US008759481B2

(12) United States Patent
Tsunoda et al.

(10) Patent No.: US 8,759,481 B2
(45) Date of Patent: Jun. 24, 2014

(54) PEPTIDE VACCINES FOR CANCERS EXPRESSING TUMOR-ASSOCIATED ANTIGENS

(71) Applicant: Oncotherapy Science, Inc., Kanagawa (JP)

(72) Inventors: Takuya Tsunoda, Kanagawa (JP); Ryuji Ohsawa, Kanagawa (JP)

(73) Assignee: OncoTherapy Science, Inc. (JP)

( * ) Notice: Subject to any disclaimer, the term of this patent is extended or adjusted under 35 U.S.C. 154(b) by 0 days.

(21) Appl. No.: 13/744,354

(22) Filed: Jan. 17, 2013

(65) Prior Publication Data

US 2013/0189291 A1 Jul. 25, 2013

Related U.S. Application Data

(60) Division of application No. 12/542,638, filed on Aug. 17, 2009, now Pat. No. 8,383,590, which is a continuation-in-part of application No. PCT/JP2008/000290, filed on Feb. 21, 2008.

(60) Provisional application No. 60/902,949, filed on Feb. 21, 2007, provisional application No. 61/089,973, filed on Aug. 19, 2008.

(51) Int. Cl.
 *C07K 16/00* (2006.01)

(52) U.S. Cl.
USPC ........... 530/326; 530/328; 530/237; 514/19.3

(58) Field of Classification Search
None
See application file for complete search history.

(56) References Cited

U.S. PATENT DOCUMENTS

| | | |
|---|---|---|
| 6,664,232 B1 | 12/2003 | Itoh |
| 6,783,961 B1 | 8/2004 | Edwards et al. |
| 6,830,885 B1 | 12/2004 | Lanctot et al. |
| 7,531,300 B2 | 5/2009 | Nakamura et al. |
| 7,727,714 B2 | 6/2010 | Nakamura et al. |
| 8,143,228 B2 | 3/2012 | Mabjeesh |
| 2003/0013649 A1 | 1/2003 | Rosen et al. |
| 2003/0082758 A1 | 5/2003 | Rosen et al. |
| 2003/0086934 A1 | 5/2003 | Botstein et al. |
| 2003/0124579 A1 | 7/2003 | Mack et al. |
| 2003/0194704 A1 | 10/2003 | Penn et al. |
| 2003/0232350 A1 | 12/2003 | Afar et al. |
| 2005/0214836 A1 | 9/2005 | Nakamura et al. |
| 2005/0259483 A1 | 11/2005 | Nakamura et al. |
| 2005/0260639 A1 | 11/2005 | Nakamura et al. |
| 2006/0024692 A1 | 2/2006 | Nakamura et al. |
| 2006/0093617 A1 | 5/2006 | Buyse et al. |
| 2006/0105333 A1 | 5/2006 | Nakamura et al. |
| 2006/0194199 A1 | 8/2006 | Nakamura et al. |
| 2006/0199179 A1 | 9/2006 | Nakamura et al. |
| 2007/0014787 A1 | 1/2007 | Ruben et al. |
| 2007/0015271 A1 | 1/2007 | Rosen et al. |
| 2007/0253954 A1 | 11/2007 | Nakamura et al. |
| 2009/0062512 A1 | 3/2009 | Hildebrand et al. |
| 2009/0162361 A1 | 6/2009 | Nakamura et al. |
| 2009/0169572 A1 | 7/2009 | Nakatsuru et al. |
| 2009/0175844 A1 | 7/2009 | Nakamura et al. |
| 2009/0191211 A1 | 7/2009 | Nakatsuru et al. |
| 2009/0202576 A1 | 8/2009 | Tahara et al. |
| 2009/0208514 A1 | 8/2009 | Nakamura et al. |
| 2009/0215683 A1 | 8/2009 | Nakamura et al. |
| 2009/0286856 A1 | 11/2009 | Nakamura et al. |
| 2009/0312264 A1 | 12/2009 | Itoh et al. |
| 2009/0317392 A1 | 12/2009 | Nakamura et al. |
| 2010/0009920 A1 | 1/2010 | Nakamura et al. |
| 2010/0204060 A1 | 8/2010 | Nakamura et al. |
| 2012/0014996 A1 | 1/2012 | Nakamura et al. |
| 2012/0264634 A1 | 10/2012 | Amersdorfer et al. |

FOREIGN PATENT DOCUMENTS

| | | |
|---|---|---|
| CN | 1073878 A | 7/1993 |
| CN | 1362263 A | 8/2002 |
| CN | 1469926 A | 1/2004 |
| CN | 1781934 A | 6/2006 |
| CN | 1872877 A | 12/2006 |
| EP | 01/29221 A2 | 12/1984 |
| EP | 0222491 A1 | 5/1987 |
| EP | 0546787 A2 | 6/1993 |
| EP | 1022286 A1 | 7/2000 |
| EP | 1757306 A1 | 2/2007 |
| EP | 1972639 A2 | 9/2008 |
| EP | 1983003 A2 | 10/2008 |
| EP | 2080812 A1 | 7/2009 |
| RU | 2283130 C2 | 9/2006 |
| TW | 2005/02247 | 1/2005 |

(Continued)

OTHER PUBLICATIONS

Ezzell (J. NIH Res. 1995 7:46).*

(Continued)

*Primary Examiner* — Sheela J Huff

(74) *Attorney, Agent, or Firm* — Kilpatrick Townsend & Stockton LLP

(57) ABSTRACT

The present invention provides peptides having an amino acid sequence as set forth in SEQ ID NO: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288, as well as peptides having the above-mentioned amino acid sequences in which 1, 2, or several (e.g., up to 5) amino acids are substituted, deleted, or added, provided the peptides possess cytotoxic T cell inducibility. The present invention also provides drugs for treating or preventing a disease associated with over-expression of the CDH3, EPHA4, ECT2, HIG2, INHBB, KIF20A, KNTC2, TTK and/or URLC10, e.g. cancers containing as an active ingredient one or more of these peptides. The peptides of the present invention find further utility as vaccines.

14 Claims, 20 Drawing Sheets

(56) References Cited

FOREIGN PATENT DOCUMENTS

| | | |
|---|---|---|
| WO | 95/28484 A1 | 10/1995 |
| WO | 98/45433 A1 | 10/1998 |
| WO | 2009/025116 A1 | 2/2000 |
| WO | 01/29221 A | 4/2001 |
| WO | 01/72295 A2 | 4/2001 |
| WO | 0144291 A2 | 6/2001 |
| WO | 01/62776 A1 | 8/2001 |
| WO | 01/64835 A2 | 9/2001 |
| WO | 02/102235 A2 | 10/2001 |
| WO | 02/08765 A2 | 1/2002 |
| WO | 02/30268 A2 | 4/2002 |
| WO | 02/078524 A2 | 10/2002 |
| WO | 02/086443 A2 | 10/2002 |
| WO | 03/080640 A1 | 10/2003 |
| WO | 2004/001072 A2 | 12/2003 |
| WO | 2004/007770 A2 | 1/2004 |
| WO | 2004/024952 A2 | 3/2004 |
| WO | 2004/024952 A2 | 3/2004 |
| WO | 2004/030615 A2 | 4/2004 |
| WO | 2004/031410 A1 | 4/2004 |
| WO | 2004/031410 A2 | 4/2004 |
| WO | 2004/031412 A2 | 4/2004 |
| WO | 2004/031413 A2 | 4/2004 |
| WO | 2004/031414 A2 | 4/2004 |
| WO | 2004/055050 A2 | 7/2004 |
| WO | 2004/058153 A2 | 7/2004 |
| WO | 2005/001138 A2 | 1/2005 |
| WO | 2005/016962 A2 | 2/2005 |
| WO | 2004/019475 A2 | 3/2005 |
| WO | 2005/019258 A2 | 3/2005 |
| WO | 2005/028676 A2 | 3/2005 |
| WO | 2005/083086 A2 | 9/2005 |
| WO | 2005/090572 A2 | 9/2005 |
| WO | 2005/097189 A1 | 10/2005 |
| WO | 2005/118626 A2 | 12/2005 |
| WO | 2006/038208 A2 | 4/2006 |
| WO | 2006/058496 A1 | 6/2006 |
| WO | 2005/091734 A2 | 8/2006 |
| WO | 2006/085684 A2 | 8/2006 |
| WO | 2006/090810 A2 | 8/2006 |
| WO | 2006/091734 A2 | 8/2006 |
| WO | 2006/093337 A1 | 9/2006 |
| WO | 2007/013480 A2 | 2/2007 |
| WO | 2007/013575 A2 | 2/2007 |
| WO | 2007/013665 A2 | 2/2007 |
| WO | 2007/013671 A2 | 2/2007 |
| WO | 2007/018047 A1 | 2/2007 |
| WO | 2007/064743 A2 | 6/2007 |
| WO | 2007/102383 A1 | 9/2007 |
| WO | 2007/102525 A1 | 9/2007 |
| WO | 2007/121147 A1 | 10/2007 |
| WO | 2007/150077 A2 | 12/2007 |
| WO | 2008/072777 A2 | 6/2008 |
| WO | 2008/102557 A1 | 8/2008 |
| WO | 2008/102906 A1 | 8/2008 |
| WO | 2009/016691 A1 | 2/2009 |
| WO | 2010/021112 A1 | 2/2010 |
| WO | 2011/039289 A1 | 4/2011 |

OTHER PUBLICATIONS

Spitler (Cancer Biotherapy, 1995, 10:1-3).*
Boon (Adv. Can. Res. 1992 58:177-210.*
Freshney (Culture of Animal Cells, A Manual of Basic Technique, Alan R. Liss, Inc., 1983, New York, p4).*
Dermer (Bio/Technology, 1994, 12:320).*
Gura (Science, 1997, 278:1041-1042).*
Jain (Sci. Am., 1994, 271:58-65).*
Adams, et al., "Prediction of binding to MHC class I molecules," *J Immunol Methods*, vol. 185(2), pp. 181-190 (Sep. 25, 1995).
Allan, et al., "Membrane motors," *Curr Opin Cell Biol.*, vol. 11(4), pp. 476-482 (Aug. 1999).
Andre, et al., "Exosomes as Potent Cell-Free Peptide-Based Vaccine. I. Dendritic Cell-Derived Exosomes Transfer Functional MHC Class I/Peptide Complexes to Dendritic Cells," *J Immunol.*, vol. 172(4), pp. 2126-2136 (Feb. 15, 2004).
Ashida, et al., "Molecular Features of the Transition from Prostatic Intraepithelial Neoplasia (PIN) to Prostate Cancer: Genome-wide Gene-expression Profiles of Prostate Cancers and PINs," *Cancer Research*, vol. 64(17), pp. 5963-5972 (Sep. 1, 2004).
Bachinsky, et al., "Mapping and binding analysis of peptides derived from the tumor associated antigen survivin for eight HLA alleles," *Cancer Immun.*, vol. 5:6. 9 pages (Mar. 22, 2005).
Belli, et al., "Vaccination of Metastatic Melanoma Patients With Autologous Tumor-Derived Heat Shock Protein gp96-Peptide Complexes: Clinical and Immunologic Findings," *J Clin. Oncol.*, vol. 20(20), pp. 4169-4180 (Oct. 15, 2002).
Belokoneva, "Immunity Retro Style," *Science and Life*, No. 1, pp. 45-48 (2004).
Bienz, et al., "Linking Colorectal Cancer to Wnt Signaling," *Cell*, vol. 103(2), pp. 311-320 (Oct. 13, 2000).
Boon, "Tumor Antigens Recognized by Cytolytic T Lymphocytes: Present Perspectives for Specific Immunotherapy," *Int J Cancer*, vol. 54(2), pp. 177-180 (May 8, 1993).
Boon, et al., "Human Tumor Antigens Recognized by T Lymphocytes," *J Exp Med.*, vol. 183(3), pp. 725-729 (Mar. 1, 1996).
Brown et al., "Activins Are Critical Modulators of Growth and Survival," *Mol. Endocrinol*, 17, pp. 2404-2417. (2003).
Butterfield, et al., "Generation of Human T-cell Responses to an HLA-A2.1-restricted Peptide Epitope Derived from α-Fetoprotein," *Cancer Res.*, vol. 59(13), pp. 3134-3142 (Jul. 1, 1999).
Coulie, et al, "Cytolytic T-cell responses of cancer patients vaccinated with a MAGE antigen," *Immunol Rev.*, vol. 188, pp. 33-42 (Oct. 2002).
Dionne, et al., "Her-2/neu altered peptide ligand-induced CTL responses: implications for peptides with increased HLA affinity and T-cell-receptor interaction," *Cancer Immunol Immunother.*, vol. 53(4), pp. 307-314 (Apr. 2004, Epub Nov. 5, 2003).
Echard, et al. "Interaction of a Golgi-Associated Kinesin-Like Protein with Rab6," et al., *Science*, vol. 279(5350), pp. 580-585 (Jan. 23, 1998).
Eloubeidi, et al., "Prognostic factors for survival in pancreatic cancer: a population-based study," *Am J Surg.*, vol. 192(3), pp. 322-329 (Sep. 2006).
Escudier, et al., "Vaccination of metastatic melanoma patients with autologous dendritic cell (DC) derived-exosomes: result of the first phase I clinical trial," *J Trans I Med.*, vol. 3(1):10, 13 pages (Mar. 2, 2005).
Falk, et al., "Allele-specific motifs revealed by sequencing of self-peptide eluted from MHC molecules," *Nature*, vol. 351(6324), pp. 290-296 (May 23, 1991).
Fujie, et al., "A Mage-1 Encoded HLA-A24-Binding Synthetic Peptide Induces Specific Anti-Tumor Cytotoxic T Lymphocytes," *Int J Cancer*, vol. 80(2), pp. 169-172 (Jan. 18, 1999).
Harada, et al., "Kinesin superfamily protein-derived peptides with the ability to induce glioma-reactive cytotoxic T lymphocytes in human leukocyte antigen-A24+glioma patients," *Oncology Reports*, vol. 17(3), pp. 629-636 (Mar. 2007).
Goonetilleke, et al., "Nationwide questionnaire survey of the contemporary surgical management of pancreatic cancer in the United Kingdom &*Ireland," *Int J Surg.*, vol. 5(3), pp. 147-151 (Jun. 2007, Epub Oct. 24, 2006).
Gross, et al., "High vaccination efficiency of low-affinity epitopes in antitumor immunotherapy," *J. Clin. Invest.*, vol. 113(3), pp. 425-433 (Feb. 2004).
Harris, "Structure and Function of the p53 Tumor Suppressor Gene: Clues for Rational Cancer Therapeutic Strategies," *J Natl Cancer Inst.*, vol. 88(20), pp. 1442-1455 (Oct. 16, 1996).
Hirokawa, et al., "Kinesin and dynein superfamily proteins in organelle transport and cell division," *Curr Opin Cell Biol.*, vol. 10(1), pp. 60-73 (Feb. 1998).
Hoffmann, et al., "The Ability of Variant Peptides to Reverse the Nonresponsiveness of T Lymphocytes to the Wild-Type Sequence $P53_{264-272}$ Epitope," *J Immunol.*, vol. 168(3), pp. 1338-1347 (Feb. 1, 2002).

(56) References Cited

OTHER PUBLICATIONS

Hung, et al, "Molecular profiling of bladder cancer: involvement of the TGF-β pathway in bladder cancer progression,"*Cancer Letters*, vol. 265, No. 1, pp. 27-38 (2008).
Imai, et al., "Identification of a novel tumor-associated antigen, RAB6KIFL, as a candidate of target for immunotherapy of pancreatic cancer," *Abstract of the Annual Meeting of the Japanese Society of Immunology*, #1-H-W15-1-0/P, vol. 38, p. 101 (2008).
Ishikawa, et al., "Cancer-Testis Antigen Lymphocyte Antigen 6 Complex Locus K Is a Serologic Biomarker and a Therapeutic Target for Lung and Esophageal Carcinomas," *Cancer Res.*, vol. 67(24), pp. 11601-11611 (Dec. 15, 2007).
Kikuchi, et al., "Identification of a SART-1-Dervied Peptide Capable of Inducing HLA-A24-Restricted and Tumor-Specific Cytotoxic T Lymphocytes," *Int J Cancer*, vol. 81 (3), pp. 459-466 (May 5, 1999).
Kondo, et al., "Prominent Roles of Secondary Anchor Residues in Peptide Binding to HLA-A24 Human Class I Molecules," *J. Immunol.*, vol. 155(9), pp. 4307-4312 (Nov. 1, 1995).
Kubo, et al., "Definition of Specific Peptide Motifs for Four Major HLA-A Alleles," *J Immunol*,. vol. 152(8), pp. 3913-3924 (Apr. 15, 1994).
Kuzushima, et al., "Efficient identification of HLA-A*2402-restricted cytomegalovirus specific CD8+ T-cell epitopes by a computer algorithm and an enzyme-linked immunospot assay,"*Blood*, vol. 98(6), pp. 1872-1881 (Sep. 15, 2001).
Lin, et al., "Molecular diagnosis of colorectal tumors by expression profiles of 50 genes expressed differentially in adenomas and carcinomas," *Oncogene*, vol. 21(26), pp. 4120-4128 (Jun. 13, 2002).
Lockhart, et al., "Treatment for Pancreatic Cancer: Current Therapy and Continued Progress," *Gastroenterology*, vol. 128(6), pp. 1642-1654 (May 2005).
Mylonas, et al., "Inhibin/activin subunits beta-A (-βA) and beta-B {-βB) are differentially localised in normal, hyperplastic and malignant human endometrial tissue," *Acta Histochem*, vol. 108(1), pp. 1-11 (2006).
Oiso, et al., "A Newly Identified Mage-3-Derived Epitope Recognized by HLA-A24-Restricted Cytotoxic T Lymphocytes," *Int J Cancer*, vol. 81(3), pp. 387-394 (May 5, 1999).
Okabe, et al., "Genome-wide Analysis of Gene Expression in Human Hepatocellular Carcinomas Using cDNA Microarray: Identification of Genes Involved in Viral Carcinogenesis and Tumor Progression," *Cancer Res.*, vol. 61 (5), pp. 2129-2137 (Mar. 1, 2001).
Parker, et al., "Scheme for Ranking Potential HLA-A2 Binding Peptides Based on Independent Binding of Individual Peptide Side-Chains," *J Immunol.*, vol. 152(1), pp. 163-175 (Jan. 1, 1994).
Rammensee, et al., "MHC ligands and peptide motifs: first listing," *Immunogenetics*, vol. 41(4), pp. 178-228 (1995).
Robertson, et al., "Inhibin/activin and ovarian cancer,"*Endocr. Relat. Cancer*, 11, pp. 35-49 (2004).
Rosenberg, et al., "Cancer immunotherapy: moving beyond current vaccines," *Nat Med.*, vol. 10(9), pp. 909-915 (Sep. 2004).
Schueler-Furman, et al., "Structure-based prediction of binding peptides to MHC class I molecules: Application to a broad range of MHC alleles," *Protein Sci.*, vol. 9(9), pp. 1838-1846 (Sep. 2000).
Sener, et al., "Pancreatic Cancer: A Report of Treatment and Survival Trends for 100,313 Patients Diagnosed from 1985-1995, Using the National Cancer Database," *J Am Coll Surg.*, vol. 189(1), pp. 1-7 (Jul. 1999).
Smeenk, et al., "Survival after surgical management of pancreatic adenocarcinoma: does curative and radical surgery truly exist?" *Langenbecks Arch Surg.*, vol. 390(2), pp. 94-103 (Apr. 2005, Epub May 14, 2004).
Stevanovic, "Identification of tumour-associated T-cell epitopes for vaccine development," *Nat. Rev. Cancer*, vol. 2(7); pp. 514-520 (2002).
Suda, et al., "Identification of secernin 1 as a novel immunotherapy target for gastric cancer using the expression profiles of cDNA microarray," *Cancer Science*, vol. 97(5), pp. 411-419 (May 2006).
Suda, et al., "Identification of human leukocyte antigen-A24-restricted epitope peptides derived from gene products upregulated in lung and esophageal cancers as novel targets for immunotherapy,"*Cancer Science*, vol. 98(11), pp. 1803-1808 (Nov. 2007).
Tanaka, et al., "Induction of Antitumor Cytotoxic T Lymphocytes with a MAGE-3-encoded Synthetic Peptide Presented by Human Leukocytes Antigen-A24," *Cancer Res.*, vol. 57(20), pp. 4465-4468 (Oct. 15, 1997).
Taniuchi, et al., "Identification and functional analysis of RAB6KIFL up-regulated in pancreatic cancer," *Abstract of the Annual Meeting of the Japanese Cancer Association*,W-135, vol. 63, p. 79 (2004).
Taniuchi, et al., "Down-regulation of RAB6KIFL/KIF20A, a Kinesin Involved with Membrance Trafficking of Discs Large Homologue 5, Can Attenuate Growth of Pancreatic Cancer," *Cancer Res.*, vol. 65(1), pp. 105-112 (Jan. 1, 2005).
Van Der Burg, et al., "Immunogenicity of Peptides Bound to MHC Class 1 Molecules Depends on the MHC-Peptide Complex Stability," *J Immunol.*, vol. 156(9), pp. 3308-3314 (May 1, 1996).
Vissers, et al., "The Renal Cell Carcinoma-associated Antigen G250 Encodes a Human Leukocyte Antigen (HLA)-A2.1-restricted Epitope Recognized by a Cytotoxic T Lymphocytes," *Cancer Res.*, vol. 59(21), pp. 5554-5559 (Nov. 1, 1999).
Worbs, et al., "Expression of the inhibin/activin subunits (-α and -βA and -βB) in normal and carcinogenic endometrial tissue: Possible immunohistochemical differentiation markers," *Oncol Reg.*, vol. 17(1), pp. 97-104 (Jan. 2007).
Yeo, et al., "Pancreaticoduodenectomy for Cancer of the Head of the Pancreas," *Ann Surg.*, vol. 221(6), pp. 721-731, discussion, pp. 731-733 (Jun. 1995).
Ying, et al., "Synthesis of human inhibin β fragments, preparation and generation of monoclonal antibodies against human inhibin-βB subunits," *Acta Pharmaceutica Sinica*, vol. 35, No. 7, pp. 505-507 (2000).
Zaremba, et al., "Identification of an Enhancer Agonist Cytotoxic T Lymphocyte Peptide from Human Carcinoembryonic Antigen," *Cancer Res.*, vol. 57(20), pp. 4570-4577 (Oct. 15, 1997).
GenBank Accession No: EAW83239.1, 3 pgs., downloaded from http://www.ncbi.nlm.nih.gov/protein/EAW83239.1 (Dec. 18, 2006).
Protein Sequence Analysis, http//vitalonic.narod.ru/biochem/index.html (English Translation at http://molbiol.ru/eng/scripts/01_18.html) (2006).
Protocol of Oral Hearing issued in related Russian Application No. 2009135020/10(049325) based on International Patent Application No. PCT/JP2008/000290, filed Feb. 21, 2008.
Supplementary European Search Report issued on Jan. 30, 2012, filed in related European Patent Application No. EP09808047.
Decision on Grant of Russian Patent Application No. 2009135020/10, 8 pages, application filed on Feb. 21, 2008.
U.S. Appl. No. 11/913,147, filed Oct. 30, 2007, 239 pages.
U.S. Appl. No. 12/671,447, filed Jul. 6, 2010, 103 pages.
U.S. Appl. No. 12/673,451, filed Feb. 2, 2010, 131 pages.
U.S. Appl. No. 12/903,961, filed Oct. 13, 2010, 46 pages.
U.S. Appl. No. 13/001,869, which is a U.S. National Phase of PCT/JP2009/003009, filed Jun. 30, 2009, 63 pages.
U.S. Appl. No. 13/002,977, filed Sep. 16, 2011, 66 pages.
U.S. Appl. No. 13/080,461, filed Apr. 5, 2011, 75 pages.
U.S. Appl. No. 13/059,618, filed Jun. 9, 2011, 43 pages.
U.S. Appl. No. 13/059,617, filed Jun. 16, 2011, 39 pages.
U.S. Appl. No. 13/125,548, filed Jul. 6, 2011, 54 pages.
U.S. Appl. No. 13/224,102, filed Sep. 1, 2011, 82 pages.
U.S. Appl. No. 13/246,639, filed Sep. 27, 2011, 164 pages.
U.S. Appl. No. 13/464,831, filed May 4, 2012, 162 pages.
U.S. Appl. No. 13/536,327, filed Jun. 28, 2012, 204 pages.
U.S. Appl. No. 13/519,127, which is a U.S. National Stage of PCT/JP2009/007333, filed Dec. 28, 2009, 59 pages.
U.S. Appl. No. 13/638,272, which is a U.S. National Stage of PCT/JP2011/001909, filed Mar. 30, 2011, 70 pages.
U.S. Appl. No. 13/320,022, which is a U.S. National Stage of PCT/JP2010/003166, filed May 10, 2010, 66 pages.
Burgess, et al., "Possible Dissociation of the Heparin-binding and Mitogenic Activities of Heparin-binding (Acidic Fibroblast) Growth Factor-1 from Its Receptor binding Activities by Site-directed Mutagenesis of a Single Lysine Residue," *J Cell Biol.*, vol. 111(5 Pt 1), pp. 2129-2138 (Nov. 1990).

(56) References Cited

OTHER PUBLICATIONS

Dermer, et al., "Another Anniversary for the War on Cancer," *Bio/Technology*, vol. 12, p. 320 (1994).

Ezzell, "Cancer "Vaccines": An Idea Whose Time Has Come?," *J NIH Res.*, vol. 7, p. 46 (1995).

Freshney, et al., Culture of Animal Cells, A Manual of Basic Technique, Alan R. Liss, Inc., New York (1983).

Gura, "Systems for Identifying New Drugs Are Often Faulty," *Science*, vol. 278(5340), pp. 1041-1042 (Nov. 7, 1997).

Jain, "Barriers to Drug Delivery in Solid Tumors," *Sci Am.*, vol. 271(1), pp. 58-65 (Jul. 1994).

Lazar, et al., "Transforming Growth Factor α: Mutation of Aspartic Acid 47 and Leucine 48 Results in Different Biological Activities," *Mol Cell Biol.*, vol. 8(3), pp. 1247-1252 (Mar. 1988).

Spitler, "Cancer Vaccines: The Interferon Analogy," *Cancer Biother.*, vol. 10(1), pp. 1-3 (1995).

Worbs, et al., "Expression of the inhibin/activin subunits (-α and -βA and -βB) in normal and carcinogenic endometrial tissue: Possible immunohistochemical differentiation markers," *Oncol Rep.*, vol. 17(1), pp. 97-104 (Jan. 2007).

Kono, et al., "Multicenter, phase II clinical trial of cancer vaccination for advanced esophageal cancer with three peptides derived from novel cancer-testis antigens," *J Transl Med.*, vol. 10:141, 9 pages (Jul. 9, 2012).

Boon, "Toward a Genetic Analysis of Tumor Rejection Antigens," *Adv Cancer Res.*, vol. 58, pp. 177-210 (1992).

De Nooij-Van, et al., "Characterization of the Human LY-6 Antigens, the Newly Annotated Member LY-6K Included, As Molecular Markers for Head-and-Neck Squamous Cell Carcinoma," *Int J Cancer*, vol. 103(6), pp. 768-774 (Mar. 1, 2003).

Dionne, et al., "Functional characterization of CTL against gp100 altered peptide ligands," *Cancer Immunol Immunother.*, vol. 52(4), pp. 199-206 (Apr. 2003, Epub Feb. 18, 2003).

Ishizaki, et al., "Inhibition of Tumor Growth with Antiangiogenic Cancer Vaccine Using Epitope Peptides Derived from Human Vascular Endothelial Growth Factor Receptor 1," *Clin Cancer Res.*, vol. 12(19), pp. 5841-5849 (Oct. 1, 2006).

Kono, et al. "Vaccination with multiple peptides derived from novel cancer-testis antigens can induce specific T-cell responses and clinical responses in advanced esophageal cancer," *Cancer Sci.*, vol. 100(8), pp. 1502-1509 (Aug. 2009, Epub May 14, 2009).

Tahara, et al., "Translational Research of cancer vaccine therapy by novel antigen peptides," *Japanese Cancer Association Symposium* (Feb. 7, 2006).

Tsunoda, et al., "Phase I clinical trial of epitope peptides based vaccine with novel tumor associate antigen, RNF43 and URLC10, found by genome-wide exploration using cDNA Microarray Profiling (GET-MAP) against colorectal cancer and esophageal cancer patients" *Annual Report 2005, Institute of Medical Science, University of Tokyo*, p. 247, No. 5 (2006).

Extended European Search Report for European Application No. 12175482.4, 5 pages, dated Jul. 31, 2013.

Extended European Search Report for European Application No. 12175487.3, 6 pages, dated Aug. 7, 2013.

Hayama, S., et al., "Activation of CDCA1-KNTC2, Members of Centromere Protein Complex, Involved in Pulmonary Carcinogenesis," *Cancer Research*, vol. 66 (21), pp. 10339-10348 (Nov. 1, 2006).

GenBank Accession No. NM_017527.3, 3 pgs., downloaded from http://www.ncbi.nlm.nih.gov/nuccore/NM_017527 (Mar. 8, 2013).

Extended European Search Report mailed on Sep. 23, 2013 for European Application No. EP12175488.1 15 pages.

Komori et al., "Identification of HLA-A2- or HLA-A24-Restricted CTL Eptitopes Possibly Useful for Flypican-3-Specific Immunotherapy of Hepatocellular Carcinoma", 2006; *Clin Cancer Res*: vol. 12, pp. 2689-2697.

\* cited by examiner a  CDH3-A24-10-248 b  CDH3-A24-10-332 c  CDH3-A24-10-470 d  CDH3-A24-9-513 e  CDH3-A24-9-406 d e f

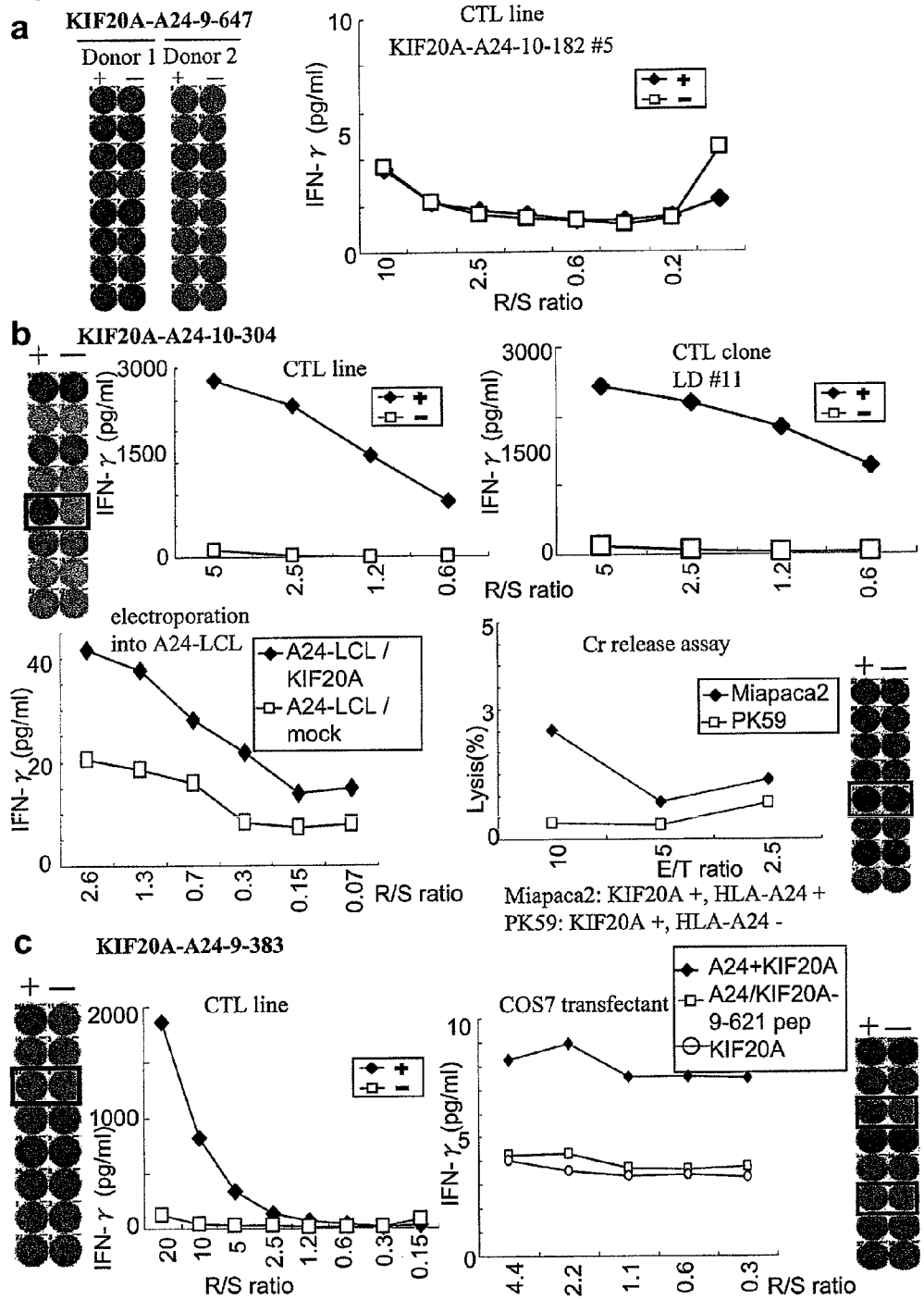

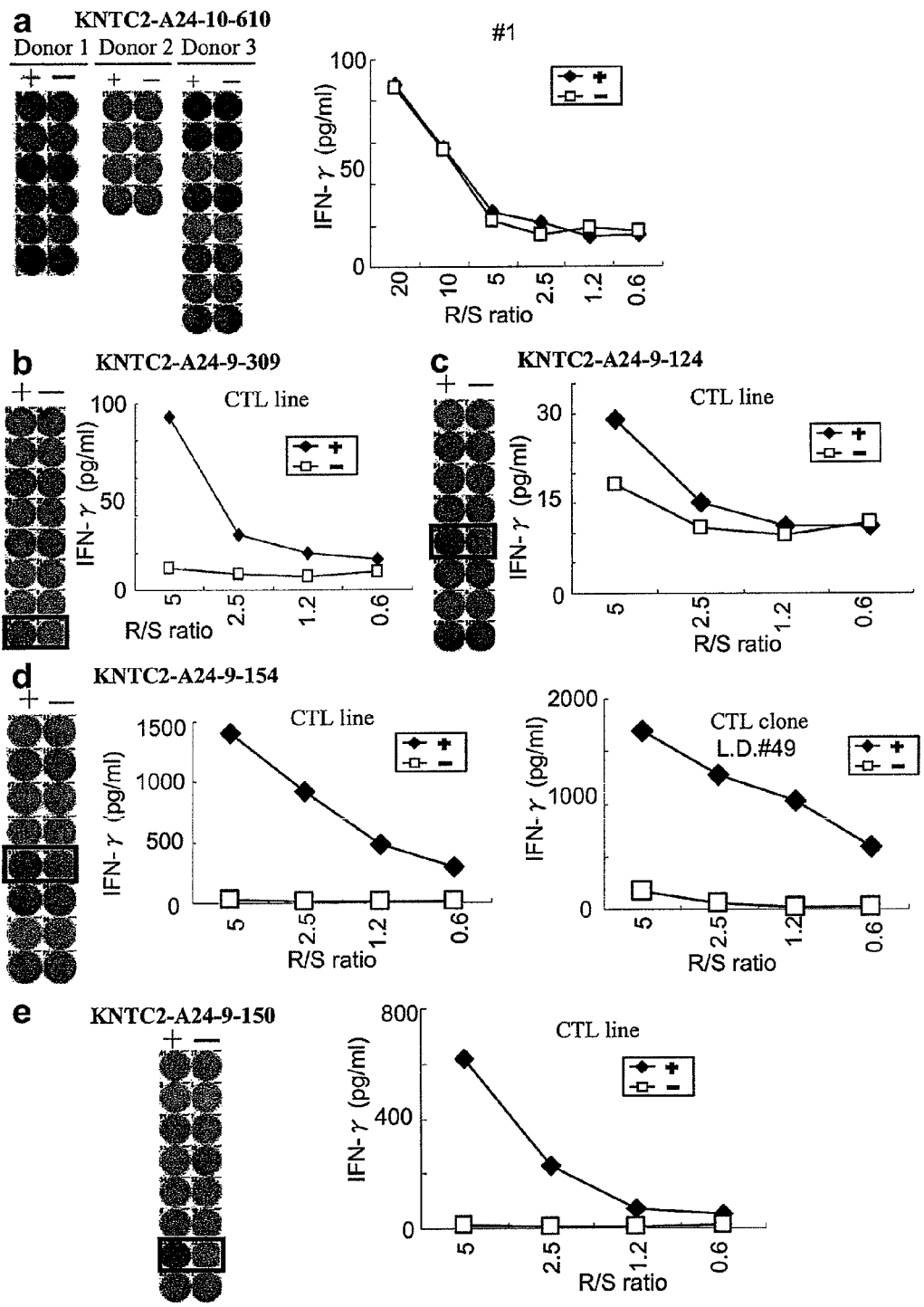

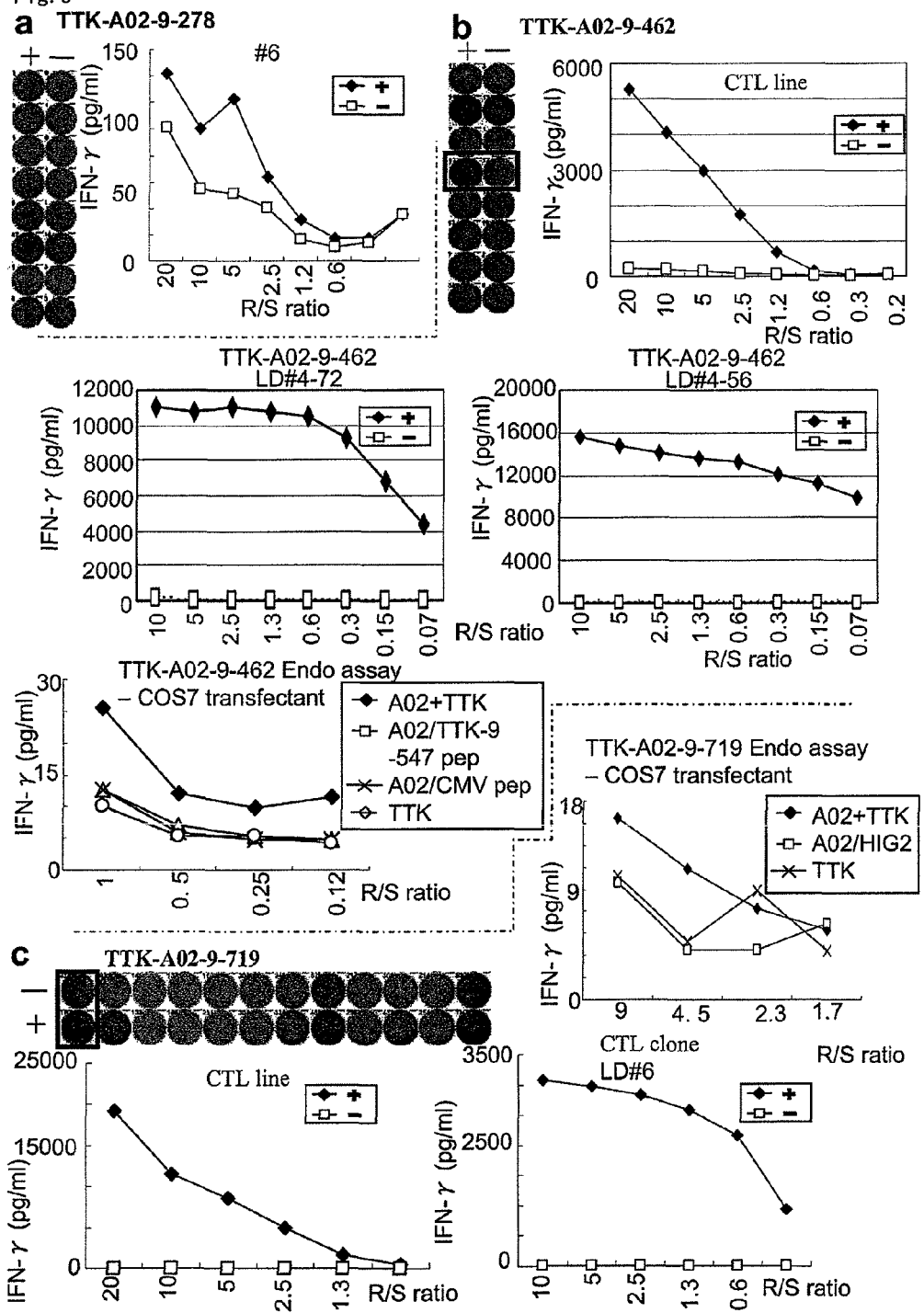

d  TTK-A02-9-547 a URLC10-A02-9-58 b URLC10-A02-9-206   c URLC10-A02-9-212 d URLC10-A02-10-211

Continuation of d

CTL line stimulated by URLC10-A02-10-211 recognized endogenously URLC10 expressed target cells with HLA-A02

INHBB-A02 ELISPOT data

INHBB-A02 CTL line

PEPTIDE VACCINES FOR CANCERS EXPRESSING TUMOR-ASSOCIATED ANTIGENS

CROSS-REFERENCES TO RELATED APPLICATIONS

This application is a division of U.S. application Ser. No. 12/542,638, filed Aug. 17, 2009, which is a continuation-in-part of PCT/JP2008/000290 (WO 2008/102557) filed Feb. 21, 2008, which claims priority to U.S. Provisional Application Ser. No. 60/902,949, filed Feb. 21, 2007. This application also claims the benefit of U.S. Provisional Application Ser. No. 61/089,973 filed Aug. 19, 2008. All of these applications are incorporated herein by reference.

REFERENCE TO A "SEQUENCE LISTING," A TABLE, OR A COMPUTER PROGRAM LISTING APPENDIX SUBMITTED ON A COMPACT DISK

This application includes a Sequence Listing as a text file named "SEQUENCE_LISTING_87331_020810USTXT.TXT" created Jan. 16, 2013 and containing 246,002 bytes. The material contained in this text file is incorporated by reference.

TECHNICAL FIELD

The present invention relates to the field of biological science, more specifically to the field of cancer therapy. In particular, the present invention relates to novel immunogenic peptides that serve as extremely effective as cancer vaccines, and drugs for treating and preventing tumors containing such peptides.

BACKGROUND ART

It has been demonstrated that $CD8^+$ cytotoxic T lymphocytes (CTLs) recognize epitope peptides derived from tumor-associated antigens (TAAs) presented on MHC class I molecules, and subsequently lyse the tumor cells. Since the discovery of the MAGE family as the first example of TAAs, many other TAAs have been discovered using immunological approaches (Boon T. (1993) Int J Cancer 54: 177-80; Boon T. et al., (1996) J Exp Med 183: 725-9; van der Bruggen P et al., (1991) Science 254: 1643-7; Brichard V et al., (1993) J Exp Med 178: 489-95; Kawakami Y et al., (1994) J Exp Med 180: 347-52.). Some of them are now in clinical development as targets of immunotherapy. TAAs discovered to date include MAGE (van der Bruggen P et al., (1991) Science 254: 1643-7.), gp100 (Kawakami Y et al., (1994) J Exp Med 180: 347-52.), SART (Shichijo S et al., (1998) J Exp Med 187:277-88.), and NY-ESO-1 (Chen Y. T. et al., (1997) Proc. Natl. Acd. Sci. USA, 94: 1914-8.). On the other hand, certain gene products demonstrated to be somewhat specifically over-expressed in tumor cells have been shown to be recognized as targets for inducing cellular immune responses. Such gene products include p53 (Umano Y et al., (2001) Br J Cancer, 84:1052-7.), HER2/neu (Tanaka H et al., (2001) Br J Cancer, 84: 94-9.), CEA (Nukaya I et al., (1999) Int. J. Cancer 80, 92-7.) and the like.

Despite significant progress in basic and clinical research concerning TAAs (Rosenberg S A et al., (1998) Nature Med, 4: 321-7; Mukherji B. et al., (1995) Proc Natl Acad Sci USA, 92: 8078-82; Hu X et al., (1996) Cancer Res, 56: 2479-83.), only a very limited number of candidate TAAs suitable for treatment of cancers are presently available. TAAs that are abundantly expressed in cancer cells, and whose expression is restricted to cancer cells, would be promising candidates as immunotherapeutic targets.

Both HLA-A24 and HLA-A0201 are common HLA alleles in the Japanese and Caucasian populations (Date Y et al., (1996) Tissue Antigens 47: 93-101; Kondo A et al., (1995) Immunol 155: 4307-12; Kubo R T et al., (1994) J Immunol 152: 3913-24; Imanishi et al., Proceeding of the eleventh International Histocompatibility Workshop and Conference Oxford University Press, Oxford, 1065 (1992); Williams F et al., (1997) Tissue Antigen 49: 129-33.). Thus, antigenic peptides of cancers presented by these HLA alleles may find particular utility in the treatment of cancers among Japanese and Caucasian patients. Further, it is known that the induction of low-affinity CTL in vitro usually results from exposure to high concentrations of peptides, generating a high level of specific peptide/MHC complexes on antigen-presenting cells (APCs), which will effectively activate these CTL (Alexander-Miller et al., (1996) Proc Natl Acad Sci USA 93: 4102-7.).

Recently, HLA class I-binding peptide sequence can be expected using algorithms (Journal of Immunological Methods, (1995), Vol. 185, pp. 181-190, J. Immunol., (1994), Vol. 152, pp. 163-175, protein science, (2000), Vol. 9, pp. 1838-1846). However, it is hard to say that the expected epitope peptide can be cut to the size and expressed on the target cell surface with HLA molecule and recognized by CTL. Moreover, the algorithm, for example BIMAS (http://bimas.dcrt.nih.gov/cgi-bin/molbio/ken_parker_comboform) (Parker K C, et al., (1994) J. Immunol.; 152(1):163-75; Kuzushima K, et al., (2001) Blood.; 98(6):1872-81.)) can suggest the HLA molecule-binding peptide, but the suggested peptide is not so rigorous (Bachinsky M M, et. al., Cancer Immun. 2005 Mar. 22; 5:6.). Thus TAA screening still remains a lot of challenges and difficulties.

Recent developments in cDNA microarray technologies have enabled the construction of comprehensive profiles of gene expression in malignant cells as compared to normal cells (Okabe, H. et al., (2001) Cancer Res., 61, 2129-37; Lin Y M. et al., (2002) Oncogene, 21; 4120-8; Hasegawa S. et al., (2002) Cancer Res 62:7012-7.). This approach enables a more thorough understanding of the complex nature of cancer cells and the mechanisms of carcinogenesis and facilitates the identification of genes whose expression is deregulated in tumors (Bienz M. et al., (2000) Cell 103, 311-20.). Among the transcripts identified as up-regulated in cancers, CDH3 (GenBank Accession No. NM_001793; SEQ ID Nos. 1, 2), EPHA4 (GenBank Accession No. L36645; SEQ ID Nos. 3, 4), ECT2 (GenBank Accession No. AY376439; SEQ ID Nos. 5, 6), HIG2 (GenBank Accession No. NM_013332; SEQ ID Nos. 7, 8) INHBB (GenBank Accession No. NM_002193; SEQ ID Nos. 9, 435, 10, 436), KIF20A (GenBank Accession No. NM_005733; SEQ ID Nos. 11, 12), KNTC2 (GenBank Accession No. AF017790; SEQ ID Nos. 13, 14), TTK (GenBank Accession No. NM_003318; SEQ ID Nos. 15, 16) and URLC10 (GenBank Accession No. NM_017527; SEQ ID Nos. 17, 18) have been recently discovered. The entire contents of the references are incorporated by reference herein. These genes are of particular interest to the present inventors, being specifically up-regulated in tumor cells of the various cancer tissues of the cases analyzed (see below). Thus, immunogenic peptides derived from CDH3, EPHA4, ECT2, HIG2, INHBB, KIF20A, KNTC2, TTK and URLC10 may find utility in selectively killing tumor cells that express such antigens. The present invention addresses these and other needs.

Since cytotoxic drugs, such as M-VAC, often cause severe adverse reactions, it is clear that thoughtful selection of novel target molecules on the basis of well-characterized mechanisms of action should be very helpful in the development of effective anti-cancer drugs having a minimized risk of side effects. Toward this goal, expression profile analyses were previously performed on various cancers and normal human tissue. Such studies led to the discovery of multiple genes that are specifically over-expressed in cancer (Lin Y M, et al., Oncogene. 2002 Jun. 13; 21:4120-8; Kitahara O, et al., Cancer Res. 2001 May 1; 61:3544-9; Suzuki C, et al., Cancer Res. 2003 Nov. 1; 63:7038-41; Ashida S, Cancer Res. 2004 Sep. 1; 64:5963-72; Ochi K, et al., Int J Oncol. 2004 March; 24(3): 647-55; Kaneta Y, et al., Int J Oncol. 2003 September; 23:681-91; Obama K, Hepatology. 2005 June; 41:1339-48; Kato T, et al., Cancer Res. 2005 Jul. 1; 65:5638-46; Kitahara O, et al., Neoplasia. 2002 July-August; 4:295-303; Saito-Hisaminato A et al., DNA Res 2002, 9: 35-45.). Examples of such genes identified as over-expressed in various cancers include, but are not limited to, CDH3, EPHA4, ECT2, HIG2, INHBB, KIF20A, KNTC2, TTK and URLC10. CDH3 has been previously identified as over-expressed in bladder cancer, cervical cancer, cholangiocellular carcinoma, colorectal cancer, endometriosis, gastric cancer, diffuse-type gastric cancer, non-small cell lung cancer (NSCLC), pancreatic cancer, soft tissue tumor and testicular tumor. EPHA4 has been identified in bladder cancer, cervical cancer, cholangiocellular carcinoma, endometriosis, diffuse-type gastric cancer, ovarian cancer, pancreatic cancer, prostate cancer and soft tissue tumor. ECT2 has been identified in bladder cancer, breast cancer, cervical cancer, cholangiocellular carcinoma, chronic myeloid leukemia (CML), colorectal cancer, esophageal cancer, NSCLC, lymphoma, prostate cancer, renal carcinoma and small cell lung cancer (SCLC). HIG2 has been identified in renal carcinoma and SCLC. INHBB has been identified in cholangiocellular carcinoma, esophageal cancer, NSCLC, renal carcinoma, SCLC and soft tissue tumor. KIF20A has been identified in bladder cancer, breast cancer, cholangiocellular carcinoma, esophageal cancer, NSCLC, pancreatic cancer, prostate cancer, renal carcinoma and SCLC. KNTC2 has been identified in bladder cancer, breast cancer, cervical cancer, cholangiocellular carcinoma, CML, colorectal cancer, esophageal cancer, NSCLC, lymphoma, osteosarcoma, ovarian cancer, pancreatic cancer, prostate cancer, renal carcinoma, SCLC and soft tissue tumor. TTK has been identified in bladder cancer, breast cancer, cervical cancer, cholangiocellular carcinoma, CML, colorectal cancer, esophageal cancer, liver cancer, NSCLC, lymphoma, osteosarcoma, prostate cancer, SCLC and soft tissue tumor. URLC10 has been identified in bladder cancer, cervical cancer, cholangiocellular carcinoma, esophageal cancer, gastric cancer, NSCLC, osteosarcoma, pancreatic cancer and SCLC.

BRIEF SUMMARY OF THE INVENTION

The present invention is based in part on the discovery of the applicable targets of immunotherapy. Because TAAs have often no immunogenicity, the discovery of appropriate targets is of extreme importance. As noted above, CDH3, EPHA4, ECT2, HIG2, INHBB, KIF20A, KNTC2, TTK and URLC10 have been identified as up-regulated in various cancers. More particularly, these genes were identified using gene expression profiling with a genome-wide cDNA microarray. As discussed above, expression of CDH3, EPHA4, ECT2, HIG2, INHBB, KIF20A, KNTC2, TTK and URLC10 has been shown to be specifically up-regulated in various tumor cells, from pancreatic cancer cells to renal cell carcinomas. As described in Table 1, CDH3 expression is validly elevated in 26 out of 34 bladder cancer, 17 out of 19 cervical cancer, all of 19 cholangiocellular carcinoma, 30 out of 34 colorectal cancer, 20 out of 21 endometriosis, 13 out of 20 gastric cancer, 7 out of 8 diffuse-type gastric cancer, 36 out of 37 NSCLC, all of 16 pancreatic cancer, all of 21 soft tissue tumor and all of 10 testicular tumor.

Table 1 further demonstrates that:

EPHA4 expression is validly elevated in 14 out of 34 bladder cancer, 8 out of 14 cervical cancer, 10 out of 25 cholangiocellular carcinoma, 5 out of 15 endometriosis, 5 out of 8 diffuse-type gastric cancer, all of 5 ovarian cancer, all 14 pancreatic cancer, 20 out of 51 prostate cancer and 14 out of 23 soft tissue tumor.

ECT2 expression is validly elevated in 17 out of 19 bladder cancer, 5 out of 12 breast cancer, all of 14 cervical cancer, all of 13 cholangiocellular carcinoma, all of 5 CML, 7 out of 8 colorectal cancer, 12 out of 16 esophageal cancer, 6 out of 16 NSCLC, 8 out of 10 lymphoma, 1 out of 1 pancreatic cancer, 10 out of 13 prostate cancer, 3 out of 6 renal carcinoma and 12 out of 13 SCLC cancer.

HIG2 expression is validly elevated in 19 out of 20 renal cancer and 7 out of 9 soft tissue tumor.

INHBB expression is validly elevated in 10 out of 21 cholangiocellular carcinoma, all of 12 esophageal cancer, 10 out of 13 NSCLC, 22 out of 24 renal carcinoma, 8 out of 14 SCLC cancer and 45 out of 49 soft tissue tumor.

KIF20A expression is validly elevated in all of 31 bladder cancer, 38 out of 61 breast cancer, 10 out of 11 cholangiocellular carcinoma, 7 out of 19 esophageal cancer, 21 out of 22 NSCLC, all of 6 ovarian cancer, 17 out of 36 prostate cancer, 6 out of 11 renal carcinoma and all of 15 SCLC.

KNTC2 expression is validly elevated in 30 out of 32 bladder cancer, 47 out of 56 breast cancer, all of 10 cervical cancer, 16 out of 22 cholangiocellular carcinoma, 17 out of 37 CML, 3 out of 10 colorectal cancer, 11 out of 46 esophagus cancer, 15 out of 19 NSCLC, 7 out of 8 lymphoma, 20 out of 24 osteosarcoma, 3 out of 5 ovarian cancer, all of 2 pancreatic cancer, 15 out of 37 prostate cancer, 14 out of 19 renal cancer, all of 15 SCLC and 40 out of 59 soft tissue tumor.

TTK expression is validly elevated in all of 27 bladder cancer, 25 out of 30 breast cancer, 15 out of 16 cervical cancer, all of 10 cholangiocellular carcinoma, 5 out of 7 CML, 6 out of 10 colorectal cancer, 24 out of 44 esophageal cancer, 8 out of 15 liver cancer, all of 12 NSCLC, all of 6 lymphoma, 13 out of 16 osteoblastoma, 12 out of 17 prostate cancer, all of 15 SCLC and 16 out of 33 soft tissue tumor.

URLC10 expression is validly elevated in all of 29 bladder cancer, 15 out of 16 cervical cancer, all of 7 cholangiocellular carcinoma, 7 out of 19 esophageal cancer, all of 3 gastric cancer, 24 out of 27 NSCLC, 15 out of 19 osteosarcoma, 4 out of 5 pancreatic cancer, 33 out of 43 soft tissue tumor.

The present invention is based, at least in part, on the identification of specific epitope peptides of the gene products of these genes (CDH3, EPHA4, ECT2, HIG2, INHBB, KIF20A, KNTC2, TTK and URLC10) which possess the ability to induce cytotoxic T lymphocytes (CTLs) specific to the corresponding molecules. As discussed in detail below, Peripheral Blood Mononuclear Cells (PBMC) of healthy donor were stimulated using HLA-A*2402 or HLA-A*0201 binding candidate peptides derived from CDH3, EPHA4, ECT2, HIG2, INHBB, KIF20A, KNTC2, TTK or URLC10. CTL clones and/or lines were then established with specific cytotoxicity against the HLA-A24 or HLA-A2 (HLA-A02)

positive target cells pulsed with each of the candidate peptides. These results demonstrate that these peptides are HLA-A24 or HLA-A2 (HLA-A02) restricted epitope peptides that can induce potent and specific immune responses against cells expressing CDH3, EPHA4, ECT2, HIG2, INHBB, KIF20A, KNTC2, TTK or URLC10.

Accordingly, the present invention provides methods for treating or preventing a disease associated with the over-expression of CDH3, EPHA4, ECT2, HIG2, INHBB, KIF20A, KNTC2, TTK or URLC10, e.g. cancer. Such methods involve the step of administering to a subject in need thereof a CDH3, EPHA4, ECT2, HIG2, INHBB, KIF20A, KNTC2, TTK and/or URLC10 polypeptides of the invention. Administration of such peptide(s) results in the induction of anti-tumor immunity. Thus, the present invention provides methods for inducing anti-tumor immunity in a subject, such methods involving the step of administering to the subject the CDH3, EPHA4, ECT2, HIG2, INHBB, KIF20A, KNTC2, TTK and/or URLC10 polypeptides, as well as pharmaceutical compositions for treating or preventing a disease associated with the over-expression of CDH3, EPHA4, ECT2, HIG2, INHBB, KIF20A, KNTC2, TTK and/or URLC10, e.g. cancer, that include the CDH3, EPHA4, ECT2, HIG2, INHBB, KIF20A, KNTC2, TTK and URLC10 polypeptides. Examples of such cancers include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

The present invention further provides methods for preventing post-surgery recurrence of the disease mentioned above.

Regarding the specific aims and objectives recited above, it will be understood by those skilled in the art that one or more aspects of this invention can meet certain objectives, while one or more other aspects can meet certain other objectives. Each objective may not apply equally, in all its respects, to every aspect of this invention. As such, the objects herein can be viewed in the alternative with respect to any one aspect of this invention.

Additional objects and features of the invention will become more fully apparent when the following detailed description is read in conjunction with the accompanying figures and examples. However, it is to be understood that both the foregoing summary of the invention and the following detailed description are of preferred embodiments, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

BRIEF DESCRIPTION OF THE DRAWINGS

Various aspects and applications of the present invention will become apparent to the skilled artisan upon consideration of the brief description of the figures and the detailed description of the present invention and its preferred embodiments which follows:

FIG. 1 depicts the results of the screening of epitope peptides, which, in turn, demonstrate that CDH3-A24-10-332 (SEQ ID NO: 34), CDH3-A24-10-470 (SEQ ID NO: 358), CDH3-A24-9-513 (SEQ ID NO: 19), CDH3-A24-9-406 (SEQ ID NO: 22), CDH3-A24-10-807 (SEQ ID NO: 30) and CDH3-A24-10-655 (SEQ ID NO: 344) show potent IFN-gamma production. "a" depicts the example of negative peptides which could not be detected CTL-inducing ability despite possible binding activity with HLA-A*2402. "b" depicts the CTL-inducing ability of CDH3-A24-10-332 (SEQ ID NO: 34). CDH3-A24-10-332 (SEQ ID NO: 34) demonstrated potent IFN-gamma production as compared to the control by IFN-gamma ELISPOT assay, and CTL line that was established from the positive well #4 shown in boxed wells, demonstrated the specific response against the target cells pulsed with the epitope peptide. "c" depicts the CTL-inducing ability of CDH3-A24-10-470 (SEQ ID NO: 358). CDH3-A24-10-470 (SEQ ID NO: 358) demonstrated potent IFN-gamma production as compared to the control by IFN-gamma ELISPOT assay, and CTL line that was established from the positive well #4 shown in boxed wells, demonstrated the specific response against the target cells pulsed with the epitope peptide. "d" depicts the CTL-inducing ability of CDH3-A24-9-513 (SEQ ID NO: 19). CDH3-A24-9-513 (SEQ ID NO: 19) demonstrated potent IFN-gamma production as compared to the control by IFN-gamma ELISPOT assay. The well #6 shown in boxed wells in left panel demonstrated the specific response against the target cells pulsed with the epitope peptide. Moreover, CTL line that was established from the positive well #5 shown in boxed wells in middle panel, demonstrated the specific response against the target cells pulsed with the epitope peptide. "e" depicts the CTL-inducing ability of CDH3-A24-9-406 (SEQ ID NO: 22). CDH3-A24-9-406 (SEQ ID NO: 22) demonstrated potent IFN-gamma production as compared to the control by IFN-gamma ELISPOT assay, and CTL line that was established from the positive well #2 shown in boxed wells, demonstrated the specific response against the target cells pulsed with the epitope peptide.

[FIG. 1-2] FIG. 1 depicts the results of the screening of epitope peptides, which, in turn, demonstrate that CDH3-A24-10-332 (SEQ ID NO: 34), CDH3-A24-10-470 (SEQ ID NO: 358), CDH3-A24-9-513 (SEQ ID NO: 19), CDH3-A24-9-406 (SEQ ID NO: 22), CDH3-A24-10-807 (SEQ ID NO: 30) and CDH3-A24-10-655 (SEQ ID NO: 344) show potent IFN-gamma production. "f" depicts the CTL-inducing ability of CDH3-A24-10-807 (SEQ ID NO: 30). CDH3-A24-10-807 (SEQ ID NO: 30) demonstrated potent IFN-gamma production as compared to the control by IFN-gamma ELISPOT assay, and CTL line and the clone were established from the positive well #5 shown in boxed wells. The established CTL clone raised against the peptide demonstrated the specific CTL activity against COS7 transfected both full length of CDH3 gene and HLA-A24 molecule (lower right graph). On the other hand, COS7 transfected full length of CDH3 but not HLA-A24 and COS7 transfected HLA-A24 but not full length of CDH3 were prepared for the negative control. The CTL clone showed high specific CTL activity against COS7 that transfected both CDH3 and HLA-A24. "g" depicts the CTL-inducing ability of CDH3-A24-10-655 (SEQ ID NO: 344). CDH3-A24-10-655 (SEQ ID NO: 344) demonstrated potent IFN-gamma production as compared to the control by IFN-gamma ELISPOT assay, and CTL line and the clone were established from the positive well #1 shown in boxed wells. The established CTL clone raised against the peptide demonstrated the specific CTL activity against COS7 transfected both full length of CDH3 gene and HLA-A24 molecule (lower right graph). On the other hand, COS7 transfected full length of CDH3 but not HLA-A24 and COS7 transfected HLA-A24 but not full length of CDH3 were prepared for the negative control. The CTL clone showed high specific CTL activity against COS7 that transfected both CDH3 and HLA-A24.

[FIG. 2] FIG. 2 depicts the results of the screening of epitope peptides, which, in turn, demonstrate that Epha4-A24-9-453 (SEQ ID NO: 41), Epha4-A24-9-5 (SEQ ID NO: 44), Epha4-A24-9-420 (SEQ ID NO: 48), Epha4-A24-9-869 (SEQ ID NO: 46), Epha4-A24-10-24 (SEQ ID NO: 78) Epha4-A02-9-501 (SEQ ID NO: 376) and Epha4-A02-9-165 (SEQ ID NO: 379) show potent IFN-gamma production. "a" depicts the example of negative peptides which could not be detected CTL-inducing ability despite possible binding activity with HLA. "b" depicts the CTL-inducing ability of Epha4-A24-9-453 (SEQ ID NO: 41). Epha4-A24-9-453 (SEQ ID NO: 41) demonstrated potent IFN-gamma production as compared to the control by IFN-gamma ELISPOT assay, and CTL line that was established from the positive well #3 shown in boxed wells, demonstrated the specific response against the target cells pulsed with the epitope peptide. "c" depicts the CTL-inducing ability of Epha4-A24-9-5 (SEQ ID NO: 44). Epha4-A24-9-5 (SEQ ID NO: 44) demonstrated potent IFN-gamma production as compared to the control by IFN-gamma ELISPOT assay, and CTL line, that was established from the positive well #2 shown in boxed wells, demonstrated the specific response against the target cells pulsed with the epitope peptide. "d" depicts the CTL-inducing ability of Epha4-A24-9-420 (SEQ ID NO: 48). Epha4-A24-9-420 (SEQ ID NO: 48) demonstrated potent IFN-gamma production as compared to the control by IFN-gamma ELISPOT assay. The well #6 shown in boxed wells in upper panel demonstrated the specific response against the target cells pulsed with the epitope peptide. Moreover CTL line that was established from the positive well #6 shown in boxed wells in middle panel, demonstrated the specific response against the target cells pulsed with the epitope peptide. "e" depicts the CTL-inducing ability of Epha4-A24-9-869 (SEQ ID NO: 46). Epha4-A24-9-869 (SEQ ID NO: 46) demonstrated potent IFN-gamma production as compared to the control by IFN-gamma ELISPOT assay, and CTL line that was established from the positive well #5 shown in boxed wells, demonstrated the specific response against the target cells pulsed with the epitope peptide. "f" depicts the CTL-inducing ability of Epha4-A24-10-24 (SEQ ID NO: 78). Epha4-A24-10-24 (SEQ ID NO: 78) demonstrated potent IFN-gamma production as compared to the control by IFN-gamma ELISPOT assay, and CTL line that was established from the positive well #4 shown in boxed wells, demonstrated the specific response against the target cells pulsed with the epitope peptide. "g" depicts the CTL-inducing ability of Epha4-A02-9-501 (SEQ ID NO: 376). Epha4-A02-9-501 (SEQ ID NO: 376) demonstrated potent IFN-gamma production as compared to the control by IFN-gamma ELISPOT assay, and CTL line and clone was established from the positive well #8 shown in boxed wells. Cytotoxic activity of the established CTL line against the target cells pulsed with the peptide was measured by Cr-release assay (CRA) (lower graph), and the CTL line had very potent specific cytotoxic activity against the target cells pulsed with the peptides. "h" depicts the CTL-inducing ability of Epha4-A02-9-165 (SEQ ID NO: 379). Epha4-A02-9-165 (SEQ ID NO: 379) demonstrated potent IFN-gamma production as compared to the control by IFN-gamma ELISPOT assay, and CTL line was established from the positive well #3 shown in boxed wells. Cytotoxic activity of the established CTL line against target cells pulsed with peptide was measured by Cr-release assay (CRA) (right graph), and the CTL line had very potent specific cytotoxic activity against the target cells pulsed with the peptides.

FIG. 3 depicts the results of the screening of epitope peptides, which, in turn, demonstrate that ECT2-A24-9-515 (SEQ ID NO: 80), ECT2-A24-10-40 (SEQ ID NO: 100) and ECT2-A24-10-101 (SEQ ID NO: 101) show potent IFN-gamma production. "a" depicts the example of negative peptides which could not be detected CTL-inducing ability despite possible binding activity with HLA. "b" depicts the CTL-inducing ability of ECT2-A24-9-515 (SEQ ID NO: 80). ECT2-A24-9-515 (SEQ ID NO: 80) demonstrated potent IFN-gamma production as compared to the control by IFN-gamma ELISPOT assay. The well #5 and #7 shown in boxed wells in left panel demonstrated the specific response against the target cells pulsed with the epitope peptide. Moreover, CTL line that was established from the positive well #7 shown in boxed wells in second panel, demonstrated the specific response against the target cells pulsed with the epitope peptide. Cytotoxic activity of the CTL line against cancer cell line, TE6 endogenously expressing ECT2 and HLA-A24 was measured by Cr-release assay (CRA), and the CTL clone had very potent cytotoxic activity against TE6. On the other hand, the effector cells did not demonstrate the cytotoxic activity of the CTL line against cancer cell line, TE5 expressing only ECT2 was not detected. "c" depicts the CTL-inducing ability of ECT2-A24-10-40 (SEQ ID NO: 100). ECT2-A24-10-40 (SEQ ID NO: 100) demonstrated potent IFN-gamma production as compared to the control by IFN-gamma ELISPOT assay, and CTL line and the clone were established from the positive well #2 shown in boxed wells. The established CTL clone raised against the peptide demonstrated specific CTL activity against COS7 transfected both full length of ECT2 gene and HLA-A24 molecule. On the other hand, COS7 transfected full length of ECT2 but not HLA-A24, COS7 transfected HLA-A24 and URLC10 gene as a substitute for full length of ECT2 and COS7 transfected HLA-A24 and pulsed with ECT2-10-101 were prepared for the negative control. The CTL clone showed high specific CTL activity against COS7 that transfected both ECT2 and HLA-A24. "d" depicts the CTL-inducing ability of ECT2-A24-10-101 (SEQ ID NO: 101). ECT2-A24-10-101 (SEQ ID NO: 101) demonstrated potent IFN-gamma production as compared to the control by IFN-gamma ELISPOT assay, and CTL line were established from the positive well #1 shown in boxed wells. The established CTL line raised against the peptide demonstrated specific CTL activity against COS7 transfected both full length of ECT2 gene and HLA-A24 molecule. COS7 transfected full length of ECT2 but not HLA-A24, COS7 transfected HLA-A24 and URLC10 gene as substitute for full length of ECT2 and COS7 transfected HLA-A24 and pulsed with ECT2-10-40 were prepared for the negative control. The CTL clone showed high specific CTL activity against COS7 that transfected both ECT2 and HLA-A24.

[FIG. 4-1] FIG. 4 depicts the results of the screening of epitope peptides, which, in turn, demonstrate that HIG2-A24-9-19 (SEQ ID NO: 110), HIG2-A24-9-22 (SEQ ID NO: 111), HIG2-A24-9-8 (SEQ ID NO: 387), HIG2-A24-10-7 (SEQ ID NO: 112), HIG2-A24-10-18 (SEQ ID NO: 394), HIG2-A02-9-15 (SEQ ID NO: 116), HIG2-A02-9-4 (SEQ ID NO: 117) and HIG2-A02-10-8 (SEQ ID NO: 121) show potent IFN-gamma production. "a" depicts the example of negative peptides which could not be detected CTL-inducing ability despite possible binding activity with HLA. "b" depicts the CTL-inducing ability of HIG2-A24-9-19 (SEQ ID NO: 110). HIG2-A24-9-19 (SEQ ID NO: 110) demonstrated potent IFN-gamma production as compared to the control by IFN-gamma ELISPOT assay, and CTL line, that was established from the positive well #6 shown in boxed wells, demonstrated the specific response against the target cells pulsed with the epitope peptide. "c" depicts the CTL-inducing ability of HIG2-A24-9-22 (SEQ ID NO: 111). HIG2-A24-9-22 (SEQ ID NO: 111) demonstrated potent IFN-gamma production as compared to the control by IFN-gamma ELISPOT assay, and CTL line and clone, that was established from the positive well #7 shown in boxed wells, demonstrated the specific response against the target cells pulsed with the epitope peptide. "d" depicts the CTL-inducing ability of HIG2-A24-9-8 (SEQ ID NO: 387). HIG2-A24-9-8 (SEQ ID NO: 387) demonstrated potent IFN-gamma production as compared to the control by IFN-gamma ELISPOT assay, and CTL line and clone, that were established from the positive well #5 shown in boxed wells, demonstrated the specific response against the target cells pulsed with the epitope peptide. "e" depicts the CTL-inducing ability of HIG2-A02-9-8 (SEQ ID NO: 114). HIG2-A02-9-8 (SEQ ID NO: 114) demonstrated potent IFN-gamma production as compared to the control by IFN-gamma ELISPOT assay, and CTL line was established from the positive well #10 shown in boxed wells. The established CTL line raised against the peptide demonstrate specific CTL activity against 293T transfected both full length of HIG2 gene and HLA-A02 molecule. 293T transfected full length of HIG2 but not HLA-A02, 293Ts transfected HLA-A02 and FoxP3 gene as substitute for full length of HIG2 and 293Ts transfected HLA-A02 and pulsed with HIG2-9-15 were prepared for the negative control. The CTL line showed high specific CTL activity against 293T that transfected both HIG2 and HLA-A02.

[FIG. 4-2] FIG. 4 depicts the results of the screening of epitope peptides, which, in turn, demonstrate that HIG2-A24-9-19 (SEQ ID NO: 110), HIG2-A24-9-22 (SEQ ID NO: 111), HIG2-A24-9-8 (SEQ ID NO: 387), HIG2-A24-10-7 (SEQ ID NO: 112), HIG2-A24-10-18 (SEQ ID NO: 394), HIG2-A02-9-15 (SEQ ID NO: 116), HIG2-A02-9-4 (SEQ ID NO: 117) and HIG2-A02-10-8 (SEQ ID NO: 121) show potent IFN-gamma production. "f" depicts the CTL-inducing ability of HIG2-A24-10-7 (SEQ ID NO: 112). HIG2-A24-10-7 (SEQ ID NO: 112) demonstrated potent IFN-gamma production as compared to the control by IFN-gamma ELISPOT assay, and CTL lines or clone, that were established from the positive well #1 and #7 shown in boxed wells, demonstrated the specific response against the target cells pulsed with the epitope peptide. "g" depicts the CTL-inducing ability of HIG2-A24-10-18 (SEQ ID NO: 394). HIG2-A24-10-18 (SEQ ID NO: 394) demonstrated potent IFN-gamma production as compared to the control by IFN-gamma ELISPOT assay, and CTL line and clone, that were established from the positive well #7 shown in boxed wells, demonstrated the specific response against the target cells pulsed with the epitope peptide. "h" depicts the CTL-inducing ability of HIG2-A02-9-15 (SEQ ID NO: 116). HIG2-A02-9-15 (SEQ ID NO: 116) demonstrated potent IFN-gamma production as compared to the control by IFN-gamma ELISPOT assay, and CTL line was established from the positive well #10 shown in boxed wells. The established CTL line raised against the peptide demonstrated specific CTL activity against COS7 transfected both full length of HIG2 gene and HLA-A02 molecule. COS7 transfected full length of HIG2 but not HLA-A02 and COS7s transfected HLA-A02 and pulsed with HIG2-9-8 peptide were prepared for the negative control. The CTL line showed high specific CTL activity against COS7 that transfected both HIG2 and HLA-A02.

[FIG. 4-3] FIG. 4 depicts the results of the screening of epitope peptides, which, in turn, demonstrate that HIG2-A24-9-19 (SEQ ID NO: 110), HIG2-A24-9-22 (SEQ ID NO: 111), HIG2-A24-9-8 (SEQ ID NO: 387), HIG2-A24-10-7 (SEQ ID NO: 112), HIG2-A24-10-18 (SEQ ID NO: 394), HIG2-A02-9-15 (SEQ ID NO: 116), HIG2-A02-9-4 (SEQ ID NO: 117) and HIG2-A02-10-8 (SEQ ID NO: 121) show potent IFN-gamma production. "i" depicts the CTL-inducing ability of HIG2-A02-9-4 (SEQ ID NO: 117). HIG2-A02-9-4 (SEQ ID NO: 117) demonstrated potent IFN-gamma production as compared to the control by IFN-gamma ELISPOT assay, and CTL line and clone were established from the positive well #10 shown in boxed wells. The established CTL line raised against the peptide demonstrated specific CTL activity against COS7 transfected both full length of HIG2 gene and HLA-A02 molecule (middle graph). Also, COS7 transfected full length of HIG2 but not HLA-A02, COS7s transfected HLA-A02 and TTK gene as substitute for full length of HIG2 and COS7s transfected HLA-A02 and pulsed with HIG2-9-8 were prepared for the negative control. Cytotoxic activity of the CTL clone against 293T, transfected both full length of HIG2 gene and HLA-A02 molecule, and cancer cell line, Caki-1 endogenously expressing HIG2 and HLA-A02 was measured by Cr-release assay (CRA) (lower graphs), and the CTL clone had very potent cytotoxic activity against the transfectant with both of HIG2 gene and HLA-A02, and Caki-1. On the other hand, the effector cells did not demonstrate the cytotoxic activity of the CTL line against 293T, transfected only HIG2 or only HLA-A02, and cancer cell line, A498 expressing only HIG2 was not detected. "j" depicts the CTL-inducing ability of HIG2-A02-10-8 (SEQ ID NO: 121). HIG2-A02-10-8 (SEQ ID NO: 121) demonstrated potent IFN-gamma production as compared to the control by IFN-gamma ELISPOT assay, and CTL line, that was established from the positive well #9 shown in boxed wells, demonstrated the specific response against the target cells pulsed with the epitope peptide.

[FIG. 5-1] FIG. 5 depicts the results of the screening of epitope peptides, which, in turn, demonstrate that INHBB-A24-9-180 (SEQ ID NO: 395), INHBB-A24-10-180 (SEQ ID NO: 133), INHBB-A24-10-305 (SEQ ID NO: 135), INHBB-A24-10-7 (SEQ ID NO: 137) and INHBB-A24-10-212 (SEQ ID NO: 426) show potent IFN-gamma production. "a" depicts the example of negative peptides which could not be detected CTL-inducing ability despite possible binding activity with HLA. "b" depicts the CTL-inducing ability of INHBB-A24-9-180 (SEQ ID NO: 395). INHBB-A24-9-180 (SEQ ID NO: 395) demonstrated potent IFN-gamma production as compared to the control by IFN-gamma ELISPOT assay, and CTL line and clone was established from the positive well #7 shown in boxed wells. Cytotoxic activity of the established CTL clone against tumor cells, Miapaca2 expressing both of INHBB and HLA-A02 was measured by Cr-release assay (CRA), and the effector cells showed high specific cytotoxic activity against Miapaca2. On the other hand, it did not show significant specific cytotoxic activity against Caki-1 expressing INHBB but not HLA-A02. "c" depicts the CTL-inducing ability of INHBB-A24-10-180 (SEQ ID NO: 133). INHBB-A24-10-180 (SEQ ID NO: 133) demonstrated potent IFN-gamma production as compared to the control by IFN-gamma ELISPOT assay, and CTL line was established from the positive well #3 shown in boxed wells. The established CTL line raised against the peptide demonstrated high specific CTL activity against 293T transfected both of full length of INHBB gene and HLA-A24 molecule. Also, 293T transfected full length of INHBB but not HLA-A24 and 293Ts transfected HLA-A24 and pulsed with INHBB-10-305 peptide were prepared for the negative control.

[FIG. 5-2] FIG. 5 depicts the results of the screening of epitope peptides, which, in turn, demonstrate that INHBB-A24-9-180 (SEQ ID NO: 395), INHBB-A24-10-180 (SEQ ID NO: 133), INHBB-A24-10-305 (SEQ ID NO: 135), INHBB-A24-10-7 (SEQ ID NO: 137) and INHBB-A24-10-212 (SEQ ID NO: 426) show potent IFN-gamma production. "d" depicts the CTL-inducing ability of INHBB-A24-10-305 (SEQ ID NO: 135). INHBB-A24-10-305 (SEQ ID NO: 135) demonstrated potent IFN-gamma production as compared to the control by IFN-gamma ELISPOT assay, and CTL line and clone were established from the positive well #2 shown in boxed wells. The established CTL clone raised against the peptide demonstrated high specific CTL activity against 293T transfected both full length of INHBB gene and HLA-A24 molecule. Also, 293T transfected full length of INHBB but HLA-A24 and 293Ts transfected HLA-A24 and pulsed with INHBB-10-180 peptide were prepared for the negative control. "e" depicts the CTL-inducing ability of INHBB-A24-10-7 (SEQ ID NO: 137)). INHBB-A24-10-7 (SEQ ID NO: 137) demonstrated potent IFN-gamma production as compared to the control by IFN-gamma ELISPOT assay, and CTL lines were established from the positive well #8 shown in boxed wells in upper panel and #2 shown in boxed wells in lower panel. The CTL line from #8 well demonstrated specific CTL activity against 293T transfected both full length of INHBB gene and HLA-A24 molecule. Also, 293T transfected full length of INHBB but not HLA-A24 and 293Ts transfected HLA-A24 and pulsed with INHBB-10-40 peptide were prepared for the negative control. "f" depicts the CTL-inducing ability of INHBB-A24-10-212 (SEQ ID NO: 426). INHBB-A24-10-212 (SEQ ID NO: 426) demonstrated potent IFN-gamma production as compared to the control by IFN-gamma ELISPOT assay, and CTL line, that was established from the positive well #1 shown in boxed wells, demonstrated the specific response against the target cells pulsed with the epitope peptide.

[FIG. 6-1] FIG. 6 depicts the results of the screening of epitope peptides, which, in turn, demonstrate that KIF20A-A24-10-304 (SEQ ID NO: 186), KIF20A-A24-9-383 (SEQ ID NO: 178), KIF20A-A24-10-66 (SEQ ID NO: 194) and KIF20A-A24-9-305 (SEQ ID NO: 174) show potent IFN-gamma production. "a" depicts the example of negative peptides which could not be detected CTL-inducing ability despite possible binding activity with HLA. "b" depicts the CTL-inducing ability of KIF20A-A24-10-304 (SEQ ID NO: 186). KIF20A-A24-10-304 (SEQ ID NO: 186) demonstrated potent IFN-gamma production as compared to the control by IFN-gamma ELISPOT assay. The well #5 shown in boxed wells in lower right panel demonstrated the specific response against the target cells pulsed with the epitope peptide. Moreover, CTL line and clone, that were established from the positive well #5 shown in boxed wells in upper left panel, also demonstrated the specific response against the target cells pulsed with the epitope peptide. The established CTL clone raised against the peptide demonstrated specific CTL activity against 24-LCL transfected full length of KIF20A gene. Also, A24-LCL transfected mock vector was prepared for the negative control. Cytotoxic activity of the CTL clone against tumor cells, Miapaca2 expressing both of KIF20A and HLA-A24 was measured by Cr-release assay (CRA), and the CTL clone had very potent specific cytotoxic activity against Miapaca2 (lower right graph). On the other hand, it did not show significant specific cytotoxic activity against PK59 expressing KIF20A but not HLA-A24. "c" depicts the CTL-inducing ability of KIF20A-A24-9-383 (SEQ ID NO: 178). KIF20A-A24-9-383 (SEQ ID NO: 178) demonstrated potent IFN-gamma production as compared to the control by IFN-gamma ELISPOT assay. The well #3 and 4 shown in boxed wells in right panel demonstrated the specific response against the target cells pulsed with the epitope peptide. Moreover, CTL line, that was established from the positive well #3 shown in boxed wells in left panel, also demonstrated the specific response against the target cells pulsed with the epitope peptide. The established CTL line demonstrated high specific CTL activity against COS7 transfected both full length of KIF20A gene and HLA-A24 molecule. Also, COS7 transfected full length of KIF20A but not HLA-A24 and COS7s transfected HLA-A24 and pulsed with KIF20A-9-621 peptide were prepared for the negative control.

[FIG. 6-2] FIG. 6 depicts the results of the screening of epitope peptides, which, in turn, demonstrate that KIF20A-A24-10-304 (SEQ ID NO: 186), KIF20A-A24-9-383 (SEQ ID NO: 178), KIF20A-A24-10-66 (SEQ ID NO: 194) and KIF20A-A24-9-305 (SEQ ID NO: 174) show potent IFN-gamma production. "d" depicts the CTL-inducing ability of KIF20A-A24-10-66 (SEQ ID NO: 194). KIF20A-A24-10-66 (SEQ ID NO: 194) demonstrated potent IFN-gamma production as compared to the control by IFN-gamma ELISPOT assay, and CTL lines, that were established from the positive well #6 shown in boxed wells in upper left panel and #3 shown in boxed wells in lower middle panel demonstrated the specific response against the target cells pulsed with the epitope peptide. Moreover, CTL clone selected from CTL line from #6 well by limiting dilution demonstrated specific CTL activity against the target cells. The established CTL clone showed specific CTL activity against COS7 transfected both full length of KIF20A gene and HLA-A24 molecule. Also, COS7 transfected full length of KIF20A but not HLA-A24, COS7s transfected HLA-A24 and URLC10 gene as substitute for full length of KIF20A and COS7 transfected HLA-A24 and pulsed with KIF20A-10-308 peptide were prepared for the negative control. "e" depicts the CTL-inducing ability of KIF20A-A24-9-305 (SEQ ID NO: 174). KIF20A-A24-9-305 (SEQ ID NO: 174) demonstrated potent IFN-gamma production as compared to the control by IFN-gamma ELISPOT assay, and CTL lines, that were established from the positive well #2 shown in boxed wells in upper left panel and #6 shown in boxed wells in lower middle panel, demonstrated the specific response against the target cells pulsed with the epitope peptide. Moreover, CTL clone selected from CTL line from #2 well by limiting dilution demonstrated specific CTL activity against the target cells. Cytotoxic activity of the CTL clone against tumor cells, PK45P expressing both of KIF20A and HLA-A24 was measured by Cr-release assay (CRA), and the CTL clone had very potent cytotoxic activity against PK45P. On the other hand, it did not show significant specific cytotoxic activity against PK59 expressing KIF20A but not HLA-A24.

[FIG. 7-1] FIG. 7 depicts the results of the screening of epitope peptides, which, in turn, demonstrate that KNTC2-A24-9-309 (SEQ ID NO: 196), KNTC2-A24-9-124 (SEQ ID NO: 202), KNTC2-A24-9-154 (SEQ ID NO: 210) KNTC2-A24-9-150 (SEQ ID NO: 213), KNTC2-A24-10-452 (SEQ ID NO: 214), KNTC2-A24-10-227 (SEQ ID NO: 217) and KNTC2-A24-10-273 (SEQ ID NO: 223) show potent IFN-gamma production. "a" depicts the example of negative peptides which could not be detected CTL-inducing ability despite possible binding activity with HLA. "b" depicts the CTL-inducing ability of KNTC2-A24-9-309 (SEQ ID NO:

196). KNTC2-A24-9-309 (SEQ ID NO: 196) demonstrated potent IFN-gamma production as compared to the control by IFN-gamma ELISPOT assay, and CTL line, that was established from the positive well #8 shown in boxed wells, demonstrated the specific response against the target cells pulsed with the epitope peptide. "c" depicts the CTL-inducing ability of KNTC2-A24-9-124 (SEQ ID NO: 202). KNTC2-A24-9-124 (SEQ ID NO: 202) demonstrated potent IFN-gamma production as compared to the control by IFN-gamma ELISPOT assay, and CTL line, that was established from the positive well #5 shown in boxed wells, demonstrated the specific response against the target cells pulsed with the epitope peptide. "d" depicts the CTL-inducing ability of KNTC2-A24-9-154 (SEQ ID NO: 210). KNTC2-A24-9-154 (SEQ ID NO: 210) demonstrated potent IFN-gamma production as compared to the control by IFN-gamma ELISPOT assay, and CTL line and clone, that were established from the positive well #5 shown in boxed wells demonstrated the specific response against the target cells pulsed with the epitope peptide. "e" depicts the CTL-inducing ability of KNTC2-A24-9-150 (SEQ ID NO: 213). KNTC2-A24-9-150 (SEQ ID NO: 213) demonstrated potent IFN-gamma production as compared to the control by IFN-gamma ELISPOT assay, and CTL line, that was established from the positive well #7 shown in boxed wells, demonstrated the specific response against the target cells pulsed with the epitope peptide.

Figure 2:
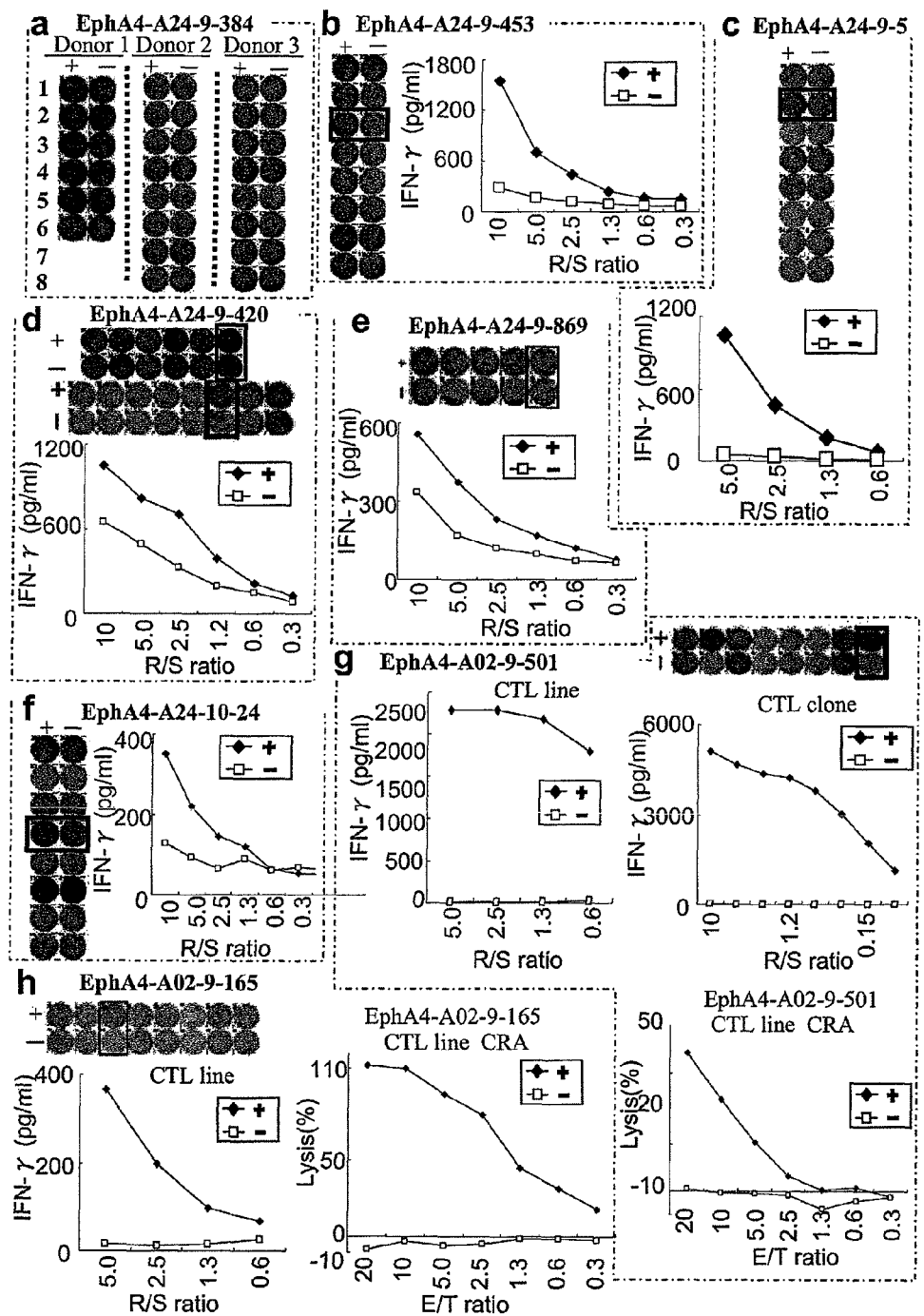
Figure 7:
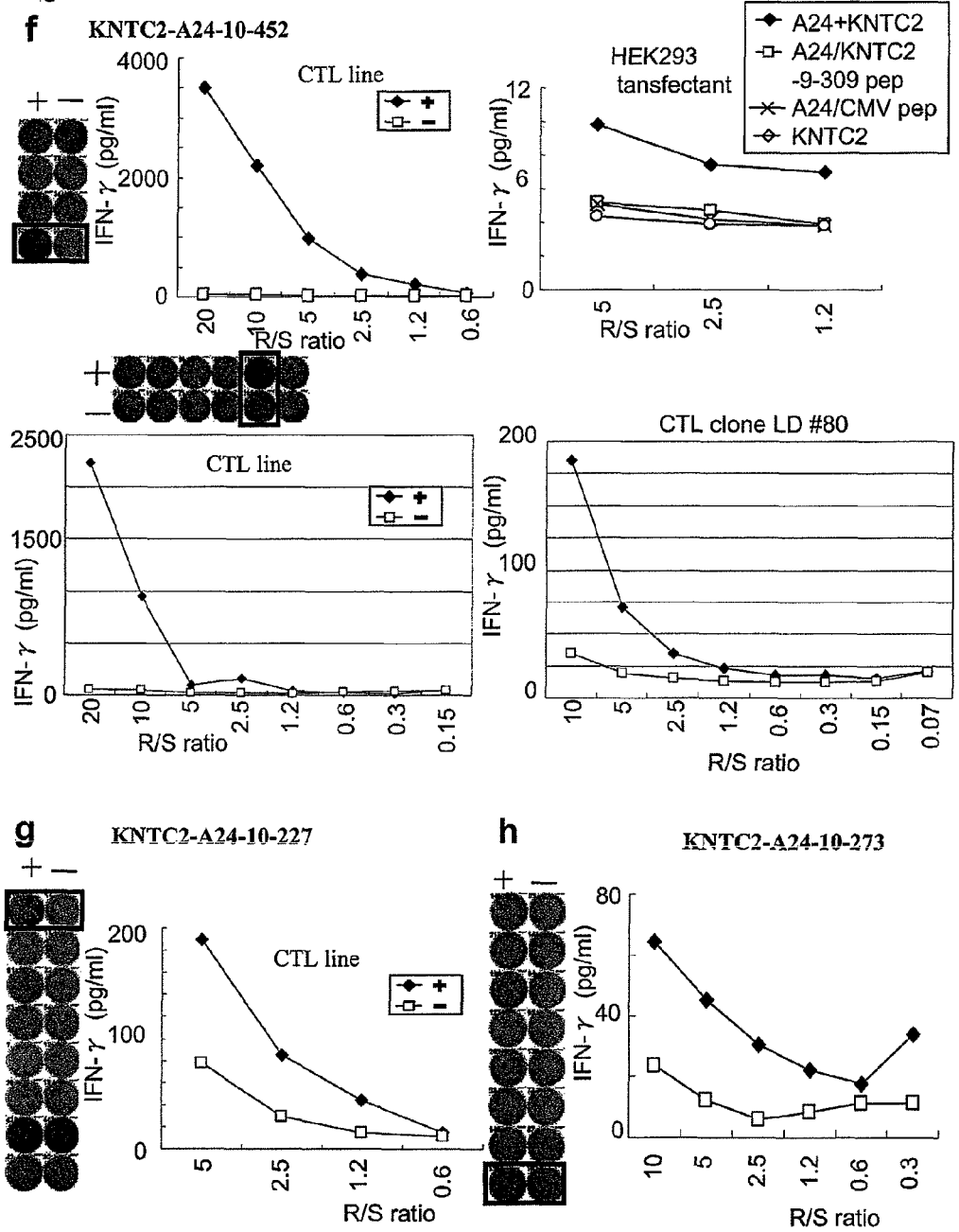

[FIG. 7-2] FIG. 7 depicts the results of the screening of epitope peptides, which, in turn, demonstrate that KNTC2-A24-9-309 (SEQ ID NO: 196), KNTC2-A24-9-124 (SEQ ID NO: 202), KNTC2-A24-9-154 (SEQ ID NO: 210) KNTC2-A24-9-150 (SEQ ID NO: 213), KNTC2-A24-10-452 (SEQ ID NO: 214), KNTC2-A24-10-227 (SEQ ID NO: 217) and KNTC2-A24-10-273 (SEQ ID NO: 223) show potent IFN-gamma production. "f" depicts the CTL-inducing ability of KNTC2-A24-10-452 (SEQ ID NO: 214). KNTC2-A24-10-452 (SEQ ID NO: 214) demonstrated potent IFN-gamma production as compared to the control by IFN-gamma ELISPOT assay, and CTL lines and clone, that were established from the positive well #4 shown in boxed wells in upper left panel and #5 shown in boxed wells in middle panel, demonstrated the specific response against the target cells pulsed with the epitope peptide. Moreover, CTL clone selected from CTL line from #5 well by limiting dilution demonstrated specific CTL activity against the target cells. The established CTL line from #4 well showed specific CTL activity against HEK293 transfected both full length of KNTC2 gene and HLA-A24 molecule. Also, HEK293 transfected full length of KNTC2 but not HLA-A24, HEK293 transfected HLA-A24 but full length of KNTC2 and HEK293 transfected HLA-A24 pulsed with KNTC-9-309 peptide were prepared for the negative control. "g" depicts the CTL-inducing ability of KNTC2-A24-10-227 (SEQ ID NO: 217). KNTC2-A24-10-227 (SEQ ID NO: 217) demonstrated potent IFN-gamma production as compared to the control by IFN-gamma ELISPOT assay, and CTL line, that was established from the positive well #1 shown in boxed well s, demonstrated the specific response against the target cells pulsed with the epitope peptide. "h" depicts the CTL-inducing ability of KNTC2-A24-10-273 (SEQ ID NO: 223). KNTC2-A24-10-273 (SEQ ID NO: 223) demonstrated potent IFN-gamma production as compared to the control by IFN-gamma ELISPOT assay, and CTL line, that was established from the positive well #8 shown in boxed wells, demonstrated the specific response against the target cells pulsed with the epitope peptide.

Figure 1:
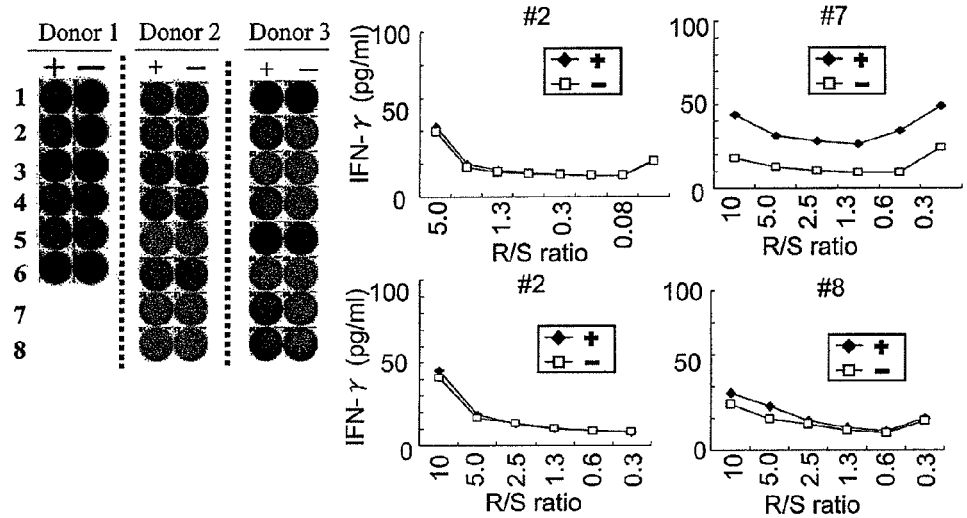
[FIG. 1-1]
Figure 1:
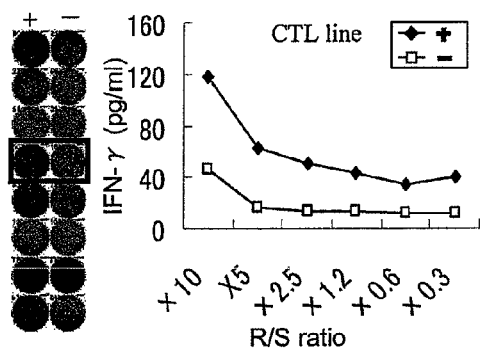
Figure 1:
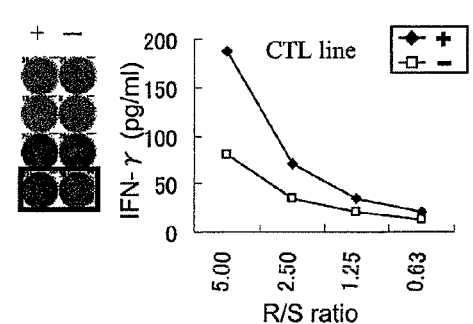
Figure 1:
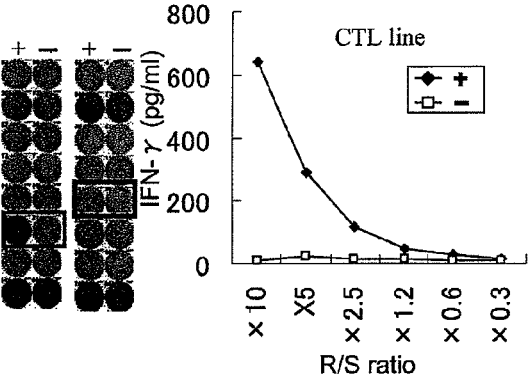
Figure 1:
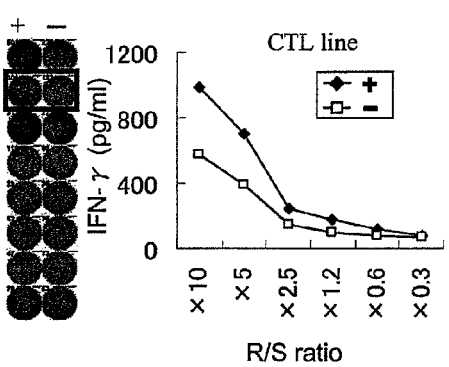
Figure 1:
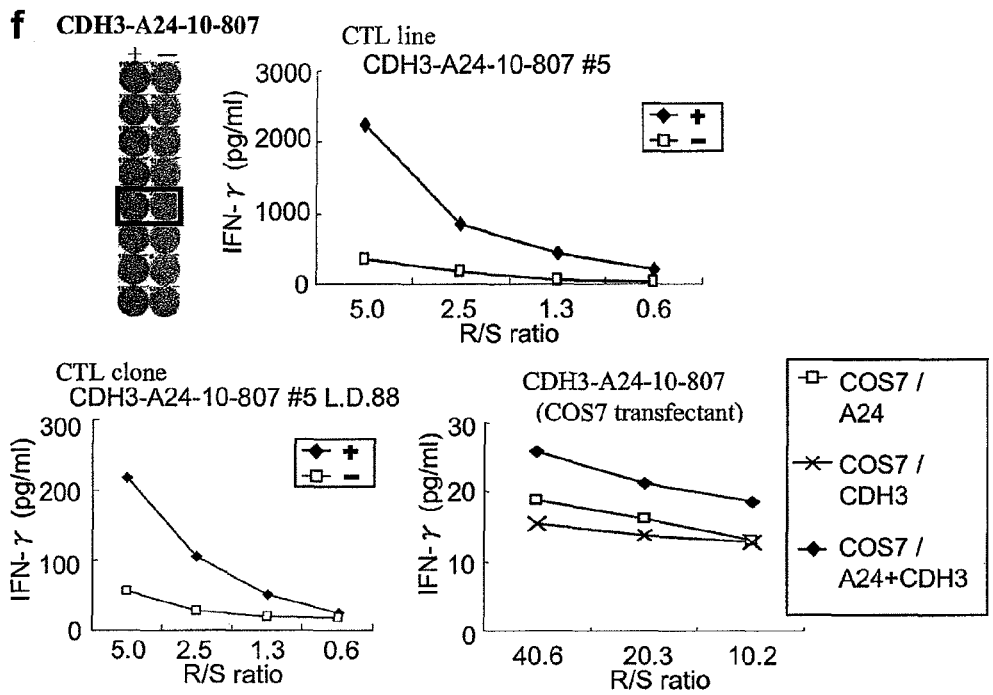
Figure 1:
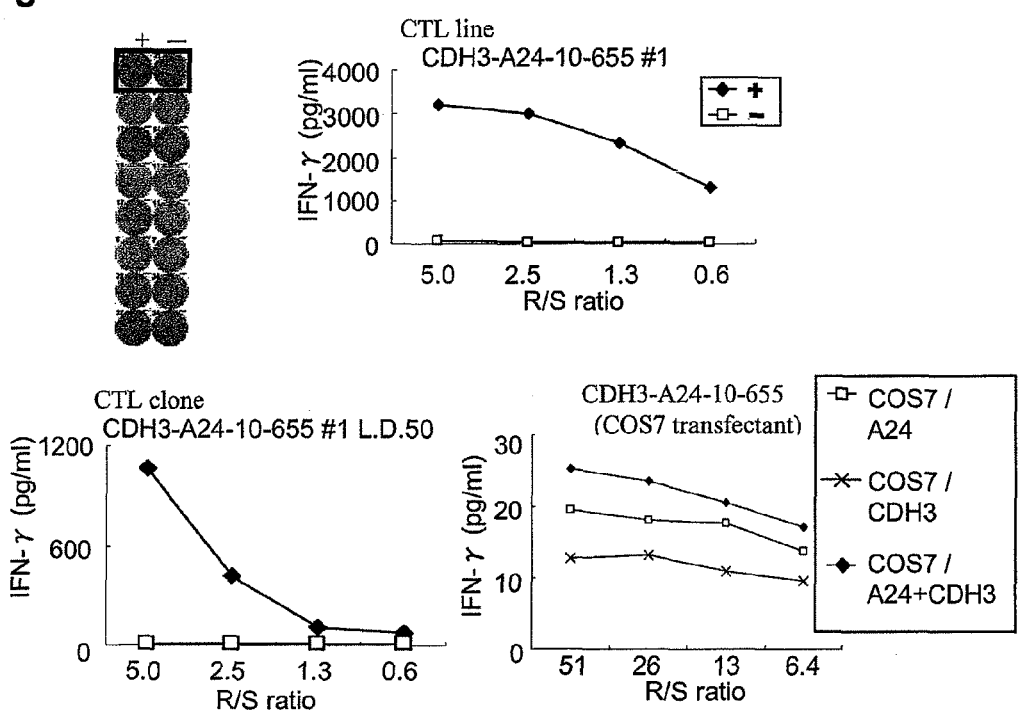
Figure 8:
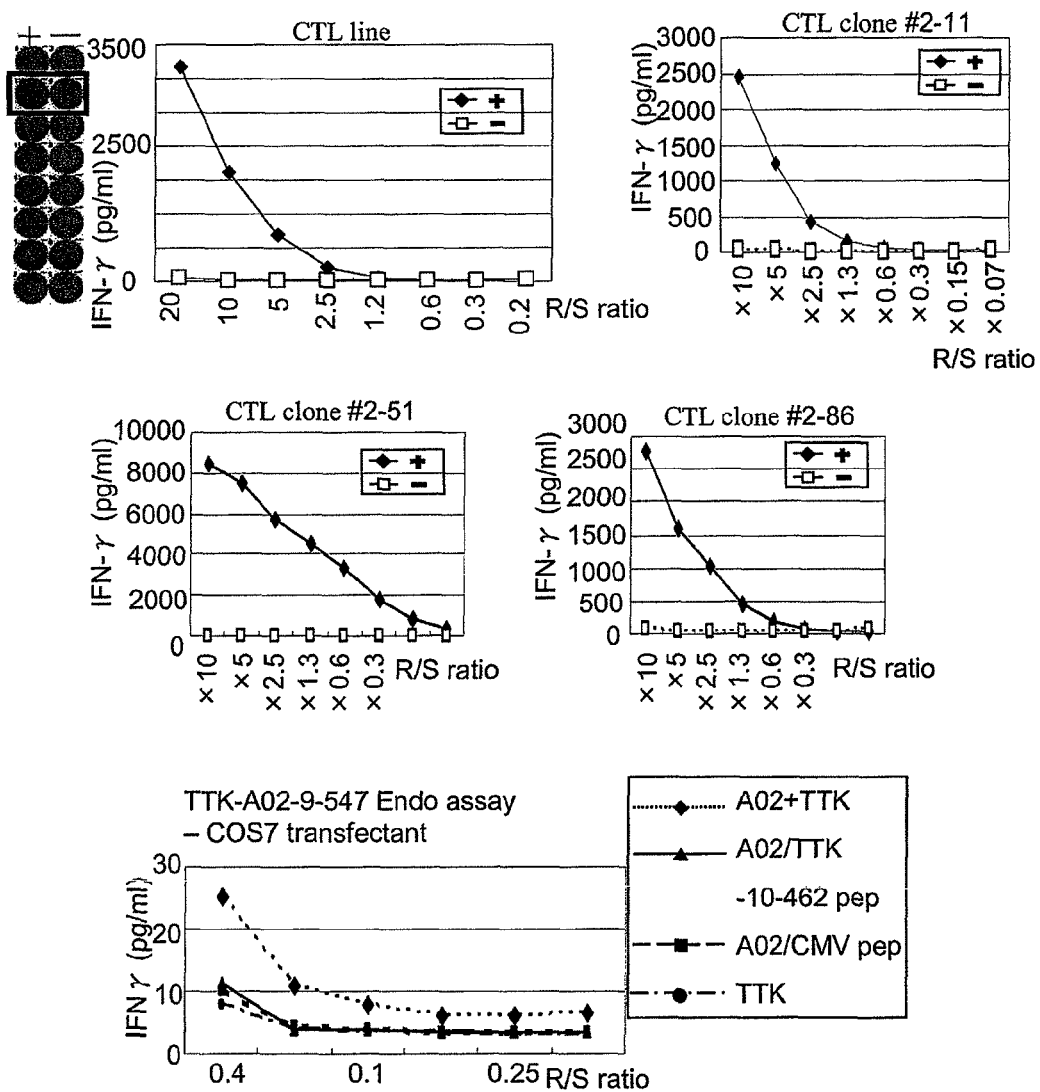
Figure 8:
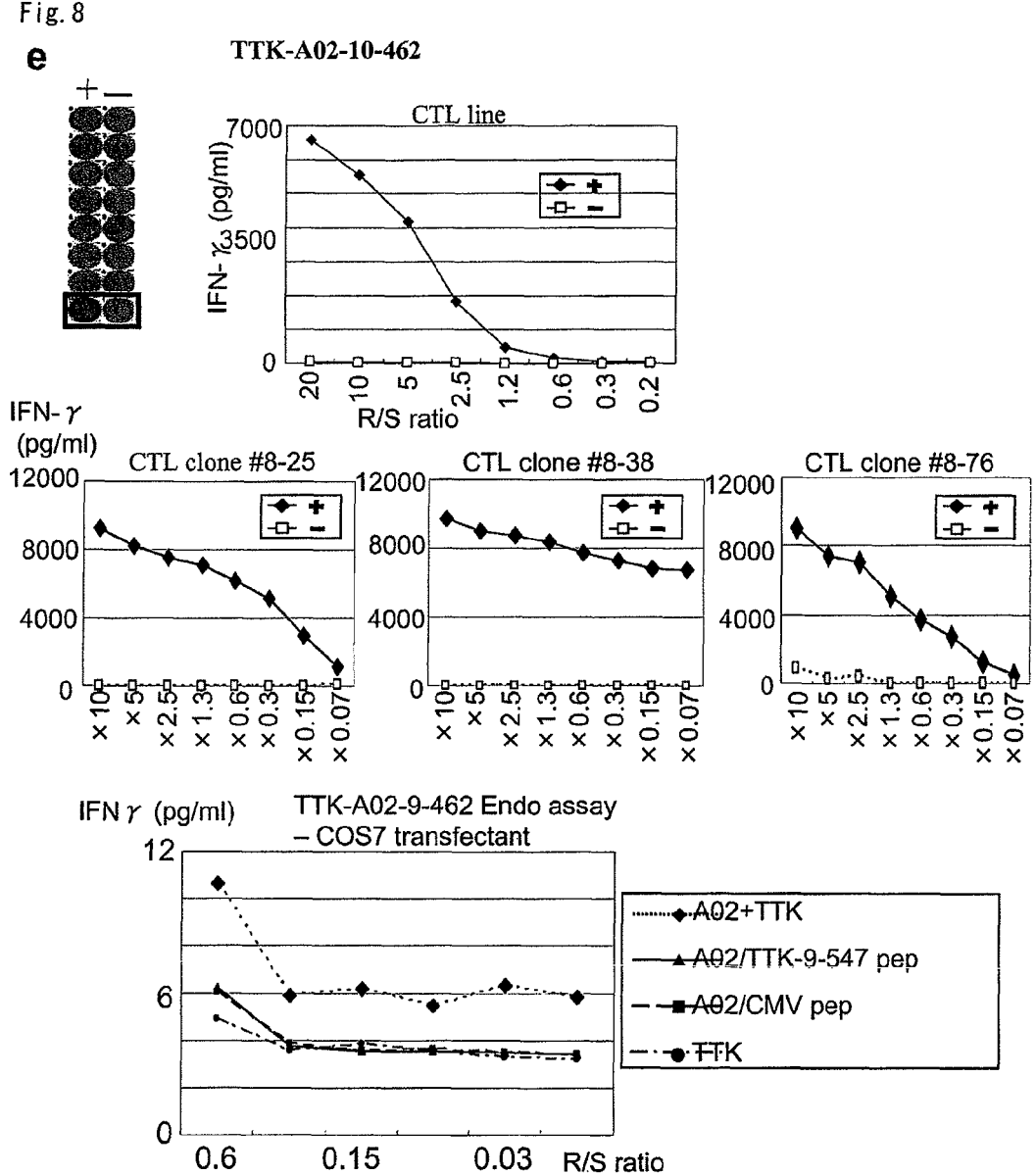

[FIG. 8-1] FIG. 8 depicts the results of the screening of epitope peptides, which, in turn, demonstrate that TTK-A02-9-462 (SEQ ID NO: 227), TTK-A02-9-719 (SEQ ID NO: 233), TTK-A02-9-547 (SEQ ID NO: 228) and TTK-A02-10-462 (SEQ ID NO: 254), show potent IFN-gamma production. "a" depicts the example of negative peptides which could not be detected CTL-inducing ability despite possible binding activity with HLA. "b" depicts the CTL-inducing ability of TTK-A02-9-462 (SEQ ID NO: 227). TTK-A02-9-462 (SEQ ID NO: 227) demonstrated potent IFN-gamma production as compared to the control by IFN-gamma ELISPOT assay, and CTL line and two clones, that were established from the positive well #4 shown in boxed wells, demonstrated the specific response against the target cells pulsed with the epitope peptide. The established CTL clone showed high specific CTL activity against COS7 transfected both full length of TTK gene and HLA-A02 molecule. Also, COS7 transfected full length of TTK but not HLA-A02, COS7s transfected HLA-A02 but not full length of TTK and COS7s transfected HLA-A02 pulsed with TTK-9-547 peptide were prepared for the negative control. "c" depicts the CTL-inducing ability of TTK-A02-9-719 (SEQ ID NO: 233). TTK-A02-9-719 (SEQ ID NO: 233) demonstrated potent IFN-gamma production as compared to the control by IFN-gamma ELISPOT assay, and CTL line and clones were established from the positive well #1 shown in boxed wells. The established CTL line showed high specific CTL activity against COS7 transfected both full length of TTK gene and HLA-A02 molecule. Also, COS7 transfected full length of TTK but not HLA-A02 and COS7s transfected HLA-A02 and HIG2 gene as substitute for full length of TTK were prepared for the negative control.

[FIG. 8-2] FIG. 8 depicts the results of the screening of epitope peptides, which, in turn, demonstrate that TTK-A02-9-462 (SEQ ID NO: 227), TTK-A02-9-719 (SEQ ID NO: 233), TTK-A02-9-547 (SEQ ID NO: 228) and TTK-A02-10-462 (SEQ ID NO: 254), show potent IFN-gamma production. "d" depicts the CTL-inducing ability of TTK-A02-9-547 (SEQ ID NO: 228). TTK-A02-9-547 (SEQ ID NO: 228) demonstrated potent IFN-gamma production as compared to the control by IFN-gamma ELISPOT assay, and CTL line and clones were established from the positive well #2 shown in boxed wells. The established CTL line showed specific CTL activity against COS7 transfected both full length of TTK gene and HLA-A02 molecule. Also, COS7 transfected full length of TTK but not HLA-A02, COS7s transfected HLA-A02 but not full length of TTK and COS7s transfected HLA-A02 and pulsed with TTK-10-462 were prepared for the negative control.

Figure 3:
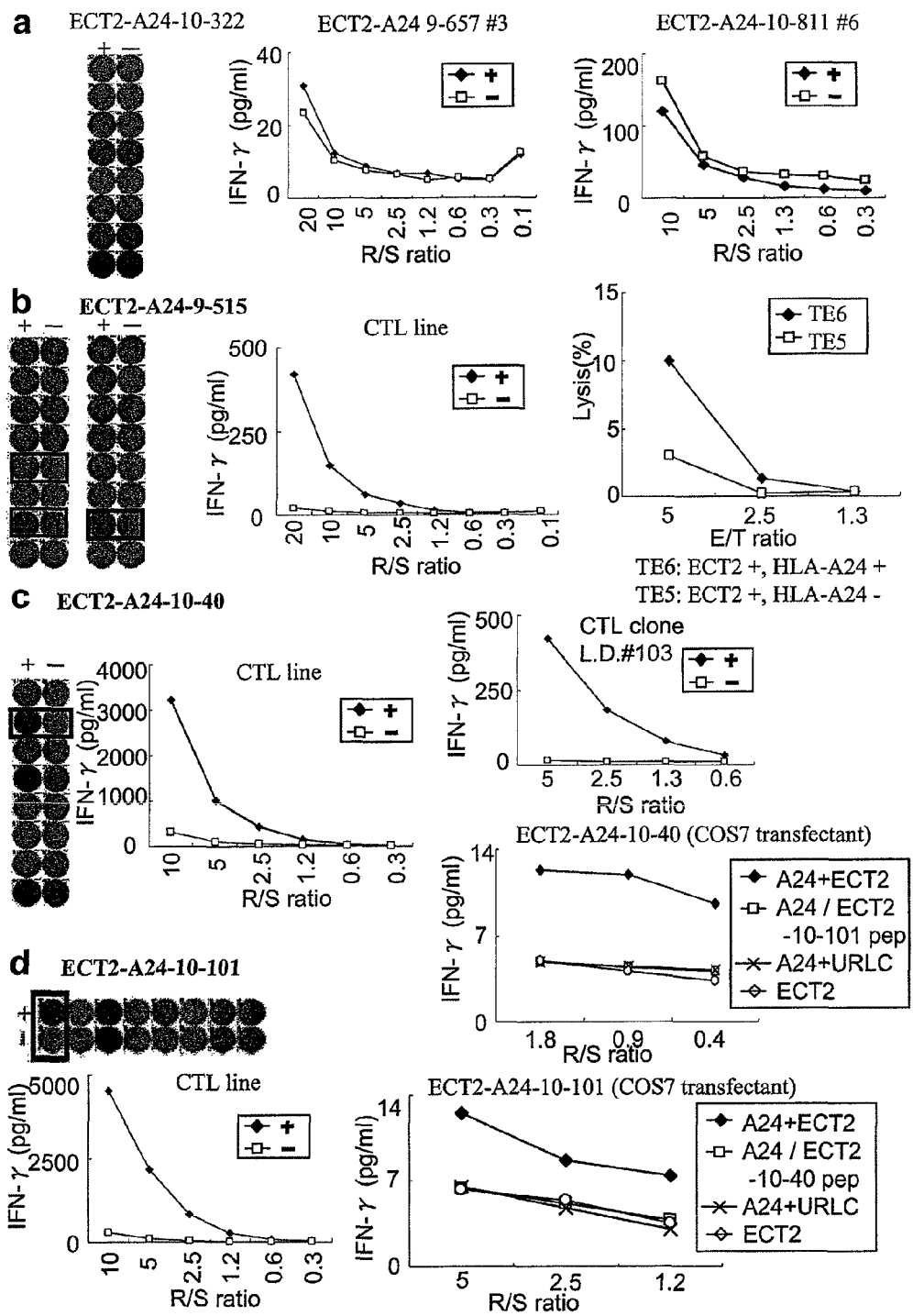
[FIG. 3]

[FIG. 8-3] FIG. 8 depicts the results of the screening of epitope peptides, which, in turn, demonstrate that TTK-A02-9-462 (SEQ ID NO: 227), TTK-A02-9-719 (SEQ ID NO: 233), TTK-A02-9-547 (SEQ ID NO: 228) and TTK-A02-10-462 (SEQ ID NO: 254), show potent IFN-gamma production. "e" depicts the CTL-inducing ability of TTK-A02-10-462 (SEQ ID NO: 254). TTK-A02-10-462 (SEQ ID NO: 254) demonstrated potent IFN-gamma production as compared to the control by IFN-gamma ELISPOT assay, and CTL line and three clones were established from the positive well #8 shown in boxed wells. The established CTL clone showed specific CTL activity against COS7 transfected both full length of TTK gene and HLA-A02 molecule. Also, COS7 transfected full length of TTK but not HLA-A02, COS7s transfected HLA-A02 but not full length of TTK and COS7s transfected HLA-A02 and pulsed with TTK-9-547 peptide were prepared for the negative control.

Figure 9:
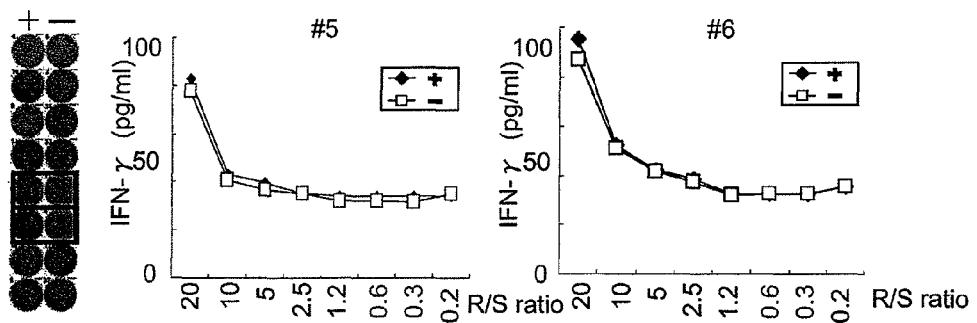
Figure 9:
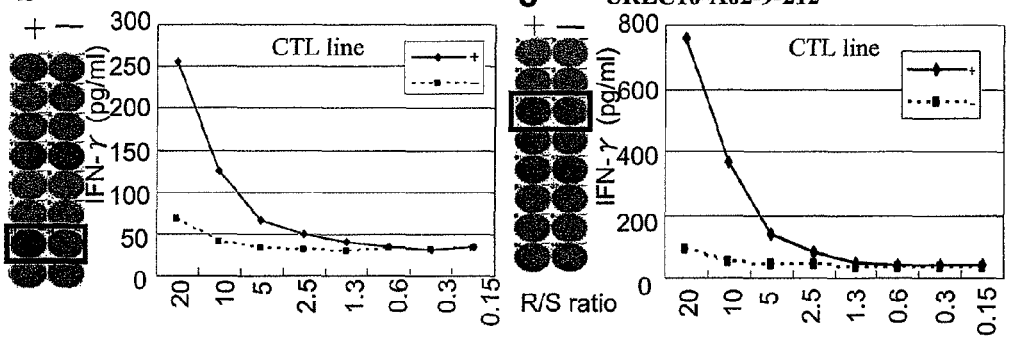
Figure 9:
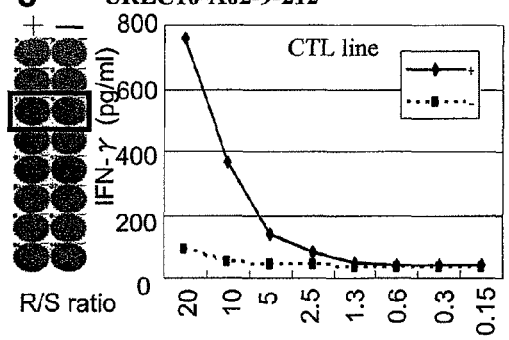
Figure 9:
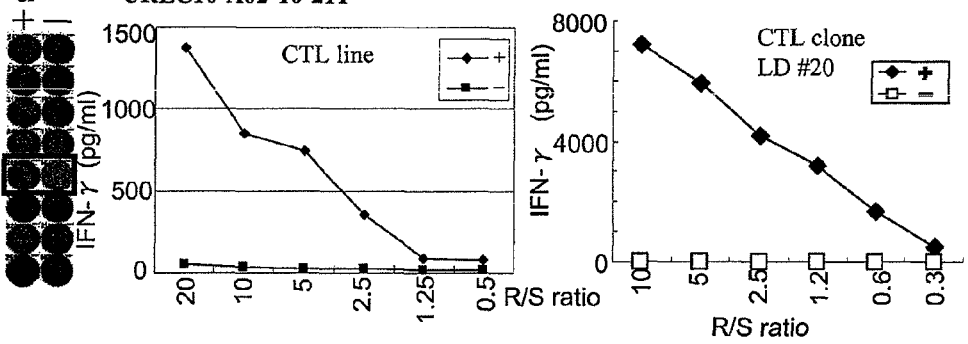
Figure 9:
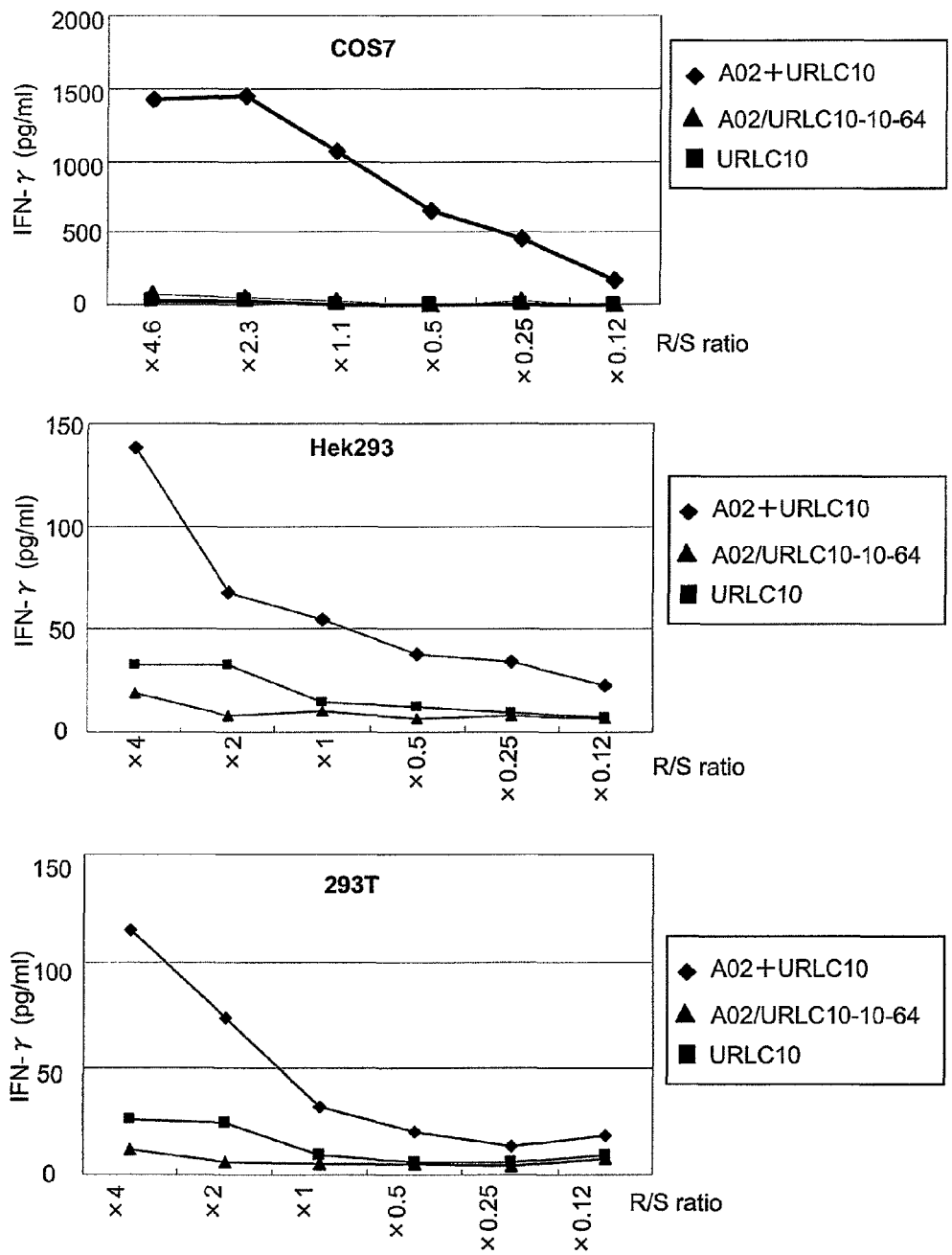

[FIG. 9-1] FIG. 9 depicts the results of the screening of epitope peptides, which, in turn, demonstrate that URLC10-A02-9-206 (SEQ ID NO: 271), URLC10-A02-9-212 (SEQ ID NO: 272) and URLC10-A02-10-211 (SEQ ID NO: 288) show potent IFN-gamma production. "a" depicts the example of negative peptides which could not be detected CTL-inducing ability despite possible binding activity with HLA. "b" depicts the CTL-inducing ability of URLC10-A02-9-206 (SEQ ID NO: 271). URLC10-A02-9-206 (SEQ ID NO: 271) demonstrated potent IFN-gamma production as compared to the control by IFN-gamma ELISPOT assay, and CTL line, that was established from the positive well #7 shown in boxed wells, demonstrated the specific response against the target cells pulsed with the epitope peptide. "c" depicts the CTL-inducing ability of URLC10-A02-9-212 (SEQ ID NO: 272). URLC10-A02-9-212 (SEQ ID NO: 272) demonstrated potent IFN-gamma production as compared to the control by IFN-gamma ELISPOT assay, and CTL line, that was established from the positive well #3 shown in boxed wells, demonstrated the specific response against the target cells pulsed with the epitope peptide. "d" depicts the CTL-inducing ability of URLC10-A02-10-211 (SEQ ID NO: 288). URLC10-A02-10-211 (SEQ ID NO: 288) demonstrated potent IFN-gamma production as compared to the control by IFN-gamma ELISPOT assay, and CTL line and clones, were established from the positive well #5 shown in boxed wells.

[FIG. 9-2] FIG. 9 depicts the results of the screening of epitope peptides, which, in turn, demonstrate that URLC10-A02-9-206 (SEQ ID NO: 271), URLC10-A02-9-212 (SEQ ID NO: 272) and URLC10-A02-10-211 (SEQ ID NO: 288) show potent IFN-gamma production. "Continuation of d" The established CTL clone showed high specific CTL activity against COS7, Hek293 and 293T which were transfected both full length of URLC10 gene and HLA-A02 molecule. Also, COS7, Hek293 or 293T which were transfected full length of URLC10 but not HLA-A02 and COS7s, Hek293s or 293Ts, which were transfected HLA-A02 and pulsed with URLC10-10-64, were prepared for the negative control. In this drawings, "+" means the peptide pulsed target, "−" means the no peptide pulsed target, "R" means Responder, "S" means Stimulator, "E" means Effector, and "T" means Target.

Figure 10:
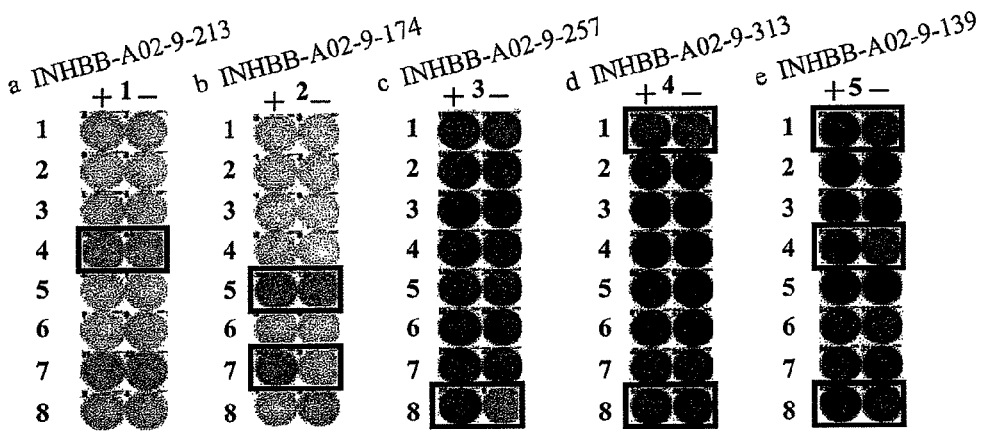
Figure 10:
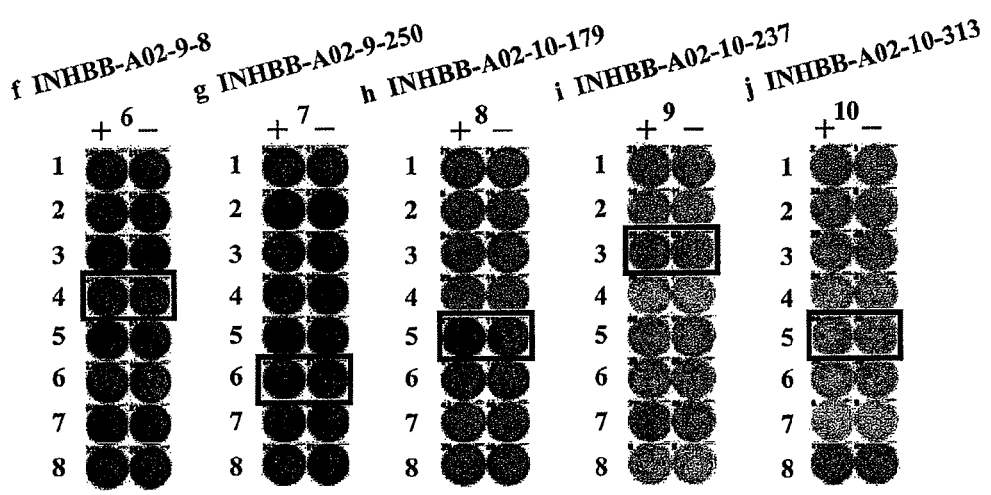
Figure 10:
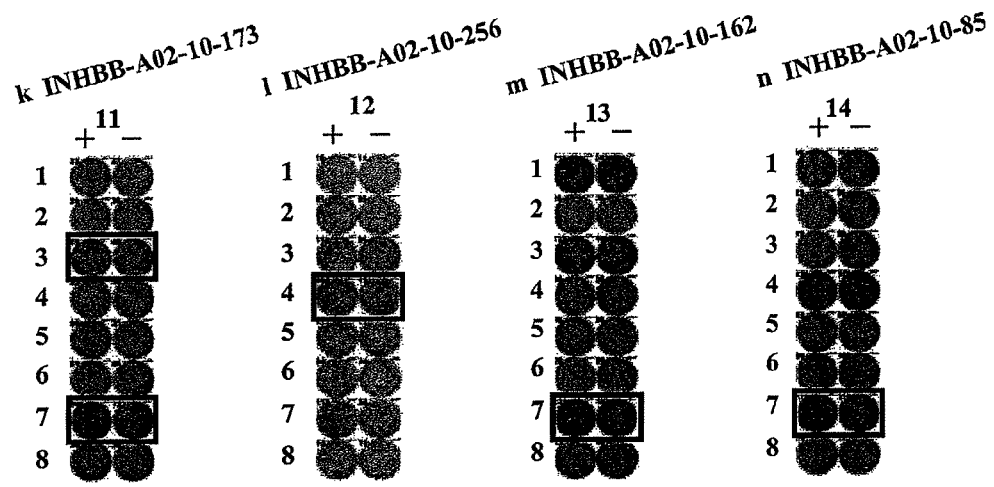

[FIG. 10] FIG. 10 includes a series of photographs, (a)-(n), depicting the results of IFN-gamma ELISPOT assay on CTLs that were induced with peptides derived from INHBB. The CTLs in well #4 stimulated with INHBB-A02-9-213 (SEQ ID NO: 143) (a), well #5 and #7 stimulated with INHBB-A02-9-174 (SEQ ID NO: 147) (b), well #8 stimulated with INHBB-A02-9-257 (SEQ ID NO: 148) (c), well #1 and #8 stimulated with INHBB-A02-9-313 (SEQ ID NO: 149) (d), well #1, #4 and #8 stimulated with INHBB-A02-9-139 (SEQ ID NO: 150) (e), well #4 stimulated with INHBB-A02-9-8 (SEQ ID NO: 152) (f), well #6 stimulated with INHBB-A02-9-250 (SEQ ID NO: 153) (g), well #5 stimulated with INHBB-A02-10-179 (SEQ ID NO: 154) (h), well #3 stimulated with INHBB-A02-10-237 (SEQ ID NO: 156) (i), well #5 stimulated with INHBB-A02-10-313 (SEQ ID NO: 160) (j), well #3 and #7 stimulated with INHBB-A02-10-173 (SEQ ID NO: 161) (k), well #4 stimulated with INHBB-A02-10-256 (SEQ ID NO: 162) (l), well #7 stimulated with INHBB-A02-10-162 (SEQ ID NO: 163) (m) and well #7 stimulated with INHBB-A02-10-85 (SEQ ID NO: 166) (n) showed potent IFN-gamma production as compared with the control respectively. In the figures, "+" indicates that the target cells in the well were pulsed with the appropriate peptide, and "−" indicates that the target cells had not been pulsed with any peptides.

Figure 11:
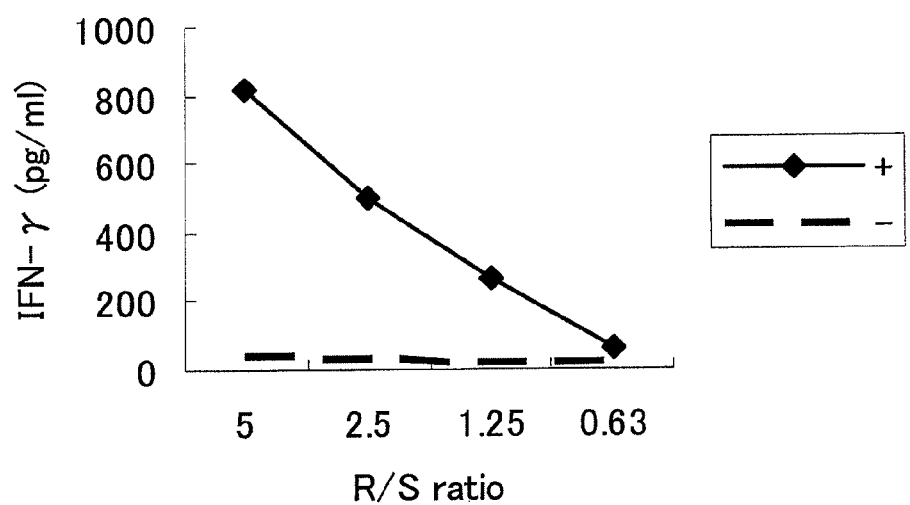

[FIG. 11] FIG. 11 depicts a line graph showing the results of establishment of CTL lines stimulated with INHBB-A02-9-174 (SEQ ID NO: 147) with IFN-gamma ELISA assay. The depicted results demonstrate that CTL line established by stimulation with the peptide showed potent IFN-gamma production as compared with the control. In the figures, "+" indicates that the target cells were pulsed with the appropriate peptide and "−" indicates that the target cells had not been pulsed with any peptides.

DETAILED DESCRIPTION OF THE INVENTION

The words "a", "an", and "the" as used herein mean "at least one" unless otherwise specifically indicated. Unless otherwise defined, all technical and scientific terms used herein have the same meaning as commonly understood by one of ordinary skill in the art to which this invention belongs.

The present invention is based in part on the discovery of applicable targets of immunotherapy. Identification of new TAAs, particularly those that induce potent and specific anti-tumor immune responses, warrants further development of the clinical application of the peptide vaccination strategy in various types of cancer (Boon T et al., (1996) J Exp Med 183: 725-9; van der Bruggen P et al., (1991) Science 254: 1643-7; Brichard V et al., (1993) J Exp Med 178: 489-95; Kawakami Y et al., (1994) J Exp Med 180: 347-52; Shichijo S et al., (1998) J Exp Med 187:277-88; Chen Y T et al., (1997) Proc. Natl. Acad. Sci. USA, 94: 1914-8; Harris C C, (1996) J Natl Cancer Inst 88:1442-55; Butterfield L H et al., (1999) Cancer Res 59:3134-42; Vissers J L et al., (1999) Cancer Res 59: 5554-9; van der Burg S H et al., (1996) J. Immunol. 156:3308-14; Tanaka F et al., (1997) Cancer Res 57:4465-8; Fujie T et al., (1999) Int J Cancer 80:169-72; Kikuchi M et al., (1999) Int J Cancer 81: 459-66; Oiso M et al., (1999) Int J Cancer 81:387-94.). Because TAAs have often no immunogenicity, discovery of fitting targets is extremely important issue.

As noted above,
CDH3 (GenBank Accession No. NM_001793; SEQ ID Nos. 1, 2),
EPHA4 (GenBank Accession No. L36645; SEQ ID Nos. 3, 4),
ECT2 (GenBank Accession No. AY376439; SEQ ID Nos. 5, 6),
HIG2 (GenBank Accession No. NM_013332; SEQ ID Nos. 7, 8)
INHBB (GenBank Accession No. NM_002193; SEQ ID Nos. 9, 435, 10, 436),
KIF20A (GenBank Accession No. NM_005733; SEQ ID Nos. 11, 12),
KNTC2 (GenBank Accession No. AF017790; SEQ ID Nos. 13, 14),
TTK (GenBank Accession No. NM_003318; SEQ ID Nos. 15, 16) and
URLC10 (GenBank Accession No. NM_017527; SEQ ID Nos. 17, 18) were previously identified as over-expressed in various cancers using cDNA microarray technologies.

In the present invention, peptides derived from CDH3, EPHA4, ECT2, HIG2, INHBB, KIF20A, KNTC2, TTK or URLC10 are shown to be TAA epitopes restricted by HLA-A24 and HLA-A2 (HLA-A02), an HLA allele commonly found in the Japanese and Caucasian populations. Specifically, using their binding affinities to HLA-A24 or HLA-A2 (HLA-A02), candidates of HLA-A24 or HLA-A2 (HLA-A02) binding peptides derived from CDH3, EPHA4, ECT2, HIG2, INHBB, KIF20A, KNTC2, TTK or URLC10 were identified. After the in vitro stimulation of T-cells by dendritic cells (DCs) loaded with these peptides, CTLs were successfully established using the following peptides.

CDH3-A24-9-513, (SEQ ID NO: 19)

CDH3-A24-9-406, (SEQ ID NO: 22)

CDH3-A24-10-807, (SEQ ID NO: 30)

CDH3-A24-10-332, (SEQ ID NO: 34)

CDH3-A24-10-655, (SEQ ID NO: 344)

CDH3-A24-10-470, (SEQ ID NO: 358)

EphA4-A24-9-453, (SEQ ID NO: 41)

EphA4-A24-9-5, (SEQ ID NO: 44)

EphA4-A24-9-869, (SEQ ID NO: 46)

EphA4-A24-9-420, (SEQ ID NO: 48)

EphA4-A24-10-24, (SEQ ID NO: 78)

EphA4-A02-9-501, (SEQ ID NO: 376)

EphA4-A02-9-165, (SEQ ID NO: 379)

ECT2-A24-9-515, (SEQ ID NO: 80)

ECT2-A24-10-40, (SEQ ID NO: 100)

ECT2-A24-10-101, (SEQ ID NO: 101)

HIG2-A24-9-19, (SEQ ID NO: 110)

HIG2-A24-9-22, (SEQ ID NO: 111)

HIG2-A24-9-8, (SEQ ID NO: 387)

HIG2-A24-10-7, (SEQ ID NO: 112)

HIG2-A24-10-18, (SEQ ID NO: 394)

HIG2-A02-9-8, (SEQ ID NO: 114)

HIG2-A02-9-15, (SEQ ID NO: 116)

HIG2-A02-9-4, (SEQ ID NO: 117)

HIG2-A02-10-8, (SEQ ID NO: 121)

INHBB-A24-9-180, (SEQ ID NO: 395)

INHBB-A24-10-180, (SEQ ID NO: 133)

-continued

INHBB-A24-10-305, (SEQ ID NO: 135)

INHBB-A24-10-7, (SEQ ID NO: 137)

INHBB-A24-10-212, (SEQ ID NO: 426)

INHBB-A02-9-213, (SEQ ID NO: 143)

INHBB-A02-9-174, (SEQ ID NO: 147)

INHBB-A02-9-257, (SEQ ID NO: 148)

INHBB-A02-9-313, (SEQ ID NO: 149)

INHBB-A02-9-139, (SEQ ID NO: 150)

INHBB-A02-9-8, (SEQ ID NO: 152)

INHBB-A02-9-250, (SEQ ID NO: 153)

INHBB-A02-10-179, (SEQ ID NO: 154)

INHBB-A02-10-237, (SEQ ID NO: 156)

INHBB-A02-10-313, (SEQ ID NO: 160)

INHBB-A02-10-173, (SEQ ID NO: 161)

INHBB-A02-10-256, (SEQ ID NO: 162)

INHBB-A02-10-162 (SEQ ID NO: 163)

INHBB-A02-10-85. (SEQ ID NO: 166)

KIF20A-A24-9-305, (SEQ ID NO: 174)

KIF20A-A24-9-383, (SEQ ID NO: 178)

KIF20A-A24-10-304, (SEQ ID NO: 186)

KIF20A-A24-10-66, (SEQ ID NO: 194)

KNTC2-A24-9-309, (SEQ ID NO: 196)

KNTC2-A24-9-124, (SEQ ID NO: 202)

KNTC2-A24-9-154, (SEQ ID NO: 210)

KNTC2-A24-9-150, (SEQ ID NO: 213)

KNTC2-A24-10-452, (SEQ ID NO: 214)

KNTC2-A24-10-227, (SEQ ID NO: 217)

KNTC2-A24-10-273, (SEQ ID NO: 223)

TTK-A02-9-462, (SEQ ID NO: 227)

TTK-A02-9-547, (SEQ ID NO: 228)

TTK-A02-9-719, (SEQ ID NO: 233)

TTK-A02-10-462, (SEQ ID NO: 254)

URLC-A02-9-206, (SEQ ID NO: 271)

URLC-A02-9-212 and (SEQ ID NO: 272)

URLC-A02-10-211 (SEQ ID NO: 288)

These peptides are epitope peptides of each TAA restricted by HLA-A24 or HLA-A2 (HLA-A02). Since these antigens are over-expressed in most cancers and are associated with tumor cell proliferation, they find utility as immunotherapeutic targets against cancers. Exemplary cancers include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

Accordingly, the present invention further provides methods of treating or preventing a disease associated with the over-expression of CDH3, EPHA4, ECT2, HIG2, INHBB, KIF20A, KNTC2, TTK and/or URLC10, e.g. cancers in a subject, such methods including the steps of administering to the subject an immunogenic peptide of less than about 40 amino acids, often less than about 20 amino acids, usually less than about 15 amino acids and having the amino acid sequence of SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288.

Alternatively, the immunogenic peptide may have an amino acid sequence as set forth in SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 in which 1, 2, or several (e.g., up to 5) amino acids are substituted, deleted or added, provided the resulting variant peptide retains the immunogenic activity (i.e., the ability to induce CTLs specific to cells expressing CDH3, EPHA4, ECT2, HIG2, INHBB, KIF20A, KNTC2, TTK and/or URLC10, e.g. cancers).

The number of residues to be substituted, deleted, or added is generally 5 amino acids or less, preferably 4 amino acids or less, more preferably 3 amino acids or less, even more preferably one or two amino acids. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. Furthermore the present invention provides methods for preventing post-surgery recurrence of these diseases mentioned above.

Variant peptides (i.e., peptides having an amino acid sequence modified by substituting, deleting, or adding one, two or several amino acid residues to an original amino acid sequence) are known to retain the original biological activity (Mark D F et al., (1984) Proc Natl Acad Sci USA 81: 5662-6; Zoller M J and Smith M, (1982) Nucleic Acids Res 10:6487-500; Dalbadie-McFarland G et al., (1982) Proc Natl Acad Sci USA 79: 6409-13.). In the context of the present invention, it is preferable that the amino acid modification results in conservation of the properties of the original amino acid side-chain (a process known as conservative amino acid substitution). Examples of properties of amino acid side chains include hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

In preferred embodiments, the immunogenic peptide is a nonapeptide (9-mer) or a decapeptide (10-mer). The present invention further provides a method of inducing anti-tumor immunity for a disease associated with the over-expression of CDH3, EPHA4, ECT2, HIG2, INHBB, KIF20A, KNTC2, TTK and/or URLC10, e.g. cancers, in a subject, such a method including the steps of administering an immunogenic peptide of the present invention, namely one having the amino acid sequence of SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288, or a variant thereof (i.e., including 1, 2, or several (e.g., up to 5) amino acid substitutions, deletions, or additions) to the subject in need thereof. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

In the context of the present invention, the subject is preferably a mammal. Exemplary mammals include, but are not limited to, e.g., a human, non-human primate, mouse, rat, dog, cat, horse, or cow. In the present invention, the peptide can be administered to a subject via an in vivo or ex vivo protocol. Furthermore, the present invention also provides use of nonapeptide or decapeptide selected from peptides having the amino acid sequence of SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 (and variants thereof) for manufacturing an immunogenic composition for treating or preventing a disease associated with the over-expression of CDH3, EPHA4, ECT2, HIG2, INHBB, KIF20A, KNTC2, TTK and/or URLC10, e.g. cancers. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

Homology analyses of the following peptides demonstrate that they do not have significant homology with the peptides derived from any known human gene products.

```
CDH3-A24-9-513,     (SEQ ID NO: 19)
CDH3-A24-9-406,     (SEQ ID NO: 22)
CDH3-A24-10-807,    (SEQ ID NO: 30)
CDH3-A24-10-332,    (SEQ ID NO: 34)
CDH3-A24-10-655,    (SEQ ID NO: 344)
CDH3-A24-10-470,    (SEQ ID NO: 358)
EphA4-A24-9-453,    (SEQ ID NO: 41)
EphA4-A24-9-5,      (SEQ ID NO: 44)
EphA4-A24-9-869,    (SEQ ID NO: 46)
EphA4-A24-9-420,    (SEQ ID NO: 48)
EphA4-A24-10-24,    (SEQ ID NO: 78)
EphA4-A02-9-501,    (SEQ ID NO: 376)
EphA4-A02-9-165,    (SEQ ID NO: 379)
ECT2-A24-9-515,     (SEQ ID NO: 80)
ECT2-A24-10-40,     (SEQ ID NO: 100)
ECT2-A24-10-101,    (SEQ ID NO: 101)
HIG2-A24-9-19,      (SEQ ID NO: 110)
HIG2-A24-9-22,      (SEQ ID NO: 111)
HIG2-A24-9-8,       (SEQ ID NO: 387)
HIG2-A24-10-7,      (SEQ ID NO: 112)
HIG2-A24-10-18,     (SEQ ID NO: 394)
HIG2-A02-9-8,       (SEQ ID NO: 114)
```

-continued

```
HIG2-A02-9-15,      (SEQ ID NO: 116)
HIG2-A02-9-4,       (SEQ ID NO: 117)
HIG2-A02-10-8,      (SEQ ID NO: 121)
INHBB-A24-9-180,    (SEQ ID NO: 395)
INHBB-A24-10-180,   (SEQ ID NO: 133)
INHBB-A24-10-305,   (SEQ ID NO: 135)
INHBB-A24-10-7,     (SEQ ID NO: 137)
INHBB-A24-10-212,   (SEQ ID NO: 426)
INHBB-A02-9-213,    (SEQ ID NO: 143)
INHBB-A02-9-174,    (SEQ ID NO: 147)
INHBB-A02-9-257,    (SEQ ID NO: 148)
INHBB-A02-9-313,    (SEQ ID NO: 149)
INHBB-A02-9-139,    (SEQ ID NO: 150)
INHBB-A02-9-8,      (SEQ ID NO: 152)
INHBB-A02-9-250,    (SEQ ID NO: 153)
INHBB-A02-10-179,   (SEQ ID NO: 154)
INHBB-A02-10-237,   (SEQ ID NO: 156)
INHBB-A02-10-313,   (SEQ ID NO: 160)
INHBB-A02-10-173,   (SEQ ID NO: 161)
INHBB-A02-10-256,   (SEQ ID NO: 162)
INHBB-A02-10-162    (SEQ ID NO: 163)
INHBB-A02-10-85.    (SEQ ID NO: 166)
KIF20A-A24-9-305,   (SEQ ID NO: 174)
KIF20A-A24-9-383,   (SEQ ID NO: 178)
KIF20A-A24-10-304,  (SEQ ID NO: 186)
KIF20A-A24-10-66,   (SEQ ID NO: 194)
KNTC2-A24-9-309,    (SEQ ID NO: 196)
```

-continued

KNTC2-A24-9-124, (SEQ ID NO: 202)

KNTC2-A24-9-154, (SEQ ID NO: 210)

KNTC2-A24-9-150, (SEQ ID NO: 213)

KNTC2-A24-10-452, (SEQ ID NO: 214)

KNTC2-A24-10-227, (SEQ ID NO: 217)

KNTC2-A24-10-273, (SEQ ID NO: 223)

TTK-A02-9-462, (SEQ ID NO: 227)

TTK-A02-9-547, (SEQ ID NO: 228)

TTK-A02-9-719, (SEQ ID NO: 233)

TTK-A02-10-462, (SEQ ID NO: 254)

URLC-A02-9-206, (SEQ ID NO: 271)

URLC-A02-9-212 (SEQ ID NO: 272)
and

URLC-A02-10-211 (SEQ ID NO: 288)

Accordingly, the possibility of unknown or undesirable immune responses with immunotherapy against these molecules is significantly reduced.

Regarding HLA antigens, the data presented here demonstrate that the uses of A-24 type or A-2 type antigens (which are said to be highly expressed among the Japanese) are favorable for obtaining effective results. The uses of subtypes such as A-2402 and A-0201 are even more preferable. Typically, in the clinic, the type of HLA antigen of the patient requiring treatment is investigated in advance, which, in turn, enables the selection of appropriate peptides having high levels of binding affinity to the patient antigen, or having cytotoxic T cell (CTL) inducibility by antigen presentation. Furthermore, in order to obtain peptides having high binding affinity and CTL inducibility, substitution, deletion, or addition of 1, 2, or several (e.g., up to 5) amino acids may be performed based on the amino acid sequence of the naturally occurring CDH3, EPHA4, ECT2, HIG2, INHBB, KIF20A, KNTC2, TTK and URLC10 partial peptide. Herein, the term "several" means refers to 5 or less, more preferably 3 or less. Furthermore, in addition to peptides that are naturally displayed, since the regularity of the sequences of peptides displayed by binding to HLA antigens is already known (Kubo R T, et al., (1994) J. Immunol., 152, 3913-24; Rammensee H G, et al., (1995) Immunogenetics. 41:178-228; Kondo A, et al., (1995) J. Immunol. 155:4307-12.), modifications based on such regularity can be performed on the immunogenic peptides of the invention. For example, peptides possessing high HLA-24 binding affinity in which the second amino acid from the N terminus substituted with phenylalanine, tyrosine, methionine, or tryptophan may be favorably used. Likewise, peptides whose C-terminal amino acid is substituted with phenylalanine, leucine, isoleucine, tryptophan, or methionine may also be used favorably. On the other hand, peptides possessing high HLA-A2 (HLA-A02) binding affinity in which the second amino acid from the N terminus substituted with leucine or methionine, and peptides whose C-terminal amino acid is substituted with valine or leucine may be used favorably. The substitution is performed not only at the terminus amino acids but also at the position of potential TCR recognition of peptides. Several studies have demonstrated that amino acid substitutions in a peptide can be equal to or better than the original, for example CAP1, $p53_{(264-272)}$, Her-2/$neu_{(369-377)}$ or $gp100_{(209-217)}$ (Zaremba et al. Cancer Res. 57, 4570-4577, 1997, T. K. Hoffmann et al. J Immunol. (2002) February 1; 168(3):1338-47, S. O. Dionne et al. Cancer Immunol Immunotherapy. (2003) 52: 199-206 and S. O. Dionne et al. Cancer Immunology, Immunotherapy (2004) 53, 307-314). Furthermore, 1 to 2 amino acids may be added to the N terminus and/or C terminus of the peptide.

However, when the peptide sequence is identical to a portion of the amino acid sequence of an endogenous or exogenous protein having a different function, side effects such as autoimmune disorders or allergic symptoms against specific substances may be induced. Therefore, it is preferable to avoid the situation wherein the immunogenic sequence matches the amino acid sequence of a known protein. This situation may be avoided by performing a homology search using available databases. If homology searches confirm that peptides in which 1, 2 or several different amino acids do not exist in nature, then the danger that modifications of the above-mentioned amino acid sequence that, for example, increase the binding affinity with HLA antigens, and/or increase the CTL inducibility can be avoided.

Although peptides having high binding affinity to the HLA antigens as described above are expected to be highly effective as cancer vaccines, the candidate peptides, which are selected according to the presence of high binding affinity as an indicator, must be examined for the actual presence of CTL inducibility. CTL inducibility may be routinely confirmed by inducing antigen-presenting cells carrying human MHC antigens (for example, B-lymphocytes, macrophages, and dendritic cells), or more specifically dendritic cells derived from human peripheral blood mononuclear leukocytes, and, after stimulation with the peptide of interest, mixing with CD8-positive cells and measuring the cytotoxic activity against the target cells. As the reaction system, transgenic animals produced to express a human HLA antigen (for example, those described in BenMohamed L, et al., (2000) Hum. Immunol.; 61(8):764-79 Related Articles, Books, Linkout.) may be used. For example, the target cells can be radio-labeled with $^{51}Cr$ and such, and cytotoxic activity can be calculated from radioactivity released from the target cells. Alternatively, it can be examined by measuring IFN-gamma produced and released by CTL in the presence of antigen-presenting cells that carry immobilized peptides, and visualizing the inhibition zone on the media using anti-IFN-gamma monoclonal antibodies.

As a result of examining the CTL inducibility of peptides as described above, it was discovered that those peptides having high binding affinity to an HLA antigen did not necessarily have high inducibility. However, nonapeptides or decapeptides selected from the group of peptides having the amino acid sequences indicated by the following peptides showed particularly high CTL inducibility.

CDH3-A24-9-513, (SEQ ID NO: 19)

CDH3-A24-9-406, (SEQ ID NO: 22)

CDH3-A24-10-807, (SEQ ID NO: 30)

-continued

CDH3-A24-10-332, (SEQ ID NO: 34)

CDH3-A24-10-655, (SEQ ID NO: 344)

CDH3-A24-10-470, (SEQ ID NO: 358)

EphA4-A24-9-453, (SEQ ID NO: 41)

EphA4-A24-9-5, (SEQ ID NO: 44)

EphA4-A24-9-869, (SEQ ID NO: 46)

EphA4-A24-9-420, (SEQ ID NO: 48)

EphA4-A24-10-24, (SEQ ID NO: 78)

EphA4-A02-9-501, (SEQ ID NO: 376)

EphA4-A02-9-165, (SEQ ID NO: 379)

ECT2-A24-9-515, (SEQ ID NO: 80)

ECT2-A24-10-40, (SEQ ID NO: 100)

ECT2-A24-10-101, (SEQ ID NO: 101)

HIG2-A24-9-19, (SEQ ID NO: 110)

HIG2-A24-9-22, (SEQ ID NO: 111)

HIG2-A24-9-8, (SEQ ID NO: 387)

HIG2-A24-10-7, (SEQ ID NO: 112)

HIG2-A24-10-18, (SEQ ID NO: 394)

HIG2-A02-9-8, (SEQ ID NO: 114)

HIG2-A02-9-15, (SEQ ID NO: 116)

HIG2-A02-9-4, (SEQ ID NO: 117)

HIG2-A02-10-8, (SEQ ID NO: 121)

INHBB-A24-9-180, (SEQ ID NO: 395)

INHBB-A24-10-180, (SEQ ID NO: 133)

INHBB-A24-10-305, (SEQ ID NO: 135)

INHBB-A24-10-7, (SEQ ID NO: 137)

INHBB-A24-10-212, (SEQ ID NO: 426)

-continued

INHBB-A02-9-213, (SEQ ID NO: 143)

INHBB-A02-9-174, (SEQ ID NO: 147)

INHBB-A02-9-257, (SEQ ID NO: 148)

INHBB-A02-9-313, (SEQ ID NO: 149)

INHBB-A02-9-139, (SEQ ID NO: 150)

INHBB-A02-9-8, (SEQ ID NO: 152)

INHBB-A02-9-250, (SEQ ID NO: 153)

INHBB-A02-10-179, (SEQ ID NO: 154)

INHBB-A02-10-237, (SEQ ID NO: 156)

INHBB-A02-10-313, (SEQ ID NO: 160)

INHBB-A02-10-173, (SEQ ID NO: 161)

INHBB-A02-10-256, (SEQ ID NO: 162)

INHBB-A02-10-162 (SEQ ID NO: 163)

INHBB-A02-10-85. (SEQ ID NO: 166)

KIF20A-A24-9-305, (SEQ ID NO: 174)

KIF20A-A24-9-383, (SEQ ID NO: 178)

KIF20A-A24-10-304, (SEQ ID NO: 186)

KIF20A-A24-10-66, (SEQ ID NO: 194)

KNTC2-A24-9-309, (SEQ ID NO: 196)

KNTC2-A24-9-124, (SEQ ID NO: 202)

KNTC2-A24-9-154, (SEQ ID NO: 210)

KNTC2-A24-9-150, (SEQ ID NO: 213)

KNTC2-A24-10-452, (SEQ ID NO: 214)

KNTC2-A24-10-227, (SEQ ID NO: 217)

KNTC2-A24-10-273, (SEQ ID NO: 223)

TTK-A02-9-462, (SEQ ID NO: 227)

TTK-A02-9-547, (SEQ ID NO: 228)

-continued

TTK-A02-9-719, (SEQ ID NO: 233)

TTK-A02-10-462, (SEQ ID NO: 254)

URLC-A02-9-206, (SEQ ID NO: 271)

URLC-A02-9-212 and (SEQ ID NO: 272)

URLC-A02-10-211 (SEQ ID NO: 288)

As noted above, the present invention provides peptides having cytotoxic T cell inducibility, namely those having the amino acid sequence of SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 or a variant thereof (i.e., those in which 1, 2, or several amino acids are substituted, deleted, or added).

It is preferable that the amino acid sequences composed of 9 or 10 amino acids indicated in SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 or a variant thereof do not match an amino acid sequence associated with another endogenous protein.

In particular, amino acid substitution to leucine or methionine at the second amino acid from the N terminus, amino acid substitution to valine or leucine at the C-terminal amino acid, and amino acid addition of 1 to 2 amino acids at the N terminus and/or C terminus are examples of preferred variants.

One of skill in the art will recognize that in addition to amino acid substitutions and additions, immunologically active fragments of the peptides may also be used in the methods of the invention. Methods for determining active fragments are well known in the art. CTL clones obtained by stimulation by these modified peptides can recognize the original peptides and cause damage for cells expressing the original peptides.

Peptides of the present invention can be prepared using well known techniques. For example, the peptides can be prepared synthetically, using either recombinant DNA technology or chemical synthesis. Peptides of the present invention may be synthesized individually or as longer polypeptides composed of two or more peptides. The peptides of the present invention are preferably isolated, i.e., substantially free of other naturally occurring host cell proteins and fragments thereof.

The peptides of the present invention may contain modifications, such as glycosylation, side chain oxidation, or phosphorylation; so long as the modifications do not destroy the biological activity of the peptides as described herein, namely the ability to binding to an HLA antigen and induce CTL. Other modifications include incorporation of D-amino acids or other amino acid mimetics that can be used, for example, to increase the serum half life of the peptides.

Moreover, this invention may contain a method of screening for a peptide which 1, 2, or several amino acids are substituted, wherein said peptide comprises an amino acid sequence selected from the group consisting of SEQ ID NO: 19, 22, 30, 34, 344, 358, 41, 44, 46, 48, 78, 80, 100, 101, 110, 111, 387, 112, 394, 395, 133, 135, 137, 426, 174, 178, 186, 194, 196, 202, 210, 213, 214, 217 or 223, said method comprising the steps of:
(a) conforming no significant sequence homology to the entire sequence of 1, 2 or several amino acids substitute;
(b) measuring the CTL inducibility of the candidate substitute peptide; and
(c) selecting the peptide which CTL inducibility is same to or higher than the original peptide.

Alternatively, this invention may contain a method of screening for a peptide which 1, 2, or several amino acids are substituted, wherein said peptide comprises an amino acid sequence selected from the group consisting of SEQ ID NO: 376, 379, 114, 116, 117, 121, 143, 147, 148, 149, 150, 152, 153, 154, 156, 160, 161, 162, 163, 166, 227, 228, 233, 254, 271, 272 or 288, said method comprising the steps of:
(a) conforming no significant sequence homology to the entire sequence of 1, 2 or several amino acids substitute;
(b) measuring the CTL inducibility of the candidate substitute peptide; and
(c) selecting the peptide which CTL inducibility is same to or higher than the original peptide.

For example, in preferred embodiments, the present invention provides a method of identifying for a peptide having an ability to induce CTL against cells expressing at least one tumor-associated antigen, wherein the tumor-associated antigen is antigen selected from the group consisting of CDH3, EPHA4, ECT2, HIG2, INHBB, KIF20A, KNTC2, TTK and URLC10, said method comprising the steps of:
(i) providing or generating at least one candidate sequence which consists of an amino acid sequence modified by substituting, deleting, or adding one, two or several amino acid residues to an original amino acid sequence, wherein the original amino acid sequence is selected from the group consisting of SEQ ID NO: 19, 22, 30, 34, 344, 358, 41, 44, 46, 48, 78, 80, 100, 101, 110, 111, 387, 112, 394, 395, 133, 135, 137, 426, 174, 178, 186, 194, 196, 202, 210, 213, 214, 217 or 223;
(ii) selecting the candidate sequence that does not have substantial significant homology with the peptides derived from any known human gene products other than said tumor-associated antigens;
(iii) contacting a peptide consisting of the candidate sequence selected in step (ii) with antigen presenting cells;
(iv) contacting the antigen presenting cells of step iii with T-cells to evaluate the ability of the peptide to stimulate the T-cells; and
(v) identifying the peptide of which CTL inducibility is same to or higher than a peptide consisting of the original amino acid sequence.

Alternatively, in preferred embodiments, the present invention provides a method of identifying for a peptide having an ability to induce CTL against cells expressing at least one tumor-associated antigen, wherein the tumor-associated antigen is antigen selected from the group consisting of CDH3, EPHA4, ECT2, HIG2, INHBB, KIF20A, KNTC2, TTK and URLC10, said method comprising the steps of:
(i) providing or generating at least one candidate sequence which consists of an amino acid sequence modified by substituting, deleting, or adding one, two or several amino acid residues to an original amino acid sequence, wherein the original amino acid sequence is selected from the group consisting of SEQ ID NO: 376, 379, 114, 116, 117, 121, 143, 147, 148, 149, 150, 152, 153, 154, 156, 160, 161, 162, 163, 166, 227, 228, 233, 254, 271, 272 or 288;

(ii) selecting the candidate sequence that does not have substantial significant homology with the peptides derived from any known human gene products other than said tumor-associated antigens;

(iii) contacting a peptide consisting of the candidate sequence selected in step (ii) with antigen presenting cells;

(iv) contacting the antigen presenting cells of step (iii) with T-cells to evaluate the ability of the peptide to stimulate the T-cells; and (v) identifying the peptide of which CTL inducibility is same to or higher than a peptide consisting of the original amino acid sequence.

Preferably, the amino acid is substituted for a different amino acid in which the properties of the amino acid side-chain are conserved (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids. In the present invention, substantial significant homology is, for example, more than 90%, preferably 95%, more preferably 99% or 100% identity with a known human gene product to be compared.

The peptides of this invention can be prepared as a combination, which includes two or more of peptides of the invention, for use as a vaccine for a disease associated with the over-expression of CDH3, EPHA4, ECT2, HIG2, INHBB, KIF20A, KNTC2, TTK and/or URLC10, e.g. cancers, such a vaccine inducing CTL in vivo. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. The peptides may be in a cocktail or may be conjugated to each other using standard techniques. For example, the peptides can be expressed as a single polypeptide sequence. The peptides in the combination may be the same or different.

By administering the peptides of this invention, the peptides are presented at a high density on the HLA antigens of antigen-presenting cells, which, in turn, induces CTLs that specifically react toward the complex formed between the displayed peptide and the HLA antigen. Alternatively, antigen-presenting cells having immobilized the peptides of this invention on their cell surface, obtained by removing dendritic cells from the subjects, may be stimulated by the peptides of this invention. Re-administration of these cells to the respective subjects induces CTL, and, as a result, aggressiveness towards the target cells can be increased.

More specifically, the present invention provides drugs for treating and/or preventing proliferation, metastasis, and such of a disease associated with the over-expression of CDH3, EPHA4, ECT2, HIG2, INHBB, KIF20A, KNTC2, TTK and/or URLC10, e.g. cancers, which include one or more of peptides of the present invention, or a polynucleotide encoding the peptides. The peptides or polynucleotides of the present invention find particular utility in the treatment of a disease associating CDH3, EPHA4, ECT2, HIG2, INHBB, KIF20A, KNTC2, TTK and/or URLC10, e.g. cancers. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

The peptides of this invention can be administered to a subject directly, as a pharmaceutical composition that has been formulated by conventional formulation methods. In such cases, in addition to the peptides of this invention, carriers, excipients, and such that are ordinarily used for drugs can be included as appropriate, without particular limitations. The immunogenic compositions of this invention may be used for treatment and prevention of a disease associated with the over-expression of CDH3, EPHA4, ECT2, HIG2, INHBB, KIF20A, KNTC2, TTK and/or URLC10, e.g. cancers. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

The immunogenic compositions for treatment and/or prevention of a disease associated with the over-expression of CDH3, EPHA4, ECT2, HIG2, INHBB, KIF20A, KNTC2, TTK and/or URLC10, e.g. cancers, which include as the active ingredient one or more peptides of the present invention, can further include an adjuvant so that cellular immunity will be established effectively. Alternatively, they may be administered with other active ingredients, such as anti-cancer agents.

The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. Suitable formulations include granules. Suitable adjuvants are described in the literature (Johnson A G. (1994) Clin. Microbiol. Rev., 7:277-89.).

Exemplary adjuvants include, but are not limited to, aluminum phosphate, aluminum hydroxide, and alum. Furthermore, liposome formulations, granular formulations in which the drug is bound to few-mc m diameter beads, and formulations in which a lipid is bound to the peptide may be conveniently used. The method of administration may be oral, intradermal, subcutaneous, intravenous injection, or such, and may include systemic administration or local administration to the vicinity of the targeted tumor.

The dose of the peptide(s) of this invention can be adjusted appropriately according to the disease to be treated, age of the patient, weight, method of administration, and such. Though the dosage is ordinarily 0.001 mg to 1000 mg, preferably 0.01 mg to 100 mg, more preferably 0.1 mg to 10 mg, preferably administered once in a few days to few months, one skilled in the art can readily select the appropriate dose and method of administration, as, the selection and optimization of these parameters is well within routine skill.

The present invention further provides intracellular vesicles called exosomes, which present complexes formed between the peptides of this invention and HLA antigens on their surface. Exosomes can be prepared, for example, by using the methods described in detail in Published Japanese Translation of International Publication Nos. Hei 11-510507 and 2000-512161, and are preferably prepared using antigen-presenting cells obtained from subjects who are targets of treatment and/or prevention. The exosomes of this invention can be inoculated as cancer vaccines, similarly to the peptides of this invention.

The type of HLA antigens used must match that of the subject requiring treatment and/or prevention. For example, in the Japanese population, HLA-A24 or HLA-A2 (HLA-A02), particularly HLA-A2402 or HLA-A0201, is often appropriate.

In some embodiments, the vaccine compositions of the present invention include a component which primes cytotoxic T lymphocytes. Lipids have been identified as agents capable of priming CTL in vivo against viral antigens. For example, palmitic acid residues can be attached to the epsilon- and alpha-amino groups of a lysine residue and then linked to an immunogenic peptide of the invention. The lipidated peptide can then be administered either directly, in a micelle or particle, incorporated into a liposome, or emulsified in an adjuvant. As another example of a lipid priming of CTL responses, *E. coli* lipoproteins, such as tripalmitoyl-S-glycerylcysteinlyseryl-serine (P3CSS), can be used to prime CTL when covalently attached to an appropriate peptide (see, e.g., Deres K, et al., (1989) Nature 342:561-4.).

The immunogenic compositions of the present invention may also include nucleic acids encoding one or more of the immunogenic peptides disclosed here. See, e.g., Wolff J A et al., (1990) Science 247:1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

The immunogenic peptides of the invention can also be expressed by viral or bacterial vectors. Examples of suitable expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another suitable vector is BCG (Bacille Calmette Guerin). BCG vectors are described in Stover C K, et al., (1991) Nature 351:456-60. A wide variety of other vectors useful for therapeutic administration or immunization e.g., adeno and adeno-associated virus vectors, retroviral vectors, *Salmonella typhi* vectors, detoxified anthrax toxin vectors, and the like, are known in the art. See, e.g., Shata M T, et al., (2000) Mol. Med. Today 6:66-71; Shedlock D J and Weiner D B., et al., (2000) J. Leukoc. Biol. 68:793-806; and Hipp J D, et al., (2000) In Vivo 14:571-85.

The present invention also provides methods of inducing antigen-presenting cells using one or more peptides of this invention. The antigen-presenting cells can be induced by inducing dendritic cells from the peripheral blood monocytes and then contacting (stimulating) them with one or more peptides of this invention in vitro, ex vivo or in vivo. When peptides of the present invention are administered to the subjects, antigen-presenting cells that have the peptides of this invention immobilized to them are induced in the body of the subject. Alternatively, after immobilizing the peptides of this invention to the antigen-presenting cells, the cells can be administered to the subject as a vaccine. For example, the ex vivo administration may include the steps of:

a: collecting antigen-presenting cells from a subject, and b: contacting the antigen-presenting cells of step a with a peptide of the present invention.

Alternatively, according to the present invention, use of the peptides of this invention for manufacturing a pharmaceutical composition inducing antigen-presenting cells is provided. Further, the present invention also provides the peptide of the present invention for inducing antigen-presenting cells. The antigen-presenting cells obtained by step b can be administered to the subject as a vaccine.

This invention also provides a method for inducing antigen-presenting cells having a high level of cytotoxic T cell inducibility, in which the method includes the step of transferring genes composed of polynucleotide(s) encoding one or more peptides of this invention to antigen-presenting cells in vitro. The introduced genes may be in the form of DNAs or RNAs. For the method of introduction, without particular limitations, various methods conventionally performed in this field, such as lipofection, electroporation, and calcium phosphate method may be suitably used. More specifically, transfection may be performed as described in Reeves M E, et al., (1996) Cancer Res., 56:5672-7; Butterfield L H, et al., (1998) J. Immunol., 161:5607-13; Boczkowski D, et al., (1996) J. Exp. Med., 184:465-72; Published Japanese Translation of International Publication No. 2000-509281. By transferring the gene into antigen-presenting cells, the gene undergoes transcription, translation, and such in the cell, and then the obtained protein is processed by MHC Class I or Class II, and proceeds through a presentation pathway to present partial peptides.

The present invention further provides methods for inducing CTL using one or more peptides of this invention. When the peptides of this invention are administered to a subject, CTL are induced in the body of the subject, and the strength of the immune system targeting the cells expressing CDH3, EPHA4, ECT2, HIG2, INHBB, KIF20A, KNTC2, TTK and/or URLC10, e.g. cancer cells in the tumor tissues is thereby enhanced.

The cancers contemplated include, but are not limited to bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor. Alternatively, the peptides of the present invention may be used in the context of an ex vivo therapeutic method, in which subject-derived antigen-presenting cells and CD8-positive cells or peripheral blood mononuclear leukocytes are contacted (stimulated) with one or more peptides of this invention in vitro, and, after inducing CTL, the cells are returned to the subject. For example, the method may include the steps of:

a: collecting antigen-presenting cells from a subject, b: contacting the antigen-presenting cells of step a with a peptide of the present invention, c: mixing the antigen-presenting cells of step b with $CD^{8+}$ T cells and co-culturing so as to induce cytotoxic T-cells, and d: collecting $CD^{8+}$ T cells from the co-culture of step c.

Alternatively, according to the present invention, use of the peptides of this invention for manufacturing a pharmaceutical composition inducing CTLs is provided. Further, the present invention also provides the peptide of the present invention for inducing CTLs. The CD$^{8+}$ T cells having cytotoxic activity obtained by step d can be administered to the subject as a vaccine.

The present invention further provides isolated cytotoxic T cells induced using the peptides of this invention. The cytotoxic T cells, induced by stimulation with an antigen-presenting cell presenting one or more peptides of this invention, are preferably derived from subjects who are the target of treatment and/or prevention, and can be administered alone or in combination with other drugs, including one or more peptides of this invention or exosomes having anti-tumor activity. The obtained cytotoxic T cells act specifically against target cells presenting the peptides of this invention, or preferably the same peptide(s) used for induction. The target cells may be cells that express CDH3, EPHA4, ECT2, HIG2, INHBB, KIF20A, KNTC2, TTK and/or URLC10 endogenously, or cells that are transfected with CDH3, EPHA4, ECT2, HIG2, INHBB, KIF20A, KNTC2, TTK and/or URLC10 genes. Cells that present the peptides of this invention on the cell surface, due to stimulation with these peptides, can also become targets of attack.

The present invention also provides antigen-presenting cells presenting complexes formed between HLA antigens and one or more peptides of this invention. The antigen-presenting cells, obtained through contact with the peptides of this invention or the nucleotides encoding such peptides, are preferably derived from subjects who are the target of treatment and/or prevention, and can be administered as vaccines, alone or in combination with other drugs, including the peptides, exosomes, or cytotoxic T cells of the present invention.

The present invention also provides a composition composed of nucleic acids encoding polypeptides that are capable of forming a subunit of a T cell receptor (TCR), and methods of using the same. The TCR subunits have the ability to form TCRs that confer specificity to T cells for tumor cells presenting CDH3, EPHA4, ECT2, HIG2, INHBB, KIF20A, KNTC2, TTK or URLC10. By using the known method in the art, the nucleic acids of alpha- and beta-chain as the TCR subunits of the CTL induced with one or more peptides of this invention may be identified (WO2007/032255 and Morgan et al., J Immunol, 171, 3288 (2003)). The derivative TCRs preferably bind target cells displaying the CDH3, EPHA4, ECT2, HIG2, INHBB, KIF20A, KNTC2, TTK or URLC10 peptide with high avidity, and optionally mediate efficient killing of target cells presenting the CDH3, EPHA4, ECT2, HIG2, INHBB, KIF20A, KNTC2, TTK or URLC10 peptide in vivo and in vitro.

The nucleic acids encoding the TCR subunits can be incorporated into suitable vectors e.g. retroviral vectors. These vectors are well known in the art. The nucleic acids or the vectors containing them usefully can be transferred into a T cell, which T cell is preferably from a patient. Advantageously, the invention provides an off-the-shelf composition allowing rapid modification of a patient's own T cells (or those of another mammal) to rapidly and easily produce modified T cells having excellent cancer cell killing properties.

Also, the present invention provides CTLs which are prepared by transduction with the nucleic acids encoding the TCR subunits polypeptides binding with CDH3, EPHA4, ECT2, HIG2, INHBB, KIF20A, KNTC2, TTK or URLC10 peptide e.g. SEQ ID NOs: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 in the context of HLA-A24 or HLA-A2 (HLA-A02). The transduced CTLs are capable of homing to cancer cells in vivo, and expanded by well known culturing method in vitro (e.g., Kawakami et al., J Immunol., 142, 3452-3461 (1989)). The T cells of the invention can be used to form an immunogenic composition useful in treating or preventing cancer in a patient in need of therapy or protection (WO2006/031221).

In the context of the present invention, the term "vaccine" (also referred to as an immunogenic composition) refers to a substance that induces anti-tumor immunity or suppresses cancers upon inoculation into animals. According to the present invention, polypeptides having the amino acid sequence of SEQ ID NO: 19, 22, 30, 34, 344, 358, 41, 44, 46, 48, 78, 80, 100, 101, 110, 111, 387, 112, 394, 395, 133, 135, 137, 426, 174, 178, 186, 194, 196, 202, 210, 213, 214, 217 or 223 were suggested to be HLA-A24 restricted epitope peptides and those of SEQ ID NO: 376, 379, 114, 116, 117, 121, 143, 147, 148, 149, 150, 152, 153, 154, 156, 160, 161, 162, 163, 166, 227, 228, 233, 254, 271, 272 or 288 were suggested to be HLA-A2 (HLA-A02) restricted epitope peptides that may induce potent and specific immune response against cells expressing CDH3, EPHA4, ECT2, HIG2, INHBB, KIF20A, KNTC2, TTK and/or URLC10, e.g. cancer cells expressing CDH3, EPHA4, ECT2, HIG2, INHBB, KIF20A, KNTC2, TTK and/or URLC10. The cancers contemplated include, but are not limited to bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

Thus, the present invention also encompasses a method of inducing anti-tumor immunity using polypeptides having the amino acid sequence of SEQ ID NO: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 143, 147, 148, 149, 150, 152, 153, 154, 156, 160, 161, 162, 163, 166, 174, 178, 186, 194, 196, 202, 210, 213, 214, 217, 223, 227, 228, 233, 254, 271, 272 or 288 or a variant thereof (i.e., including 1, 2, or several (e.g., up to 5) amino acid substitutions, deletions, or additions). In general, anti-tumor immunity includes immune responses such as follows:

an induction of cytotoxic lymphocytes against tumors containing cells expressing CDH3, EPHA4, ECT2, HIG2, INHBB, KIF20A, KNTC2, TTK and/or URLC10, an induction of antibodies that recognize tumors containing cells expressing CDH3, EPHA4, ECT2, HIG2, INHBB, KIF20A, KNTC2, TTK and/or URLC10, and an induction of anti-tumor cytokine production.

Therefore, when a certain peptide induces any one of these immune responses upon inoculation into an animal, the peptide is decided to have anti-tumor immunity inducing effect. The induction of the anti-tumor immunity by a peptide can be detected by observing in vivo or in vitro the response of the immune system in the host against the peptide.

For example, a method for detecting the induction of cytotoxic T lymphocytes is well known. A foreign substance that enters the living body is presented to T cells and B cells by the action of antigen-presenting cells (APCs). T cells that respond to the antigen presented by APC in antigen specific manner differentiate into cytotoxic T cells (also referred to as cytotoxic T lymphocytes or CTLs) due to stimulation by the antigen, and then proliferate; this process is referred to herein as "activation" of T cells. Therefore, CTL induction by a certain peptide can be evaluated by presenting the peptide to a T cell by APC, and detecting the induction of CTL. Furthermore, APCs have the effect of activating CD4+ T cells, CD8+ T cells, macrophages, eosinophils and NK cells. Since CD4+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, it is well known to evaluate the degree of tumor cell damage using 3H-thymidine uptake activity or LDH (lactose dehydrogenase)-release as the indicator. Furthermore, it can be also examined by measuring IFN-gamma produced and released by CTL in the presence of antigen-presenting cells that carry immobilized peptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against cells expressed CDH3, EPHA4, ECT2, HIG2, INHBB, KIF20A, KNTC2, TTK and/or URLC10 are useful as vaccines against diseases associating CDH3, EPHA4, ECT2, HIG2, INHBB, KIF20A, KNTC2, TTK and/or URLC10, e.g. cancers. Furthermore, APC that have acquired the ability to induce CTL against a disease associated with the over-expression of CDH3, EPHA4, ECT2, HIG2, INHBB, KIF20A, KNTC2, TTK and/or URLC10, e.g. cancers, by contacting with the polypeptides are useful as vaccines against the disease. Furthermore, CTL that have acquired cytotoxicity due to presentation of the polypeptide antigens by APC can be also used as vaccines against a disease associating CDH3, EPHA4, ECT2, HIG2, INHBB, KIF20A, KNTC2, TTK and/or URLC10, e.g. cancers. Such therapeutic methods for a disease associating CDH3, EPHA4, ECT2, HIG2, INHBB, KIF20A, KNTC2, TTK and/or URLC10, e.g. cancers, using anti-tumor immunity due to APC and CTL, are referred to as cellular immunotherapy. The cancers contemplated include, but are not limited to, bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

Generally, when using a polypeptide for cellular immunotherapy, efficiency of the CTL-induction can be increased by combining a plurality of polypeptides having different structures and contacting them with DC. Therefore, when stimulating DC with protein fragments, it is advantageous to use a mixture of multiple types of fragments.

The induction of anti-tumor immunity by a polypeptide can be further confirmed by observing the induction of antibody production against tumors. For example, when antibodies against a polypeptide are induced in a laboratory animal immunized with the polypeptide, and when growth, proliferation and/or metastasis of tumor cells is suppressed by those antibodies, the polypeptide is determined to induce anti-tumor immunity.

Anti-tumor immunity can be induced by administering a vaccine of this invention, and the induction of anti-tumor immunity enables treatment and prevention of a disease associated with the over-expression of CDH3, EPHA4, ECT2, HIG2, INHBB, KIF20A, KNTC2, TTK and/or URLC10, e.g. cancers. Therapy against or prevention of the onset of a disease associated with the over-expression of CDH3, EPHA4, ECT2, HIG2, INHBB, KIF20A, KNTC2, TTK and/or URLC10, e.g. cancers, may include inhibition of the growth of cells expressing CDH3, EPHA4, ECT2, HIG2, INHBB, KIF20A, KNTC2, TTK and/or URLC10, e.g. cancer cells, involution of these cells and suppression of occurrence of these cells, e.g. cancer cells. Decrease in mortality of individuals having a disease associating CDH3, EPHA4, ECT2, HIG2, INHBB, KIF20A, KNTC2, TTK and/or URLC10, e.g. cancers, decrease of the disease markers in the blood, alleviation of detectable symptoms accompanying the disease and such are also included in the therapy or prevention of the disease, e.g. cancers. Such therapeutic and preventive effects are preferably statistically significant, for example, observed at a significance level of 5% or less, wherein the therapeutic or preventive effect of a vaccine against a disease associating CDH3, EPHA4, ECT2, HIG2, INHBB, KIF20A, KNTC2, TTK and/or URLC10, e.g. cancers, is compared to a control without vaccine administration. For example, Student's t-test, the Mann-Whitney U-test or ANOVA may be used for determining statistical significance.

In that the present invention provides a method for treating, or preventing a disease associated with the over-expression of CDH3, EPHA4, ECT2, HIG2, INHBB, KIF20A, KNTC2, TTK and/or URLC10, e.g. cancers, the therapeutic compounds or compositions may be administered prophylactically or therapeutically to subjects suffering from or at risk of (or susceptible to) developing the disease. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

In the context of cancer treatment, the term "efficacious" refers to a treatment that leads to a decrease in size, prevalence or metastatic potential of cancer in a subject. When a treatment is applied prophylactically, "efficacious" means that the treatment retards or prevents occurrence of cancer or alleviates a clinical symptom of cancer. The assessment of cancer can be made using standard clinical protocols. Furthermore, the efficaciousness of a treatment may be determined in association with any known method for diagnosing or treating cancer. For example, cancer can be diagnosed histopathologically or by identifying symptomatic anomalies.

The above-mentioned peptide, having immunological activity, or a polynucleotide or vector encoding such a peptide, may be combined with an adjuvant. An adjuvant refers to a compound that enhances the immune response against the peptide when administered together (or successively) with the peptide having immunological activity. Examples of suitable adjuvants include cholera toxin, *salmonella* toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

When using APC or CTL as the vaccine of this invention, a disease associated with the over-expression of CDH3, EPHA4, ECT2, HIG2, INHBB, KIF20A, KNTC2, TTK and/or URLC10, e.g. cancers, can be treated or prevented, for example, by the ex vivo method. More specifically, PBMCs of the subject receiving treatment or prevention are collected, contacted ex vivo with a peptide of the present invention. Following the induction of APC or CTL, the cells may be administered to the subject. APC can be also induced by introducing a vector encoding the peptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of diseases in other individuals.

Aspects of the present invention are described in the following examples, which are presented only to illustrate the present invention and to assist one of ordinary skill in making and using the same. The examples are not intended in any way to otherwise limit the scope of the invention.

Although methods and materials similar or equivalent to those described herein can be used in the practice or testing of the present invention, suitable methods and materials are described below.

EXAMPLES

Hereinafter, the present invention is exemplified, but not restricted, by the following Examples. However, materials, methods and such described herein only illustrate aspects of the invention and in no way are intended to limit the scope of the present invention. As such, materials, methods and such similar or equivalent to those described therein may be used in the practice or testing of the present invention.

Example 1

Materials and Methods

Cell Lines

A24-LCL cells (HLA-A24), human B-lymphoblastoid cell line, was established by transforming with Epstain-barr virus. T2 cell, COS7, A498, Caki-2 and HEK 293 were purchased from ATCC. Caki-1 and MIAPaca-2 were purchased from JCRB. PK-45P, PK-59, TE-5 and TE-6 were purchased from TKG. 293 T was purchased from GenHunter.

Candidate Selection of Peptide Derived from CDH3, EPHA4, ECT2, HIG2, INHBB, KIF20A, KNTC2, TTK and URLC10

9-mer and 10-mer peptides derived from CDH3, EPHA4, ECT2, HIG2, INHBB, KIF20A, KNTC2, TTK or URLC10 that bind to HLA-A*2402 or HLA-A*0201 molecule were predicted using the binding prediction software "BIMAS" (http://bimas.dcrt.nih.gov/cgi-bin/molbio/ken_parker_comboform) (Parker K C, et al., (1994) J Immunol; 152(1):163-75; Kuzushima K, et al., (2001) Blood.; 98(6):1872-81.). These peptides were synthesized by Sigma (Sapporo, Japan) according to the standard solid phase synthesis method and purified by reversed phase HPLC. The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce CTL responses against peptides presented on HLA. DCs were generated in vitro as described elsewhere (Nukaya I et al., (1999) Int. J. Cancer 80, 92-7, Tsai V et al., (1997) J. Immunol 158:1796-802.). Briefly, peripheral blood mononuclear cells (PBMCs) isolated from a normal volunteer (HLA-A*2402 and/or HLA-A*0201) by Ficoll-Paque (Pharmacia) solution were separated by adherence to a plastic tissue culture flask (Becton Dickinson) so as to enrich them for the monocyte fraction. The monocyte-enriched population was cultured in the presence of 1000 U/ml of GM-CSF (Genzyme) and 1000 U/ml of IL-4 (Genzyme) in AIM-V (Invitrogen) containing 2% heat-inactivated autologous serum (AS). After 7 days in the culture, the cytokine-generated DCs were pulsed with 20 micro g/ml of the synthesized peptides in the presence of 3 micro g/ml of beta 2-microglobulin for 4 hrs at 20 degrees C. in AIM-V. These peptide-pulsed DCs were then inactivated by MMC (30 micro g/ml for 30 mins) and mixed at a 1:20 ratio with autologous CD8$^+$ T cells, obtained by positive selection with Dynabeads M-450 CD8 (Dynal) and DETACHa BEAD™ (Dynal). These cultures were set up in 48-well plates (Corning); each well contained $1.5 \times 10^4$ peptide-pulsed DCs, $3 \times 10^5$ CD8$^+$ T cells and 10 ng/ml of IL-7 (Genzyme) in 0.5 ml of AIM-V/2% AS. Three days later, these cultures were supplemented with IL-2 (CHIRON) to a final concentration of 20 IU/ml. On day 7 and 14, the T cells were further restimulated with the autologous peptide-pulsed DCs. The DCs were prepared each time by the same way described above. CTL was tested against peptide-pulsed A24-LCL cells or T2 cells after the 3rd round of peptide stimulation on day 21.

CTL Expansion Procedure

CTLs were expanded in culture using the method similar to that described by Riddell S R, et al., (Walter E A et al., (1995) N Engl J Med 333:1038-44; Riddel S R, et al., (1996) Nature Med. 2:216-23.). A total $5 \times 10^4$ of CTLs were resuspended in 25 ml of AIM-V/5% AS with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS containing 30 IU/ml of IL-2 on days 5, 8 and 11.

Establishment of CTL Clones

The dilutions were made to have 0.3, 1, and 3 CTLs/well in 96 round-bottomed micro titer plate (Nalge Nunc International). CTLs were cultured with $7 \times 10^4$ cells/well of 2 kinds of human B-lymphoblastoid cell lines, 30 ng/ml of anti-CD3 antibody, and 125 U/ml of IL-2 in total of 150 micro l/well of AIM-V containing 5% AS. 50 micro l/well of IL-2 was added to the medium 10 days later so that IL-2 became 125 U/ml in the final concentration. CTL activity of CTLs was tested on the 14th day, and CTL clones were expanded using the same method above.

Specific CTL Activity

To examine the specific CTL activity, IFN-gamma ELISPOT assay and IFN-gamma ELISA assay were performed. Briefly, peptide-pulsed A24-LCL or T2 cell ($1\times10^4$/well) was prepared as stimulator cells. Cultured Cells in 48 wells or CTL clones after limiting dilution were used as responder cells. IFN-gamma ELISPOT assay and ELISA assay were performed under manufacture procedure.

Establishment of the Cells Forcibly Expressing Either or Both of the Target Gene and HLA-A02 or HLA-A24

The cDNA encoding an open reading frame of target genes or HLA-A02 or HLA-A24 was amplified by PCR. The PCR-amplified product was cloned into pcDNA3.1 myc-His vector (Invitrogen). The plasmids were transfected into the target cells, HLA-A02 and HLA-A24-null normal human cell line COS7 or 293T using lipofectamine (Invitrogen) according to the manufacturer's recommended procedures. Alternatively, the plasmid contained the target genes were transfected into A24-LCL by electroporation using GenePulserII (Biorad). Briefly, $2.5\times10^6$ A24-LCL cells were pulsed with 10 mcg prasmid at 140V and 1000 micro F. After 2 days from transfection, the transfected cells were treated with Cell dissociation solution and used as the target cells for CTL activity assay.

Cytotoxicity Assay

Cytotoxic activity was evaluated by a four-hour $^{51}$Cr release assay. The target cells were pulsed with a 20 micro g/mL concentration of peptide overnight. The target cells were labeled with 100 micro Ci of $Na_2^{51}CrO_4$ at 37 degrees C. for one hour, and then washed three times with RPMI1640. The target cells ($1\times10^4$/100 micro L) and 100 micro L of effector cells at various numbers with a total volume of 200 micro L were placed into a round-bottomed 96-well microtiter plate (Corning), and cultured at 37 degrees C. in a $CO_2$ incubator for four hours. After culturing, 100 micro L of the supernatant was collected from each well, and measured the radioactivity using a gamma counter. Spontaneous release was the radioactivity from the target cells with medium in the absence of effector cells, and maximum release was the radioactivity from the target cells with 1 M HCl.

The Percentage of specific cytotoxicity was determined by calculating as following formula:

% Specific lysis=[(experimental release−spontaneous release)/(maximum release−spontaneous release)]×100.

Results

Enhanced CDH3, EPHA4, ECT2, HIG2, INHBB, KIF20A, KNTC2, TTK and URLC10 Expression in Cancers The global gene expression profile data obtained from various cancers using cDNA-microarray revealed that the expression of the following genes was elevated.

CDH3 (GenBank Accession No. NM_001793; SEQ ID Nos. 1, 2),

EPHA4 (GenBank Accession No. L36645; SEQ ID Nos. 3, 4),

ECT2 (GenBank Accession No. AY376439; SEQ ID Nos. 5, 6),

HIG2 (GenBank Accession No. NM_013332; SEQ ID Nos. 7, 8),

INHBB (GenBank Accession No. NM_002193; SEQ ID Nos. 9, 435, 10, 436),

KIF20A (GenBank Accession No. NM_005733; SEQ ID Nos. 11, 12),

KNTC2 (GenBank Accession No. AF017790; SEQ ID Nos. 13, 14),

TTK (GenBank Accession No. NM_003318; SEQ ID Nos. 15, 16) and

URLC10 (GenBank Accession No. NM_017527; SEQ ID Nos. 17, 18)

CDH3 expression was validly elevated in the following cancers in comparison with corresponding normal tissue.

26 out of 34 bladder cancer,
17 out of 19 cervical cancer,
19 out of 19 cholangiocellular carcinoma,
30 out of 34 colorectal cancer,
20 out of 21 endometriosis,
13 out of 20 gastric cancer,
7 out of 8 diffuse-type gastric cancer,
36 out of 37 NSCLC,
16 out of 16 pancreatic cancer,
21 out of 21 soft tissue tumor and
10 out of 10 testicular tumor EPHA4 expression was validly elevated in the following cancers in comparison with corresponding normal tissue.

14 out of 34 bladder cancer,
8 out of 14 cervical cancer,
10 out of 25 cholangiocellular carcinoma,
5 out of 15 endometriosis,
5 out of 8 diffuse-type gastric cancer,
5 out of 5 ovarian cancer,
14 out of 14 pancreatic cancer,
20 out of 51 prostate cancer and
14 out of 23 soft tissue tumor ECT2 expression was validly elevated in the following cancers in comparing with corresponding normal tissue.

17 out of 19 bladder cancer,
5 out of 12 breast cancer,
14 out of 14 cervical cancer,
13 out of 13 cholangiocellular carcinoma,
5 out of 5 CML,
7 out of 8 colorectal cancer,
12 out of 16 esophageal cancer,
6 out of 16 NSCLC,
8 out of 10 lymphoma,
1 out of 1 pancreatic cancer,
10 out of 13 prostate cancer,
3 out of 6 renal carcinoma and
12 out of 13 SCLC cancer HIG2 expression was validly elevated in 19 out of 20 renal cancer and 7 out of 9 soft tissue tumor in comparing with corresponding normal tissue.

INHBB expression was validly elevated in the following cancers in comparing with corresponding normal tissue.

10 out of 21 cholangiocellular carcinoma,
12 out of 12 esophageal cancer,
10 out of 13 NSCLC,
22 out of 24 renal carcinoma,
8 out of 14 SCLC cancer and
45 out of 49 soft tissue tumor KIF20A expression was validly elevated in the following cancers in comparing with corresponding normal tissue.

31 out of 31 bladder cancer,
38 out of 61 breast cancer,
10 out of 11 cholangiocellular carcinoma,
7 out of 19 esophageal cancer,
21 out of 22 NSCLC,
6 out of 6 ovarian cancer, 17 out of 36 prostate cancer,
6 out of 11 renal carcinoma and
15 out of 15 SCLC KNTC2 expression was validly elevated in the following cancers in comparing with corresponding normal tissue.
30 out of 32 bladder cancer,
47 out of 56 breast cancer,
10 out of 10 cervical cancer,
16 out of 22 cholangiocellular carcinoma,
17 out of 37 CML,
3 out of 10 colorectal cancer,
11 out of 46 esophagus cancer,
15 out of 19 NSCLC,
7 out of 8 lymphoma,
20 out of 24 osteosarcoma,
3 out of 5 ovarian cancer,
2 out of 2 pancreatic cancer,
15 out of 37 prostate cancer,
14 out of 19 renal carcinoma,
15 out of 15 SCLC and
40 out of 59 soft tissue tumor TTK expression was validly elevated in the following cancers in comparing with corresponding normal tissue.
27 out of 27 bladder cancer,
25 out of 30 breast cancer,
15 out of 16 cervical cancer,
10 out of 10 cholangiocellular carcinoma,
5 out of 7 CML,
6 out of 10 colorectal cancer,
24 out of 44 esophageal cancer,
8 out of 15 liver cancer,
12 out of 12 NSCLC,
6 out of 6 lymphoma,
13 out of 16 osteoblastoma,
12 out of 17 prostate cancer,
15 out of 15 SCLC and
16 out of 33 soft tissue tumor URLC10 expression was validly elevated in the following cancers in comparing with corresponding normal tissue
29 out of 29 bladder cancer,
15 out of 16 cervical cancer,
7 out of 7 cholangiocellular carcinoma,
7 out of 19 esophageal cancer,
3 out of 3 gastric cancer, 24 out of 27 NSCLC,
15 out of 19 osteosarcoma,
4 out of 5 pancreatic cancer,
33 out of 43 soft tissue tumor.

TABLE 1

Ratio of cases observed up-regulation of CDH3, EPHA4, ECT2, HIG2, INHBB, KIF20A, KNTC2, TTK or URLC10 in cancerous tissue as compared to normal corresponding tissue

| | CDH3 | EPHA4 | ECT2 | HIG2 | INHBB |
|---|---|---|---|---|---|
| Bladder cancer | 26/34 | 14/34 | 17/19 | — | — |
| Breast cancer | — | — | 5/12 | — | — |
| Cervical cancer | 17/19 | 8/14 | 14/14 | — | — |
| Cholangiocellular carcinoma | 19/19 | 10/25 | 13/13 | — | 10/21 |
| CML | — | — | 5/5 | — | — |
| Colectal cancer | 30/34 | — | 7/8 | — | — |
| Endometriosis | 20/21 | 5/15 | — | — | — |
| Esophageal cancer | — | — | 12/16 | — | 12/12 |
| Gastric cancer | 13/20 | — | — | — | — |
| Diffuse-type Gastric cancer | 7/8 | 5/8 | — | — | — |
| Liver cancer | — | — | — | — | — |
| non-small cell lung cancer | 36/37 | — | 6/16 | — | 10/13 |
| Lymphoma | — | — | 8/10 | — | — |
| Osteosarcoma | — | — | — | — | — |

TABLE 1-continued

Ratio of cases observed up-regulation of CDH3, EPHA4, ECT2, HIG2, INHBB, KIF20A, KNTC2, TTK or URLC10 in cancerous tissue as compared to normal corresponding tissue

| | CDH3 | EPHA4 | ECT2 | HIG2 | INHBB |
|---|---|---|---|---|---|
| Ovarian cancer | — | 5/5 | — | — | — |
| Pancreatic cancer | 16/16 | 14/14 | 1/1 | — | — |
| Prostate cancer | — | 20/51 | 10/13 | — | — |
| Renal carcinoma | — | — | 3/6 | 19/20 | 22/24 |
| Small cell lung cancer | — | — | 12/13 | — | 8/14 |
| Soft tissue tumor | 21/21 | 14/23 | — | 7/9 | 45/49 |
| Testicular tumor | 10/10 | — | — | — | — |

| | KIF20A | KNTC2 | TTK | URLC10 |
|---|---|---|---|---|
| Bladder cancer | 31/31 | 30/32 | 27/27 | 29/29 |
| Breast cancer | 38/61 | 47/56 | 25/30 | — |
| Cervical cancer | — | 10/10 | 15/16 | 15/16 |
| Cholangiocellular carcinoma | 10/11 | 16/22 | 10/10 | 7/7 |
| CML | — | 17/37 | 5/7 | — |
| Colectal cancer | — | 3/10 | 6/10 | — |
| Endometriosis | — | — | — | — |
| Esophageal cancer | 7/19 | 11/46 | 24/44 | 7/19 |
| Gastric cancer | — | — | — | 3/3 |
| Diffuse-type Gastric cancer | — | — | — | — |
| Liver cancer | — | — | 8/15 | — |
| non-small cell lung cancer | 21/22 | 15/19 | 12/12 | 24/27 |
| Lymphoma | — | 7/8 | 6/6 | — |
| Osteosarcoma | — | 20/24 | 13/16 | 15/19 |
| Ovarian cancer | — | 3/5 | — | — |
| Pancreatic cancer | 6/6 | 2/2 | — | 4/5 |
| Prostate cancer | 17/36 | 15/37 | 12/17 | — |
| Renal carcinoma | 6/11 | 14/19 | — | — |
| Small cell lung cancer | 15/15 | 15/15 | 15/15 | — |
| Soft tissue tumor | — | 40/59 | 16/33 | 33/43 |
| Testicular tumor | — | — | — | — |

Prediction of HLA-A24 or HLA-A2 (HLA-A02) Binding Peptides Derived from CDH3, EPHA4, ECT2, HIG2, INHBB, KIF20A, KNTC2, TTK or URLC10

Table 2 sets forth the HLA-A*2402 binding peptides for CDH3 in order of binding affinity. Table 2A sets forth 9-mer peptides derived from CDH3 and Table 2B sets forth 10-mer peptides derived from CDH3.

Table 3 sets forth the HLA-A*2402 and HLA-A*0201 binding peptides for EPHA4 in order of binding affinity. Table 3A sets forth the HLA-A*2402 binding 9-mer peptides derived from EPHA4, Table 3B shows the HLA-A*2402 binding 10-mer peptides derived from EPHA4 and Table 3C sets forth the HLA-A*0201 binding 9-mer peptides derived from EPHA4.

Table 4 sets forth the HLA-A*2402 binding peptides for ECT2 in order of binding affinity. Table 4A sets forth 9-mer peptides derived from ECT2 and Table 4B shows 10-mer peptides derived from ECT2.

Table 5 sets forth the HLA-A*2402 and HLA-A*0201 binding peptides for HIG2, Table 5A sets forth the HLA-A*2402 binding 9-mer peptides derived from HIG2, Table 5B sets forth the HLA-A*2402 binding 10-mer peptides derived from HIG2, Table 5C sets forth the HLA-A*0201 binding 9-mer peptides derived from HIG2, and Table 5D sets forth HLA-A*0201 binding 10-mer peptides derived from HIG2.

Table 6 sets forth the HLA-A*2402 and HLA-A*0201 binding peptides for INHBB, Table 6A shows the HLA-A*2402 binding 9-mer peptides derived from INHBB, Table 6B sets forth the HLA-A*2402 binding 10-mer peptides derived from INHBB, Table 6C sets forth the HLA-A*0201 binding 9-mer peptides derived from INHBB, and Table 6D sets forth HLA-A*0201 binding 10-mer peptides derived from INHBB.

Table 7 sets forth the HLA-A*2402 binding peptides for KIF20A in order of binding affinity. Table 7A sets forth 9-mer peptides derived from KIF20A and Table 7B sets forth 10-mer peptides derived from KIF20A.

Table 8 sets forth the HLA-A*2402 binding peptides for KNTC2 in order of binding affinity. Table 8A sets forth 9-mer peptides derived from KNTC2 and Table 8B sets forth 10-mer peptides derived from KNTC2.

Table 9 sets forth the HLA-A*0201 binding peptides for TTK in order of binding affinity. Table 9A sets forth 9-mer peptides derived from TTK and Table 9B sets forth 10-mer peptides derived from TTK.

Table 10 sets forth the HLA-A*0201 binding peptides for URLC10 in order of binding affinity. Table 10A sets forth 9-mer peptides derived from URLC10 and Table 10B sets forth 10-mer peptides derived from URLC10.

Explanation and definition about the terms in tables

Start position indicates the number of amino acid from N-terminal.

Binding score is derived from "BIMAS" described in Materials and Methods.

Positive donor number indicates the number of donors whose CD8+-T-cells can be induced to the specific CTL by the ex vivo stimulation with antigen-presenting cells. This is shown as (positive donor number/whole donor number).

Positive well number indicates the number of wells where specific IFN-gamma production can be detected by IFN-gamma ELISPOT assay. 4 to 8 wells can be prepared from one donor. This is shown as (positive wells number/the number of whole wells tested by IFN-gamma ELISPOT assay).

Positive CTL line indicates the number of CTL line established from positive wells. The generation of CTL line is determined by ELISA. This is shown as (established CTL line number/the number of positive wells tested by IFN-gamma ELISPOT assay).

No positive donor is not defined by no detectable positive wells, but by no established CTL line.

The peptides showed by bold character in tables possesses the stimulation activity of the T cells.

No data at positive donor number, positive well number and positive CTL line indicating "–" means that the peptides can't be synthesized for any reason.

TABLE 2A

| \multicolumn{6}{c}{HLA-A*2402 binding 9-mer peptides derived from CDH3} | | | | | |
|---|---|---|---|---|---|
| Strat position | Amino acid sequence | Binding score | Positive donor number | Positive well number | Positive CTL line | SEQ ID NO. |
| 513 | IYEVMVLAM | 37.5 | 1/3 | | | 19 |
| 667 | LFLLLVLLL | 36 | – | – | – | 20 |
| 30 | VFREAEVTL | 24 | 0/3 | 1/22 | 0/1 | 21 |
| 406 | LYVEVTNEA | 16.632 | 1/3 | | | 22 |
| 332 | KYEAHVPEN | 16.5 | 0/3 | 1/22 | 0/1 | 23 |
| 180 | KYELFGHAV | 15 | 0/3 | 1/22 | 0/1 | 24 |
| 85 | RSLKERNPL | 14.4 | 0/3 | 1/22 | 0/1 | 25 |
| 5 | RGPLASLLL | 12 | 0/3 | 2/22 | 0/2 | 26 |
| 652 | KGGFILPVL | 11.2 | 0/3 | 0/22 | – | 27 |
| 248 | TYNGVVAYS | 10.5 | 0/3 | 2/22 | 0/2 | 28 |
| 65 | LFSTDNDDF | 10 | 0/3 | 0/22 | – | 29 |
| 94 | KIFPSKRIL | 9.6 | 0/1 | 0/8 | – | 306 |
| 221 | RGSVLEGVL | 9.6 | 0/1 | 0/8 | – | 307 |
| 668 | FLLLVLLLL | 8.4 | – | – | – | 308 |
| 754 | IGNFIIENL | 8.4 | – | – | – | 309 |
| 311 | TAVAVVEIL | 8.4 | 0/1 | 0/8 | – | 310 |
| 557 | NQSPVRQVL | 8.064 | 0/1 | 0/8 | – | 311 |
| 611 | KQDTYDVHL | 8 | 0/1 | 0/8 | – | 312 |
| 781 | DYEGSGSDA | 7.5 | 0/1 | 0/8 | – | 313 |
| 165 | GWLLLNKPL | 7.2 | 0/1 | 0/8 | – | 314 |
| 656 | ILPVLGAVL | 7.2 | 0/1 | 0/8 | – | 315 |
| 770 | TAPPYDTLL | 7.2 | 0/1 | 0/8 | – | 316 |
| 602 | VVLSLKKFL | 7.2 | 0/1 | 0/8 | – | 317 |
| 665 | ALLFLLLVL | 7.2 | – | – | – | 318 |
| 410 | VTNEAPFVL | 7.2 | 0/1 | 0/8 | – | 319 |

TABLE 2A-continued

HLA-A*2402 binding 9-mer peptides derived from CDH3

| Strat position | Amino acid sequence | Binding score | Positive donor number | Positive well number | Positive CTL line | SEQ ID NO. |
|---|---|---|---|---|---|---|
| 662 | AVLALLFLL | 7.2 | — | — | — | 320 |
| 613 | DTYDVHLSL | 6.72 | 0/1 | 0/8 | — | 321 |
| 6 | GPLASLLLL | 6 | 0/1 | 0/8 | — | 322 |
| 564 | VLNITDKDL | 6 | 0/1 | 0/8 | — | 323 |
| 159 | AVEKETGWL | 6 | 0/1 | 0/8 | — | 324 |
| 511 | NNIYEVMVL | 6 | 0/1 | 0/8 | — | 325 |
| 11 | LLLLQVCWL | 6 | - | - | — | 326 |
| 57 | GCPGQEPAL | 6 | 0/1 | 0/8 | — | 327 |
| 293 | EYTLTIQAT | 6 | 0/1 | 0/8 | — | 328 |
| 79 | ETVQERRSL | 6 | 0/1 | 0/8 | — | 329 |
| 475 | SYRILRDPA | 6 | 0/1 | 0/8 | — | 330 |
| 493 | GQVTAVGTL | 6 | 0/1 | 0/8 | — | 331 |
| 661 | GAVLALLFL | 6 | 0/1 | 0/8 | — | 332 |
| 388 | GILTTRKGL | 6 | 0/1 | 0/8 | — | 333 |
| 382 | HPESNQGIL | 6 | 0/1 | 0/8 | — | 334 |
| 663 | VLALLFLLL | 5.76 | — | — | — | 335 |
| 598 | EGDTVVLSL | 5.6 | 0/1 | 0/8 | — | 336 |
| 278 | TISVISSGL | 5.6 | 0/1 | 2/8 | 0/2 | 337 |
| 659 | VLGAVLALL | 5.6 | 0/1 | 0/8 | — | 338 |
| 811 | EWGSRFKKL | 5.28 | 0/1 | 0/8 | — | 339 |
| 445 | KVVEVQEGI | 5.04 | 0/1 | 0/8 | — | 340 |
| 614 | TYDVHLSLS | 5 | 0/1 | 0/8 | — | 341 |
| 142 | FYSITGPGA | 5 | 0/1 | 0/8 | — | 342 |
| 246 | IYTYNGVVA | 5 | 0/1 | 0/8 | — | 343 |

TABLE 2B

HLA-A*2402 binding 10-mer peptides derived from CDH3

| strat position | sequence | Binding Score | positive donor number | positive well number | positive CTL line | SEQ ID NO |
|---|---|---|---|---|---|---|
| 807 | DYLNeWGSRF | 150 | 1/3 | | | 30 |
| 248 | TYNGvVAYSI | 105 | 0/3 | 4/22 | 0/4 | 31 |
| 667 | LFLLlVLLLL | 42 | — | — | — | 32 |
| 397 | DFEAkNQHTL | 30 | 0/3 | 2/22 | 0/2 | 33 |
| 332 | KYEAhVPENA | 21 | 1/3 | | | 34 |
| 180 | KYELFGHAVS | 15 | 0/3 | 2/22 | 0/2 | 35 |
| 510 | RNNIYEVMVL | 12 | 0/3 | 4/22 | 0/4 | 36 |
| 5 | RGPLASLLLL | 12 | 0/3 | 1/22 | 0/1 | 37 |

TABLE 2B-continued

HLA-A*2402 binding 10-mer peptides derived from CDH3

| start position | sequence | Binding Score | positive donor number | positive well number | positive CTL line | SEQ ID NO |
|---|---|---|---|---|---|---|
| 477 | RILRDPAGWL | 12 | 0/3 | 1/22 | 0/1 | 38 |
| 556 | CNQSPVRQVL | 10.08 | 0/3 | 2/22 | 0/2 | 39 |
| 655 | FILPvLGAVL | 8.64 | 1/3 | | | 344 |
| 662 | AVLAILFLLL | 8.64 | — | — | — | 345 |
| 277 | GTISvISSGL | 8.4 | 0/3 | 0/20 | — | 346 |
| 781 | DYEGsGSDAA | 7.5 | 0/3 | 0/20 | — | 347 |
| 601 | TVVLsLKKFL | 7.2 | 0/3 | 3/20 | 0/3 | 348 |
| 158 | FAVEkETGWL | 7.2 | 0/3 | 0/20 | — | 349 |
| 665 | ALLFlLLVLL | 7.2 | — | — | — | 350 |
| 259 | SQEPkDPHDL | 7.2 | 0/3 | 0/20 | — | 351 |
| 664 | LALLfLLLVL | 7.2 | — | — | — | 352 |
| 42 | GAEQePGQAL | 7.2 | 0/3 | 1/20 | 0/1 | 353 |
| 661 | GAVLaLLFLL | 7.2 | — | — | — | 354 |
| 595 | VNEEgDTVVL | 7.2 | 0/2 | 0/12 | — | 355 |
| 340 | NAVGhEVQRL | 7.2 | 0/2 | 0/12 | — | 356 |
| 411 | TNEApFVLKL | 6.6 | 0/2 | 0/12 | — | 357 |
| 470 | ENQKiSYRIL | 6 | 1/2 | | | 358 |
| 10 | SLLLlQVCWL | 6 | 0/2 | 1/12 | 0/1 | 359 |
| 721 | GLEArPEVVL | 6 | 0/2 | 2/12 | 0/2 | 360 |
| 345 | EVQRlTVTDL | 6 | 0/2 | 4/12 | 0/4 | 361 |
| 2 | GLPRgPLASL | 6 | 0/2 | 3/12 | 0/3 | 362 |
| 657 | LPVLgAVLAL | 6 | — | — | — | 363 |
| 563 | QVLNiTDKDL | 6 | 0/2 | 1/12 | 0/1 | 364 |
| 159 | AVEKeTGWLL | 6 | 0/2 | 2/12 | 0/2 | 365 |
| 492 | SGQVtAVGTL | 6 | 0/2 | — | — | 366 |
| 387 | QGILtTRKGL | 6 | 0/2 | — | — | 367 |
| 525 | SPPTtGTGTL | 6 | 0/2 | 2/12 | 0/2 | 368 |
| 358 | NSPAwRATYL | 6 | 0/2 | 2/12 | 0/2 | 369 |
| 122 | GPFPqRLNQL | 5.76 | 0/2 | 3/12 | 0/3 | 370 |
| 753 | EIGNfIIENL | 5.6 | 0/2 | 1/12 | 0/1 | 371 |
| 310 | TTAVaVVEIL | 5.6 | — | — | — | 372 |
| 246 | IYTYnGVVAY | 5 | 0/2 | 2/12 | 0/2 | 373 |
| 805 | DYDYlNEWGS | 5 | 0/2 | 0/12 | — | 374 |

TABLE 3A

HLA-A*2402 binding 9-mer peptides derived from EPHA4

| strat position | sequence | Binding Score | positive donor number | positive well number | positive CTL line | SEQ ID NO |
|---|---|---|---|---|---|---|
| 97 | VYIEIKFTL | 504 | 0/2 | 1/16 | 0/1 | 40 |
| 453 | RYSVALAWL | 400 | 2/3 | | | 41 |
| 25 | VYPANEVTL | 300 | 0/3 | 0/22 | — | 42 |
| 384 | HYTPQQNGL | 288 | 0/3 | 1/22 | 0/1 | 43 |
| 5 | FYFALFSCL | 288 | 1/2 | | | 44 |
| 519 | GYGDFSEPL | 240 | 0/3 | 3/22 | 0/3 | 45 |
| 869 | KFGQIVNML | 67.2 | 1/3 | | | 46 |
| 777 | AYTTRGGKI | 55 | 0/3 | 1/22 | 0/1 | 47 |
| 420 | KYNPNPDQS | 18 | 1/3 | | | 48 |
| 749 | RNILVNSNL | 16.8 | 0/3 | 1/22 | 0/1 | 49 |
| 734 | KYLSDMSYV | 15 | 0/3 | 0/22 | — | 50 |
| 879 | KLIRNPNSL | 14.4 | 0/3 | 0/22 | — | 51 |
| 926 | RYKDNFTAA | 14.4 | 0/3 | 0/22 | — | 52 |
| 834 | KAIEEGYRL | 14.4 | 0/3 | 0/22 | — | 53 |
| 574 | KYSKAKQEA | 13.2 | 0/3 | 0/22 | — | 54 |
| 184 | AFQDVGACI | 12.6 | 0/3 | 1/22 | 0/1 | 55 |
| 252 | WLVPIGNCL | 12.096 | 0/3 | 0/22 | — | 56 |
| 326 | RPPSAPLNL | 12 | 0/3 | 0/22 | — | 57 |
| 203 | KCPLTVRNL | 12 | 0/3 | 0/22 | — | 58 |
| 360 | SYNVVCKKC | 11.55 | 0/3 | 0/22 | — | 59 |

TABLE 3B

HLA-A*2402 binding 10-mer peptides derived from EPHA4

| strat position | sequence | Binding Score | positive donor number | positive well number | positive CTL line | SEQ ID NO |
|---|---|---|---|---|---|---|
| 25 | VYPANEVTLL | 300 | 0/3 | 0/22 | — | 60 |
| 244 | MYCGADGEWL | 200 | 0/3 | 1/22 | 0/1 | 61 |
| 657 | GYTDKQRRDF | 120 | 0/3 | 1/22 | 0/1 | 62 |
| 5 | FYFAlFSCLF | 100 | — | — | — | 63 |
| 102 | KFTLRDCNSL | 48 | 0/3 | 1/22 | 0/1 | 64 |
| 818 | SYGERPYWDM | 30 | 0/3 | 2/22 | 0/2 | 65 |
| 4 | IFYFALFSCL | 28.8 | — | — | — | 66 |
| 808 | SYGIVMWEVM | 25 | — | — | — | 67 |
| 630 | EFGEVCSGRL | 24 | 0/3 | 0/22 | — | 68 |
| 420 | KYNPNPDQSV | 21.6 | 0/3 | 0/22 | — | 69 |
| 930 | NFTAAGYTTL | 20 | 0/2 | 0/16 | — | 70 |
| 675 | QFDHPNIIHL | 20 | 0/3 | 0/22 | — | 71 |

TABLE 3B-continued

HLA-A*2402 binding 10-mer peptides derived from EPHA4

| strat position | sequence | Binding Score | positive donor number | positive well number | positive CTL line | SEQ ID NO |
|---|---|---|---|---|---|---|
| 708 | AFLRKNDGRF | 15 | 0/3 | 0/22 | — | 72 |
| 579 | KQEADEEKHL | 12 | 0/3 | 1/22 | 0/1 | 73 |
| 727 | RGIGSGMKYL | 12 | 0/3 | 0/22 | — | 74 |
| 96 | RVYIEIKFTL | 11.2 | 0/2 | 1/16 | 0/1 | 75 |
| 507 | SYVFHVRART | 10.5 | 0/3 | 1/22 | 0/1 | 76 |
| 251 | EWLVPIGNCL | 10.08 | 0/3 | 0/22 | — | 77 |
| 24 | RVYPANEVTL | 9.6 | 1/3 | | | 78 |
| 699 | EYMENGSLDA | 9 | 0/3 | 0/22 | — | 79 |

TABLE 3C

HLA-A*0201 binding 9-mer peptides derived from EPHA4

| strat position | sequence | Binding Score | positive donor number | positive well number | positive CTL line | SEQ ID NO |
|---|---|---|---|---|---|---|
| 8 | ALFSCLFGI | 514.942 | — | — | — | 375 |
| 501 | GLNPLTSYV | 382.536 | 1/1 | | | 376 |
| 12 | CLFGICDAV | 126.098 | 0/1 | 1/5 | 0/1 | 377 |
| 977 | QMHGRMVPV | 115.534 | 0/1 | 1/5 | 0/1 | 378 |
| 165 | KLNTEIRDV | 111.979 | 1/1 | | | 379 |
| 252 | WLVPIGNCL | 98.267 | 0/1 | 1/5 | 0/1 | 380 |
| 879 | KLIRNPNSL | 74.768 | 0/1 | 1/5 | 0/1 | 381 |
| 559 | VVILIAAFV | 56.902 | — | — | — | 382 |
| 812 | VMWEVMSYG | 39.386 | 0/1 | 0/5 | — | 383 |
| 728 | GIGSGMKYL | 37.157 | 0/1 | 0/5 | — | 384 |
| 750 | NILVNSNLV | 35.385 | 0/1 | 1/5 | 0/1 | 385 |
| 937 | TTLEAVVHV | 33.705 | 0/1 | 1/5 | 0/1 | 386 |

TABLE 4A

HLA-A*2402 binding 9-mer peptides derived from ECT2

| strat position | sequence | Binding Score | positive donor number | positive well number | positive CTL line | SEQ ID NO |
|---|---|---|---|---|---|---|
| 515 | TYPPFVNFF | 216 | 1/1 | | | 80 |
| 140 | LYCTSMMNL | 200 | 0/1 | 0/8 | — | 81 |
| 298 | LYVVKQEWF | 150 | 0/1 | 0/8 | — | 82 |
| 435 | NYVNILATI | 105 | 0/1 | 0/8 | — | 83 |
| 773 | IYTADPESF | 100 | 0/1 | 0/8 | — | 84 |
| 110 | LYKADCRVI | 50 | 0/1 | 0/8 | — | 85 |
| 739 | SFQMTSDEL | 33 | 0/1 | 0/8 | — | 86 |
| 504 | IFLKYSKDL | 30 | 0/1 | 0/8 | — | 87 |

TABLE 4A-continued

HLA-A*2402 binding 9-mer peptides derived from ECT2

| strat position | sequence | Binding Score | positive donor number | positive well number | positive CTL line | SEQ ID NO |
|---|---|---|---|---|---|---|
| 867 | FFERRSHTL | 30 | 0/1 | 0/8 | — | 88 |
| 178 | DFNSKVTHL | 30 | 0/1 | 0/8 | — | 89 |
| 61 | KQEELIKAL | 17.28 | 0/1 | 0/8 | — | 90 |
| 657 | RGEQVTLFL | 16.8 | 0/1 | 2/8 | 0/2 | 91 |
| 568 | RLPSVALLL | 16.8 | 0/1 | 0/8 | — | 92 |
| 550 | KPECGRQSL | 14.4 | 0/1 | 0/8 | — | 93 |
| 470 | IFGSIPDIF | 14 | 0/1 | 0/8 | — | 94 |
| 116 | RVIGPPVVL | 12 | 0/1 | 0/8 | — | 95 |
| 507 | KYSKDLVKT | 11 | 0/1 | 0/8 | — | 96 |
| 223 | DFYAAVDDF | 10 | 0/1 | 0/8 | — | 97 |

TABLE 4B

HLA-A*2402 binding 10-mer peptides derived from ECT2

| strat position | sequence | Binding Score | positive donor number | positive well number | positive CTL line | SEQ ID NO |
|---|---|---|---|---|---|---|
| 322 | LYEKaNTPEL | 330 | 0/1 | 0/8 | — | 98 |
| 435 | NYVNiLATII | 90 | 0/1 | 0/8 | — | 99 |
| 40 | SYVEeEMPQI | 90 | 1/1 | | | 100 |
| 101 | DFQDsVFNDL | 72.576 | 1/1 | | | 101 |
| 866 | SFFErRSHTL | 24 | 0/1 | 0/8 | — | 102 |
| 811 | SFSKtPKRAL | 20 | 0/1 | 1/8 | 0/1 | 103 |
| 268 | KYLPlGDERC | 18 | 0/1 | 0/8 | — | 104 |
| 84 | EFEGlDSPEF | 16.5 | 0/1 | 1/8 | 0/1 | 105 |
| 236 | KVPPfQDCIL | 14.4 | 0/1 | 0/8 | — | 106 |
| 728 | RPPTeQANVL | 14.4 | 0/1 | 0/8 | — | 107 |
| 507 | KYSKdLVKTY | 12 | 0/1 | 0/8 | — | 108 |
| 281 | VVEEnIVKDL | 10.08 | 0/1 | 0/8 | — | 109 |

TABLE 5A

HLA-A*2402 binding 9-mer peptides derived from HIG2

| strat position | sequence | Binding Score | positive donor number | positive well number | positive CTL line | SEQ ID NO |
|---|---|---|---|---|---|---|
| 19 | IFVRVMESL | 42 | 1/3 | | | 110 |
| 22 | RVMESLEGL | 14.4 | 1/3 | | | 111 |
| 8 | YLLGVVLTL | 8.4 | 1/3 | | | 387 |
| 7 | LYLLGVVLT | 7.5 | 0/2 | 3/15 | 0/3 | 388 |
| 23 | VMESLEGLL | 7.2 | 0/2 | 0/16 | — | 389 |
| 9 | LLGVVLTLL | 5.6 | — | — | — | 390 |

TABLE 5B

HLA-A*2402 binding 10-mer peptides derived from HIG2

| strat position | sequence | Binding Score | positive donor number | positive well number | positive CTL line | SEQ ID NO |
|---|---|---|---|---|---|---|
| 7 | LYLLGVVLTL | 420 | 1/3 | | | 112 |
| 22 | RVMESLEGLL | 17.28 | 0/3 | 4/24 | 0/4 | 113 |
| 8 | YLLGVVLTLL | 8.4 | — | — | — | 391 |
| 5 | LNLYLLGVVL | 7.2 | 0/2 | 0/12 | — | 392 |
| 46 | LANTEPTKGL | 6 | 0/2 | 0/14 | — | 393 |
| 18 | SIFVRVMESL | 5.6 | 1/2 | | | 394 |

TABLE 5C

HLA-A*0201 binding 9-mer peptides derived from HIG2

| strat position | sequence | Binding Score | positive donor number | positive well number | positive CTL line | SEQ ID NO |
|---|---|---|---|---|---|---|
| 8 | YLLGVVLTL | 836.253 | 1/1 | | | 114 |
| 13 | VLTLLSIFV | 650.311 | 0/1 | 0/12 | — | 115 |
| 15 | TLLSIFVRV | 488.951 | 1/1 | | | 116 |
| 4 | VLNLYLLGV | 271.948 | 1/1 | | | 117 |
| 9 | LLGVVLTLL | 83.527 | 0/1 | 0/12 | — | 118 |
| 22 | RVMESLEGL | 31.957 | 0/1 | 0/12 | — | 119 |
| 6 | NLYLLGVVL | 28.027 | 0/1 | 0/12 | — | 120 |

TABLE 5D

HLA-A*0201 binding 10-mer peptides derived from HIG2

| strat position | sequence | Binding Score | positive donor number | positive well number | positive CTL line | SEQ ID NO |
|---|---|---|---|---|---|---|
| 8 | YLLGvVLTLL | 836.253 | 1/1 | | | 121 |
| 12 | VVLTlLSIFV | 210.538 | — | — | — | 122 |
| 29 | GLLEsPSPGT | 113.047 | 0/1 | 0/12 | — | 123 |
| 6 | NLYLlGVVLT | 54.847 | — | — | — | 124 |
| 4 | VLNLyLLGVV | 14.495 | 0/1 | 0/12 | — | 125 |
| 15 | TLLSiFVRVM | 13.174 | 0/1 | 0/12 | — | 126 |
| 18 | SIFVrVMESL | 12.248 | 0/1 | 0/12 | — | 127 |
| 14 | LTLLsIFVRV | 11.545 | — | — | — | 128 |

TABLE 6A

HLA-A*2402 binding 9-mer peptides derived from INHBB

| strat position | sequence | Binding Score | positive donor number | positive well number | positive CTL line | SEQ ID NO |
|---|---|---|---|---|---|---|
| 383 | LYFDDEYNI | 60 | 0/3 | 0/20 | — | 129 |
| 238 | LFERGERRL | 30 | 0/3 | 1/19 | 0/1 | 130 |

TABLE 6A-continued

HLA-A*2402 binding 9-mer peptides derived from INHBB

| strat position | sequence | Binding Score | positive donor number | positive well number | positive CTL line | SEQ ID NO |
|---|---|---|---|---|---|---|
| 7 | RALGAACLL | 12 | 0/3 | 0/21 | — | 131 |
| 388 | EYNIVKRDV | 10.5 | 0/3 | 0/18 | — | 132 |
| 180 | LYLKLLPYV | 9 | 1/2 | | | 395 |
| 163 | ISNEGNQNL | 8.64 | 0/1 | 0/8 | — | 396 |
| 223 | RSGWHTFPL | 8 | 0/1 | 0/6 | — | 397 |
| 176 | ASLWLYLKL | 7.92 | 0/1 | 0/7 | — | 398 |
| 338 | AYLAGVPGS | 7.5 | 0/1 | 1/7 | 0/1 | 399 |
| 213 | NMVEKRVDL | 7.2 | 0/1 | 0/8 | — | 400 |
| 102 | AMVTALRKL | 6.6 | 0/1 | 0/8 | — | 401 |
| 250 | VQCDSCQEL | 6.336 | 0/1 | 0/8 | — | 402 |
| 369 | NSCCIPTKL | 6.16 | 0/1 | 0/8 | — | 403 |
| 330 | NYCEGSCPA | 6 | 0/1 | 0/7 | — | 404 |
| 172 | FVVQASLWL | 6 | 0/1 | 0/8 | — | 405 |
| 355 | VNQYRMRGL | 6 | 0/1 | 0/8 | — | 406 |
| 307 | QFFIDFRLI | 6 | 0/1 | 0/7 | — | 407 |
| 14 | LLLLAAGWL | 6 | — | — | — | 408 |
| 306 | QQFFIDFRL | 5.6 | 0/1 | 0/6 | — | 409 |
| 170 | NLFVVQASL | 5.6 | 0/1 | 0/7 | — | 410 |
| 327 | YYGNYCEGS | 5 | 0/1 | 1/8 | 0/1 | 411 |

TABLE 6B

HLA-A*2402 binding 10-mer peptides derived from INHBB

| strat position | sequence | Binding Score | positive donor number | positive well number | positive CTL line | SEQ ID NO |
|---|---|---|---|---|---|---|
| 180 | LYLKLLPYVL | 360 | 1/3 | | | 133 |
| 171 | LFVVQASLWL | 30 | — | — | — | 134 |
| 305 | RQQFFIDFRL | 16.8 | 1/3 | | | 135 |
| 73 | DFLEAVKRHI | 12.6 | 0/3 | 4/20 | 0/4 | 136 |
| 7 | RALGAACLLL | 12 | 1/3 | | | 137 |
| 273 | RPFVVQARL | 11.2 | 0/3 | 1/20 | 0/1 | 138 |
| 338 | AYLAGVPGSA | 10 | 0/3 | 2/20 | 0/2 | 139 |
| 169 | QNLFvVQASL | 8.4 | 0/1 | 1/6 | 0/1 | 412 |
| 249 | DVQCdSCQEL | 7.92 | 0/1 | 4/6 | 0/4 | 413 |
| 383 | LYFDdEYNIV | 7.2 | 0/1 | 0/6 | — | 415 |
| 229 | FPLTeAIQAL | 7.2 | 0/1 | 1/6 | 0/1 | 416 |
| 299 | RTNLcCRQQF | 7.2 | 0/1 | 5/6 | 0/5 | 417 |

TABLE 6B-continued

HLA-A*2402 binding 10-mer peptides derived from INHBB

| strat position | sequence | Binding Score | positive donor number | positive well number | positive CTL line | SEQ ID NO |
|---|---|---|---|---|---|---|
| 101 | AAMVtALRKL | 6.6 | 0/1 | 2/6 | 0/2 | 418 |
| 368 | VNSCcIPTKL | 6.16 | 0/1 | 2/6 | 0/2 | 419 |
| 13 | CLLLlAAGWL | 6 | — | — | — | 420 |
| 354 | VVNQyRMRGL | 6 | 0/1 | 0/6 | — | 421 |
| 150 | DGLAsSRVRL | 6 | 0/1 | 2/6 | 0/2 | 422 |
| 293 | GLECdGRTNL | 6 | 0/1 | 0/6 |  | 423 |
| 330 | NYCEgSCPAY | 6 | 0/1 | 1/6 | 0/1 | 424 |
| 176 | ASLWlYLKLL | 6 | 0/1 | 1/6 | 0/1 | 425 |
| 212 | WNMVeKRVDL | 6 | 1/1 |  |  | 426 |
| 74 | FLEAvKRHIL | 6 | 0/1 | 2/6 | 0/2 | 427 |
| 331 | YCEGsCPAYL | 6 | 0/1 | 1/6 | 0/1 | 428 |
| 77 | AVKRhILSRL | 5.6 | 0/1 | 1/6 | 0/1 | 429 |
| 175 | QASLwLYLKL | 5.28 | 0/1 | 2/6 | 0/2 | 430 |
| 326 | GYYGnYCEGS | 5 | 0/1 | 1/6 | 0/1 | 431 |
| 159 | LYFFiSNEGN | 5 | 0/1 | 4/6 | 0/4 | 432 |
| 327 | YYGNyCEGSC | 5 | 0/1 | 1/6 | 0/1 | 433 |

TABLE 6C

HLA-A*0201 binding 9-mer peptides derived from INHBB

| strat position | sequence | Binding Score | positive donor number | positive well number | positive CTL line | SEQ ID NO |
|---|---|---|---|---|---|---|
| 177 | SLWLYLKLL | 407.808 | 0/1 | 0/8 |  | 140 |
| 14 | LLLLAAGWL | 96.074 | — | — | — | 141 |
| 170 | NLFVVQASL | 79.041 | 0/1 | 0/8 |  | 142 |
| 213 | NMVEKRVDL | 63.256 | 0/1 | 0/8 |  | 143 |
| 172 | FVVQASLWL | 47.291 | 0/1 | 0/8 |  | 144 |
| 306 | QQFFIDFRL | 46.48 | 0/1 | 0/8 |  | 145 |
| 281 | RLGDSRHRI | 42.774 | 0/1 | 0/8 |  | 146 |
| 174 | VQASLWLYL | 34.427 | 0/1 | 0/8 |  | 147 |
| 257 | ELAVVPVFV | 28.69 | 0/1 | 1/8 | 0/1 | 148 |
| 313 | RLIGWNDWI | 28.116 | 0/1 | 1/8 | 0/1 | 149 |
| 139 | RVSEIISFA | 22.546 | 0/1 | 3/8 | 0/3 | 150 |
| 151 | GLASSRVRL | 21.362 | 0/1 | 0/8 |  | 151 |
| 8 | ALGAACLLL | 21.362 | 0/1 | 1/8 | 0/1 | 152 |
| 250 | VQCDSCQEL | 15.096 | 0/1 | 1/8 | 0/1 | 153 |

TABLE 6D

HLA-A*0201 binding 10-mer peptides derived from INHBB

| strat position | sequence | Binding Score | positive donor number | positive well number | positive CTL line | SEQ ID NO |
|---|---|---|---|---|---|---|
| 179 | WLYLKLLPYV | 12951.1 | 0/1 | 1/8 | 0/1 | 154 |
| 301 | NLCCRQQFFI | 332.806 | 0/1 | 0/8 | | 155 |
| 237 | ALFERGERRL | 64.814 | 0/1 | 0/8 | | 156 |
| 382 | MLYFDDEYNI | 56.754 | 0/1 | 0/8 | | 157 |
| 13 | CLLLLAAGWL | 56.514 | — | — | — | 158 |
| 8 | ALGAACLLLL | 49.134 | — | — | — | 159 |
| 313 | RLIGWNDWII | 32.081 | 0/1 | 0/8 | | 160 |
| 173 | VVQASLWLYL | 29.711 | 0/1 | 2/8 | 0/2 | 161 |
| 256 | QELAVVPVFV | 27.521 | 0/1 | 0/8 | | 162 |
| 162 | FISNEGNQNL | 13.512 | 0/1 | 1/8 | 0/1 | 163 |
| 305 | RQQFFIDFRL | 12.562 | 0/1 | 0/8 | | 164 |
| 362 | GLNPGTVNSC | 11.426 | 0/1 | 0/7 | | 165 |
| 85 | RLQMRGRPNI | 10.433 | 0/1 | 1/8 | 0/1 | 166 |
| 69 | RVDGDFLEAV | 10.425 | 0/1 | 0/8 | | 167 |

TABLE 7A

HLA-A*2402 binding 9-mer peptides derived from KIF20A

| strat position | sequence | Binding Score | positive donor number | positive well number | positive CTL line | SEQ ID NO |
|---|---|---|---|---|---|---|
| 308 | IYNELLYDL | 432 | 0/2 | 0/14 | — | 168 |
| 621 | MYEEKLNIL | 432 | 0/2 | 0/14 | — | 169 |
| 67 | VYLRVRPLL | 420 | 0/2 | 0/14 | — | 170 |
| 499 | KFSAIASQL | 56 | 0/2 | 0/14 | — | 171 |
| 304 | SFFEIYNEL | 44.352 | 0/2 | 0/14 | — | 172 |
| 187 | IFNSLQGQL | 36 | 0/2 | 0/14 | — | 173 |
| 305 | FFEIYNELL | 30 | 1/2 | | | 174 |
| 23 | MFESTAADL | 30 | 0/2 | 0/14 | — | 175 |
| 256 | SFDSGIAGL | 20 | 0/2 | 0/14 | — | 176 |
| 298 | RFSIWISFF | 20 | — | — | — | 177 |
| 383 | IFSIRILHL | 20 | 1/2 | | | 178 |
| 647 | KIEELEALL | 17.28 | 0/2 | 0/14 | — | 179 |
| 625 | KLNILKESL | 14.4 | 0/2 | 0/14 | — | 180 |
| 695 | KLQQCKAEL | 13.2 | 0/2 | 0/14 | — | 181 |
| 726 | FTIDVDKKL | 11.088 | 0/2 | 0/14 | — | 182 |
| 688 | QLQEVKAKL | 11.088 | 0/2 | 0/14 | — | 183 |

TABLE 7B

HLA-A*2402 binding 10-mer peptides derived from KIF20A

| strat position | sequence | Binding Score | positive donor number | positive well number | positive CTL line | SEQ ID NO |
|---|---|---|---|---|---|---|
| 308 | IYNElLYDLL | 432 | 0/2 | 0/14 | — | 184 |
| 182 | RSLAlIFNSL | 24.192 | 0/2 | 1/14 | 0/1 | 185 |
| 304 | SFFEiYNELL | 24 | 1/2 | | | 186 |
| 742 | RLLRtELQKL | 15.84 | 0/2 | 0/14 | — | 187 |
| 739 | KNIRlLRTEL | 15.84 | 0/2 | 0/14 | — | 188 |
| 218 | RQEEmKKLSL | 14.4 | 0/2 | 2/14 | 0/2 | 189 |
| 70 | RVRPlLPSEL | 12.672 | 0/2 | 0/14 | — | 190 |
| 871 | RILRsRRSPL | 12 | 0/2 | 0/14 | — | 191 |
| 89 | RIENvETLVL | 12 | 0/2 | 1/14 | 0/1 | 192 |
| 364 | KNQSfASTHL | 12 | 0/2 | 0/14 | — | 193 |
| 66 | KVYLrVRPLL | 11.2 | 1/2 | | | 194 |
| 60 | DSMEkVKVYL | 10.08 | 0/2 | 0/14 | — | 195 |

TABLE 8A

HLA-A*2402 binding 9-mer peptides derived from KNTC2

| strat position | sequence | Binding Score | positive donor number | positive well number | positive CTL line | SEQ ID NO |
|---|---|---|---|---|---|---|
| 309 | KYQAYMSNL | 600 | 1/3 | | | 196 |
| 457 | VYVPLKELL | 432 | 0/3 | 0/18 | — | 197 |
| 414 | EYHKLARKL | 264 | 0/3 | 0/18 | — | 198 |
| 139 | SYELPDTKF | 165 | 0/3 | 0/18 | — | 199 |
| 629 | KYEKKATLI | 150 | 0/3 | 0/18 | — | 200 |
| 400 | KYARGKEAI | 100 | 0/3 | 1/18 | 0/1 | 201 |
| 124 | DFLKIFTFL | 50.4 | 1/3 | | | 202 |
| 134 | GFLCPSYEL | 33 | 0/3 | 0/18 | — | 203 |
| 257 | LFNVDAFKL | 33 | 0/3 | 0/18 | — | 204 |
| 242 | SFDEMNAEL | 26.4 | 0/3 | 0/18 | — | 205 |
| 128 | IFTFLYGFL | 24 | 0/3 | 0/18 | — | 206 |
| 146 | KFEEEVPRI | 18 | 0/3 | 1/18 | 0/1 | 207 |
| 368 | RINHERNEL | 15.84 | 0/3 | 1/18 | 0/1 | 208 |
| 235 | SFMSGADSF | 15 | 0/3 | 0/18 | — | 209 |
| 154 | IFKDLGYPF | 14.4 | 1/3 | | | 210 |
| 563 | EYQLVVQTT | 12.6 | 0/3 | 0/18 | — | 211 |
| 474 | KALNKKMGL | 12 | 0/3 | 1/18 | 0/1 | 212 |
| 150 | EVPRIFKDL | 10.08 | 1/3 | | | 213 |

TABLE 8B

HLA-A*2402 binding 10-mer peptides derived from KNTC2

| strat position | sequence | Binding Score | positive donor number | positive well number | positive CTL line | SEQ ID NO |
|---|---|---|---|---|---|---|
| 452 | KYRAQVYVPL | 560 | 2/3 | | | 214 |
| 610 | EYEECMSEDL | 360 | 0/3 | 1/18 | 0/1 | 215 |
| 360 | KYSVADIERI | 100 | 0/3 | 0/18 | — | 216 |
| 227 | DYTIKCYESF | 100 | 1/3 | | | 217 |
| 146 | KFEEEVPRIF | 50.4 | 0/3 | 0/18 | — | 218 |
| 90 | AFIQQCIRQL | 30 | 0/3 | 0/18 | — | 219 |
| 20 | RSQDVNKQGL | 17.28 | 0/3 | 1/18 | 0/1 | 220 |
| 501 | RTLKEEVQKL | 15.84 | 0/3 | 0/18 | — | 221 |
| 403 | RGKEAIETQL | 13.44 | 0/3 | 1/18 | 0/1 | 222 |
| 273 | RALNEQIARL | 12 | 1/3 | | | 223 |
| 563 | EYQLVVQTTT | 10.5 | 0/3 | 3/22 | 0/3 | 224 |
| 467 | ETEEEINKAL | 10.08 | 0/3 | 1/22 | 0/1 | 225 |
| 541 | LLESTVNQGL | 10.08 | 0/3 | 1/22 | 0/1 | 226 |

TABLE 9A

HLA-A*0201 binding 9-mer peptides derived from TTK

| strat position | sequence | Binding Score | positive donor number | positive well number | positive CTL line | SEQ ID NO |
|---|---|---|---|---|---|---|
| 462 | YMSCFRTPV | 878.055 | 1/1 | | | 227 |
| 547 | KQIYAIKYV | 312.218 | 1/1 | | | 228 |
| 630 | NMLEAVHTI | 262.897 | 0/1 | 1/8 | 0/1 | 229 |
| 278 | LLNSPDCDV | 118.238 | 0/1 | 1/8 | 0/1 | 230 |
| 498 | ILATPLQNL | 83.527 | 0/1 | 0/8 | — | 231 |
| 811 | YVLGQLVGL | 73.172 | 0/1 | 0/8 | — | 232 |
| 719 | SLGCILYYM | 62.845 | 1/2 | | | 233 |
| 670 | QMQPDTTSV | 50.232 | 0/1 | 0/8 | — | 234 |
| 804 | GTTEEMKYV | 50.102 | 0/1 | 0/8 | — | 235 |
| 654 | LIVDGMLKL | 47.088 | 0/1 | 1/8 | 0/1 | 236 |
| 363 | SLLAKLEET | 31.074 | 0/1 | 0/8 | — | 237 |
| 790 | YVQIQTHPV | 27.995 | 0/1 | 0/8 | — | 238 |
| 785 | LLAHPYVQI | 26.604 | 0/1 | 0/8 | — | 239 |
| 86 | KLIGRYSQA | 26.082 | 0/1 | 0/8 | — | 240 |
| 186 | NLNLQKKQL | 21.362 | 0/1 | 0/8 | — | 241 |
| 671 | MQPDTTSVV | 20.152 | 0/1 | 0/8 | — | 242 |
| 577 | KLQQHSDKI | 17.892 | 0/1 | 0/8 | — | 243 |
| 142 | FAFVHISFA | 14.856 | 0/1 | 0/8 | — | 244 |

TABLE 9A-continued

HLA-A*0201 binding 9-mer peptides derived from TTK

| strat position | sequence | Binding Score | positive donor number | positive well number | positive CTL line | SEQ ID NO |
|---|---|---|---|---|---|---|
| 322 | CELRNLKSV | 11.509 | 0/1 | 0/8 | — | 245 |
| 824 | SILKAAKTL | 10.868 | 0/1 | 0/8 | — | 246 |

TABLE 9B

HLA-A*0201 binding 10-mer peptides derived from TTK

| strat position | sequence | Binding Score | positive donor number | positive well number | positive CTL line | SEQ ID NO |
|---|---|---|---|---|---|---|
| 68 | LLLKLEKNSV | 437.482 | 0/1 | 0/8 | — | 247 |
| 277 | NLLNSPDCDV | 257.342 | 0/1 | 0/8 | — | 248 |
| 653 | FLIVDGMLKL | 226.014 | 0/1 | 0/8 | — | 249 |
| 423 | TTFEQPVFSV | 195.487 | 0/1 | 0/8 | — | 250 |
| 542 | VLNEKKQIYA | 190.448 | 0/1 | 0/8 | — | 251 |
| 658 | GMLKLIDFGI | 161.697 | 0/1 | 0/8 | — | 252 |
| 194 | LLSEEEKKNL | 148.896 | 0/1 | 0/8 | — | 253 |
| 462 | YMSCFRTPVV | 94.738 | 1/1 | | | 254 |
| 57 | MMANNPEDWL | 70.685 | 0/1 | 0/8 | — | 255 |
| 600 | MVMECGNIDL | 48.205 | 0/1 | 0/8 | — | 256 |
| 689 | YMPPEAIKDM | 37.961 | 0/1 | 0/8 | — | 257 |
| 86 | KLIGRYSQAI | 36.515 | 0/1 | 0/8 | — | 258 |
| 669 | NQMQPDTTSV | 26.092 | 0/1 | 1/8 | 0/1 | 259 |
| 497 | QILATPLQNL | 24.997 | 0/1 | 0/8 | — | 260 |
| 654 | LIVDGMLKLI | 22.997 | 0/1 | 0/8 | — | 261 |
| 186 | NLNLQKKQLL | 21.362 | 0/1 | 1/8 | 0/1 | 262 |
| 670 | QMQPDTTSVV | 20.595 | 0/1 | 0/8 | — | 263 |
| 803 | KGTTEEMKYV | 20.102 | 0/1 | 0/8 | — | 264 |
| 11 | LTIDSIMNKV | 15.486 | 0/1 | 0/8 | — | 265 |
| 577 | KLQQHSDKII | 14.971 | 0/1 | 0/8 | — | 266 |

TABLE 10A

HLA-A*0201 binding 9-mer peptides derived from URLC10

| strat position | sequence | Binding Score | positive donor number | positive well number | positive CTL line | SEQ ID NO |
|---|---|---|---|---|---|---|
| 131 | KIFPRFFMV | 1364.78 | 0/1 | 0/8 | — | 267 |
| 204 | GLWLAILLL | 407.808 | 0/1 | 0/8 | — | 268 |
| 65 | LLVVALPRV | 271.948 | 0/1 | 0/8 | — | 269 |
| 60 | ALLALLLVV | 242.674 | — | — | — | 270 |

TABLE 10A-continued

HLA-A*0201 binding 9-mer peptides derived from URLC10

| strat position | sequence | Binding Score | positive donor number | positive well number | positive CTL line | SEQ ID NO |
|---|---|---|---|---|---|---|
| 206 | WLAILLLLA | 52.561 | 1/1 | | | 271 |
| 212 | LLASIAAGL | 36.316 | 1/1 | | | 272 |
| 210 | LLLLASIAA | 31.249 | 0/1 | 0/8 | — | 273 |
| 137 | FMVAKQCSA | 16.505 | 0/1 | 2/8 | 0/2 | 274 |
| 58 | TMALLALLL | 15.428 | 0/1 | 2/8 | 0/2 | 275 |
| 59 | MALLALLLV | 13.975 | 0/1 | 2/8 | 0/2 | 276 |
| 209 | ILLLLASIA | 12.812 | 0/1 | 0/8 | — | 434 |
| 208 | AILLLLASI | 12.208 | — | — | — | 277 |
| 69 | ALPRVWTDA | 8.446 | 0/1 | 0/8 | — | 278 |
| 197 | SMGESCGGL | 8.223 | 0/1 | 0/8 | — | 279 |
| 61 | LLALLLVVA | 7.964 | — | — | — | 280 |
| 67 | VVALPRVWT | 6.097 | 0/1 | 0/8 | — | 281 |
| 72 | RVWTDANLT | 5.412 | 0/1 | 0/8 | — | 282 |
| 160 | FLLEEPMPF | 5.2 | 0/1 | 1/8 | 0/1 | 283 |
| 62 | LALLLVVAL | 4.292 | 0/1 | 0/8 | — | 284 |
| 57 | GTMALLALL | 2.525 | 0/1 | 1/8 | 0/1 | 285 |

TABLE 10B

HLA-A*0201 binding 10-mer peptides derived from URLC10

| strat position | sequence | Binding Score | positive donor number | positive well number | positive CTL line | SEQ ID NO |
|---|---|---|---|---|---|---|
| 64 | LLLVVALPRV | 1006.21 | 0/1 | 0/8 | — | 286 |
| 204 | GLWLAILLLL | 407.808 | 0/1 | 1/8 | 0/1 | 287 |
| 211 | LLLASIAAGL | 134.369 | 1/1 | | | 288 |
| 258 | TMALLALLLV | 115.534 | — | — | — | 289 |
| 61 | LLALLLVVAL | 83.527 | — | — | — | 290 |
| 160 | FLLEEPMPFF | 65.782 | 0/1 | 0/8 | — | 291 |
| 209 | ILLLLASIAA | 31.249 | 0/1 | 0/8 | — | 292 |
| 131 | KIFPRFFMVA | 26.186 | 0/1 | 0/8 | — | 293 |
| 60 | ALLALLLVVA | 17.334 | — | — | — | 294 |
| 66 | LVVALPRVWT | 6.097 | 0/1 | 0/8 | — | 295 |
| 59 | MALLALLLVV | 5.73 | — | — | — | 296 |
| 2 | RLQRPRQAPA | 4.968 | 0/1 | 1/8 | 0/1 | 297 |
| 112 | CQNPRRCKWT | 4.156 | 0/1 | 0/8 | — | 298 |
| 72 | RVWTDANLTA | 3.608 | 0/1 | 0/8 | — | 299 |
| 53 | WAPLGTMALL | 3.139 | 0/1 | 0/8 | — | 300 |
| 121 | TEPYCVIAAV | 3.111 | 0/1 | 0/8 | — | 301 |

TABLE 10B-continued

HLA-A*0201 binding 10-mer peptides derived from URLC10

| strat position | sequence | Binding Score | positive donor number | positive well number | positive CTL line | SEQ ID NO |
|---|---|---|---|---|---|---|
| 162 | LEEPMPFFYL | 2.739 | 0/1 | 1/8 | 0/1 | 302 |
| 181 | LEGPPINSSV | 2.299 | 0/1 | 2/8 | 0/2 | 303 |
| 170 | YLKCCKIRYC | 2.024 | 0/1 | 0/8 | – | 304 |
| 130 | VKIFPRFFMV | 1.81 | 0/1 | 0/8 | – | 305 |

Stimulation of the T Cells Using the Predicted Peptides from CDH3 Restricted with HLA-A*2402 and Establishment for CTL Lines Stimulated with CDH3 Derived Peptides CTLs for those peptides derived from CDH3 were generated according to the protocols set forth in "Materials and Methods" section above. Resulting that CTLs having detectable specific CTL activity, as determined by IFN-gamma ELISPOT assay, are shown in FIG. 1. In particular, CDH3-A24-9-513 (SEQ ID NO: 19), CDH3-A24-9-406 (SEQ ID NO: 22), CDH3-A24-10-807 (SEQ ID NO: 30), CDH3-A24-10-332 (SEQ ID NO: 34), CDH3-A24-10-655 (SEQ ID NO: 344) and CDH3-A24-10-470 (SEQ ID NO: 358) demonstrated potent IFN-gamma production as compared to the control by IFN-gamma ELISPOT assay, and the cells in the positive well number #5 stimulated with SEQ ID NO: 19, #2 with SEQ ID NO: 22, #5 with SEQ ID NO: 30, #4 with SEQ ID NO: 34, #1 with SEQ ID NO: 344 and #4 with SEQ ID NO: 358 were expanded and CTL lines were established. Those CTL lines having higher specific CTL activities against the peptide-pulsed target as compared to the activities against target without peptide pulse were determined by ELISA. Results are shown in FIG. 1. While, other peptides shown in table 2 could not establish the CTL lines despite possible binding activity with HLA-A*2402. For example, the typical negative peptide (CDH3-A24-10-248) were shown in FIG. 1a. In this invention, the peptides which could establish CTL line were selected as potent CTL stimulation peptide.

Establishment for CTL Clones Stimulated with CDH3 Derived Peptides

Furthermore, the limiting dilution from these CTL lines was performed according to the protocols set forth in the "Materials and Methods" section above. The establishment of CTL clones from CDH3-A24-10-807 (SEQ ID NO: 30) #5 and CDH3-A24-10-655 (SEQ ID NO: 344) #1 CTL line are shown in FIGS. 1f and g. CTL clones had potent and specific CTL activities against the peptide-pulsed target as compared to the activities against target without peptide pulse.

Specific CTL Activity Against the Target Cells Expressing CDH3 and HLA-A*2402

The established CTL line raised against these peptides were examined for their ability to recognize the target cells expressing CDH3 and HLA-A*2402. Specific CTL activity against COS7 transfected with both full length CDH3 gene and the HLA-A*2402 molecule, which serves as a specific model for the target cells endogenously express CDH3 and HLA-A*2402, was tested using as effector cells the CTL lines raised by CDH3-A24-10-807 (SEQ ID NO: 30) and CDH3-A24-10-655 (SEQ ID NO: 344). COS7 transfected with full length CDH3 but not HLA-A*2402 and COS7 transfected with HLA-A*2402 but not full length CDH3 were prepared as controls. The CTL clones demonstrated the highest specific CTL activity against COS7 that was transfected with both CDH3 and HLA-A2402 (FIGS. 1f and g).

These results clearly demonstrate that CDH3-A24-10-807 (SEQ ID NO: 30) and CDH3-A24-10-655 (SEQ ID NO: 344) are naturally expressed on the target cell surface with HLA-A2402 molecule and recognize CTL. Furthermore, these peptides are epitope peptides, which may serve as cancer vaccines targeting CDH3 expressed tumors.

Stimulation of the T Cells Using the Predicted Peptides from EPHA4 Restricted with HLA-A*2402 or HLA-A*0201, and Establishment for CTL Lines Stimulated with EPHA4 Derived Peptides CTLs for those peptides derived from EphA4 were generated by IFN-gamma ELISPOT assay. Resulting that CTLs having detectable specific CTL activity, as determined by IFN-gamma ELISPOT assay, are shown in FIG. 2. In particular, EphA4-A24-9-453 (SEQ ID NO: 41), EphA4-A24-9-5 (SEQ ID NO: 44), EphA4-A24-9-869 (SEQ ID NO: 46), EphA4-A24-9-420 (SEQ ID NO: 48), EphA4-A24-10-24 (SEQ ID NO: 78), EphA4-A02-9-501 (SEQ ID NO: 376) and EphA4-A02-9-165 (SEQ ID NO: 379) demonstrated potent IFN-gamma production by IFN-gamma ELISPOT assay, and the cells in the positive well number #3 stimulated with EphA4-A24-9-453 (SEQ ID NO: 41), #2 with EphA4-A24-9-5 (SEQ ID NO: 44), #5 with EphA4-A24-9-869 (SEQ ID NO: 46), #6 with EphA4-A24-9-420 (SEQ ID NO: 48), #4 with EphA4-A24-10-24 (SEQ ID NO: 78), #8 with EphA4-A02-9-501 (SEQ ID NO: 376) and #3 with EphA4-A02-9-165 (SEQ ID NO: 379) were expanded and CTL lines were established. Those CTL lines having higher specific CTL activities against the peptide-pulsed target as compared to the activities against target without peptide pulse were determined by ELISA. Especially, CTL lines stimulated with EphA4-A02-9-501 (SEQ ID NO: 376) and EphA4-A02-9-165 (SEQ ID NO: 379) were tested by 51Cr-release assay according to the protocols set forth in the "Materials and Methods" section above. Results are shown in FIG. 2a-h. While, other peptides shown in table 3 could not establish the CTL lines despite possible binding activity with HLA-A*2402 or HLA-A*0201. For example, the typical negative peptide (EphA4-A24-9-384) were shown in FIG. 2a. In this invention, the peptides which could establish CTL line were selected as potent CTL stimulation peptides.

Stimulation of the T Cells Using the Predicted Peptides from ECT2 Restricted with HLA-A*2402, and Establishment for CTL Lines Stimulated with ECT2 Derived Peptides CTLs for those peptides derived from ECT2 were generated according to the protocols set forth in the "Materials and Methods" section above. Resulting CTLs having detectable specific CTL activity as determined by an IFN-gamma ELISPOT assay are shown in FIG. 3. In particular, ECT2-

A24-9-515 (SEQ ID NO: 80), ECT2-A24-10-40 (SEQ ID NO: 100) and ECT2-A24-10-101 (SEQ ID NO: 101) showed potent IFN-gamma production, and the cells in the positive well number #7 stimulated with ECT2-A24-9-515 (SEQ ID NO: 80), #2 with ECT2-A24-10-40 (SEQ ID NO: 100) and #1 with ECT2-A24-10-101 (SEQ ID NO: 101) were expanded and CTL lines were established. Those CTL lines having higher specific CTL activities against the peptide-pulsed target as compared to the activities against target without peptide pulse were determined by ELISA. Results are shown in FIG. 3a-d. While, other peptides shown in table 4 could not establish the CTL lines despite possible binding activity with HLA-A*2402. For example, the typical negative peptide (ECT2-A24-10-322, ECT2-A24-9-657 and ECT2-A24-10-811) were shown in FIG. 2a. In this invention, the peptides which could establish CTL line were selected as potent CTL stimulation peptide.

Establishment for CTL Clones Stimulated with ECT2 Derived Peptides

Furthermore, the limiting dilution from these CTL lines was performed according to the protocols set forth in the "Materials and Methods" section above. The establishment of CTL clones from ECT2-A24-10-40 (SEQ ID NO: 100) #2 CTL line are shown in FIG. 3c. CTL clones had potent and specific CTL activities against the peptide-pulsed target as compared to the activities against target without peptide pulse.

Specific CTL Activity Against the Target Cells Expressing ECT2 and HLA-A*2402

The established CTL line raised against these peptides were examined for their ability to recognize the target cells expressing ECT2 and HLA-A*2402. Specific CTL activity against COS7 transfected with both full length ECT2 gene and the HLA-A*2402 molecule, which serves as a specific model for the target cells endogenously express ECT2 and HLA-A*2402, was tested using as effector cells the CTL clone raised by ECT2-A24-10-40 (SEQ ID NO: 100) and the CTL line raised by ECT2-A24-10-101 (SEQ ID NO: 101). COS7 transfected with full length ECT2 but not HLA-A*2402 and COS7 transfected with HLA-A*2402 but not full length ECT2 (replaced other gene e.g. URLC10 or INHBB) were prepared as controls. The CTL line demonstrating the highest specific CTL activity against COS7 that was transfected with both ECT2 and HLA-A2402 (FIGS. 3c and d).

These results clearly demonstrate that ECT2-A24-10-40 (SEQ ID NO: 100) and ECT2-A24-10-101 (SEQ ID NO: 101) are naturally expressed on the target cell surface with HLA-A2402 molecule and recognize CTL. Furthermore, these peptides are epitope peptides, which may serve as cancer vaccines targeting ECT2 expressed tumors.

Cytotoxic Activity Against Cancer Cell Line Endogenously Expressing HLA-A*2402 and ECT2

Furthermore, Cytotoxic activity was examined by cytotoxicity assay according to the protocols set forth in the "Materials and Methods" section above. As a result, as shown in FIG. 3b, CTL clone stimulated with ECT2-A24-9-515 (SEQ ID NO: 80) showed remarkably high cytotoxic effect towards HLA-A24-positive and ECT-positive cancer cell lines TE6, compared to that towards HLA-A24-negative and ECT-positive cancer cell lines TE5.

Figure 4:
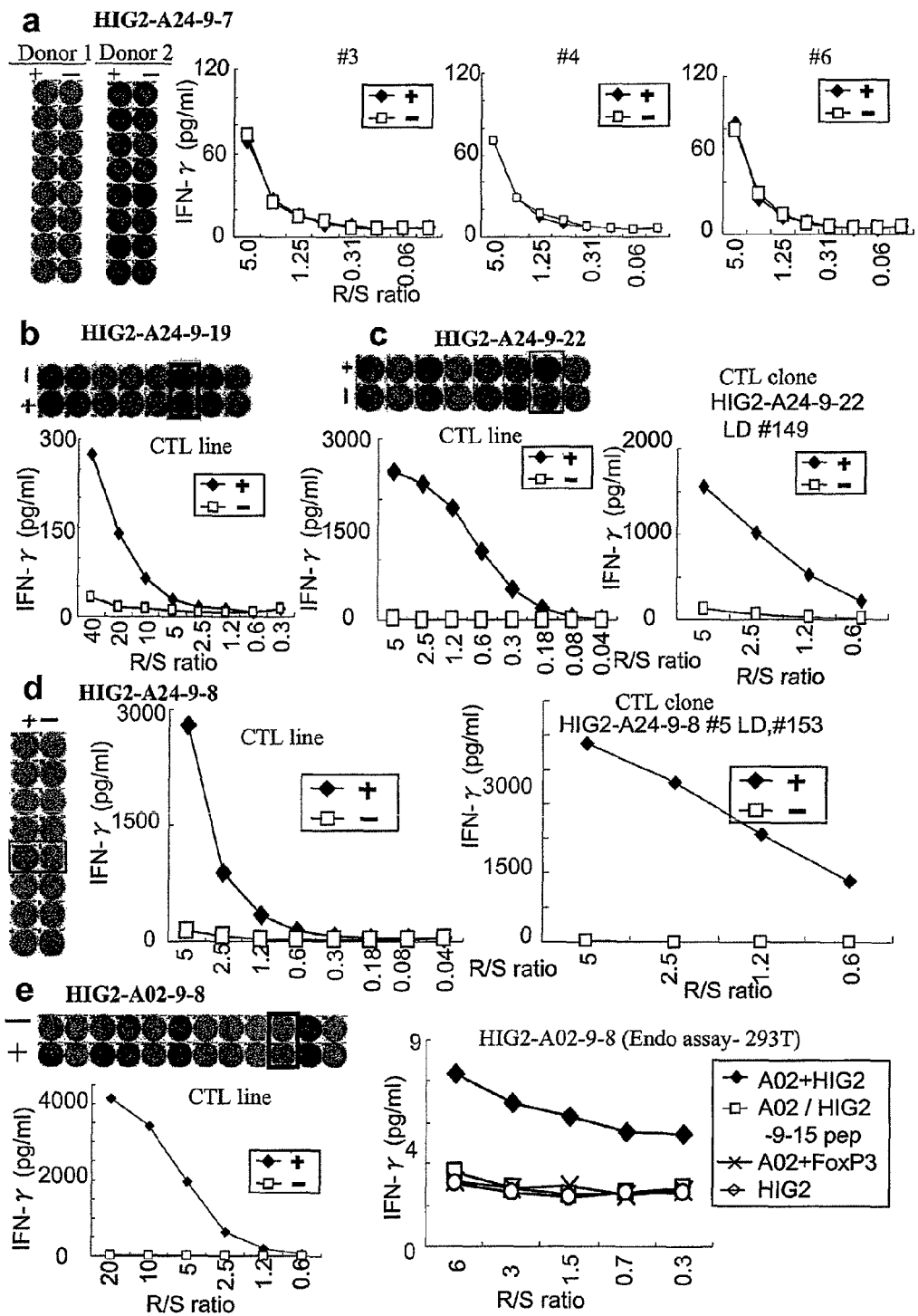
Figure 4:
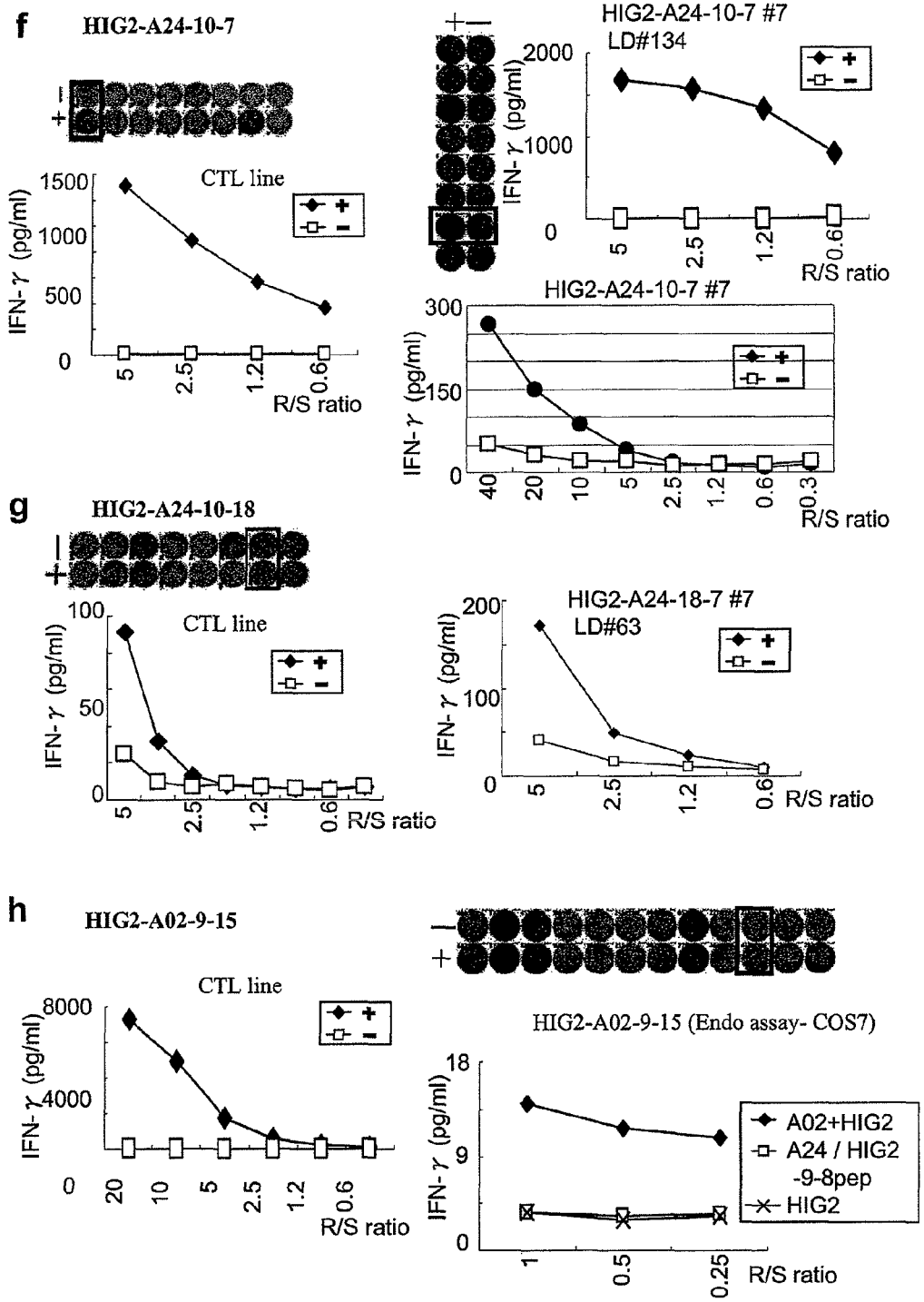
Figure 4:
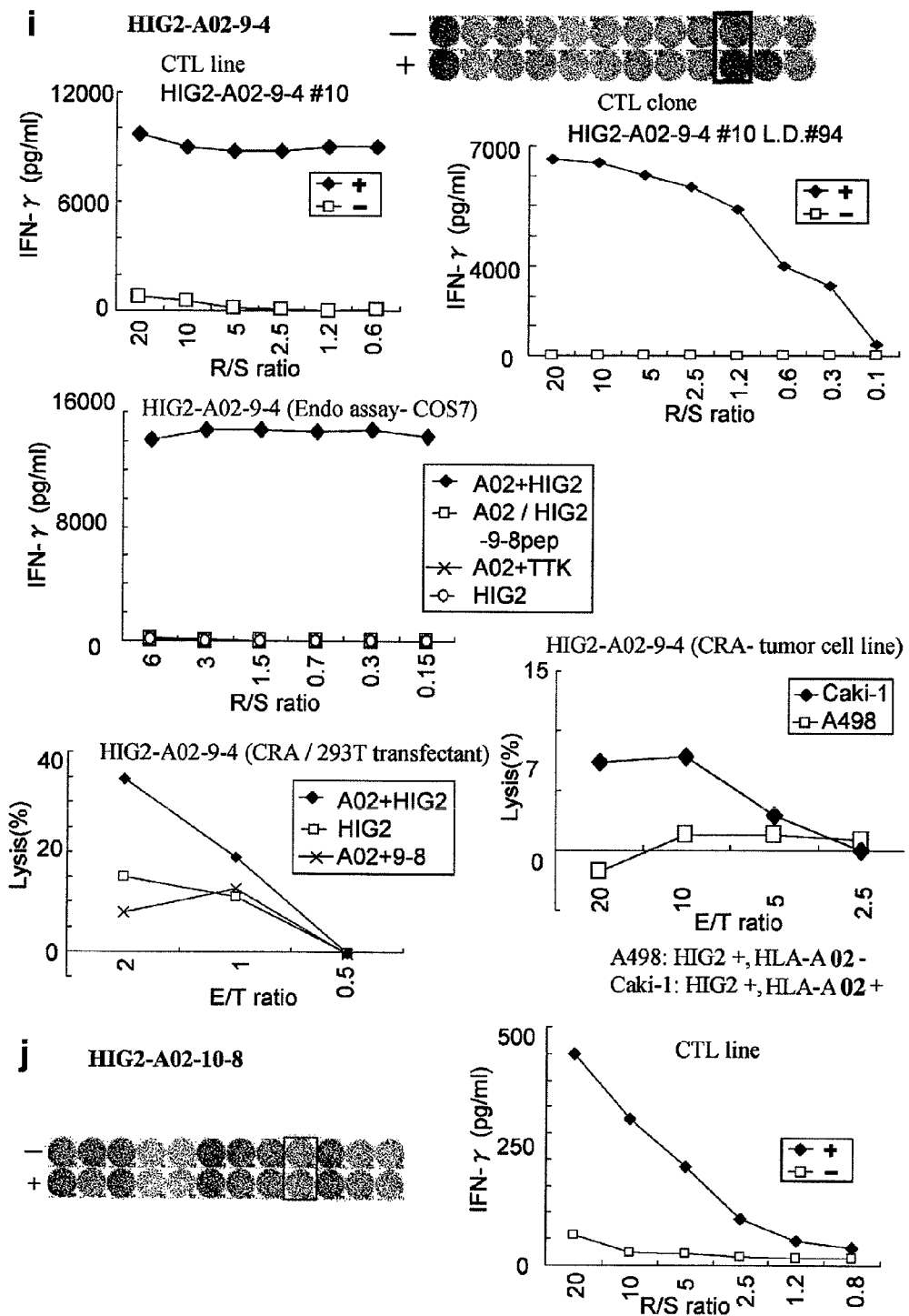

Stimulation of the T Cells Using the Predicted Peptides from HIG2 Restricted with HLA-A*2402 or HLA-A*0201, and Establishment for CTL Lines Stimulated with HIG2 Derived Peptides CTLs for those peptides derived from HIG2 were generated according to the protocols set forth in the "Materials and Methods" section above. Resulting CTLs having detectable specific CTL activity as determined by an IFN-gamma ELISPOT assay are shown in FIG. 4. In particular, HIG2-A24-9-19 (SEQ ID NO: 110), HIG2-A24-9-22 (SEQ ID NO: 111), HIG2-A24-9-8 (SEQ ID NO: 387), HIG2-A24-10-7 (SEQ ID NO: 112), HIG2-A24-10-18 (SEQ ID NO: 394), HIG2-A02-9-8 (SEQ ID NO: 114), HIG2-A02-9-15 (SEQ ID NO: 116), HIG2-A02-9-4 (SEQ ID NO: 117) and HIG2-A02-10-8 (SEQ ID NO: 121) demonstrated potent IFN-gamma production by IFN-gamma ELISPOT assay, and the cells in the positive well number #6 stimulated with HIG2-A24-9-19 (SEQ ID NO: 110), #7 with HIG2-A24-9-22 (SEQ ID NO: 111), #5 with HIG2-A24-9-8 (SEQ ID NO: 387), #1 with HIG2-A24-10-7 (SEQ ID NO: 112), #7 with HIG2-A24-10-18 (SEQ ID NO: 394), #10 with HIG2-A02-9-8 (SEQ ID NO: 114), #10 with HIG2-A02-9-15 (SEQ ID NO: 116), #10 with HIG2-A02-9-4 (SEQ ID NO: 117) and #9 with HIG2-A02-10-8 (SEQ ID NO: 121) were expanded and CTL lines were established. Those CTL lines having higher specific CTL activities against the peptide-pulsed target as compared to the activities against target without peptide pulse were determined by ELISA. Results are shown in FIG. 4a-j. While, other peptides shown in table 5 could not establish the CTL lines despite possible binding activity with HLA-A*2402. For example, the typical negative peptide (HIG2-A24-9-7) were shown in FIG. 4a. In this invention, the peptides which could establish CTL line were selected as potent CTL stimulation peptide.

Establishment for CTL Clones Stimulated with HIG2 Derived Peptides

Furthermore, the limiting dilution from these CTL lines was performed according to the protocols set forth in the "Materials and Methods" section above. The establishment of CTL clones from HIG2-A24-9-22 (SEQ ID NO: 111) #7 CTL line, HIG2-A24-9-8 (SEQ ID NO: 387) #5 CTL line, HIG2-A24-10-7 (SEQ ID NO: 112) #1 CTL line, HIG2-A24-10-18 (SEQ ID NO: 394) #7 CTL line and HIG2-A02-9-4 (SEQ ID NO: 117) #10 CTL line are shown in FIGS. 4c, e, f, g and i. CTL clones had potent and specific CTL activities against the peptide-pulsed target as compared to the activities against target without peptide pulse.

Specific CTL Activity Against the Target Cells Expressing HIG2 and HLA-A*0201

The established CTL line raised against these peptides were examined for their ability to recognize the target cells expressing HIG2 and HLA-A*0201. Specific CTL activity against 293T or COS7 transfected with both full length HIG2 gene and the HLA-A*0201 molecule, which serves as a specific model for the target cells endogenously express HIG2 and HLA-A*0201, was tested using as effector cells the CTL lines raised by HIG2-A02-9-8 (SEQ ID NO: 114), HIG2-A02-9-15 (SEQ ID NO: 116) and the CTL clone raised by HIG2-A02-9-4 (SEQ ID NO: 117). 293T or COS7 transfected with full length ECT2 but not HLA-A*0201 and 293T or COS7 transfected with HLA-A*0201 but not full length ECT2 (or replaced other gene e.g. FoxP3 or TTK) were prepared as controls. The CTL line demonstrating the highest specific CTL activity against 293T or COS7 that was transfected with both ECT2 and HLA-A*0201 (FIGS. 4e, h and i).

These results clearly demonstrate that HIG2-A02-9-8 (SEQ ID NO: 114), HIG2-A02-9-15 (SEQ ID NO: 116) and HIG2-A02-9-4 (SEQ ID NO: 117) are naturally expressed on the target cell surface with HLA-A2402 or HLA-A0201 molecule and recognize CTL. Furthermore, these peptides are epitope peptides, which may serve as cancer vaccines targeting HIG2 expressed tumors.

Cytotoxic Activity Against Cancer Cell Line Endogenously Expressing HLA-A*0201 and HIG2

Furthermore, Cytotoxic activity was examined by cytotoxicity assay according to the protocols set forth in the "Materials and Methods" section above. As a result, as shown in FIG. 4i, CTL clone stimulated with HIG2-A02-9-4 (SEQ ID NO: 117) showed remarkably high cytotoxic effect towards HLA-A02-positive and HIG2-positive cancer cell lines CAki-1, compared to that towards HLA-A02-negative and HIG2-positive cancer cell lines A498.

Figure 5:
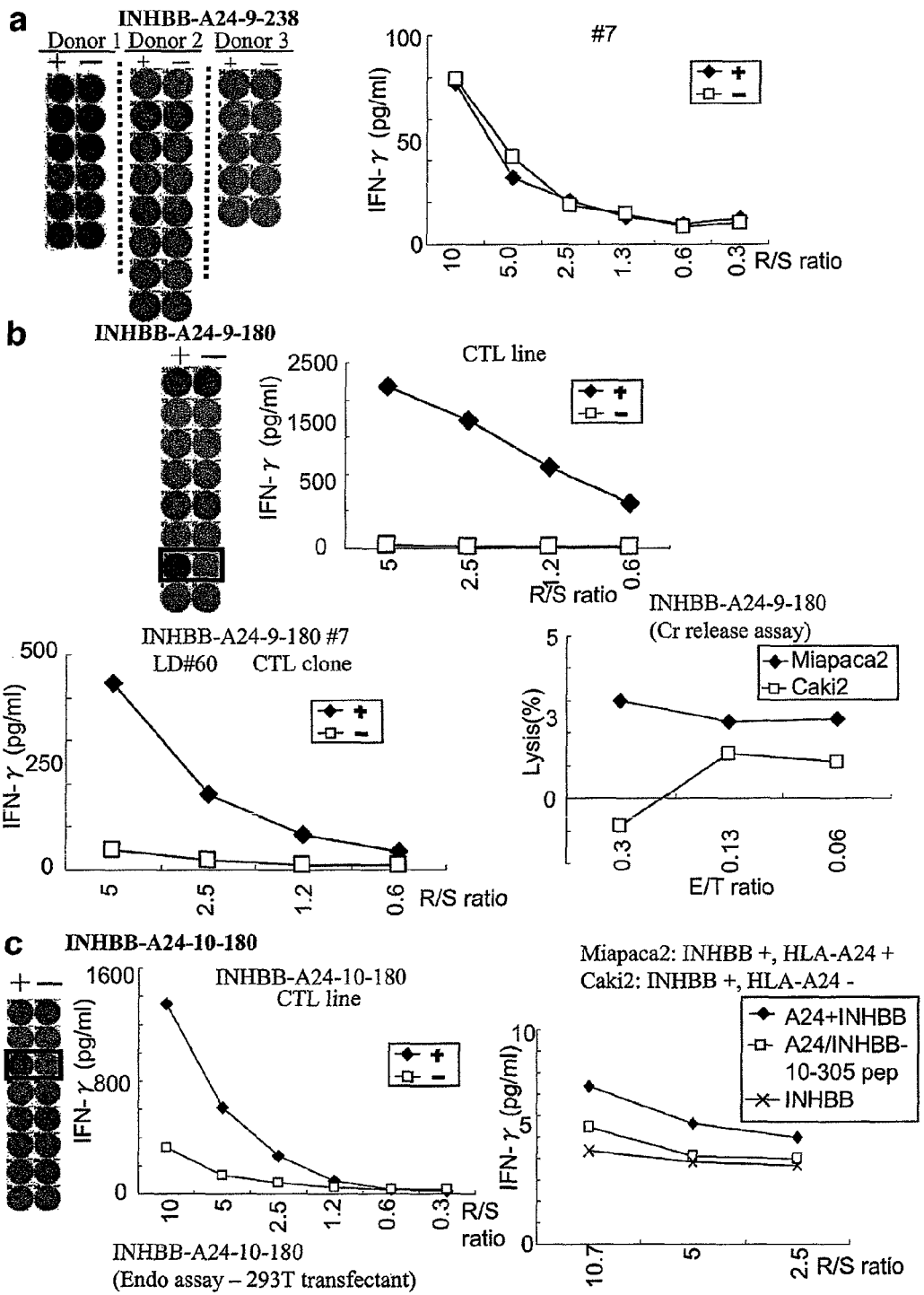
Figure 5:
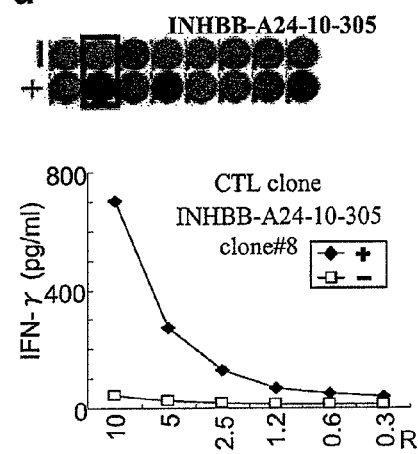
Figure 5:
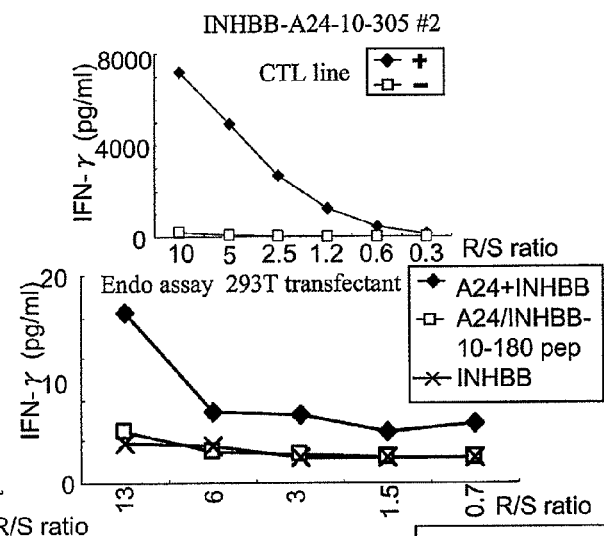
Figure 5:
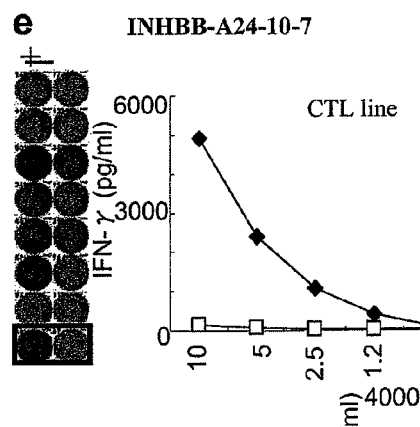
Figure 5:
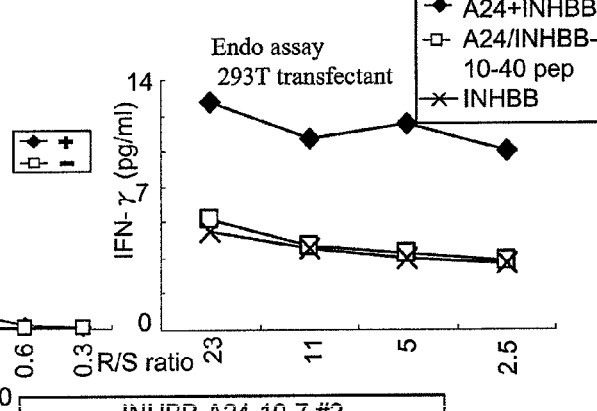
Figure 5:
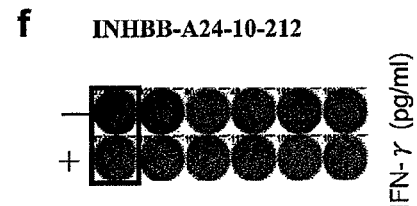
Figure 5:
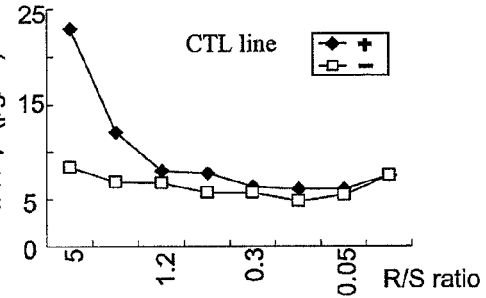

Stimulation of the T Cells Using the Predicted Peptides from INHBB Restricted with HLA-A*2402 or HLA-A*0201, and Establishment for CTL Lines Stimulated with INHBB Derived Peptides CTLs for those peptides derived from INHBB were generated according to the protocols set forth in the "Materials and Methods" section above. Resulting CTLs having detectable specific CTL activity as determined by an IFN-gamma ELISPOT assay are shown in FIG. 5. In particular, INHBB-A24-9-180 (SEQ ID NO: 395), INHBB-A24-10-180 (SEQ ID NO: 133), INHBB-A24-10-305 (SEQ ID NO: 135), INHBB-A24-10-7 (SEQ ID NO: 137) and INHBB-A24-10-212 (SEQ ID NO: 426) demonstrated potent IFN-gamma production by IFN-gamma ELISPOT assay, and the cells in the positive well number #7 stimulated with INHBB-A24-9-180 (SEQ ID NO: 395), #3 with INHBB-A24-10-180 (SEQ ID NO: 133), #2 with INHBB-A24-10-305 (SEQ ID NO: 135), #8 and #2 with INHBB-A24-10-7 (SEQ ID NO: 137) and #1 with INHBB-A24-10-212 (SEQ ID NO: 426) were expanded and CTL lines were established. Those CTL lines having higher specific CTL activities against the peptide-pulsed target as compared to the activities against target without peptide pulse were determined by ELISA. Results are shown in FIG. 5b-e. While, other peptides shown in table 6 could not establish the CTL lines despite possible binding activity with HLA-A*2402 and HLA*0201. For example, the typical negative peptide (INHBB-A24-9-238) were shown in FIG. 5a. In this invention, the peptides which could establish CTL line were selected as potent CTL stimulation peptide.

Establishment for CTL Clones Stimulated with INHBB Derived Peptides

Furthermore, the limiting dilution from these CTL lines was performed according to the protocols set forth in the "Materials and Methods" section above. The establishment of CTL clones from INHBB-A24-9-180 (SEQ ID NO: 395) #7 CTL line, and INHBB-A24-10-305 (SEQ ID NO: 135) #2 CTL line are shown in FIGS. 5b and d. CTL clones had potent and specific CTL activities against the peptide-pulsed target as compared to the activities against target without peptide pulse.

Specific CTL Activity Against the Target Cells Expressing INHBB and HLA-A*2402

The established CTL line raised against these peptides were examined for their ability to recognize the target cells expressing INHBB and HLA-A*2402. Specific CTL activity against 293T transfected with both full length INHBB gene and the HLA-A*2402 molecule, which serves as a specific model for the target cells endogenously express INHBB and HLA-A*2402, was tested using as effector cells the CTL lines raised by INHBB-A24-10-180 (SEQ ID NO: 133) and INHBB-A24-10-7 (SEQ ID NO: 137) and the CTL clone raised by INHBB-A24-10-305 (SEQ ID NO: 135), 293T transfected with full length INHBB but not HLA-A*2402 and 293T transfected with HLA-A*2402 but not full length INHBB were prepared as controls. The CTL line demonstrating the highest specific CTL activity against 293T was that transfected with both INHBB and HLA-A*2402 (FIGS. 5c, d and e).

These results clearly demonstrate that INHBB-A24-10-305 (SEQ ID NO: 135), INHBB-A24-10-180 (SEQ ID NO: 133) and INHBB-A24-10-7 (SEQ ID NO: 137) are naturally expressed on the target cell surface with HLA-A2402 molecule and recognize CTL. Furthermore, these peptides are epitope peptides, which may serve as cancer vaccines targeting INHBB expressed tumors.

Cytotoxic Activity Against Cancer Cell Line Endogenously Expressing HLA-A*2402 and INHBB Furthermore, Cytotoxic activity was performed by cytotoxicity assay according to the protocols set forth in the "Materials and Methods" section above. As a result, as shown in FIG. 5b, CTL clone stimulated with INHBB-A24-9-180 (SEQ ID NO: 395) showed remarkably high cytotoxic effect towards HLA-A24-positive and INHBB-positive cancer cell lines MIAPaca2, compared to that towards HLA-A24-negative and INHBB-positive cancer cell lines CAki-2.

Figure 6:
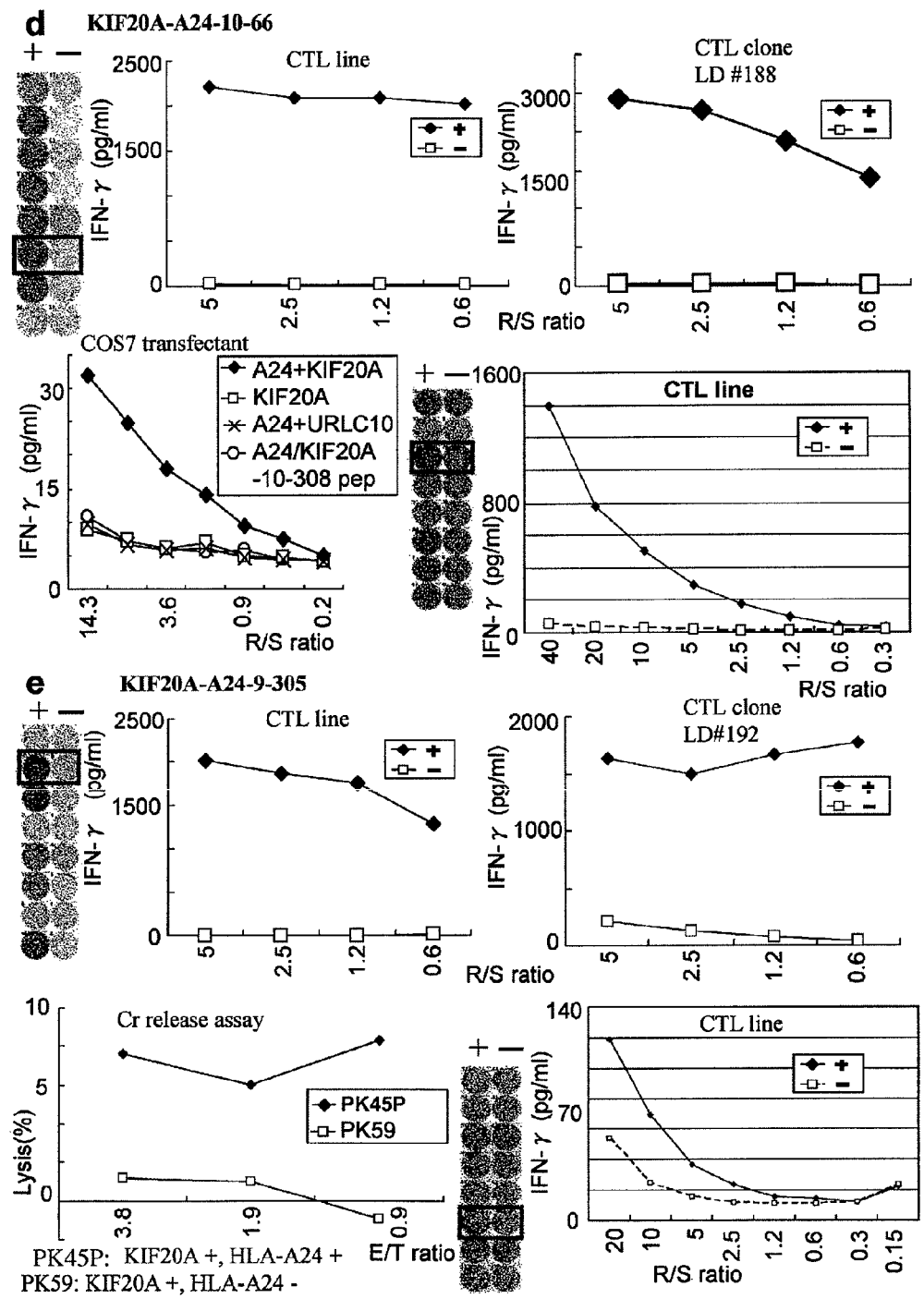

Stimulation of the T Cells Using the Predicted Peptides from KIF20A Restricted with HLA-A*2402, and Establishment for CTL Lines Stimulated with KIF20A Derived Peptides CTLs for those peptides derived from KIF20A were generated according to the protocols set forth in the "Materials and Methods" section above. Resulting CTLs having detectable specific CTL activity as determined by an IFN-gamma ELISPOT assay are shown in FIG. 6. In particular, KIF20A-A24-9-305 (SEQ ID NO: 174), KIF20A-A24-9-383 (SEQ ID NO: 178), KIF20A-A24-10-304 (SEQ ID NO: 186) and KIF20A-A24-10-66 (SEQ ID NO: 194) demonstrated potent IFN-gamma production by IFN-gamma ELISPOT assay, and the cells in the positive well number #2 stimulated with KIF20A-A24-9-305 (SEQ ID NO: 174), #3 with KIF20A-A24-9-383 (SEQ ID NO: 178), #5 with KIF20A-A24-10-304 (SEQ ID NO: 186) and #6 with KIF20A-A24-10-66 (SEQ ID NO: 194) were expanded and CTL lines were established. Those CTL lines having higher specific CTL activities against the peptide-pulsed target as compared to the activities against target without peptide pulse were determined by ELISA. Results are shown in FIG. 6a-e. While, other peptides shown in table 7 could not establish the CTL lines despite possible binding activity with HLA-A*2402. For example, the typical negative peptide (KIF20A-A24-9-647 and KIF20A-A24-10-182) were shown in FIG. 6a. In this invention, the peptides which could establish CTL line were selected as potent CTL stimulation peptide.

Establishment for CTL Clones Stimulated with KIF20A Derived Peptides

Furthermore, the limiting dilution from these CTL lines was performed according to the protocols set forth in the "Materials and Methods" section above. The establishment of CTL clones from KIF20A-A24-9-305 (SEQ ID NO: 174) #2 CTL line, KIF20A-A24-10-304 (SEQ ID NO: 186) #5 CTL line and KIF20A-A24-10-66 (SEQ ID NO: 194) #6 CTL line are shown in FIGS. 6b, d and e. CTL clones had potent and specific CTL activities against the peptide-pulsed target as compared to the activities against target without peptide pulse.

Specific CTL Activity Against the Target Cells Expressing KIF20A and HLA-A*2402

The established CTL line raised against these peptides were examined for their ability to recognize the target cells expressing KIF20A and HLA-A*2402. Specific CTL activity against COS7 transfected with both full length KIF20A gene and the HLA-A*2402 molecule and A24-LCL transfected by electroporation with full length KIF20A gene, which serve as a specific model for the target cells endogenously express KIF20A and HLA-A*2402, was tested using as effector cells the CTL lines raised by KIF20A-A24-9-383 (SEQ ID NO: 178) and KIF20A-A24-10-304 (SEQ ID NO: 186) and the CTL clone raised by KIF20A-A24-10-66 (SEQ ID NO: 194). COS7 transfected with full length KIF20A but not HLA-A*2402 and COS7 transfected with HLA-A*2402 but not full length KIF20A (or replaced full length URLC10 gene), COS7 transfected with HLA-A*2402 and pulsed with KIF20A-10-308, and A24-LCL transfected with mock vector were prepared as controls. The CTL line demonstrated the highest specific CTL activity against COS7 that was transfected with both KIF20A and HLA-A*2402 (FIGS. 6b, c and d). Alternatively, the CTL line stimulated with KIF20A-A24-10-304 (SEQ ID NO: 186) demonstrated against A24-LCL transfected with KIF20A.

These results clearly demonstrate that KIF20A-A24-9-383 (SEQ ID NO: 178), KIF20A-A24-10-304 (SEQ ID NO: 186) and KIF20A-A24-10-66 (SEQ ID NO: 194) is naturally expressed on the target cell surface with HLA-A2402 molecule and recognize CTL. Furthermore, these peptides are epitope peptides, which may serve as cancer vaccines targeting KIF20A expressed tumors.

Cytotoxic Activity Against Cancer Cell Line Endogenously Expressing HLA-A*2402 and KIF20A Furthermore, Cytotoxic activity was examined by cytotoxicity assay according to the protocols set forth in the "Materials and Methods" section above. As a result, as shown in FIG. 6b and e, CTL clone stimulated with KIF20A-A24-9-305 (SEQ ID NO: 174) or KIF20A-A24-10-304 (SEQ ID NO: 186) showed remarkably high cytotoxic effect towards HLA-A24-positive and KIF20A-positive cancer cell lines PK45P or MIAPaca2 respectively, compared to that towards HLA-A24-negative and KIF20A-positive cancer cell lines PK59.

Stimulation of the T Cells Using the Predicted Peptides from KNTC2 Restricted with HLA-A*2402, and Establishment for CTL Lines Stimulated with KNTC2 Derived Peptides CTLs for those peptides derived from KNTC2 were generated according to the protocols set forth in the "Materials and Methods" section above. Resulting CTLs having detectable specific CTL activity as determined by an IFN-gamma ELISPOT assay are shown in FIG. 7. In particular, KNTC2-A24-9-309 (SEQ ID NO: 196), KNTC2-A24-9-124 (SEQ ID NO: 202), KNTC2-A24-9-154 (SEQ ID NO: 210), KNTC2-A24-9-150 (SEQ ID NO: 213), KNTC2-A24-10-452 (SEQ ID NO: 214), KNTC2-A24-10-227 (SEQ ID NO: 217) and KNTC2-A24-10-273 (SEQ ID NO: 223) demonstrated potent IFN-gamma production by IFN-gamma ELISPOT assay, and the cells in the positive well number #8 stimulated with KNTC2-A24-9-309 (SEQ ID NO: 196), #5 with KNTC2-A24-9-124 (SEQ ID NO: 202), #5 with KNTC2-A24-9-154 (SEQ ID NO: 210), #7 with KNTC2-A24-9-150 (SEQ ID NO: 213), #4 and #5 with KNTC2-A24-10-452 (SEQ ID NO: 214), #1 with KNTC2-A24-10-227 (SEQ ID NO: 217) and #8 with KNTC2-A24-10-273 (SEQ ID NO: 223) were expanded and CTL lines were established. Those CTL lines having higher specific CTL activities against the peptide-pulsed target as compared to the activities against target without peptide pulse were determined by ELISA. Results are shown in FIG. 7a-h. While, other peptides shown in table 8 could not establish the CTL lines despite possible binding activity with HLA-A*2402. For example, the typical negative peptide (KNTC2-A24-10-610) were shown in FIG. 7a. In this invention, the peptides which could establish CTL line were selected as potent CTL stimulation peptide.

Establishment for CTL Clones Stimulated with KNTC2 Derived Peptides

Furthermore, the limiting dilution from these CTL lines was performed according to the protocols set forth in the "Materials and Methods" section above. The establishment of CTL clones from KNTC2-A24-9-154 (SEQ ID NO: 210) #5 CTL line and KNTC2-A24-10-452 (SEQ ID NO: 214) #5 CTL line are shown in FIGS. 7d and f. CTL clones had potent and specific CTL activities against the peptide-pulsed target as compared to the activities against target without peptide pulse.

Specific CTL Activity Against the Target Cells Expressing KNTC2 and HLA-A*2402

The established CTL line raised against these peptides were examined for their ability to recognize the target cells expressing KNTC2 and HLA-A*2402. Specific CTL activity against HEK293 transfected with both full length KNTC2 gene and the HLA-A*2402 molecule which serves as a specific model for the target cells endogenously express KNTC2 and HLA-A*2402, was tested using as effector cells the CTL clones raised by KNTC2-A24-10-452 (SEQ ID NO: 214). HEK293 transfected with full length KNTC2 but not HLA-A*2402, HEK293 transfected with HLA-A*2402 but not full length KNTC2 and HEK293 transfected with HLA-A*2402 and pulsed with KNTC2-9-309 were prepared as controls. The CTL line demonstrating the highest specific CTL activity against HEK293 was that transfected with both KNTC2 and HLA-A*2402 (FIG. 7f).

These results clearly demonstrate that KNTC2-A24-10-452 (SEQ ID NO: 214) is naturally expressed on the target cell surface with HLA-A2402 molecule and recognize CTL. Furthermore, these peptides are epitope peptides, which may serve as cancer vaccines targeting KNTC2 expressed tumors.

Stimulation of the T Cells Using the Predicted Peptides from TTK Restricted with HLA-A*0201, and Establishment for CTL Lines Stimulated with TTK Derived Peptides CTLs for those peptides derived from TTK were generated according to the protocols set forth in the "Materials and Methods" section above. Resulting CTLs having detectable specific CTL activity as determined by an IFN-gamma ELISPOT assay are shown in FIG. 8. As depicted in FIG. 8b-d, TTK-A2-9-462 (SEQ ID NO: 227), TTK-A2-9-547 (SEQ ID NO: 228), TTK-A2-9-719 (SEQ ID NO: 233) and TTK-A2-10-462 (SEQ ID NO: 254) demonstrated potent IFN-gamma production by IFN-gamma ELISPOT assay, and the cells in the positive well number #4 stimulated with TTK-A2-9-462 (SEQ ID NO: 227), #2 with TTK-A2-9-547 (SEQ ID NO: 228), #1 with TTK-A2-9-719 (SEQ ID NO: 233) and #8 with TTK-A2-10-462 (SEQ ID NO: 254) were expanded. Those CTL lines having higher specific CTL activities against the peptide-pulsed target as compared to the activities against target without peptide pulse were determined by ELISA. While, other peptides shown in table 9 could not establish the CTL lines despite possible binding activity with HLA-A*0201. For example, the typical negative peptide (TTK-A2-9-278) were shown in FIG. 8a. In this invention, the peptides which could establish CTL line were selected as potent CTL stimulation peptide.

Establishment for CTL Clones Stimulated with TTK Derived Peptides

Furthermore, the limiting dilution from these CTL lines was performed according to the protocols set forth in the "Materials and Methods" section above. The establishment of CTL clones from TTK-A2-9-462 (SEQ ID NO: 227) #4 CTL line, TTK-A2-9-547 (SEQ ID NO: 228) #2 CTL line, TTK-A2-9-719 (SEQ ID NO: 233) #1 CTL line and TTK-A2-10-462 (SEQ ID NO: 254) #8 CTL line were shown in FIGS. 8d, c, d and e. CTL clones had potent and specific CTL activities against the peptide-pulsed target as compared to the activities against target without peptide pulse.

Specific CTL Activity Against the Target Cells Expressing TTK and HLA-A*0201

The established CTL clone raised against these peptides were examined for their ability to recognize the target cells endogenously expressing TTK and HLA-A*0201. Specific CTL activity against COS7 transfected with both the full length TTK gene and the HLA-A*0201 molecule, which is a specific model for the target cells endogenously express TTK and HLA-A*0201, was tested using as effector cells the CTL clones raised by TTK-A2-9-462 (SEQ ID NO: 227), TTK-A02-9-547 (SEQ ID NO: 228), TTK-A2-9-719 (SEQ ID NO: 233) and TTK-A2-10-462 (SEQ ID NO: 254). COS7 transfected with full length TTK but HLA-A*0201, COS7 transfected HLA-A*0201 but not full length of TTK (or replaced full length HIG2 gene) and COS7 transfected with HLA-A*0201 and pulsed with different target epitope peptide, were prepared as controls. The CTL Clone had the highest specific CTL activity against COS7 that was transfected with both TTK and HLA-A*0201 (FIGS. 8b, c, d and e).

These results clearly demonstrate that TTK-A2-9-462 (SEQ ID NO: 227), TTK-A02-9-547 (SEQ ID NO: 228), TTK-A2-9-719 (SEQ ID NO: 233) and TTK-A02-10-462 (SEQ ID NO: 254) are naturally expressed on the target cell surface with HLA-A2 (HLA-A02) molecule and recognize CTL. Furthermore, these peptides are epitope peptides, which may serve as cancer vaccines targeting TTK expressed tumors.

Stimulation of the T Cells Using the Predicted Peptides from URLC10 Restricted with HLA-A*0201, and Establishment for CTL Lines Stimulated with URLC10 Derived Peptides CTLs for those peptides derived from URLC10 were generated according to the protocols set forth in the "Materials and Methods" section above. Resulting CTLs having detectable specific CTL activity as determined by IFN-gamma ELISPOT assay are shown in FIG. 9. As shown in FIG. 9b-d, URLC-A2-9-206 (SEQ ID NO: 271), URLC-A2-9-212 (SEQ ID NO: 272) and URLC-A2-10-211 (SEQ ID NO: 288) demonstrated potent IFN-gamma production by IFN-gamma ELISPOT assay, and the cells in the positive well number #7 stimulated with URLC-A2-9-206 (SEQ ID NO: 271), #3 with URLC-A2-9-212 (SEQ ID NO: 272) and #5 with URLC-A2-10-211 (SEQ ID NO: 288) were expanded. Those CTL lines having higher specific CTL activities against the peptide-pulsed target as compared to the activities against target without peptide pulse were determined by ELISA. While, other peptides shown in table 10 could not establish the CTL lines despite possible binding activity with HLA-A*0201. For example, the typical negative peptide (URLC-A2-9-58) were shown in FIG. 9a. In this invention, the peptide which could establish CTL line were selected as potent CTL stimulation peptide.

Specific CTL Activity Against the Target Cells Expressing URLC10 and HLA-A*0201

The established CTL line raised against these peptides were examined for their ability to recognize the target cells endogenously expressing URLC10 and HLA-A*0201. Specific CTL activity against COS7, Hek293 and 293T transfected with both full length URLC10 gene and the HLA-A*0201 molecule, which serves as a specific model for the target cells endogenously express URLC10 and HLA-A*0201, was tested using as effector cells the CTL line raised by URLC10-A02-10-211. COS7, Hek293 or 293T transfected with full length URLC10 but not HLA-A*0201 (replaced HLA-A*2402), COS7, Hek293 or 293T transfected with HLA-A*0201 but not full length URLC10 and COS7 transfected with HLA-A*0201 and pulsed with different target epitope peptide (URLC10-A02-10-64) were prepared as controls. The CTL line demonstrating the highest specific CTL activity against COS7, Hek293 or 293T was that transfected with both URLC10 and HLA-A*0201 (FIG. 9-2).

These results clearly demonstrate that URLC10-A02-10-211 is naturally expressed on the target cell surface with HLA-A*0201 molecule and recognizes CTL. Furthermore, this peptide was epitope peptides, which may utilize cancer vaccine targeting URLC10 expressed tumors.

Homology Analysis of the Antigen Peptides

The CTL clones established against the following peptides showed potent specific CTL activity.

| | |
|---|---|
| CDH3-A24-9-513, | (SEQ ID NO: 19) |
| CDH3-A24-9-406, | (SEQ ID NO: 22) |
| CDH3-A24-10-807, | (SEQ ID NO: 30) |
| CDH3-A24-10-332, | (SEQ ID NO: 34) |
| CDH3-A24-10-655, | (SEQ ID NO: 344) |
| CDH3-A24-10-470, | (SEQ ID NO: 358) |
| EphA4-A24-9-453, | (SEQ ID NO: 41) |
| EphA4-A24-9-5, | (SEQ ID NO: 44) |
| EphA4-A24-9-869, | (SEQ ID NO: 46) |
| EphA4-A24-9-420, | (SEQ ID NO: 48) |
| EphA4-A24-9-10-24, | (SEQ ID NO: 78) |
| EphA4-A02-9-501, | (SEQ ID NO: 376) |
| EphA4-A02-9-165, | (SEQ ID NO: 379) |
| ECT2-A24-9-515, | (SEQ ID NO: 80) |
| ECT2-A24-10-40, | (SEQ ID NO: 100) |
| ECT2-A24-10-101, | (SEQ ID NO: 101) |
| HIG2-A24-9-19, | (SEQ ID NO: 110) |
| HIG2-A24-9-22, | (SEQ ID NO: 111) |
| HIG2-A24-9-8, | (SEQ ID NO: 387) |
| HIG2-A24-10-7, | (SEQ ID NO: 112) |
| HIG2-A24-10-18, | (SEQ ID NO: 394) |

-continued

| | |
|---|---|
| HIG2-A02-9-8, | (SEQ ID NO: 114) |
| HIG2-A02-9-15, | (SEQ ID NO: 116) |
| HIG2-A02-9-4, | (SEQ ID NO: 117) |
| HIG2-A02-10-8, | (SEQ ID NO: 121) |
| INHBB-A24-9-180, | (SEQ ID NO: 395) |
| INHBB-A24-10-180, | (SEQ ID NO: 133) |
| INHBB-A24-10-305, | (SEQ ID NO: 135) |
| INHBB-A24-10-7, | (SEQ ID NO: 137) |
| INHBB-A24-10-212, | (SEQ ID NO: 426) |
| KIF20A-A24-9-305, | (SEQ ID NO: 174) |
| KIF20A-A24-9-383, | (SEQ ID NO: 178) |
| KIF20A-A24-10-304, | (SEQ ID NO: 186) |
| KIF20A-A24-10-66, | (SEQ ID NO: 194) |
| KNTC2-A24-10-309, | (SEQ ID NO: 196) |
| KNTC2-A24-10-124, | (SEQ ID NO: 202) |
| KNTC2-A24-10-154, | (SEQ ID NO: 210) |
| KNTC2-A24-10-150, | (SEQ ID NO: 213) |
| KNTC2-A24-10-452, | (SEQ ID NO: 214) |
| KNTC2-A24-10-227, | (SEQ ID NO: 217) |
| KNTC2-A24-10-273, | (SEQ ID NO: 223) |
| TTK-A02-9-462, | (SEQ ID NO: 227) |
| TTK-A02-9-547, | (SEQ ID NO: 228) |
| TTK-A02-9-719, | (SEQ ID NO: 233) |
| TTK-A02-10-462, | (SEQ ID NO: 254) |
| URLC-A02-9-206, | (SEQ ID NO: 271) |
| URLC-A02-9-212 and | (SEQ ID NO: 272) |
| URLC-A02-10-211 | (SEQ ID NO: 288) |

This suggests that the sequences of SEQ ID NO: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 174, 178, 186, 194, 196, 202, 210, 213, 214, 217, 223, 227, 228, 233, 254, 271, 272 or 288 are homologous to the peptides derived from other molecules, which are known to sensitize human immune system.

To exclude this possibility, homology analysis was performed with the peptide sequences as queries using BLAST algorithm (http://www.ncbi.nlm.nih.gov/blast/blast.cgi). No significant sequence homology was revealed.

These results suggest that the sequences of SEQ ID NO: 19, 22, 30, 34, 344, 358, 41, 44, 46, 48, 78, 376, 379, 80, 100, 101, 110, 111, 387, 112, 394, 114, 116, 117, 121, 395, 133, 135, 137, 426, 174, 178, 186, 194, 196, 202, 210, 213, 214, 217, 223, 227, 228, 233, 254, 271, 272 or 288 are unique and thus possess a low risk of raising unintended immunologic response to any unrelated molecule.

Example 2

Materials and Methods

Cell Lines

H2 (HLA-A02), human B-lymphoblastoid cell line, and COS7 were purchased from ATCC.

Candidate Selection of Peptides Derived from INHBB 9-mer and 10-mer peptides derived from INHBB that bind to HLA-A*0201 molecules were predicted using binding prediction software "BIMAS" (www-bimas.cit.nih.gov/molbio/hla_bind), which algorithms had been described by Parker K C et al. (J Immunol 1994, 152(1): 163-75) and Kuzushima K et al. (Blood 2001, 98(6): 1872-81). These peptides were synthesized by Sigma (Sapporo, Japan) or Biosynthesis Inc. (Lewisville, Tex.) according to a standard solid phase synthesis method and purified by reversed phase high performance liquid chromatography (HPLC). The purity (>90%) and the identity of the peptides were determined by analytical HPLC and mass spectrometry analysis, respectively. Peptides were dissolved in dimethylsulfoxide (DMSO) at 20 mg/ml and stored at −80 degrees C.

In Vitro CTL Induction

Monocyte-derived dendritic cells (DCs) were used as antigen-presenting cells (APCs) to induce cytotoxic T lymphocyte (CTL) responses against peptides presented on human leukocyte antigen (HLA). DCs were generated in vitro as described elsewhere (Nakahara S et al., Cancer Res 2003 Jul. 15, 63(14): 4112-8). Specifically, peripheral blood mononuclear cells (PBMCs) isolated from a normal volunteer (HLA-A*0201 positive) by Ficoll-Plaque (Pharmacia) solution were separated by adherence to a plastic tissue culture dish (Becton Dickinson) so as to enrich them as the monocyte fraction. The monocyte-enriched population was cultured in the presence of 1000 U/ml of granulocyte-macrophage colony-stimulating factor (GM-CSF) (R&D System) and 1000 U/ml of interleukin (IL)-4 (R&D System) in AIM-V Medium (Invitrogen) containing 2% heat-inactivated autologous serum (AS). After 7 days of culture, the cytokine-induced DCs were pulsed with 20 mcg/ml of each of the synthesized peptides in the presence of 3 mcg/ml of beta2-microglobulin for 3 hr at 37 degrees C. in AIM-V Medium. The generated cells appeared to express DC-associated molecules, such as CD80, CD83, CD86 and HLA class II, on their cell surfaces (data not shown). These peptide-pulsed DCs were then inactivated by Mitomycin C (MMC) (30 mcg/ml for 30 min) and mixed at a 1:20 ratio with autologous CD8+ T cells, obtained by positive selection with CD8 Positive Isolation Kit (Dynal). These cultures were set up in 48-well plates (Corning); each well contained $1.5\times10^4$ peptide-pulsed DCs, $3\times10^5$ CD8+ T cells and 10 ng/ml of IL-7 (R&D System) in 0.5 ml of AIM-V/2% AS medium. Three days later, these cultures were supplemented with IL-2 (CHIRON) to a final concentration of 20 IU/ml. On day 7 and 14, the T cells were further stimulated with the autologous peptide-pulsed DCs. The DCs were prepared each time by the same way described above. CTL was tested against peptide-pulsed T2 cells after the 3rd round of peptide stimulation on day 21 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

CTL Expansion Procedure

CTLs were expanded in culture using the method similar to the one described by Riddell et al. (Walter E A et al., N Engl J Med 1995 Oct. 19, 333(16): 1038-44; Riddell S R et al., Nat Med 1996 Feb., 2(2): 216-23). A total of $5\times10^4$ CTLs were suspended in 25 ml of AIM-V/5% AS medium with 2 kinds of human B-lymphoblastoid cell lines, inactivated by MMC, in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS medium containing 30 IU/ml of IL-2 on days 5, 8 and 11 (Tanaka H et al., Br J Cancer 2001 Jan. 5, 84(1): 94-9; Umano Y et al., Br J Cancer 2001 Apr. 20, 84(8): 1052-7; Uchida N et al., Clin Cancer Res 2004 Dec. 15, 10(24): 8577-86; Suda T et al., Cancer Sci 2006 May, 97(5): 411-9; Watanabe T et al., Cancer Sci 2005 August, 96(8): 498-506).

Specific CTL Activity

To examine specific CTL activity, interferon (IFN)-gamma enzyme-linked immunospot (ELISPOT) assay and IFN-gamma enzyme-linked immunosorbent assay (ELISA) were performed. Specifically, peptide-pulsed T2 ($1\times10^4$/well) was prepared as stimulator cells. Cultured cells in 48 wells were used as responder cells. IFN-gamma ELISPOT assay and IFN-gamma ELISA assay were performed under manufacture procedure.

Results

Stimulation of the T Cells Using the Predicted Peptides from INHBB Restricted with HLA-A0201 and Establishment for CTL Lines Stimulated with INHBB Derived Peptides CTLs for those peptides derived from INHBB were generated according to the protocols set forth in "Materials and Methods" section above. Resulting CTLs having detectable specific CTL activity, as determined by IFN-gamma ELISPOT assay, are shown in FIG. 10. INHBB-A02-9-213 (SEQ ID NO: 143), INHBB-A02-9-174 (SEQ ID NO: 147), INHBB-A02-9-257 (SEQ ID NO: 148), INHBB-A02-9-313 (SEQ ID NO: 149), INHBB-A02-9-139 (SEQ ID NO: 150), INHBB-A02-9-8 (SEQ ID NO: 152), INHBB-A02-9-250 (SEQ ID NO: 153), INHBB-A02-10-179 (SEQ ID NO: 154), INHBB-A02-10-237 (SEQ ID NO: 156), INHBB-A02-10-313 (SEQ ID NO: 160), INHBB-A02-10-173 (SEQ ID NO: 161), INHBB-A02-10-256 (SEQ ID NO: 162), INHBB-A02-10-162 (SEQ ID NO: 163) and INHBB-A02-10-85 (SEQ ID NO: 166) demonstrated potent IFN-gamma production as compared to the control by IFN-gamma ELISPOT assay. Furthermore, the cells in the positive well number #7 stimulated with SEQ ID NO: 147, were expanded and CTL line was established. The CTL line having higher specific CTL activity against the peptide-pulsed target as compared to the activity against target without peptide pulse was determined by IFN-gamma ELISA (FIG. 11). The results herein demonstrate that the CTL line demonstrated potent IFN-gamma production against the target cells pulsed with corresponding peptide as compared to target cells without peptide pulse. In the context of the present invention, the peptides which could establish CTL line were selected as potent CTL stimulation peptide.

In conclusion, novel HLA-A02 epitope peptides derived from INHBB were identified and demonstrated to be applicable for cancer immunotherapy.

DISCUSSION

Identification of new TAAs, particularly those that induce potent and specific anti-tumor immune responses, warrants further development of the clinical application of peptide vaccination strategies in various types of cancer (Boon T. et al., (1996) J Exp Med 183: 725-9; van der Bruggen P et al., (1991) Science 254: 1643-7; Brichard V et al., (1993) J Exp Med 178: 489-95; Kawakami Y et al., (1994) J Exp Med 180: 347-52; Shichijo S et al., (1998) J Exp Med 187:277-88; Chen Y T et al., (1997) Proc. Natl. Acad. Sci. USA, 94: 1914-8; Harris C C., (1996) J Natl Cancer Inst 88:1442-5; Butterfield L H et al., (1999) Cancer Res 59:3134-42; Vissers J L et al., (1999) Cancer Res 59: 5554-9; van der Burg S H et al., (1996) J. Immunol 156:3308-14; Tanaka F et al., (1997) Cancer Res 57:4465-8; Fujie T et al., (1999) Int J Cancer 80:169-72; Kikuchi M et al., (1999) Int J Cancer 81: 459-66; Oiso M et al., (1999) Int J Cancer 81:387-94.).

cDNA microarray technologies can disclose comprehensive profiles of gene expression of malignant cells (Lin Y M, et al., Oncogene. 2002 Jun. 13; 21:4120-8; Kitahara O, et al., Cancer Res. 2001 May 1; 61:3544-9; Suzuki C, et al., Cancer Res. 2003 Nov. 1; 63:7038-41; Ashida S, Cancer Res. 2004 Sep. 1; 64:5963-72; Ochi K, et al., Int J Oncol. 2004 March; 24(3):647-55; Kaneta Y, et al., Int J Oncol. 2003 September; 23:681-91; Obama K, Hepatology. 2005 June; 41:1339-48; Kato T, et al., Cancer Res. 2005 Jul. 1; 65:5638-46; Kitahara O, et al., Neoplasia. 2002 July-August; 4:295-303; Saito-Hisaminato A et al., DNA Res 2002, 9: 35-45.) and, find utility in the identification of potential TAAs. Among the transcripts that are up-regulated in various cancers, novel human genes, termed CDH3, EPHA4, ECT2, HIG2, INHBB, KIF20A, KNTC2, TTK and URLC10, were identified using these technologies.

As demonstrated above, CDH3, EPHA4, ECT2, HIG2, INHBB, KIF20A, KNTC2, TTK and URLC10, are overexpressed in various cancers but show minimal expression in normal tissues. In addition, these genes have been shown to have a significant function related to cell proliferation. Thus, peptides derived from CDH3, EPHA4, ECT2, HIG2, INHBB, KIF20A, KNTC2, TTK and URLC10 can serve as TAA epitopes, which, in turn, can be used to induce significant and specific immune responses against cancer cells.

Thus, as CDH3, EPHA4, ECT2, HIG2, INHBB, KIF20A, KNTC2, TTK and URLC10 are novel TAAs, vaccines using these epitope peptides find utility as immunotherapeutics against various carcinomas or other disease expressing these molecules.

INDUSTRIAL APPLICABILITY

The present invention identifies new TAAs, particularly those which induce potent and specific anti-tumor immune responses. Such TAAs warrants further development as peptide vaccines against diseases associated with the over-expression of CDH3, EPHA4, ECT2, HIG2, INHBB, KIF20A, KNTC2, TTK and/or, URLC10 e.g. cancers. All patents, patent applications, and publications cited herein are incorporated by reference.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

[Sequence list] ONC-A0704Psq.txt

What is claimed is:

1. An isolated peptide of (a) or (b) below:
   (a) an isolated peptide of less than about 15 amino acids having cytotoxic T cell inducibility, said peptide comprising the amino acid sequence of SEQ ID NO: 174;
   (b) an isolated peptide of less than about 15 amino acids having cytotoxic T cell inducibility, wherein said peptide comprises an amino acid sequence of SEQ ID NO: 174 in which 1 or 2 amino acids are substituted, deleted, or added.

2. The peptide of claim 1, wherein the peptide is selected from the group consisting of:
   (a) an isolated peptide consisting of the amino acid sequence of SEQ ID NO: 174; and (b) an isolated peptide having cytotoxic T cell inducibility, wherein said peptide consists of an amino acid sequence of SEQ ID NO: 174 in which 1 or 2 amino acids are substituted, deleted, or added.

3. The peptide of claim 1, wherein the second amino acid from the N-terminus is phenylalanine, tyrosine, methionine, or tryptophan.

4. The peptide of claim 1, wherein the C-terminal amino acid is phenylalanine, leucine, isoleucine, tryptophan, or methionine.

5. The peptide of claim 3, wherein the C-terminal amino acid is phenylalanine, leucine, isoleucine, tryptophan, or methionine.

6. A pharmaceutical composition comprising a peptide of claim 1.

7. A method of inducing antigen-presenting cells having a high cytotoxic T cell inducibility, said method comprising the step of contacting an antigen-presenting cell with a peptide of claim 1.

8. A method of inducing cytotoxic T cells by contacting a T cell with a peptide of claim 1.

9. A method of inducing antigen-presenting cells having high cytotoxic T cell inducibility, said method comprising the step of transferring a gene comprising a polynucleotide encoding a peptide of claim 1 to an antigen-presenting cell.

10. A method of inducing a cytotoxic T cell, said method comprising the steps of:
    (a) contacting an antigen-presenting cell with a peptide of claim 1, and
    (b) mixing the antigen-presenting cells of step (a) with a CD8$^+$ T cell and co-culturing.

11. A composition for inducing an immune response against a cell expressing the gene of SEQ ID NO: 11, wherein the composition comprises a peptide of claim 1 as an active ingredient.

12. The composition of claim 11, wherein the cell expressing the gene of SEQ ID NO: 11 is a cancer cell.

13. The composition of claim 12, wherein the cancer is selected from the group consisting of bladder cancer, breast cancer, cervical cancer, cholangiocellular carcinoma, CML, colorectal cancer, endometriosis, esophageal cancer, gastric cancer, diffused type gastric cancer, liver cancer, NSCLC, lymphoma, osteosarcoma, ovarian cancer, pancreatic cancer, prostate cancer, renal carcinoma, SCLC, soft tissue tumor and testicular tumor.

14. The composition of claim 13, formulated for administration to a subject whose HLA antigen is HLA-A24.

* * * * *

```
SEQUENCE LISTING

<160> NUMBER OF SEQ ID NOS: 436

<210> SEQ ID NO 1
<211> LENGTH: 3649
<212> TYPE: DNA
<213> ORGANISM: Homo sapiens
<220> FEATURE:
<221> NAME/KEY: CDS
<222> LOCATION: (508)..(2997)

<400> SEQUENCE: 1
cccgctgtag ccgcgtgtgg gaggacgcac gggcctgctt caaagctttg ggataacagc      60
gcctccgggg gataatgaat gcggagcctc cgttttcagt cgacttcaga tgtgtctcca     120
cttttttccg ctgtagccgc aaggcaagga aacatttctc ttcccgtact gaggaggctg     180
aggagtgcac tgggtgttct tttctcctct aacccagaac tgcgagacag aggctgagtc     240
cctgtaaaga acagctccag aaaagccagg agagcgcagg agggcatccg ggaggccagg     300
aggggttcgc tggggcctca accgcaccca catcggtccc acctgcgagg gggcgggacc     360
tcgtggcgct ggaccaatca gcacccacct gcgctcacct ggcctcctcc cgctggctcc     420 cggggggctgc ggtgctcaaa ggggcaagag ctgagcggaa caccgcccg ccgtcgcggc      480 agctgcttca cccctctctc tgcagcc atg ggg ctc cct cgt gga cct ctc gcg     534
                               Met Gly Leu Pro Arg Gly Pro Leu Ala
                                 1               5 tct ctc ctc ctt ctc cag gtt tgc tgg ctg cag tgc gcg gcc tcc gag       582
Ser Leu Leu Leu Leu Gln Val Cys Trp Leu Gln Cys Ala Ala Ser Glu
 10                  15                  20                  25 ccg tgc cgg gcg gtc ttc agg gag gct gaa gtg acc ttg gag gcg gga       630
Pro Cys Arg Ala Val Phe Arg Glu Ala Glu Val Thr Leu Glu Ala Gly
                 30                  35                  40 ggc gcg gag cag gag ccc ggc cag gcg ctg ggg aaa gta ttc atg ggc       678
Gly Ala Glu Gln Glu Pro Gly Gln Ala Leu Gly Lys Val Phe Met Gly
             45                  50                  55 tgc cct ggg caa gag cca gct ctg ttt agc act gat aat gat gac ttc       726
Cys Pro Gly Gln Glu Pro Ala Leu Phe Ser Thr Asp Asn Asp Asp Phe
         60                  65                  70 act gtg cgg aat ggc gag aca gtc cag gaa aga agg tca ctg aag gaa       774
Thr Val Arg Asn Gly Glu Thr Val Gln Glu Arg Arg Ser Leu Lys Glu
     75                  80                  85 agg aat cca ttg aag atc ttc cca tcc aaa cgt atc tta cga aga cac       822
Arg Asn Pro Leu Lys Ile Phe Pro Ser Lys Arg Ile Leu Arg Arg His
 90                  95                 100                 105 aag aga gat tgg gtg gtt gct cca ata tct gtc cct gaa aat ggc aag       870
Lys Arg Asp Trp Val Val Ala Pro Ile Ser Val Pro Glu Asn Gly Lys
                110                 115                 120 ggt ccc ttc ccc cag aga ctg aat cag ctc aag tct aat aaa gat aga       918
Gly Pro Phe Pro Gln Arg Leu Asn Gln Leu Lys Ser Asn Lys Asp Arg
            125                 130                 135 gac acc aag att ttc tac agc atc acg ggg ccg ggg gca gac agc ccc       966
```

```
              Asp Thr Lys Ile Phe Tyr Ser Ile Thr Gly Pro Gly Ala Asp Ser Pro
                      140                 145                 150 cct gag ggt gtc ttc gct gta gag aag gag aca ggc tgg ttg ttg ttg        1014
Pro Glu Gly Val Phe Ala Val Glu Lys Glu Thr Gly Trp Leu Leu Leu
    155                 160                 165 aat aag cca ctg gac cgg gag gag att gcc aag tat gag ctc ttt ggc        1062
Asn Lys Pro Leu Asp Arg Glu Glu Ile Ala Lys Tyr Glu Leu Phe Gly
170                 175                 180                 185 cac gct gtg tca gag aat ggt gcc tca gtg gag gac ccc atg aac atc        1110
His Ala Val Ser Glu Asn Gly Ala Ser Val Glu Asp Pro Met Asn Ile
                190                 195                 200 tcc atc atc gtg acc gac cag aat gac cac aag ccc aag ttt acc cag        1158
Ser Ile Ile Val Thr Asp Gln Asn Asp His Lys Pro Lys Phe Thr Gln
            205                 210                 215 gac acc ttc cga ggg agt gtc tta gag gga gtc cta cca ggt act tct        1206
Asp Thr Phe Arg Gly Ser Val Leu Glu Gly Val Leu Pro Gly Thr Ser
        220                 225                 230 gtg atg cag gtg aca gcc acg gat gag gat gat gcc atc tac acc tac        1254
Val Met Gln Val Thr Ala Thr Asp Glu Asp Asp Ala Ile Tyr Thr Tyr
235                 240                 245 aat ggg gtg gtt gct tac tcc atc cat agc caa gaa cca aag gac cca        1302
Asn Gly Val Val Ala Tyr Ser Ile His Ser Gln Glu Pro Lys Asp Pro
250                 255                 260                 265 cac gac ctc atg ttc acc att cac cgg agc aca ggc acc atc agc gtc        1350
His Asp Leu Met Phe Thr Ile His Arg Ser Thr Gly Thr Ile Ser Val
                270                 275                 280 atc tcc agt ggc ctg gac cgg gaa aaa gtc cct gag tac aca ctg acc        1398
Ile Ser Ser Gly Leu Asp Arg Glu Lys Val Pro Glu Tyr Thr Leu Thr
            285                 290                 295 atc cag gcc aca gac atg gat ggg gac ggc tcc acc acc acg gca gtg        1446
Ile Gln Ala Thr Asp Met Asp Gly Asp Gly Ser Thr Thr Thr Ala Val
        300                 305                 310 gca gta gtg gag atc ctt gat gcc aat gac aat gct ccc atg ttt gac        1494
Ala Val Val Glu Ile Leu Asp Ala Asn Asp Asn Ala Pro Met Phe Asp
315                 320                 325 ccc cag aag tac gag gcc cat gtg cct gag aat gca gtg ggc cat gag        1542
Pro Gln Lys Tyr Glu Ala His Val Pro Glu Asn Ala Val Gly His Glu
330                 335                 340                 345 gtg cag agg ctg acg gtc act gat ctg gac gcc ccc aac tca cca gcg        1590
Val Gln Arg Leu Thr Val Thr Asp Leu Asp Ala Pro Asn Ser Pro Ala
                350                 355                 360 tgg cgt gcc acc tac ctt atc atg ggc ggt gac gac ggg gac cat ttt        1638
Trp Arg Ala Thr Tyr Leu Ile Met Gly Gly Asp Asp Gly Asp His Phe
            365                 370                 375 acc atc acc acc cac cct gag agc aac cag ggc atc ctg aca acc agg        1686
Thr Ile Thr Thr His Pro Glu Ser Asn Gln Gly Ile Leu Thr Thr Arg
        380                 385                 390 aag ggt ttg gat ttt gag gcc aaa aac cag cac acc ctg tac gtt gaa        1734
Lys Gly Leu Asp Phe Glu Ala Lys Asn Gln His Thr Leu Tyr Val Glu
395                 400                 405 gtg acc aac gag gcc cct ttt gtg ctg aag ctc cca acc tcc aca gcc        1782
Val Thr Asn Glu Ala Pro Phe Val Leu Lys Leu Pro Thr Ser Thr Ala
410                 415                 420                 425 acc ata gtg gtc cac gtg gag gat gtg aat gag gca cct gtg ttt gtc        1830
Thr Ile Val Val His Val Glu Asp Val Asn Glu Ala Pro Val Phe Val
                430                 435                 440 cca ccc tcc aaa gtc gtt gag gtc cag gag ggc atc ccc act ggg gag        1878
Pro Pro Ser Lys Val Val Glu Val Gln Glu Gly Ile Pro Thr Gly Glu
            445                 450                 455 cct gtg tgt gtc tac act gca gaa gac cct gac aag gag aat caa aag        1926
```

```
                Pro Val Cys Val Tyr Thr Ala Glu Asp Pro Asp Lys Glu Asn Gln Lys
                            460                 465                 470 atc agc tac cgc atc ctg aga gac cca gca ggg tgg cta gcc atg gac       1974
Ile Ser Tyr Arg Ile Leu Arg Asp Pro Ala Gly Trp Leu Ala Met Asp
475                 480                 485 cca gac agt ggg cag gtc aca gct gtg ggc acc ctc gac cgt gag gat       2022
Pro Asp Ser Gly Gln Val Thr Ala Val Gly Thr Leu Asp Arg Glu Asp
490                 495                 500                 505 gag cag ttt gtg agg aac aac atc tat gaa gtc atg gtc ttg gcc atg       2070
Glu Gln Phe Val Arg Asn Asn Ile Tyr Glu Val Met Val Leu Ala Met
                510                 515                 520 gac aat gga agc cct ccc acc act ggc acg gga acc ctt ctg cta aca       2118
Asp Asn Gly Ser Pro Pro Thr Thr Gly Thr Gly Thr Leu Leu Leu Thr
                    525                 530                 535 ctg att gat gtc aat gac cat ggc cca gtc cct gag ccc cgt cag atc       2166
Leu Ile Asp Val Asn Asp His Gly Pro Val Pro Glu Pro Arg Gln Ile
                540                 545                 550 acc atc tgc aac caa agc cct gtg cgc cag gtg ctg aac atc acg gac       2214
Thr Ile Cys Asn Gln Ser Pro Val Arg Gln Val Leu Asn Ile Thr Asp
555                 560                 565 aag gac ctg tct ccc cac acc tcc cct ttc cag gcc cag ctc aca gat       2262
Lys Asp Leu Ser Pro His Thr Ser Pro Phe Gln Ala Gln Leu Thr Asp
570                 575                 580                 585 gac tca gac atc tac tgg acg gca gag gtc aac gag gaa ggt gac aca       2310
Asp Ser Asp Ile Tyr Trp Thr Ala Glu Val Asn Glu Glu Gly Asp Thr
                590                 595                 600 gtg gtc ttg tcc ctg aag aag ttc ctg aag cag gat aca tat gac gtg       2358
Val Val Leu Ser Leu Lys Lys Phe Leu Lys Gln Asp Thr Tyr Asp Val
                    605                 610                 615 cac ctt tct ctg tct gac cat ggc aac aaa gag cag ctg acg gtg atc       2406
His Leu Ser Leu Ser Asp His Gly Asn Lys Glu Gln Leu Thr Val Ile
                620                 625                 630 agg gcc act gtg tgc gac tgc cat ggc cat gtc gaa acc tgc cct gga       2454
Arg Ala Thr Val Cys Asp Cys His Gly His Val Glu Thr Cys Pro Gly
                635                 640                 645 ccc tgg aag gga ggt ttc atc ctc cct gtg ctg ggg gct gtc ctg gct       2502
Pro Trp Lys Gly Gly Phe Ile Leu Pro Val Leu Gly Ala Val Leu Ala
650                 655                 660                 665 ctg ctg ttc ctc ctg ctg gtg ctg ctt ttg ttg gtg aga aag aag cgg       2550
Leu Leu Phe Leu Leu Leu Val Leu Leu Leu Val Arg Lys Lys Arg
                    670                 675                 680 aag atc aag gag ccc ctc cta ctc cca gaa gat gac acc cgt gac aac       2598
Lys Ile Lys Glu Pro Leu Leu Leu Pro Glu Asp Asp Thr Arg Asp Asn
                685                 690                 695 gtc ttc tac tat ggc gaa gag ggg ggt ggc gaa gag gac cag gac tat       2646
Val Phe Tyr Tyr Gly Glu Glu Gly Gly Gly Glu Glu Asp Gln Asp Tyr
                700                 705                 710 gac atc acc cag ctc cac cga ggt ctg gag gcc agg ccg gag gtg gtt       2694
Asp Ile Thr Gln Leu His Arg Gly Leu Glu Ala Arg Pro Glu Val Val
                    715                 720                 725 ctc cgc aat gac gtg gca cca acc atc atc ccg aca ccc atg tac cgt       2742
Leu Arg Asn Asp Val Ala Pro Thr Ile Ile Pro Thr Pro Met Tyr Arg
730                 735                 740                 745 cct cgg cca gcc aac cca gat gaa atc ggc aac ttt ata att gag aac       2790
Pro Arg Pro Ala Asn Pro Asp Glu Ile Gly Asn Phe Ile Ile Glu Asn
                    750                 755                 760 ctg aag gcg gct aac aca gac ccc aca gcc ccg ccc tac gac acc ctc       2838
Leu Lys Ala Ala Asn Thr Asp Pro Thr Ala Pro Pro Tyr Asp Thr Leu
                765                 770                 775 ttg gtg ttc gac tat gag ggc agc ggc tcc gac gcc gcg tcc ctg agc       2886
```

```
Leu Val Phe Asp Tyr Glu Gly Ser Gly Ser Asp Ala Ala Ser Leu Ser
            780                 785                 790 tcc ctc acc tcc tcc gcc tcc gac caa gac caa gat tac gat tat ctg    2934
Ser Leu Thr Ser Ser Ala Ser Asp Gln Asp Gln Asp Tyr Asp Tyr Leu
        795                 800                 805 aac gag tgg ggc agc cgc ttc aag aag ctg gca gac atg tac ggt ggc    2982
Asn Glu Trp Gly Ser Arg Phe Lys Lys Leu Ala Asp Met Tyr Gly Gly
810                 815                 820                 825 ggg gag gac gac tag gcggcctgcc tgcagggctg gggaccaaac gtcaggccac    3037
Gly Glu Asp Asp agagcatctc caaggggtct cagttccccc ttcagctgag gacttcggag cttgtcagga    3097
agtggccgta gcaacttggc ggagacaggc tatgagtctg acgttagagt ggtggcttcc    3157
ttagcctttc aggatggagg aatgtgggca gtttgacttc agcactgaaa acctctccac    3217
ctgggccagg gttgcctcag aggccaagtt tccagaagcc tcttacctgc cgtaaaatgc    3277
tcaaccctgt gtcctgggcc tgggcctgct gtgactgacc tacagtggac tttctctctg    3337
gaatggaacc ttcttaggcc tcctggtgca acttaatttt ttttttttaat gctatcttca    3397 aaacgttaga gaaagttctt caaaagtgca gcccagagct gctgggccca ctggccgtcc    3457
tgcatttctg gtttccagac cccaatgcct cccattcgga tggatctctg cgttttata    3517 ctgagtgtgc ctaggttgcc ccttattttt tattttccct gttgcgttgc tatagatgaa    3577
gggtgaggac aatcgtgtat atgtactaga acttttttat taaagaaact tttcccagaa    3637
aaaaaaaaaa aa                                                      3649

<210> SEQ ID NO 2
<211> LENGTH: 829
<212> TYPE: PRT
<213> ORGANISM: Homo sapiens

<400> SEQUENCE: 2

Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Glu Pro Gly
        35                  40                  45

Gln Ala Leu Gly Lys Val Phe Met Gly Cys Pro Gly Gln Glu Pro Ala
    50                  55                  60

Leu Phe Ser Thr Asp Asn Asp Asp Phe Thr Val Arg Asn Gly Glu Thr
65                  70                  75                  80

Val Gln Glu Arg Arg Ser Leu Lys Glu Arg Asn Pro Leu Lys Ile Phe
                85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
    130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190
```

-continued

Ala Ser Val Glu Asp Pro Met Asn Ile Ser Ile Val Thr Asp Gln
        195                 200                 205

Asn Asp His Lys Pro Lys Phe Thr Gln Asp Thr Phe Arg Gly Ser Val
210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
                260                 265                 270

His Arg Ser Thr Gly Thr Ile Ser Val Ile Ser Ser Gly Leu Asp Arg
            275                 280                 285

Glu Lys Val Pro Glu Tyr Thr Leu Thr Ile Gln Ala Thr Asp Met Asp
            290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
            355                 360                 365

Met Gly Gly Asp Asp Gly Asp His Phe Thr Ile Thr Thr His Pro Glu
370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                405                 410                 415

Val Leu Lys Leu Pro Thr Ser Thr Ala Thr Ile Val Val His Val Glu
            420                 425                 430

Asp Val Asn Glu Ala Pro Val Phe Val Pro Pro Ser Lys Val Val Glu
        435                 440                 445

Val Gln Glu Gly Ile Pro Thr Gly Glu Pro Val Cys Val Tyr Thr Ala
    450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495

Ala Val Gly Thr Leu Asp Arg Glu Asp Glu Gln Phe Val Arg Asn Asn
            500                 505                 510

Ile Tyr Glu Val Met Val Leu Ala Met Asp Asn Gly Ser Pro Pro Thr
            515                 520                 525

Thr Gly Thr Gly Thr Leu Leu Leu Thr Leu Ile Asp Val Asn Asp His
530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
                565                 570                 575

Ser Pro Phe Gln Ala Gln Leu Thr Asp Asp Ser Asp Ile Tyr Trp Thr
            580                 585                 590

Ala Glu Val Asn Glu Glu Gly Asp Thr Val Val Leu Ser Leu Lys Lys
            595                 600                 605

Phe Leu Lys Gln Asp Thr Tyr Asp Val His Leu Ser Leu Ser Asp His
610                 615                 620

```
Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
            645                 650                 655

Leu Pro Val Leu Gly Ala Val Leu Ala Leu Leu Phe Leu Leu Leu Val
                660                 665                 670

Leu Leu Leu Leu Val Arg Lys Lys Arg Lys Ile Lys Glu Pro Leu Leu
            675                 680                 685

Leu Pro Glu Asp Asp Thr Arg Asp Asn Val Phe Tyr Tyr Gly Glu Glu
        690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
            740                 745                 750

Glu Ile Gly Asn Phe Ile Ile Glu Asn Leu Lys Ala Ala Asn Thr Asp
        755                 760                 765

Pro Thr Ala Pro Pro Tyr Asp Thr Leu Leu Val Phe Asp Tyr Glu Gly
    770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
            820                 825

<210> SEQ ID NO 3
<211> LENGTH: 3107
<212> TYPE: DNA
<213> ORGANISM: Homo sapiens
<220> FEATURE:
<221> NAME/KEY: CDS
<222> LOCATION: (34)..(2994)

<400> SEQUENCE: 3
aagcggcagg agcagcgttg gcaccggcga acc atg gct ggg att ttc tat ttc      54
                                    Met Ala Gly Ile Phe Tyr Phe
                                    1               5 gcc cta ttt tcg tgt ctc ttc ggg att tgc gac gct gtc aca ggt tcc     102
Ala Leu Phe Ser Cys Leu Phe Gly Ile Cys Asp Ala Val Thr Gly Ser
        10                  15                  20 agg gta tac ccc gcg aat gaa gtt acc tta ttg gat tcc aga tct gtt     150
Arg Val Tyr Pro Ala Asn Glu Val Thr Leu Leu Asp Ser Arg Ser Val
25                  30                  35 cag gga gaa ctt ggg tgg ata gca agc cct ctg gaa gga ggg tgg gag     198
Gln Gly Glu Leu Gly Trp Ile Ala Ser Pro Leu Glu Gly Gly Trp Glu
40                  45                  50                  55 gaa gtg agt atc atg gat gaa aaa aat aca cca atc cga acc tac caa     246
Glu Val Ser Ile Met Asp Glu Lys Asn Thr Pro Ile Arg Thr Tyr Gln
                60                  65                  70 gtg tgc aat gtg atg gaa ccc agc cag aat aac tgg cta cga act gat     294
Val Cys Asn Val Met Glu Pro Ser Gln Asn Asn Trp Leu Arg Thr Asp
            75                  80                  85 tgg atc acc cga gaa ggg gct cag agg gtg tat att gag att aaa ttc     342
Trp Ile Thr Arg Glu Gly Ala Gln Arg Val Tyr Ile Glu Ile Lys Phe
        90                  95                  100 acc ttg agg gac tgc aat agt ctt ccg ggc gtc atg ggg act tgc aag     390
```

```
            Thr Leu Arg Asp Cys Asn Ser Leu Pro Gly Val Met Gly Thr Cys Lys
                105                 110                 115 gag acg ttt aac ctg tac tac tat gaa tca gac aac gac aaa gag cgt       438
Glu Thr Phe Asn Leu Tyr Tyr Tyr Glu Ser Asp Asn Asp Lys Glu Arg
120                 125                 130                 135 ttc atc aga gag aac cag ttt gtc aaa att gac acc att gct gct gat       486
Phe Ile Arg Glu Asn Gln Phe Val Lys Ile Asp Thr Ile Ala Ala Asp
                140                 145                 150 gag agc ttc acc caa gtg gac att ggt gac aga atc atg aag ctg aac       534
Glu Ser Phe Thr Gln Val Asp Ile Gly Asp Arg Ile Met Lys Leu Asn
        155                 160                 165 acc gag atc cgg gat gta ggg cca tta agc aaa aag ggg ttt tac ctg       582
Thr Glu Ile Arg Asp Val Gly Pro Leu Ser Lys Lys Gly Phe Tyr Leu
                170                 175                 180 gct ttt cag gat gtg ggg gcc tgc atc gcc ctg gta tca gtc cgt gtg       630
Ala Phe Gln Asp Val Gly Ala Cys Ile Ala Leu Val Ser Val Arg Val
185                 190                 195 ttc tat aaa aag tgt cca ctc aca gtc cgc aat ctg gcc cag ttt cct       678
Phe Tyr Lys Lys Cys Pro Leu Thr Val Arg Asn Leu Ala Gln Phe Pro
200                 205                 210                 215 gac acc atc aca ggg gct gat acg tct tcc ctg gtg gaa gtt cga ggc       726
Asp Thr Ile Thr Gly Ala Asp Thr Ser Ser Leu Val Glu Val Arg Gly
                220                 225                 230 tcc tgt gtc aac aac tca gaa gag aaa gat gtg cca aaa atg tac tgt       774
Ser Cys Val Asn Asn Ser Glu Glu Lys Asp Val Pro Lys Met Tyr Cys
                235                 240                 245 ggg gca gat ggt gaa tgg ctg gta ccc att ggc aac tgc cta tgc aac       822
Gly Ala Asp Gly Glu Trp Leu Val Pro Ile Gly Asn Cys Leu Cys Asn
        250                 255                 260 gct ggg cat gag gag cgg agc gga gaa tgc caa gct tgc aaa att gga       870
Ala Gly His Glu Glu Arg Ser Gly Glu Cys Gln Ala Cys Lys Ile Gly
265                 270                 275 tat tac aag gct ctc tcc acg gat gcc acc tgt gcc aag tgc cca ccc       918
Tyr Tyr Lys Ala Leu Ser Thr Asp Ala Thr Cys Ala Lys Cys Pro Pro
280                 285                 290                 295 cac agc tac tct gtc tgg gaa gga gcc acc tcg tgc acc tgt gac cga       966
His Ser Tyr Ser Val Trp Glu Gly Ala Thr Ser Cys Thr Cys Asp Arg
                300                 305                 310 ggc ttt ttc aga gct gac aac gat gct gcc tct atg ccc tgc acc cgt      1014
Gly Phe Phe Arg Ala Asp Asn Asp Ala Ala Ser Met Pro Cys Thr Arg
                315                 320                 325 cca cca tct gct ccc ctg aac ttg att tca aat gtc aac gag aca tct      1062
Pro Pro Ser Ala Pro Leu Asn Leu Ile Ser Asn Val Asn Glu Thr Ser
        330                 335                 340 gtg aac ttg gaa tgg agt agc cct cag aat aca ggt ggc cgc cag gac      1110
Val Asn Leu Glu Trp Ser Ser Pro Gln Asn Thr Gly Gly Arg Gln Asp
345                 350                 355 att tcc tat aat gtg gta tgc aag aaa tgt gga gct ggt gac ccc agc      1158
Ile Ser Tyr Asn Val Val Cys Lys Lys Cys Gly Ala Gly Asp Pro Ser
360                 365                 370                 375 aag tgc cga ccc tgt gga agt ggg gtc cac tac acc cca cag cag aat      1206
Lys Cys Arg Pro Cys Gly Ser Gly Val His Tyr Thr Pro Gln Gln Asn
                380                 385                 390 ggc ttg aag acc acc aaa gtc tcc atc act gac ctc cta gct cat acc      1254
Gly Leu Lys Thr Thr Lys Val Ser Ile Thr Asp Leu Leu Ala His Thr
        395                 400                 405 aat tac acc ttt gaa atc tgg gct gtg aat gga gtg tcc aaa tat aac      1302
Asn Tyr Thr Phe Glu Ile Trp Ala Val Asn Gly Val Ser Lys Tyr Asn
                410                 415                 420 cct aac cca gac caa tca gtt tct gtc act gtg acc acc aac caa gca      1350
```

|     |     |     |     |     |     |     |     |     |     |     |     |     |     |      |
| --- | --- | --- | --- | --- | --- | --- | --- | --- | --- | --- | --- | --- | --- | ---- |
| Pro | Asn | Pro | Asp | Gln | Ser | Val | Ser | Val | Thr | Val | Thr | Thr | Asn | Gln Ala |
|     | 425 |     |     |     | 430 |     |     |     | 435 |     |     |     |     |      |

```
gca cca tca tcc att gct ttg gtc cag gct aaa gaa gtc aca aga tac      1398
Ala Pro Ser Ser Ile Ala Leu Val Gln Ala Lys Glu Val Thr Arg Tyr
440             445                 450                 455 agt gtg gca ctg gct tgg ctg gaa cca gat cgg ccc aat ggg gta atc      1446
Ser Val Ala Leu Ala Trp Leu Glu Pro Asp Arg Pro Asn Gly Val Ile
                460                 465                 470 ctg gaa tat gaa gtc aag tat tat gag aag gat cag aat gag cga agc      1494
Leu Glu Tyr Glu Val Lys Tyr Tyr Glu Lys Asp Gln Asn Glu Arg Ser
            475                 480                 485 tat cgt ata gtt cgg aca gct gcc agg aac aca gat atc aaa ggc ctg      1542
Tyr Arg Ile Val Arg Thr Ala Ala Arg Asn Thr Asp Ile Lys Gly Leu
        490                 495                 500 aac cct ctc act tcc tat gtt ttc cac gtg cga gcc agg aca gca gct      1590
Asn Pro Leu Thr Ser Tyr Val Phe His Val Arg Ala Arg Thr Ala Ala
    505                 510                 515 ggc tat gga gac ttc agt gag ccc ttg gag gtt aca acc aac aca gtg      1638
Gly Tyr Gly Asp Phe Ser Glu Pro Leu Glu Val Thr Thr Asn Thr Val
520                 525                 530                 535 cct tcc cgg atc att gga gat ggg gct aac tcc aca gtc ctt ctg gtc      1686
Pro Ser Arg Ile Ile Gly Asp Gly Ala Asn Ser Thr Val Leu Leu Val
                540                 545                 550 tct gtc tcg ggc agt gtg gtg ctg gtg gta att ctc att gca gct ttt      1734
Ser Val Ser Gly Ser Val Val Leu Val Val Ile Leu Ile Ala Ala Phe
            555                 560                 565 gtc atc agc cgg aga cgg agt aaa tac agt aaa gcc aaa caa gaa gcg      1782
Val Ile Ser Arg Arg Arg Ser Lys Tyr Ser Lys Ala Lys Gln Glu Ala
        570                 575                 580 gat gaa gag aaa cat ttg aat caa ggt gta aga aca tat gtg gac ccc      1830
Asp Glu Glu Lys His Leu Asn Gln Gly Val Arg Thr Tyr Val Asp Pro
    585                 590                 595 ttt acg tac gaa gat ccc aac caa gca gtg cga gag ttt gcc aaa gaa      1878
Phe Thr Tyr Glu Asp Pro Asn Gln Ala Val Arg Glu Phe Ala Lys Glu
600                 605                 610                 615 att gac gca tcc tgc att aag att gaa aaa gtt ata gga gtt ggt gaa      1926
Ile Asp Ala Ser Cys Ile Lys Ile Glu Lys Val Ile Gly Val Gly Glu
                620                 625                 630 ttt ggt gag gta tgc agt ggg cgt ctc aaa gtg cct ggc aag aga gag      1974
Phe Gly Glu Val Cys Ser Gly Arg Leu Lys Val Pro Gly Lys Arg Glu
            635                 640                 645 atc tgt gtg gct atc aag act ctg aaa gct ggt tat aca gac aaa cag      2022
Ile Cys Val Ala Ile Lys Thr Leu Lys Ala Gly Tyr Thr Asp Lys Gln
        650                 655                 660 agg aga gac ttc ctg agt gag gcc agc atc atg gga cag ttt gac cat      2070
Arg Arg Asp Phe Leu Ser Glu Ala Ser Ile Met Gly Gln Phe Asp His
    665                 670                 675 ccg aac atc att cac ttg gaa ggc gtg gtc act aaa tgt aaa cca gta      2118
Pro Asn Ile Ile His Leu Glu Gly Val Val Thr Lys Cys Lys Pro Val
680                 685                 690                 695 atg atc ata aca gag tac atg gag aat ggc tcc ttg gat gca ttc ctc      2166
Met Ile Ile Thr Glu Tyr Met Glu Asn Gly Ser Leu Asp Ala Phe Leu
                700                 705                 710 agg aaa aat gat ggc aga ttt aca gtc att cag ctg gtg ggc atg ctt      2214
Arg Lys Asn Asp Gly Arg Phe Thr Val Ile Gln Leu Val Gly Met Leu
            715                 720                 725 cgt ggc att ggg tct ggg atg aag tat tta tct gat atg agc tat gtg      2262
Arg Gly Ile Gly Ser Gly Met Lys Tyr Leu Ser Asp Met Ser Tyr Val
        730                 735                 740 cat cgt gat ctg gcc gca cgg aac atc ctg gtg aac agc aac ttg gtc      2310
```

-continued

| | | |
|---|---|---|
| His Arg Asp Leu Ala Ala Arg Asn Ile Leu Val Asn Ser Asn Leu Val<br>745 750 755 | | |
| tgc aaa gtg tct gat ttt ggc atg tcc cga gtg ctt gag gat gat ccg<br>Cys Lys Val Ser Asp Phe Gly Met Ser Arg Val Leu Glu Asp Asp Pro<br>760 765 770 775 | 2358 | |
| gaa gca gct tac acc acc agg ggt ggc aag att cct atc cgg tgg act<br>Glu Ala Ala Tyr Thr Thr Arg Gly Gly Lys Ile Pro Ile Arg Trp Thr<br>780 785 790 | 2406 | |
| gcg cca gaa gca att gcc tat cgt aaa ttc aca tca gca agt gat gta<br>Ala Pro Glu Ala Ile Ala Tyr Arg Lys Phe Thr Ser Ala Ser Asp Val<br>795 800 805 | 2454 | |
| tgg agc tat gga atc gtt atg tgg gaa gtg atg tcg tac ggg gag agg<br>Trp Ser Tyr Gly Ile Val Met Trp Glu Val Met Ser Tyr Gly Glu Arg<br>810 815 820 | 2502 | |
| ccc tat tgg gat atg tcc aat caa gat gtg att aaa gcc att gag gaa<br>Pro Tyr Trp Asp Met Ser Asn Gln Asp Val Ile Lys Ala Ile Glu Glu<br>825 830 835 | 2550 | |
| ggc tat cgg tta ccc cct cca atg gac tgc ccc att gcg ctc cac cag<br>Gly Tyr Arg Leu Pro Pro Pro Met Asp Cys Pro Ile Ala Leu His Gln<br>840 845 850 855 | 2598 | |
| ctg atg cta gac tgc tgg cag aag gag agg agc gac agg cct aaa ttt<br>Leu Met Leu Asp Cys Trp Gln Lys Glu Arg Ser Asp Arg Pro Lys Phe<br>860 865 870 | 2646 | |
| ggg cag att gtc aac atg ttg gac aaa ctc atc cgc aac ccc aac agc<br>Gly Gln Ile Val Asn Met Leu Asp Lys Leu Ile Arg Asn Pro Asn Ser<br>875 880 885 | 2694 | |
| ttg aag agg aca ggg acg gag agc tcc aga cct aac act gcc ttg ttg<br>Leu Lys Arg Thr Gly Thr Glu Ser Ser Arg Pro Asn Thr Ala Leu Leu<br>890 895 900 | 2742 | |
| gat cca agc tcc cct gaa ttc tct gct gtg gta tca gtg ggc gat tgg<br>Asp Pro Ser Ser Pro Glu Phe Ser Ala Val Val Ser Val Gly Asp Trp<br>905 910 915 | 2790 | |
| ctc cag gcc att aaa atg gac cgg tat aag gat aac ttc aca gct gct<br>Leu Gln Ala Ile Lys Met Asp Arg Tyr Lys Asp Asn Phe Thr Ala Ala<br>920 925 930 935 | 2838 | |
| ggt tat acc aca cta gag gct gtg gtg cac gtg aac cag gag gac ctg<br>Gly Tyr Thr Thr Leu Glu Ala Val Val His Val Asn Gln Glu Asp Leu<br>940 945 950 | 2886 | |
| gca aga att ggt atc aca gcc atc acg cac cag aat aag att ttg agc<br>Ala Arg Ile Gly Ile Thr Ala Ile Thr His Gln Asn Lys Ile Leu Ser<br>955 960 965 | 2934 | |
| agt gtc cag gca atg cga acc caa atg cag cag atg cac ggc aga atg<br>Ser Val Gln Ala Met Arg Thr Gln Met Gln Gln Met His Gly Arg Met<br>970 975 980 | 2982 | |
| gtt ccc gtc tga gccagtactg aataaactca aaactcttga aattagttta<br>Val Pro Val<br>985 | 3034 | |
| cctcatccat gcactttaat tgaagaactg cactttttt acttcgtctt cgccctctga | 3094 | |
| aattaaagaa atg | 3107 | |

<210> SEQ ID NO 4
<211> LENGTH: 986
<212> TYPE: PRT
<213> ORGANISM: Homo sapiens

<400> SEQUENCE: 4

Met Ala Gly Ile Phe Tyr Phe Ala Leu Phe Ser Cys Leu Phe Gly Ile
1               5                   10                  15

Cys Asp Ala Val Thr Gly Ser Arg Val Tyr Pro Ala Asn Glu Val Thr
            20                  25                  30

-continued

```
Leu Leu Asp Ser Arg Ser Val Gln Gly Glu Leu Gly Trp Ile Ala Ser
        35                  40                  45

Pro Leu Glu Gly Gly Trp Glu Glu Val Ser Ile Met Asp Glu Lys Asn
 50                  55                  60

Thr Pro Ile Arg Thr Tyr Gln Val Cys Asn Val Met Glu Pro Ser Gln
 65                  70                  75                  80

Asn Asn Trp Leu Arg Thr Asp Trp Ile Thr Arg Glu Gly Ala Gln Arg
                 85                  90                  95

Val Tyr Ile Glu Ile Lys Phe Thr Leu Arg Asp Cys Asn Ser Leu Pro
                100                 105                 110

Gly Val Met Gly Thr Cys Lys Glu Thr Phe Asn Leu Tyr Tyr Tyr Glu
                115                 120                 125

Ser Asp Asn Asp Lys Glu Arg Phe Ile Arg Glu Asn Gln Phe Val Lys
        130                 135                 140

Ile Asp Thr Ile Ala Ala Asp Glu Ser Phe Thr Gln Val Asp Ile Gly
145                 150                 155                 160

Asp Arg Ile Met Lys Leu Asn Thr Glu Ile Arg Asp Val Gly Pro Leu
                165                 170                 175

Ser Lys Lys Gly Phe Tyr Leu Ala Phe Gln Asp Val Gly Ala Cys Ile
                180                 185                 190

Ala Leu Val Ser Val Arg Val Phe Tyr Lys Lys Cys Pro Leu Thr Val
                195                 200                 205

Arg Asn Leu Ala Gln Phe Pro Asp Thr Ile Thr Gly Ala Asp Thr Ser
        210                 215                 220

Ser Leu Val Glu Val Arg Gly Ser Cys Val Asn Asn Ser Glu Glu Lys
225                 230                 235                 240

Asp Val Pro Lys Met Tyr Cys Gly Ala Asp Gly Glu Trp Leu Val Pro
                245                 250                 255

Ile Gly Asn Cys Leu Cys Asn Ala Gly His Glu Glu Arg Ser Gly Glu
                260                 265                 270

Cys Gln Ala Cys Lys Ile Gly Tyr Tyr Lys Ala Leu Ser Thr Asp Ala
        275                 280                 285

Thr Cys Ala Lys Cys Pro Pro His Ser Tyr Ser Val Trp Glu Gly Ala
 290                 295                 300

Thr Ser Cys Thr Cys Asp Arg Gly Phe Phe Arg Ala Asp Asn Asp Ala
305                 310                 315                 320

Ala Ser Met Pro Cys Thr Arg Pro Pro Ser Ala Pro Leu Asn Leu Ile
                325                 330                 335

Ser Asn Val Asn Glu Thr Ser Val Asn Leu Glu Trp Ser Ser Pro Gln
                340                 345                 350

Asn Thr Gly Gly Arg Gln Asp Ile Ser Tyr Asn Val Val Cys Lys Lys
        355                 360                 365

Cys Gly Ala Gly Asp Pro Ser Lys Cys Arg Pro Cys Gly Ser Gly Val
 370                 375                 380

His Tyr Thr Pro Gln Gln Asn Gly Leu Lys Thr Thr Lys Val Ser Ile
385                 390                 395                 400

Thr Asp Leu Leu Ala His Thr Asn Tyr Thr Phe Glu Ile Trp Ala Val
                405                 410                 415

Asn Gly Val Ser Lys Tyr Asn Pro Asn Pro Asp Gln Ser Val Ser Val
                420                 425                 430

Thr Val Thr Thr Asn Gln Ala Ala Pro Ser Ser Ile Ala Leu Val Gln
        435                 440                 445

Ala Lys Glu Val Thr Arg Tyr Ser Val Ala Leu Ala Trp Leu Glu Pro
```

```
              450                 455                 460
Asp Arg Pro Asn Gly Val Ile Leu Glu Tyr Glu Val Lys Tyr Tyr Glu
465                 470                 475                 480

Lys Asp Gln Asn Glu Arg Ser Tyr Arg Ile Val Arg Thr Ala Ala Arg
                485                 490                 495

Asn Thr Asp Ile Lys Gly Leu Asn Pro Leu Thr Ser Tyr Val Phe His
                500                 505                 510

Val Arg Ala Arg Thr Ala Ala Gly Tyr Gly Asp Phe Ser Glu Pro Leu
                515                 520                 525

Glu Val Thr Thr Asn Thr Val Pro Ser Arg Ile Ile Gly Asp Gly Ala
                530                 535                 540

Asn Ser Thr Val Leu Leu Val Ser Val Ser Gly Ser Val Val Leu Val
545                 550                 555                 560

Val Ile Leu Ile Ala Ala Phe Val Ile Ser Arg Arg Ser Lys Tyr
                565                 570                 575

Ser Lys Ala Lys Gln Glu Ala Asp Glu Glu Lys His Leu Asn Gln Gly
                580                 585                 590

Val Arg Thr Tyr Val Asp Pro Phe Thr Tyr Glu Asp Pro Asn Gln Ala
                595                 600                 605

Val Arg Glu Phe Ala Lys Glu Ile Asp Ala Ser Cys Ile Lys Ile Glu
610                 615                 620

Lys Val Ile Gly Val Gly Glu Phe Gly Glu Val Cys Ser Gly Arg Leu
625                 630                 635                 640

Lys Val Pro Gly Lys Arg Glu Ile Cys Val Ala Ile Lys Thr Leu Lys
                645                 650                 655

Ala Gly Tyr Thr Asp Lys Gln Arg Arg Asp Phe Leu Ser Glu Ala Ser
                660                 665                 670

Ile Met Gly Gln Phe Asp His Pro Asn Ile Ile His Leu Glu Gly Val
                675                 680                 685

Val Thr Lys Cys Lys Pro Val Met Ile Ile Thr Glu Tyr Met Glu Asn
                690                 695                 700

Gly Ser Leu Asp Ala Phe Leu Arg Lys Asn Asp Gly Arg Phe Thr Val
705                 710                 715                 720

Ile Gln Leu Val Gly Met Leu Arg Gly Ile Gly Ser Gly Met Lys Tyr
                725                 730                 735

Leu Ser Asp Met Ser Tyr Val His Arg Asp Leu Ala Ala Arg Asn Ile
                740                 745                 750

Leu Val Asn Ser Asn Leu Val Cys Lys Val Ser Asp Phe Gly Met Ser
                755                 760                 765

Arg Val Leu Glu Asp Asp Pro Glu Ala Ala Tyr Thr Thr Arg Gly Gly
770                 775                 780

Lys Ile Pro Ile Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
                805                 810                 815

Val Met Ser Tyr Gly Glu Arg Pro Tyr Trp Asp Met Ser Asn Gln Asp
                820                 825                 830

Val Ile Lys Ala Ile Glu Glu Gly Tyr Arg Leu Pro Pro Pro Met Asp
                835                 840                 845

Cys Pro Ile Ala Leu His Gln Leu Met Leu Asp Cys Trp Gln Lys Glu
                850                 855                 860

Arg Ser Asp Arg Pro Lys Phe Gly Gln Ile Val Asn Met Leu Asp Lys
865                 870                 875                 880
```

-continued

```
Leu Ile Arg Asn Pro Asn Ser Leu Lys Arg Thr Gly Thr Glu Ser Ser
                885                 890                 895

Arg Pro Asn Thr Ala Leu Leu Asp Pro Ser Ser Pro Glu Phe Ser Ala
            900                 905                 910

Val Val Ser Val Gly Asp Trp Leu Gln Ala Ile Lys Met Asp Arg Tyr
        915                 920                 925

Lys Asp Asn Phe Thr Ala Ala Gly Tyr Thr Thr Leu Glu Ala Val Val
    930                 935                 940

His Val Asn Gln Glu Asp Leu Ala Arg Ile Gly Ile Thr Ala Ile Thr
945                 950                 955                 960

His Gln Asn Lys Ile Leu Ser Ser Val Gln Ala Met Arg Thr Gln Met
                965                 970                 975

Gln Gln Met His Gly Arg Met Val Pro Val
            980                 985
```

<210> SEQ ID NO 5
<211> LENGTH: 4349
<212> TYPE: DNA
<213> ORGANISM: Homo sapiens
<220> FEATURE:
<221> NAME/KEY: CDS
<222> LOCATION: (445)..(3093)

<400> SEQUENCE: 5

```
tttttgaatc ggttgtggcg gccgcggcga ggaatggcgg tatttgtgag aggagtcggc      60
gtttgaagag gtggaactcc tagggctttt ttgagagtga cggagtctac ctcttgttac    120
ctagactgga gtgcagtggc acgatctcgg ctcactgcaa cctctgcctc ccgggttcaa    180
gcgattctcc tgcctcagcc tcctgagtag ctgggattac aggtgcctgc caccaagccc    240
agctaatttt tgtatttta gtagagatgg ggtttcattg tgttggccag gctggtctcg    300
aactcctgac ctcgtgatcc gcccgccttg gcctcccaaa gtgctaggat tacaagtgtg    360
agccaccgcg tccggccttt caaatggtat ttttgatttt cctcttccag tccttaaagc    420
agctgattta gaagaataca aatc atg gct gaa aat agt gta tta aca tcc      471
                        Met Ala Glu Asn Ser Val Leu Thr Ser
                         1               5 act act ggg agg act agc ttg gca gac tct tcc att ttt gat tct aaa     519
Thr Thr Gly Arg Thr Ser Leu Ala Asp Ser Ser Ile Phe Asp Ser Lys
 10              15                  20                  25 gtt act gag att tcc aag gaa aac tta ctt att gga tct act tca tat     567
Val Thr Glu Ile Ser Lys Glu Asn Leu Leu Ile Gly Ser Thr Ser Tyr
             30                  35                  40 gta gaa gag atg cct cag att gaa aca aga gtg ata ttg gtt caa gaa     615
Val Glu Glu Met Pro Gln Ile Glu Thr Arg Val Ile Leu Val Gln Glu
         45                  50                  55 gct gga aaa caa gaa gaa ctt ata aaa gcc tta aag gac att aaa gtg     663
Ala Gly Lys Gln Glu Glu Leu Ile Lys Ala Leu Lys Asp Ile Lys Val
     60                  65                  70 ggc ttt gta aag atg gag tca gtg gaa gaa ttt gaa ggt ttg gat tct     711
Gly Phe Val Lys Met Glu Ser Val Glu Glu Phe Glu Gly Leu Asp Ser
 75                  80                  85 ccg gaa ttt gaa aat gta ttt gta gtc acg gac ttt cag gat tct gtc     759
Pro Glu Phe Glu Asn Val Phe Val Val Thr Asp Phe Gln Asp Ser Val
 90                  95                 100                 105 ttt aat gac ctc tac aag gct gat tgt aga gtt att gga cca cca gtt     807
Phe Asn Asp Leu Tyr Lys Ala Asp Cys Arg Val Ile Gly Pro Pro Val
            110                 115                 120 gta tta aat tgt tca caa aaa gga gag cct ttg cca ttt tca tgt cgc     855
Val Leu Asn Cys Ser Gln Lys Gly Glu Pro Leu Pro Phe Ser Cys Arg
```

```
                    125                 130                 135
ccg ttg tat tgt aca agt atg atg aat cta gta cta tgc ttt act gga    903
Pro Leu Tyr Cys Thr Ser Met Met Asn Leu Val Leu Cys Phe Thr Gly
        140                 145                 150 ttt agg aaa aaa gaa gaa cta gtc agg ttg gtg aca ttg gtc cat cac    951
Phe Arg Lys Lys Glu Glu Leu Val Arg Leu Val Thr Leu Val His His
155                 160                 165 atg ggt gga gtt att cga aaa gac ttt aat tca aaa gtt aca cat ttg    999
Met Gly Gly Val Ile Arg Lys Asp Phe Asn Ser Lys Val Thr His Leu
170                 175                 180                 185 gtg gca aat tgt aca caa gga gaa aaa ttc agg gtt gct gtg agt cta   1047
Val Ala Asn Cys Thr Gln Gly Glu Lys Phe Arg Val Ala Val Ser Leu
        190                 195                 200 ggt act cca att atg aag cca gaa tgg att tat aaa gct tgg gaa agg   1095
Gly Thr Pro Ile Met Lys Pro Glu Trp Ile Tyr Lys Ala Trp Glu Arg
        205                 210                 215 cgg aat gaa cag gat ttc tat gca gca gtt gat gac ttt aga aat gaa   1143
Arg Asn Glu Gln Asp Phe Tyr Ala Ala Val Asp Asp Phe Arg Asn Glu
        220                 225                 230 ttt aaa gtt cct cca ttt caa gat tgt att tta agt ttc ctg gga ttt   1191
Phe Lys Val Pro Pro Phe Gln Asp Cys Ile Leu Ser Phe Leu Gly Phe
235                 240                 245 tca gat gaa gag aaa acc aat atg gaa gaa atg act gaa atg caa gga   1239
Ser Asp Glu Glu Lys Thr Asn Met Glu Glu Met Thr Glu Met Gln Gly
250                 255                 260                 265 ggt aaa tat tta ccg ctt gga gat gaa aga tgc act cac ctt gta gtt   1287
Gly Lys Tyr Leu Pro Leu Gly Asp Glu Arg Cys Thr His Leu Val Val
        270                 275                 280 gaa gag aat ata gta aaa gat ctt ccc ttt gaa cct tca aag aaa ctt   1335
Glu Glu Asn Ile Val Lys Asp Leu Pro Phe Glu Pro Ser Lys Lys Leu
        285                 290                 295 tat gtt gtc aag caa gag tgg ttc tgg gga agc att caa atg gat gcc   1383
Tyr Val Val Lys Gln Glu Trp Phe Trp Gly Ser Ile Gln Met Asp Ala
        300                 305                 310 cga gct gga gaa act atg tat tta tat gaa aag gca aat act cct gag   1431
Arg Ala Gly Glu Thr Met Tyr Leu Tyr Glu Lys Ala Asn Thr Pro Glu
        315                 320                 325 ctc aag aaa tca gtg tca atg ctt tct cta aat acc cct aac agc aat   1479
Leu Lys Lys Ser Val Ser Met Leu Ser Leu Asn Thr Pro Asn Ser Asn
330                 335                 340                 345 cgc aaa cga cgt cgt tta aaa gaa aca ctt gct cag ctt tca aga gag   1527
Arg Lys Arg Arg Arg Leu Lys Glu Thr Leu Ala Gln Leu Ser Arg Glu
        350                 355                 360 aca gac gtg tca cca ttt cca ccc cgt aag cgc cca tca gct gag cat   1575
Thr Asp Val Ser Pro Phe Pro Pro Arg Lys Arg Pro Ser Ala Glu His
        365                 370                 375 tcc ctt tcc ata ggg tca ctc cta gat atc tcc aac aca cca gag tct   1623
Ser Leu Ser Ile Gly Ser Leu Leu Asp Ile Ser Asn Thr Pro Glu Ser
        380                 385                 390 agc att aac tat gga gac acc cca aag tct tgt act aag tct tct aaa   1671
Ser Ile Asn Tyr Gly Asp Thr Pro Lys Ser Cys Thr Lys Ser Ser Lys
        395                 400                 405 agc tcc act cca gtt cct tca aag cag tca gca agg tgg caa gtt gca   1719
Ser Ser Thr Pro Val Pro Ser Lys Gln Ser Ala Arg Trp Gln Val Ala
410                 415                 420                 425 aaa gag ctt tat caa act gaa agt aat tat gtt aat ata ttg gca aca   1767
Lys Glu Leu Tyr Gln Thr Glu Ser Asn Tyr Val Asn Ile Leu Ala Thr
        430                 435                 440 att att cag tta ttt caa gta cca ttg gaa gag gaa gga caa cgt ggt   1815
Ile Ile Gln Leu Phe Gln Val Pro Leu Glu Glu Glu Gly Gln Arg Gly
```

-continued

```
                    445                 450                 455
gga cct atc ctt gca cca gag gag att aag act att ttt ggt agc atc      1863
Gly Pro Ile Leu Ala Pro Glu Glu Ile Lys Thr Ile Phe Gly Ser Ile
        460                 465                 470 cca gat atc ttt gat gta cac act aag ata aag gat gat ctt gaa gac      1911
Pro Asp Ile Phe Asp Val His Thr Lys Ile Lys Asp Asp Leu Glu Asp
    475                 480                 485 ctt ata gtt aat tgg gat gag agc aaa agc att ggt gac att ttt ctg      1959
Leu Ile Val Asn Trp Asp Glu Ser Lys Ser Ile Gly Asp Ile Phe Leu
490                 495                 500                 505 aaa tat tca aaa gat ttg gta aaa acc tac cct ccc ttt gta aac ttc      2007
Lys Tyr Ser Lys Asp Leu Val Lys Thr Tyr Pro Pro Phe Val Asn Phe
                510                 515                 520 ttt gaa atg agc aag gaa aca att att aaa tgt gaa aaa cag aaa cca      2055
Phe Glu Met Ser Lys Glu Thr Ile Ile Lys Cys Glu Lys Gln Lys Pro
            525                 530                 535 aga ttt cat gct ttt ctc aag ata aac caa gca aaa cca gaa tgt gga      2103
Arg Phe His Ala Phe Leu Lys Ile Asn Gln Ala Lys Pro Glu Cys Gly
        540                 545                 550 cgg cag agc ctt gtt gaa ctt ctt atc cga cca gta cag agg tta ccc      2151
Arg Gln Ser Leu Val Glu Leu Leu Ile Arg Pro Val Gln Arg Leu Pro
    555                 560                 565 agt gtt gca tta ctt tta aat gat ctt aag aag cat aca gct gat gaa      2199
Ser Val Ala Leu Leu Leu Asn Asp Leu Lys Lys His Thr Ala Asp Glu
570                 575                 580                 585 aat cca gac aaa agc act tta gaa aaa gct att gga tca ctg aag gaa      2247
Asn Pro Asp Lys Ser Thr Leu Glu Lys Ala Ile Gly Ser Leu Lys Glu
                590                 595                 600 gta atg acg cat att aat gag gat aag aga aaa aca gaa gct caa aag      2295
Val Met Thr His Ile Asn Glu Asp Lys Arg Lys Thr Glu Ala Gln Lys
            605                 610                 615 caa att ttt gat gtt gtt tat gaa gta gat gga tgc cca gct aat ctt      2343
Gln Ile Phe Asp Val Val Tyr Glu Val Asp Gly Cys Pro Ala Asn Leu
        620                 625                 630 tta tct tct cac cga agc tta gta cag cgg gtt gaa aca att tct cta      2391
Leu Ser Ser His Arg Ser Leu Val Gln Arg Val Glu Thr Ile Ser Leu
    635                 640                 645 ggt gag cac ccc tgt gac aga gga gaa caa gta act ctc ttc ctc ttc      2439
Gly Glu His Pro Cys Asp Arg Gly Glu Gln Val Thr Leu Phe Leu Phe
650                 655                 660                 665 aat gat tgc cta gag ata gca aga aaa cgg cac aag gtt att ggc act      2487
Asn Asp Cys Leu Glu Ile Ala Arg Lys Arg His Lys Val Ile Gly Thr
                670                 675                 680 ttt agg agt cct cat ggc caa acc cga ccc cca gct tct ctt aag cat      2535
Phe Arg Ser Pro His Gly Gln Thr Arg Pro Pro Ala Ser Leu Lys His
            685                 690                 695 att cac cta atg cct ctt tct cag att aag aag gta ttg gac ata aga      2583
Ile His Leu Met Pro Leu Ser Gln Ile Lys Lys Val Leu Asp Ile Arg
        700                 705                 710 gag aca gaa gat tgc cat aat gct ttt gcc ttg ctt gtg agg cca cca      2631
Glu Thr Glu Asp Cys His Asn Ala Phe Ala Leu Leu Val Arg Pro Pro
    715                 720                 725 aca gag cag gca aat gtg cta ctc agt ttc cag atg aca tca gat gaa      2679
Thr Glu Gln Ala Asn Val Leu Leu Ser Phe Gln Met Thr Ser Asp Glu
730                 735                 740                 745 ctt cca aaa gaa aac tgg cta aag atg ctg tgt cga cat gta gct aac      2727
Leu Pro Lys Glu Asn Trp Leu Lys Met Leu Cys Arg His Val Ala Asn
                750                 755                 760 acc att tgt aaa gca gat gct gag aat ctt att tat act gct gat cca      2775
Thr Ile Cys Lys Ala Asp Ala Glu Asn Leu Ile Tyr Thr Ala Asp Pro
```

```
gaa tcc ttt gaa gta aat aca aaa gat atg gac agt aca ttg agt aga      2823
Glu Ser Phe Glu Val Asn Thr Lys Asp Met Asp Ser Thr Leu Ser Arg
            780                 785                 790 gca tca aga gca ata aaa aag act tca aaa aag gtt aca aga gca ttc      2871
Ala Ser Arg Ala Ile Lys Lys Thr Ser Lys Lys Val Thr Arg Ala Phe
    795                 800                 805 tct ttc tcc aaa act cca aaa aga gct ctt cga agg gct ctt atg aca      2919
Ser Phe Ser Lys Thr Pro Lys Arg Ala Leu Arg Arg Ala Leu Met Thr
810                 815                 820                 825 tcc cac ggc tca gtg gag gga aga agt cct tcc agc aat gat aag cat      2967
Ser His Gly Ser Val Glu Gly Arg Ser Pro Ser Ser Asn Asp Lys His
                830                 835                 840 gta atg agt cgt ctt tct agc aca tca tca tta gca ggt atc cct tct      3015
Val Met Ser Arg Leu Ser Ser Thr Ser Ser Leu Ala Gly Ile Pro Ser
            845                 850                 855 ccc tcc ctt gtc agc ctt cct tcc ttc ttt gaa agg aga agt cat acg      3063
Pro Ser Leu Val Ser Leu Pro Ser Phe Phe Glu Arg Arg Ser His Thr
        860                 865                 870 tta agt aga tct aca act cat ttg ata tga agcgttacca aaatcttaaa        3113
Leu Ser Arg Ser Thr Thr His Leu Ile
    875                 880 ttatagaaat gtatagacac ctcatactca aataagaaac tgacttaaat ggtacttgta    3173
attagcacgt tggtgaaagc tggaaggaag ataaataaca ctaaactatg ctatttgatt    3233
tttcttcttg aaagagtaag gtttacctgt tacattttca agttaattca tgtaaaaaat    3293
gatagtgatt ttgatgtaat ttatctcttg tttgaatctg tcattcaaag gccaataatt    3353
taagttgcta tcagctgata ttagtagctt tgcaaccctg atagagtaaa taaattttat    3413
gggtgggtgc caaatactgc tgtgaatcta tttgtatagt atccatgaat gaatttatgg    3473
aaatagatat ttgtgcagct caatttatgc agagattaaa tgacatcata atactggatg    3533
aaaacttgca tagaattctg attaaatagt gggtctgttt cacatgtgca gtttgaagta    3593
tttaaataac cactcctttc acagtttatt ttcttctcaa gcgttttcaa gatctagcat    3653
gtggatttta aaagatttgc cctcattaac aagaataaca tttaaggag attgtttcaa     3713 aatattttg caaattgaga taaggacaga aagattgaga acattgtat attttgcaaa      3773 aacaagatgt ttgtagctgt ttcagagaga gtacggtata tttatggtaa ttttatccac    3833
tagcaaatct tgatttagtt tgatagtcgt cgtcggaatt ttattttgaa ggataagacc    3893
atgggaaaat tgtggtaaag actgtttgta cccttcatga ataattctg aagttgccat     3953 cagtttact aatcttctgt gaaatgcata gatatgcgca tgttcaactt tttattgtgg     4013
tcttataatt aaatgtaaaa ttgaaaattc atttgctgtt tcaaagtgtg atatctttca    4073
caatagcctt tttatagtca gtaattcaga ataatcaagt tcatatggat aaatgcattt    4133
ttatttccta tttctttagg gagtgctaca aatgtttgtc acttaaattt caagtttctg    4193
ttttaatagt taactgacta tagattgttt tctatgccat gtatgtgcca cttctgagag    4253
tagtaaatga ctctttgcta catttttaaaa gcaattgtat tagtaagaac tttgtaaata   4313
aatacctaaa acccaagtgt aaaaaaaaaa aaaaaa                              4349
```

<210> SEQ ID NO 6
<211> LENGTH: 882
<212> TYPE: PRT
<213> ORGANISM: Homo sapiens

<400> SEQUENCE: 6

-continued

```
Met Ala Glu Asn Ser Val Leu Thr Ser Thr Thr Gly Arg Thr Ser Leu
1               5                   10                  15

Ala Asp Ser Ser Ile Phe Asp Ser Lys Val Thr Glu Ile Ser Lys Glu
            20                  25                  30

Asn Leu Leu Ile Gly Ser Thr Ser Tyr Val Glu Glu Met Pro Gln Ile
            35                  40                  45

Glu Thr Arg Val Ile Leu Val Gln Glu Ala Gly Lys Gln Glu Glu Leu
            50                  55                  60

Ile Lys Ala Leu Lys Asp Ile Lys Val Gly Phe Val Lys Met Glu Ser
65                  70                  75                  80

Val Glu Glu Phe Glu Gly Leu Asp Ser Pro Gly Phe Glu Asn Val Phe
                85                  90                  95

Val Val Thr Asp Phe Gln Asp Ser Val Phe Asn Asp Leu Tyr Lys Ala
            100                 105                 110

Asp Cys Arg Val Ile Gly Pro Pro Val Val Leu Asn Cys Ser Gln Lys
            115                 120                 125

Gly Glu Pro Leu Pro Phe Ser Cys Arg Pro Leu Tyr Cys Thr Ser Met
130                 135                 140

Met Asn Leu Val Leu Cys Phe Thr Gly Phe Arg Lys Lys Glu Glu Leu
145                 150                 155                 160

Val Arg Leu Val Thr Leu Val His His Met Gly Gly Val Ile Arg Lys
            165                 170                 175

Asp Phe Asn Ser Lys Val Thr His Leu Val Ala Asn Cys Thr Gln Gly
            180                 185                 190

Glu Lys Phe Arg Val Ala Val Ser Leu Gly Thr Pro Ile Met Lys Pro
            195                 200                 205

Glu Trp Ile Tyr Lys Ala Trp Glu Arg Arg Asn Glu Gln Asp Phe Tyr
            210                 215                 220

Ala Ala Val Asp Asp Phe Arg Asn Glu Phe Lys Val Pro Pro Phe Gln
225                 230                 235                 240

Asp Cys Ile Leu Ser Phe Leu Gly Phe Ser Asp Glu Glu Lys Thr Asn
                245                 250                 255

Met Glu Glu Met Thr Glu Met Gln Gly Gly Lys Tyr Leu Pro Leu Gly
            260                 265                 270

Asp Glu Arg Cys Thr His Leu Val Val Glu Glu Asn Ile Val Lys Asp
            275                 280                 285

Leu Pro Phe Glu Pro Ser Lys Lys Leu Tyr Val Val Lys Gln Glu Trp
            290                 295                 300

Phe Trp Gly Ser Ile Gln Met Asp Ala Arg Ala Gly Glu Thr Met Tyr
305                 310                 315                 320

Leu Tyr Glu Lys Ala Asn Thr Pro Glu Leu Lys Lys Ser Val Ser Met
            325                 330                 335

Leu Ser Leu Asn Thr Pro Asn Ser Asn Arg Lys Arg Arg Arg Leu Lys
            340                 345                 350

Glu Thr Leu Ala Gln Leu Ser Arg Glu Thr Asp Val Ser Pro Phe Pro
            355                 360                 365

Pro Arg Lys Arg Pro Ser Ala Glu His Ser Leu Ser Ile Gly Ser Leu
370                 375                 380

Leu Asp Ile Ser Asn Thr Pro Glu Ser Ser Ile Asn Tyr Gly Asp Thr
385                 390                 395                 400

Pro Lys Ser Cys Thr Lys Ser Ser Lys Ser Ser Thr Pro Val Pro Ser
            405                 410                 415

Lys Gln Ser Ala Arg Trp Gln Val Ala Lys Glu Leu Tyr Gln Thr Glu
            420                 425                 430
```

```
Ser Asn Tyr Val Asn Ile Leu Ala Thr Ile Ile Gln Leu Phe Gln Val
        435                 440                 445

Pro Leu Glu Glu Glu Gly Gln Arg Gly Gly Pro Ile Leu Ala Pro Glu
450                 455                 460

Glu Ile Lys Thr Ile Phe Gly Ser Ile Pro Asp Ile Phe Asp Val His
465                 470                 475                 480

Thr Lys Ile Lys Asp Asp Leu Glu Asp Leu Ile Val Asn Trp Asp Glu
                485                 490                 495

Ser Lys Ser Ile Gly Asp Ile Phe Leu Lys Tyr Ser Lys Asp Leu Val
            500                 505                 510

Lys Thr Tyr Pro Pro Phe Val Asn Phe Phe Glu Met Ser Lys Glu Thr
        515                 520                 525

Ile Ile Lys Cys Glu Lys Gln Lys Pro Arg Phe His Ala Phe Leu Lys
        530                 535                 540

Ile Asn Gln Ala Lys Pro Glu Cys Gly Arg Gln Ser Leu Val Glu Leu
545                 550                 555                 560

Leu Ile Arg Pro Val Gln Arg Leu Pro Ser Val Ala Leu Leu Leu Asn
                565                 570                 575

Asp Leu Lys Lys His Thr Ala Asp Glu Asn Pro Asp Lys Ser Thr Leu
            580                 585                 590

Glu Lys Ala Ile Gly Ser Leu Lys Glu Val Met Thr His Ile Asn Glu
        595                 600                 605

Asp Lys Arg Lys Thr Glu Ala Gln Lys Gln Ile Phe Asp Val Val Tyr
        610                 615                 620

Glu Val Asp Gly Cys Pro Ala Asn Leu Leu Ser Ser His Arg Ser Leu
625                 630                 635                 640

Val Gln Arg Val Glu Thr Ile Ser Leu Gly Glu His Pro Cys Asp Arg
                645                 650                 655

Gly Glu Gln Val Thr Leu Phe Leu Phe Asn Asp Cys Leu Glu Ile Ala
            660                 665                 670

Arg Lys Arg His Lys Val Ile Gly Thr Phe Arg Ser Pro His Gly Gln
        675                 680                 685

Thr Arg Pro Pro Ala Ser Leu Lys His Ile His Leu Met Pro Leu Ser
        690                 695                 700

Gln Ile Lys Lys Val Leu Asp Ile Arg Glu Thr Glu Asp Cys His Asn
705                 710                 715                 720

Ala Phe Ala Leu Leu Val Arg Pro Pro Thr Glu Gln Ala Asn Val Leu
                725                 730                 735

Leu Ser Phe Gln Met Thr Ser Asp Glu Leu Pro Lys Glu Asn Trp Leu
            740                 745                 750

Lys Met Leu Cys Arg His Val Ala Asn Thr Ile Cys Lys Ala Asp Ala
        755                 760                 765

Glu Asn Leu Ile Tyr Thr Ala Asp Pro Glu Ser Phe Glu Val Asn Thr
        770                 775                 780

Lys Asp Met Asp Ser Thr Leu Ser Arg Ala Ser Arg Ala Ile Lys Lys
785                 790                 795                 800

Thr Ser Lys Lys Val Thr Arg Ala Phe Ser Phe Ser Lys Thr Pro Lys
                805                 810                 815

Arg Ala Leu Arg Arg Ala Leu Met Thr Ser His Gly Ser Val Glu Gly
            820                 825                 830

Arg Ser Pro Ser Ser Asn Asp Lys His Val Met Ser Arg Leu Ser Ser
        835                 840                 845

Thr Ser Ser Leu Ala Gly Ile Pro Ser Pro Ser Leu Val Ser Leu Pro
```

```
                850             855             860
Ser Phe Phe Glu Arg Arg Ser His Thr Leu Ser Arg Ser Thr Thr His
865                 870             875             880

Leu Ile

<210> SEQ ID NO 7
<211> LENGTH: 1372
<212> TYPE: DNA
<213> ORGANISM: Homo sapiens
<220> FEATURE:
<221> NAME/KEY: CDS
<222> LOCATION: (206)..(397)

<400> SEQUENCE: 7
gcacgagggc gcttttgtct ccggtgagtt ttgtggcggg aagcttctgc gctggtgctt        60
agtaaccgac tttcctccgg actcctgcac gacctgctcc tacagccggc gatccactcc       120
cggctgttcc cccggagggt ccagaggcct ttcagaagga gaaggcagct ctgtttctct       180
gcagaggagt agggtccttt cagcc atg aag cat gtg ttg aac ctc tac ctg         232
                             Met Lys His Val Leu Asn Leu Tyr Leu
                              1               5 tta ggt gtg gta ctg acc cta ctc tcc atc ttc gtt aga gtg atg gag         280
Leu Gly Val Val Leu Thr Leu Leu Ser Ile Phe Val Arg Val Met Glu
 10              15                  20                  25 tcc cta gaa ggc tta cta gag agc cca tcg cct ggg acc tcc tgg acc         328
Ser Leu Glu Gly Leu Leu Glu Ser Pro Ser Pro Gly Thr Ser Trp Thr
                30                  35                  40 acc aga agc caa cta gcc aac aca gag ccc acc aag ggc ctt cca gac         376
Thr Arg Ser Gln Leu Ala Asn Thr Glu Pro Thr Lys Gly Leu Pro Asp
             45                  50                  55 cat cca tcc aga agc atg tga taagacctcc ttccatactg gccatatttt            427
His Pro Ser Arg Ser Met
              60 ggaacactga cctagacatg tccagatggg agtcccattc ctagcagaca agctgagcac       487 cgttgtaacc agagaactat tactaggcct tgaagaacct gtctaactgg atgctcattg       547 cctgggcaag gcctgtttag gccggttgcg gtggctcatg cctgtaatcc tagcactttg       607 ggaggctgag gtgggtggat cacctgaggt caggagttcg agaccagcct gccaacatg        667 gcgaaacccc atctctacta aaaatacaaa agttagctgg gtgtggtggc agaggcctgt       727 aatcccagtt ccttgggagg ctgaggcggg agaattgctt gaacccgggg acggaggttg       787 cagtgaaccg agatcgcact gctgtaccca gcctgggcca cagtgcaaga ctccatctca       847 aaaaaaaaaa gaaaagaaaa agcctgttta atgcacaggt gtgagtggat tgcttatggc       907 tatgagatag gttgatctcg cccttacccc ggggtctggt gtatgctgtg ctttcctcag       967 cagtatggct ctgacatctc ttagatgtcc caacttcagc tgttgggaga tggtgatatt      1027 ttcaacccta cttcctaaac atctgtctgg ggttccttta gtcttgaatg tcttatgctc      1087 aattatttgg tgttgagcct ctcttccaca agagctcctc catgtttgga tagcagttga      1147 agaggttgtg tgggtgggct gttgggagtg aggatggagt gttcagtgcc catttctcat      1207 tttacatttt aaagtcgttc ctccaacata gtgtgtattg gtctgaaggg ggtggtggga      1267 tgccaaagcc tgctcaagtt atggacattg tggccaccat gtggcttaaa tgattttttc      1327 taactaataa agtggaatat atatttcaaa aaaaaaaaaa aaaaa                      1372

<210> SEQ ID NO 8
<211> LENGTH: 63
<212> TYPE: PRT
```

<213> ORGANISM: Homo sapiens

<400> SEQUENCE: 8

Met Lys His Val Leu Asn Leu Tyr Leu Leu Gly Val Val Leu Thr Leu
1               5                   10                  15

Leu Ser Ile Phe Val Arg Val Met Glu Ser Leu Glu Gly Leu Leu Glu
            20                  25                  30

Ser Pro Ser Pro Gly Thr Ser Trp Thr Thr Arg Ser Gln Leu Ala Asn
        35                  40                  45

Thr Glu Pro Thr Lys Gly Leu Pro Asp His Pro Ser Arg Ser Met
    50                  55                  60

<210> SEQ ID NO 9
<211> LENGTH: 3516
<212> TYPE: DNA
<213> ORGANISM: Homo sapiens
<220> FEATURE:
<221> NAME/KEY: CDS
<222> LOCATION: (767)..(1990)

<400> SEQUENCE: 9

```
ggatcctgga gacaactttg ccgtgtgacg cgccgggagg actgcagggc ccgcggccga      60
gggctcggcg ccgcctgtga gcgggcccgc gcggccggct ctcccgggca ccaagcttgc     120
tccgcgccac tgcccgccgg cccgcggcga ggacgacctg cccgtctccg ccgccggcgg     180
cccttcctgg cgcgaggcag tgagggcgag gcgctcaggt gcgagcgcgg ggccccgccg     240
cagcgcccgc cgcagcgccg cgccaagccg cccccggctc cgctccgggg ggctccagcg     300
ccttcgcttc cgtctcagcc aagttgcgtg acccgctctt tcgccacctt ccccagccg     360 ccggccgaac cgccgctccc actgacgctg cttttcgcttc acccgaaccg gggctgcggg     420 gccccgacg cggaaaggat ggggagaagg ctgcagatgc cgaggcgccc cgagacgccc     480
gtgcggcagt gacccgcgac ctcgcccccg cccggcgcgc cctcgggcc ccgggggccc     540 tcggcgcccc ttccctgccg cgcgggaacc cccgaggccc ggccggcccc ctcccctgc     600 gagcggcgg cagccctccc ggcggcgggg cgggcggagg cccgggcggg cgcgggcgcg     660 ggcggggcg gggcggggcg gcgcgcccgg agcccggagc ccggccctgc gctcggctcg     720
```

```
actcggctcg cctcgcggcg ggcgccctcg tcgccagcgg cgcacc atg gac ggg    775
                                                  Met Asp Gly
                                                  1 ctg ccc ggt cgg gcg ctg ggg gcc gcc tgc ctt ctg ctg ctg gcg gcc    823
Leu Pro Gly Arg Ala Leu Gly Ala Ala Cys Leu Leu Leu Leu Ala Ala
    5                   10                  15 ggc tgg ctg ggg cct gag gcc tgg ggc tca ccc acg ccc ccg ccg acg    871
Gly Trp Leu Gly Pro Glu Ala Trp Gly Ser Pro Thr Pro Pro Pro Thr
20                  25                  30                  35 cct gcc gcg ccg ccg cca ccc ccg cca ccc gga gcc ccg ggt ggc tcg    919
Pro Ala Ala Pro Pro Pro Pro Pro Pro Gly Ala Pro Gly Gly Ser
            40                  45                  50 cag gac acc tgt acg tcg tgc ggc ggc ttc cgg cgg cca gag gag ctc    967
Gln Asp Thr Cys Thr Ser Cys Gly Gly Phe Arg Arg Pro Glu Glu Leu
        55                  60                  65 ggc cga gtg gac ggc gac ttc ctg gag gcg gtg aag cgg cac atc ttg    1015
Gly Arg Val Asp Gly Asp Phe Leu Glu Ala Val Lys Arg His Ile Leu
    70                  75                  80 agc cgc ctg cag atg cgg ggc cgg ccc aac atc acg cac gcc gtg cct    1063
Ser Arg Leu Gln Met Arg Gly Arg Pro Asn Ile Thr His Ala Val Pro
85                  90                  95 aag gcc gcc atg gtc acg gcc ctg cgc aag ctg cac gcg ggc aag gtg    1111
```

```
                                        -continued

Lys Ala Ala Met Val Thr Ala Leu Arg Lys Leu His Ala Gly Lys Val
100                 105                 110                 115 cgc gag gac ggc cgc gtg gag atc ccg cac ctc gac ggc cac gcc agc    1159
Arg Glu Asp Gly Arg Val Glu Ile Pro His Leu Asp Gly His Ala Ser
                    120                 125                 130 ccg ggc gcc gac ggc cag gag cgc gtt tcc gaa atc atc agc ttc gcc    1207
Pro Gly Ala Asp Gly Gln Glu Arg Val Ser Glu Ile Ile Ser Phe Ala
                135                 140                 145 gag aca gat ggc ctc gcc tcc tcc cgg gtc cgc cta tac ttc ttc atc    1255
Glu Thr Asp Gly Leu Ala Ser Ser Arg Val Arg Leu Tyr Phe Phe Ile
            150                 155                 160 tcc aac gaa ggc aac cag aac ctg ttt gtg gtc cag gcc agc ctg tgg    1303
Ser Asn Glu Gly Asn Gln Asn Leu Phe Val Val Gln Ala Ser Leu Trp
        165                 170                 175 ctt tac ctg aaa ctc ctg ccc tac gtc ctg gag aag ggc agc cgg cgg    1351
Leu Tyr Leu Lys Leu Leu Pro Tyr Val Leu Glu Lys Gly Ser Arg Arg
180                 185                 190                 195 aag gtg cgg gtc aaa gtg tac ttc cag gag cag ggc cac ggt gac agg    1399
Lys Val Arg Val Lys Val Tyr Phe Gln Glu Gln Gly His Gly Asp Arg
                    200                 205                 210 tgg aac atg gtg gag aag agg gtg gac ctc aag cgc agc ggc tgg cat    1447
Trp Asn Met Val Glu Lys Arg Val Asp Leu Lys Arg Ser Gly Trp His
                215                 220                 225 acc ttc cca ctc acg gag gcc atc cag gcc ttg ttt gag cgg ggc gag    1495
Thr Phe Pro Leu Thr Glu Ala Ile Gln Ala Leu Phe Glu Arg Gly Glu
            230                 235                 240 cgg cga ctc aac cta gac gtg cag tgt gac agc tgc cag gag ctg gcc    1543
Arg Arg Leu Asn Leu Asp Val Gln Cys Asp Ser Cys Gln Glu Leu Ala
245                 250                 255 gtg gtg ccg gtg ttc gtg gac cca ggc gaa gag tcg cac cga ccc ttt    1591
Val Val Pro Val Phe Val Asp Pro Gly Glu Glu Ser His Arg Pro Phe
260                 265                 270                 275 gtg gtg gtg cag gct cgg ctg ggc gac agc agg cac cgc att cgc aag    1639
Val Val Val Gln Ala Arg Leu Gly Asp Ser Arg His Arg Ile Arg Lys
                280                 285                 290 cga ggc ctg gag tgc gat ggc cgg acc aac ctc tgt tgc agg caa cag    1687
Arg Gly Leu Glu Cys Asp Gly Arg Thr Asn Leu Cys Cys Arg Gln Gln
                295                 300                 305 ttc ttc att gac ttc cgc ctc atc ggc tgg aac gac tgg atc ata gca    1735
Phe Phe Ile Asp Phe Arg Leu Ile Gly Trp Asn Asp Trp Ile Ile Ala
            310                 315                 320 ccc acc ggc tac tac ggc aac tac tgt gag ggc agc tgc cca gcc tac    1783
Pro Thr Gly Tyr Tyr Gly Asn Tyr Cys Glu Gly Ser Cys Pro Ala Tyr
        325                 330                 335 ctg gca ggg gtc ccc ggc tct gcc tcc tcc ttc cac acg gct gtg gtg    1831
Leu Ala Gly Val Pro Gly Ser Ala Ser Ser Phe His Thr Ala Val Val
340                 345                 350                 355 aac cag tac cgc atg cgg ggt ctg aac ccc ggc acg gtg aac tcc tgc    1879
Asn Gln Tyr Arg Met Arg Gly Leu Asn Pro Gly Thr Val Asn Ser Cys
                360                 365                 370 tgc att ccc acc aag ctg agc acc atg tcc atg ctg tac ttc gat gat    1927
Cys Ile Pro Thr Lys Leu Ser Thr Met Ser Met Leu Tyr Phe Asp Asp
                375                 380                 385 gag tac aac atc gtc aag cgg gac gtg ccc aac atg att gtg gag gag    1975
Glu Tyr Asn Ile Val Lys Arg Asp Val Pro Asn Met Ile Val Glu Glu
            390                 395                 400 tgc ggc tgc gcc tga cagtgcaagg caggggcacg tggtggggc acggagggca    2030
Cys Gly Cys Ala
        405 gtcccgggtg ggcttcttcc agccccccgc gggaacgggg tacacggtgg gctgagtaca   2090
```

```
gtcattctgt tgggctgtgg agatagtgcc agggtgcggc ctgagatatt tttctacagc    2150
ttcatagagc aaccagtcaa aaccagagcg agaaccctca actgacatga aatactttaa    2210
aatgcacacg tagccacgca cagccagacg catcctgcca cccacacagc agcctccagg    2270
ataccagcaa atggatgcgg tgacaaatgg cagcttagct acaaatgcct gtcagtcgga    2330
gagaatgggg tgagcagcca ccattccacc agctggcccg ccacgtctc gaagttgcgc     2390 cttcccgagc acacataaaa gcacaaagac agagacgcag agagagagag agagccacgg    2450
agaggaaaag cagatgcagg ggtggggagc gcagctcggc ggaggctgcg tgtgccccgt    2510 ggctttttacc aggcctgctc tgcctggctc gatgtctgct tcttcccagc ctgggatcct   2570
tcgtgcttca aggcctgggg agcctgtcct tccatgccct tgtcgaggga aagagaccca    2630
gaaaggacac aacccgtcag agacctggga gcagggcaa tgaccgtttg actgtttgtg     2690
gcttgggcct ctgacatgac ttatgtgtgt gtgtgttttt ggggtgggga gggagggaga    2750 gaagagggggg ctaaatttga tgctttaact gatctccaac agttgacagg tcatccttgc   2810
cagttgtata actgaaaaag gacttttcta ccaggtatga ccttttaagt gaaaatctga    2870
attgttctaa atgaaagaa aaaaagttgc aatctgtgcc cttcattggg gacattcctc     2930
taggactggt ttggggacgg gtgggaatga cccctaggca aggggatgag accgcaggag    2990
gaaatggcgg ggaggtggca ttcttgaact gctgaggatg gggggtgtcc cctcagcgga    3050
ggccaaggga ggggagcagc ctagttggtc ttggagagat ggggaaggct ttcagctgat    3110
ttgcagaagt tgcccatgtg ggcccaacca tcagggctgg ccgtggacgt ggcccctgcc    3170
cactcacctg cccgcctgcc cgcccgcccg catagcactt gcagacctgc ctgaacgcac    3230
atgacatagc acttgccgat ctgcgtgtgc ccagaagtgg cccttggccg agcgccgaac    3290
tcgctcgccc tctagatgtc caagtgccac gtgaactatg caatttaaag ggttgaccca    3350
cactagacga aactggactc gtacgactct ttttatattt tttatacttg aaatgaaatc    3410
ctttgcttct tttttaagcg aatgattgct tttaatgttt gcactgattt agttgcatga    3470
ttagtcagaa actgccattt gaaaaaaaag ttatttttat agcagc                   3516
```

<210> SEQ ID NO 10
<211> LENGTH: 407
<212> TYPE: PRT
<213> ORGANISM: Homo sapiens

<400> SEQUENCE: 10

Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Ser Pro Thr Pro
            20                  25                  30

Pro Pro Thr Pro Ala Ala Pro Pro Pro Pro Pro Pro Gly Ala Pro
        35                  40                  45

Gly Gly Ser Gln Asp Thr Cys Thr Ser Cys Gly Gly Phe Arg Arg Pro
    50                  55                  60

Glu Glu Leu Gly Arg Val Asp Gly Asp Phe Leu Glu Ala Val Lys Arg
65                  70                  75                  80

His Ile Leu Ser Arg Leu Gln Met Arg Gly Arg Pro Asn Ile Thr His
                85                  90                  95

Ala Val Pro Lys Ala Ala Met Val Thr Ala Leu Arg Lys Leu His Ala
            100                 105                 110

Gly Lys Val Arg Glu Asp Gly Arg Val Glu Ile Pro His Leu Asp Gly
        115                 120                 125

```
His Ala Ser Pro Gly Ala Asp Gly Gln Glu Arg Val Ser Glu Ile Ile
            130                 135                 140

Ser Phe Ala Glu Thr Asp Gly Leu Ala Ser Ser Arg Val Arg Leu Tyr
145                 150                 155                 160

Phe Phe Ile Ser Asn Glu Gly Asn Gln Asn Leu Phe Val Val Gln Ala
                165                 170                 175

Ser Leu Trp Leu Tyr Leu Lys Leu Leu Pro Tyr Val Leu Glu Lys Gly
            180                 185                 190

Ser Arg Arg Lys Val Arg Val Lys Val Tyr Phe Gln Glu Gln Gly His
        195                 200                 205

Gly Asp Arg Trp Asn Met Val Glu Lys Arg Val Asp Leu Lys Arg Ser
    210                 215                 220

Gly Trp His Thr Phe Pro Leu Thr Glu Ala Ile Gln Ala Leu Phe Glu
225                 230                 235                 240

Arg Gly Glu Arg Leu Asn Leu Asp Val Gln Cys Asp Ser Cys Gln
                245                 250                 255

Glu Leu Ala Val Val Pro Val Phe Val Asp Pro Gly Glu Glu Ser His
            260                 265                 270

Arg Pro Phe Val Val Gln Ala Arg Leu Gly Asp Ser Arg His Arg
                275                 280                 285

Ile Arg Lys Arg Gly Leu Glu Cys Asp Gly Arg Thr Asn Leu Cys Cys
    290                 295                 300

Arg Gln Gln Phe Phe Ile Asp Phe Arg Leu Ile Gly Trp Asn Asp Trp
305                 310                 315                 320

Ile Ile Ala Pro Thr Gly Tyr Tyr Gly Asn Tyr Cys Glu Gly Ser Cys
                325                 330                 335

Pro Ala Tyr Leu Ala Gly Val Pro Gly Ser Ala Ser Ser Phe His Thr
            340                 345                 350

Ala Val Val Asn Gln Tyr Arg Met Arg Gly Leu Asn Pro Gly Thr Val
        355                 360                 365

Asn Ser Cys Cys Ile Pro Thr Lys Leu Ser Thr Met Ser Met Leu Tyr
    370                 375                 380

Phe Asp Asp Glu Tyr Asn Ile Val Lys Arg Asp Val Pro Asn Met Ile
385                 390                 395                 400

Val Glu Glu Cys Gly Cys Ala
                405

<210> SEQ ID NO 11
<211> LENGTH: 2972
<212> TYPE: DNA
<213> ORGANISM: Homo sapiens
<220> FEATURE:
<221> NAME/KEY: CDS
<222> LOCATION: (28)..(2700)

<400> SEQUENCE: 11
tcttcggacc taggctgccc tgccgtc atg tcg caa ggg atc ctt tct ccg cca    54
                                Met Ser Gln Gly Ile Leu Ser Pro Pro
                                  1               5 gcg ggc ttg ctg tcc gat gac gat gtc gta gtt tct ccc atg ttt gag    102
Ala Gly Leu Leu Ser Asp Asp Asp Val Val Val Ser Pro Met Phe Glu
 10              15                  20                  25 tcc aca gct gca gat ttg ggg tct gtg gta cgc aag aac ctg cta tca    150
Ser Thr Ala Ala Asp Leu Gly Ser Val Val Arg Lys Asn Leu Leu Ser
             30                  35                  40 gac tgc tct gtc gtc tct acc tcc cta gag gac aag cag cag gtt cca    198
Asp Cys Ser Val Val Ser Thr Ser Leu Glu Asp Lys Gln Gln Val Pro
```

-continued

```
               45                  50                  55
tct gag gac agt atg gag aag gtg aaa gta tac ttg agg gtt agg ccc         246
Ser Glu Asp Ser Met Glu Lys Val Lys Val Tyr Leu Arg Val Arg Pro
            60                  65                  70 ttg tta cct tca gag ttg gaa cga cag gaa gat cag ggt tgt gtc cgt         294
Leu Leu Pro Ser Glu Leu Glu Arg Gln Glu Asp Gln Gly Cys Val Arg
 75                  80                  85 att gag aat gtg gag acc ctt gtt cta caa gca ccc aag gac tcg ttt         342
Ile Glu Asn Val Glu Thr Leu Val Leu Gln Ala Pro Lys Asp Ser Phe
 90                  95                 100                 105 gcc ctg aag agc aat gaa cgg gga att ggc caa gcc aca cac agg ttc         390
Ala Leu Lys Ser Asn Glu Arg Gly Ile Gly Gln Ala Thr His Arg Phe
                   110                 115                 120 acc ttt tcc cag atc ttt ggg cca gaa gtg gga cag gca tcc ttc ttc         438
Thr Phe Ser Gln Ile Phe Gly Pro Glu Val Gly Gln Ala Ser Phe Phe
                125                 130                 135 aac cta act gtg aag gag atg gta aag gat gta ctc aaa ggg cag aac         486
Asn Leu Thr Val Lys Glu Met Val Lys Asp Val Leu Lys Gly Gln Asn
            140                 145                 150 tgg ctc atc tat aca tat gga gtc act aac tca ggg aaa acc cac acg         534
Trp Leu Ile Tyr Thr Tyr Gly Val Thr Asn Ser Gly Lys Thr His Thr
155                 160                 165 att caa ggt acc atc aag gat gga ggg att ctc ccc cgg tcc ctg gcg         582
Ile Gln Gly Thr Ile Lys Asp Gly Gly Ile Leu Pro Arg Ser Leu Ala
170                 175                 180                 185 ctg atc ttc aat agc ctc caa ggc caa ctt cat cca aca cct gat ctg         630
Leu Ile Phe Asn Ser Leu Gln Gly Gln Leu His Pro Thr Pro Asp Leu
                   190                 195                 200 aag ccc ttg ctc tcc aat gag gta atc tgg cta gac agc aag cag atc         678
Lys Pro Leu Leu Ser Asn Glu Val Ile Trp Leu Asp Ser Lys Gln Ile
                205                 210                 215 cga cag gag gaa atg aag aag ctg tcc ctg cta aat gga ggc ctc caa         726
Arg Gln Glu Glu Met Lys Lys Leu Ser Leu Leu Asn Gly Gly Leu Gln
            220                 225                 230 gag gag gag ctg tcc act tcc ttg aag agg agt gtc tac atc gaa agt         774
Glu Glu Glu Leu Ser Thr Ser Leu Lys Arg Ser Val Tyr Ile Glu Ser
235                 240                 245 cgg ata ggt acc agc acc agc ttc gac agt ggc att gct ggg ctc tct         822
Arg Ile Gly Thr Ser Thr Ser Phe Asp Ser Gly Ile Ala Gly Leu Ser
250                 255                 260                 265 tct atc agt cag tgt acc agc agc cag ctg gat gaa aca agt cat         870
Ser Ile Ser Gln Cys Thr Ser Ser Gln Leu Asp Glu Thr Ser His
                   270                 275                 280 cga tgg gca cag cca gac act gcc cca cta cct gtc ccg gca aac att         918
Arg Trp Ala Gln Pro Asp Thr Ala Pro Leu Pro Val Pro Ala Asn Ile
                285                 290                 295 cgc ttc tcc atc tgg atc tca ttc ttt gag atc tac aac gaa ctg ctt         966
Arg Phe Ser Ile Trp Ile Ser Phe Phe Glu Ile Tyr Asn Glu Leu Leu
            300                 305                 310 tat gac cta tta gaa ccg cct agc caa cag cgc aag agg cag act ttg        1014
Tyr Asp Leu Leu Glu Pro Pro Ser Gln Gln Arg Lys Arg Gln Thr Leu
315                 320                 325 cgg cta tgc gag gat caa aat ggc aat ccc tat gtg aaa gat ctc aac        1062
Arg Leu Cys Glu Asp Gln Asn Gly Asn Pro Tyr Val Lys Asp Leu Asn
330                 335                 340                 345 tgg att cat gtg caa gat gct gag gag gcc tgg aag ctc cta aaa gtg        1110
Trp Ile His Val Gln Asp Ala Glu Glu Ala Trp Lys Leu Leu Lys Val
                   350                 355                 360 ggt cgt aag aac cag agc ttt gcc agc acc cac ctc aac cag aac tcc        1158
Gly Arg Lys Asn Gln Ser Phe Ala Ser Thr His Leu Asn Gln Asn Ser
```

```
                       365                 370                 375
agc cgc agt cac agc atc ttc tca atc agg atc cta cac ctt cag ggg       1206
Ser Arg Ser His Ser Ile Phe Ser Ile Arg Ile Leu His Leu Gln Gly
        380                 385                 390 gaa gga gat ata gtc ccc aag atc agc gag ctg tca ctc tgt gat ctg       1254
Glu Gly Asp Ile Val Pro Lys Ile Ser Glu Leu Ser Leu Cys Asp Leu
395                 400                 405 gct ggc tca gag cgc tgc aaa gat cag aag agt ggt gaa cgg ttg aag       1302
Ala Gly Ser Glu Arg Cys Lys Asp Gln Lys Ser Gly Glu Arg Leu Lys
410                 415                 420                 425 gaa gca gga aac att aac acc tct cta cac acc ctg ggc cgc tgt att       1350
Glu Ala Gly Asn Ile Asn Thr Ser Leu His Thr Leu Gly Arg Cys Ile
                430                 435                 440 gct gcc ctt cgt caa aac cag cag aac cgg tca aag cag aac ctg gtt       1398
Ala Ala Leu Arg Gln Asn Gln Gln Asn Arg Ser Lys Gln Asn Leu Val
            445                 450                 455 ccc ttc cgt gac agc aag ttg act cga gtg ttc caa ggt ttc ttc aca       1446
Pro Phe Arg Asp Ser Lys Leu Thr Arg Val Phe Gln Gly Phe Phe Thr
        460                 465                 470 ggc cga ggc cgt tcc tgc atg att gtc aat gtg aat ccc tgt gca tct       1494
Gly Arg Gly Arg Ser Cys Met Ile Val Asn Val Asn Pro Cys Ala Ser
475                 480                 485 acc tat gat gaa act ctt cat gtg gcc aag ttc tca gcc att gct agc       1542
Thr Tyr Asp Glu Thr Leu His Val Ala Lys Phe Ser Ala Ile Ala Ser
490                 495                 500                 505 cag ctt gtg cat gcc cca cct atg caa ctg gga ttc cca tcc ctg cac       1590
Gln Leu Val His Ala Pro Pro Met Gln Leu Gly Phe Pro Ser Leu His
                510                 515                 520 tcg ttc atc aag gaa cat agt ctt cag gta tcc ccc agc tta gag aaa       1638
Ser Phe Ile Lys Glu His Ser Leu Gln Val Ser Pro Ser Leu Glu Lys
            525                 530                 535 ggg gct aag gca gac aca ggc ctt gat gat gat att gaa aat gaa gct       1686
Gly Ala Lys Ala Asp Thr Gly Leu Asp Asp Asp Ile Glu Asn Glu Ala
        540                 545                 550 gac atc tcc atg tat ggc aaa gag gag ctc cta caa gtt gtg gaa gcc       1734
Asp Ile Ser Met Tyr Gly Lys Glu Glu Leu Leu Gln Val Val Glu Ala
555                 560                 565 atg aag aca ctg ctt ttg aag gaa cga cag gaa aag cta cag ctg gag       1782
Met Lys Thr Leu Leu Leu Lys Glu Arg Gln Glu Lys Leu Gln Leu Glu
570                 575                 580                 585 atg cat ctc cga gat gaa att tgc aat gag atg gta gaa cag atg caa       1830
Met His Leu Arg Asp Glu Ile Cys Asn Glu Met Val Glu Gln Met Gln
                590                 595                 600 cag cgg gaa cag tgg tgc agt gaa cat ttg gac acc caa aag gaa cta       1878
Gln Arg Glu Gln Trp Cys Ser Glu His Leu Asp Thr Gln Lys Glu Leu
            605                 610                 615 ttg gag gaa atg tat gaa gaa aaa cta aat atc ctc aag gag tca ctg       1926
Leu Glu Glu Met Tyr Glu Glu Lys Leu Asn Ile Leu Lys Glu Ser Leu
        620                 625                 630 aca agt ttt tac caa gaa gag att cag gag cgg gat gaa aag att gaa       1974
Thr Ser Phe Tyr Gln Glu Glu Ile Gln Glu Arg Asp Glu Lys Ile Glu
635                 640                 645 gag cta gaa gct ctc ttg cag gaa gcc aga caa cag tca gtg gcc cat       2022
Glu Leu Glu Ala Leu Leu Gln Glu Ala Arg Gln Gln Ser Val Ala His
650                 655                 660                 665 cag caa tca ggg tct gaa ttg gcc cta cgg cgg tca caa agg ttg gca       2070
Gln Gln Ser Gly Ser Glu Leu Ala Leu Arg Arg Ser Gln Arg Leu Ala
                670                 675                 680 gct tct gcc tcc acc cag cag ctt cag gag gtt aaa gct aaa tta cag       2118
Ala Ser Ala Ser Thr Gln Gln Leu Gln Glu Val Lys Ala Lys Leu Gln
```

```
                        685               690                695
cag tgc aaa gca gag cta aac tct acc act gaa gag ttg cat aag tat    2166
Gln Cys Lys Ala Glu Leu Asn Ser Thr Thr Glu Glu Leu His Lys Tyr
            700                 705                 710 cag aaa atg tta gaa cca cca ccc tca gcc aag ccc ttc acc att gat    2214
Gln Lys Met Leu Glu Pro Pro Pro Ser Ala Lys Pro Phe Thr Ile Asp
    715                 720                 725 gtg gac aag aag tta gaa gag ggc cag aag aat ata agg ctg ttg cgg    2262
Val Asp Lys Lys Leu Glu Glu Gly Gln Lys Asn Ile Arg Leu Leu Arg
730                 735                 740                 745 aca gag ctt cag aaa ctt ggt gag tct ctc caa tca gca gag aga gct    2310
Thr Glu Leu Gln Lys Leu Gly Glu Ser Leu Gln Ser Ala Glu Arg Ala
                750                 755                 760 tgt tgc cac agc act ggg gca gga aaa ctt cgt caa gcc ttg acc act    2358
Cys Cys His Ser Thr Gly Ala Gly Lys Leu Arg Gln Ala Leu Thr Thr
            765                 770                 775 tgt gat gac atc tta atc aaa cag gac cag act ctg gct gaa ctg cag    2406
Cys Asp Asp Ile Leu Ile Lys Gln Asp Gln Thr Leu Ala Glu Leu Gln
        780                 785                 790 aac aac atg gtg cta gtg aaa ctg gac ctt cgg aag aag gca gca tgt    2454
Asn Asn Met Val Leu Val Lys Leu Asp Leu Arg Lys Lys Ala Ala Cys
795                 800                 805 att gct gag cag tat cat act gtg ttg aaa ctc caa ggc cag gtt tct    2502
Ile Ala Glu Gln Tyr His Thr Val Leu Lys Leu Gln Gly Gln Val Ser
810                 815                 820                 825 gcc aaa aag cgc ctt ggt acc aac cag gaa aat cag caa cca aac caa    2550
Ala Lys Lys Arg Leu Gly Thr Asn Gln Glu Asn Gln Gln Pro Asn Gln
                830                 835                 840 caa cca cca ggg aag aaa cca ttc ctt cga aat tta ctt ccc cga aca    2598
Gln Pro Pro Gly Lys Lys Pro Phe Leu Arg Asn Leu Leu Pro Arg Thr
            845                 850                 855 cca acc tgc caa agc tca aca gac tgc agc cct tat gcc cgg atc cta    2646
Pro Thr Cys Gln Ser Ser Thr Asp Cys Ser Pro Tyr Ala Arg Ile Leu
        860                 865                 870 cgc tca cgg cgt tcc cct tta ctc aaa tct ggg cct ttt ggc aaa aag    2694
Arg Ser Arg Arg Ser Pro Leu Leu Lys Ser Gly Pro Phe Gly Lys Lys
875                 880                 885 tac taa ggctgtgggg aaagagaaga gcagtcatgg ccctgaggtg ggtcagctac     2750
Tyr
890 tctcctgaag aaataggtct cttttatgct ttaccatata tcaggaatta tatccaggat  2810 gcaatactca gacactagct tttttctcac ttttgtatta taaccaccta tgtaatctca  2870 tgttgttgtt tttttttatt tacttatatg atttctatgc acacaaaaac agttatatta  2930 aagatattat tgttcacatt ttttattgaa aaaaaaaaa aa                      2972

<210> SEQ ID NO 12
<211> LENGTH: 890
<212> TYPE: PRT
<213> ORGANISM: Homo sapiens

<400> SEQUENCE: 12

Met Ser Gln Gly Ile Leu Ser Pro Pro Ala Gly Leu Leu Ser Asp Asp
1               5                   10                  15

Asp Val Val Ser Pro Met Phe Glu Ser Thr Ala Ala Asp Leu Gly
            20                  25                  30

Ser Val Val Arg Lys Asn Leu Leu Ser Asp Cys Ser Val Val Ser Thr
        35                  40                  45

Ser Leu Glu Asp Lys Gln Gln Val Pro Ser Glu Asp Ser Met Glu Lys
```

```
                50                  55                  60
Val Lys Val Tyr Leu Arg Val Arg Pro Leu Leu Pro Ser Glu Leu Glu
 65                  70                  75                  80

Arg Gln Glu Asp Gln Gly Cys Val Arg Ile Glu Asn Val Glu Thr Leu
                 85                  90                  95

Val Leu Gln Ala Pro Lys Asp Ser Phe Ala Leu Lys Ser Asn Glu Arg
                100                 105                 110

Gly Ile Gly Gln Ala Thr His Arg Phe Thr Phe Ser Gln Ile Phe Gly
                115                 120                 125

Pro Glu Val Gly Gln Ala Ser Phe Phe Asn Leu Thr Val Lys Glu Met
130                 135                 140

Val Lys Asp Val Leu Lys Gly Gln Asn Trp Leu Ile Tyr Thr Tyr Gly
145                 150                 155                 160

Val Thr Asn Ser Gly Lys Thr His Thr Ile Gln Gly Thr Ile Lys Asp
                165                 170                 175

Gly Gly Ile Leu Pro Arg Ser Leu Ala Leu Ile Phe Asn Ser Leu Gln
                180                 185                 190

Gly Gln Leu His Pro Thr Pro Asp Leu Lys Pro Leu Leu Ser Asn Glu
                195                 200                 205

Val Ile Trp Leu Asp Ser Lys Gln Ile Arg Gln Glu Met Lys Lys
                210                 215                 220

Leu Ser Leu Leu Asn Gly Gly Leu Gln Glu Glu Leu Ser Thr Ser
225                 230                 235                 240

Leu Lys Arg Ser Val Tyr Ile Glu Ser Arg Ile Gly Thr Ser Thr Ser
                245                 250                 255

Phe Asp Ser Gly Ile Ala Gly Leu Ser Ser Ile Ser Gln Cys Thr Ser
                260                 265                 270

Ser Ser Gln Leu Asp Glu Thr Ser His Arg Trp Ala Gln Pro Asp Thr
                275                 280                 285

Ala Pro Leu Pro Val Pro Ala Asn Ile Arg Phe Ser Ile Trp Ile Ser
                290                 295                 300

Phe Phe Glu Ile Tyr Asn Glu Leu Leu Tyr Asp Leu Leu Glu Pro Pro
305                 310                 315                 320

Ser Gln Gln Arg Lys Arg Gln Thr Leu Arg Leu Cys Glu Asp Gln Asn
                325                 330                 335

Gly Asn Pro Tyr Val Lys Asp Leu Asn Trp Ile His Val Gln Asp Ala
                340                 345                 350

Glu Glu Ala Trp Lys Leu Leu Lys Val Gly Arg Lys Asn Gln Ser Phe
                355                 360                 365

Ala Ser Thr His Leu Asn Gln Asn Ser Ser Arg Ser His Ser Ile Phe
                370                 375                 380

Ser Ile Arg Ile Leu His Leu Gln Gly Glu Gly Asp Ile Val Pro Lys
385                 390                 395                 400

Ile Ser Glu Leu Ser Leu Cys Asp Leu Ala Gly Ser Glu Arg Cys Lys
                405                 410                 415

Asp Gln Lys Ser Gly Glu Arg Leu Lys Glu Ala Gly Asn Ile Asn Thr
                420                 425                 430

Ser Leu His Thr Leu Gly Arg Cys Ile Ala Ala Leu Arg Gln Asn Gln
                435                 440                 445

Gln Asn Arg Ser Lys Gln Asn Leu Val Pro Phe Arg Asp Ser Lys Leu
                450                 455                 460

Thr Arg Val Phe Gln Gly Phe Phe Thr Gly Arg Gly Arg Ser Cys Met
465                 470                 475                 480
```

```
Ile Val Asn Val Asn Pro Cys Ala Ser Thr Tyr Asp Glu Thr Leu His
                485                 490                 495

Val Ala Lys Phe Ser Ala Ile Ala Ser Gln Leu Val His Ala Pro Pro
            500                 505                 510

Met Gln Leu Gly Phe Pro Ser Leu His Ser Phe Ile Lys Glu His Ser
        515                 520                 525

Leu Gln Val Ser Pro Ser Leu Glu Lys Gly Ala Lys Ala Asp Thr Gly
    530                 535                 540

Leu Asp Asp Asp Ile Glu Asn Glu Ala Asp Ile Ser Met Tyr Gly Lys
545                 550                 555                 560

Glu Glu Leu Leu Gln Val Val Glu Ala Met Lys Thr Leu Leu Leu Lys
                565                 570                 575

Glu Arg Gln Glu Lys Leu Gln Leu Glu Met His Leu Arg Asp Glu Ile
            580                 585                 590

Cys Asn Glu Met Val Glu Gln Met Gln Gln Arg Glu Gln Trp Cys Ser
        595                 600                 605

Glu His Leu Asp Thr Gln Lys Glu Leu Leu Glu Glu Met Tyr Glu Glu
    610                 615                 620

Lys Leu Asn Ile Leu Lys Glu Ser Leu Thr Ser Phe Tyr Gln Glu Glu
625                 630                 635                 640

Ile Gln Glu Arg Asp Glu Lys Ile Glu Glu Leu Glu Ala Leu Leu Gln
                645                 650                 655

Glu Ala Arg Gln Gln Ser Val Ala His Gln Gln Ser Gly Ser Glu Leu
            660                 665                 670

Ala Leu Arg Arg Ser Gln Arg Leu Ala Ala Ser Ala Ser Thr Gln Gln
        675                 680                 685

Leu Gln Glu Val Lys Ala Lys Leu Gln Gln Cys Lys Ala Glu Leu Asn
    690                 695                 700

Ser Thr Thr Glu Glu Leu His Lys Tyr Gln Lys Met Leu Glu Pro Pro
705                 710                 715                 720

Pro Ser Ala Lys Pro Phe Thr Ile Asp Val Asp Lys Lys Leu Glu Glu
                725                 730                 735

Gly Gln Lys Asn Ile Arg Leu Leu Arg Thr Glu Leu Gln Lys Leu Gly
            740                 745                 750

Glu Ser Leu Gln Ser Ala Glu Arg Ala Cys Cys His Ser Thr Gly Ala
        755                 760                 765

Gly Lys Leu Arg Gln Ala Leu Thr Thr Cys Asp Asp Ile Leu Ile Lys
    770                 775                 780

Gln Asp Gln Thr Leu Ala Glu Leu Gln Asn Asn Met Val Leu Val Lys
785                 790                 795                 800

Leu Asp Leu Arg Lys Lys Ala Ala Cys Ile Ala Glu Gln Tyr His Thr
                805                 810                 815

Val Leu Lys Leu Gln Gly Gln Val Ser Ala Lys Lys Arg Leu Gly Thr
            820                 825                 830

Asn Gln Glu Asn Gln Gln Pro Asn Gln Gln Pro Pro Gly Lys Lys Pro
        835                 840                 845

Phe Leu Arg Asn Leu Leu Pro Arg Thr Pro Thr Cys Gln Ser Ser Thr
    850                 855                 860

Asp Cys Ser Pro Tyr Ala Arg Ile Leu Arg Ser Arg Arg Ser Pro Leu
865                 870                 875                 880

Leu Lys Ser Gly Pro Phe Gly Lys Lys Tyr
                885                 890

<210> SEQ ID NO 13
```

-continued

```
<211> LENGTH: 2150
<212> TYPE: DNA
<213> ORGANISM: Homo sapiens
<220> FEATURE:
<221> NAME/KEY: CDS
<222> LOCATION: (105)..(2033)

<400> SEQUENCE: 13
ctcgagccac gaaggcccg ctgtcctgtc tagcagatac ttgcacggtt tacagaaatt      60
cggtccctgg gtcgtgtcag gaaactggaa aaaaggtcat aagc atg aag cgc agt    116
                                                  Met Lys Arg Ser
                                                  1 tca gtt tcc agc ggt ggt gct ggc cgc ctc tcc atg cag gag tta aga      164
Ser Val Ser Ser Gly Gly Ala Gly Arg Leu Ser Met Gln Glu Leu Arg
 5              10                  15                  20 tcc cag gat gta aat aaa caa ggc ctc tat acc cct caa acc aaa gag     212
Ser Gln Asp Val Asn Lys Gln Gly Leu Tyr Thr Pro Gln Thr Lys Glu
            25                  30                  35 aaa cca acc ttt gga aag ttg agt ata aac aaa ccg aca tct gaa aga     260
Lys Pro Thr Phe Gly Lys Leu Ser Ile Asn Lys Pro Thr Ser Glu Arg
        40                  45                  50 aaa gtc tcg cta ttt ggc aaa aga act agt gga cat gga tcc cgg aat     308
Lys Val Ser Leu Phe Gly Lys Arg Thr Ser Gly His Gly Ser Arg Asn
    55                  60                  65 agt caa ctt ggt ata ttt tcc agt tct gag aaa atc aag gac ccg aga     356
Ser Gln Leu Gly Ile Phe Ser Ser Ser Glu Lys Ile Lys Asp Pro Arg
70                  75                  80 cca ctt aat gac aaa gca ttc att cag cag tgt att cga caa ctc tgt     404
Pro Leu Asn Asp Lys Ala Phe Ile Gln Gln Cys Ile Arg Gln Leu Cys
85                  90                  95                 100 gag ttt ctt aca gaa aat ggt tat gca cat aat gtg tcc atg aaa tct     452
Glu Phe Leu Thr Glu Asn Gly Tyr Ala His Asn Val Ser Met Lys Ser
                105                 110                 115 cta caa gct ccc tct gtt aaa gac ttc ctg aag atc ttc aca ttt ctt     500
Leu Gln Ala Pro Ser Val Lys Asp Phe Leu Lys Ile Phe Thr Phe Leu
            120                 125                 130 tat ggc ttc ctg tgc ccc tca tac gaa ctt cct gac aca aag ttt gaa     548
Tyr Gly Phe Leu Cys Pro Ser Tyr Glu Leu Pro Asp Thr Lys Phe Glu
        135                 140                 145 gaa gag gtt cca aga atc ttt aaa gac ctt ggg tat cct ttt gca cta     596
Glu Glu Val Pro Arg Ile Phe Lys Asp Leu Gly Tyr Pro Phe Ala Leu
    150                 155                 160 tcc aaa agc tcc atg tac aca gtg ggg gct cct cat aca tgg cct cac     644
Ser Lys Ser Ser Met Tyr Thr Val Gly Ala Pro His Thr Trp Pro His
165                 170                 175                 180 att gtg gca gcc tta gtt tgg cta ata gac tgc atc aag ata cat act     692
Ile Val Ala Ala Leu Val Trp Leu Ile Asp Cys Ile Lys Ile His Thr
                185                 190                 195 gcc atg aaa gaa agc tca cct tta ttt gat gat ggg cag cct tgg gga    740
Ala Met Lys Glu Ser Ser Pro Leu Phe Asp Asp Gly Gln Pro Trp Gly
            200                 205                 210 gaa gaa act gaa gat gga att atg cat aat aag ttg ttt ttg gac tac    788
Glu Glu Thr Glu Asp Gly Ile Met His Asn Lys Leu Phe Leu Asp Tyr
        215                 220                 225 acc ata aaa tgc tat gag agt ttt atg agt ggt gcc gac agc ttt gat    836
Thr Ile Lys Cys Tyr Glu Ser Phe Met Ser Gly Ala Asp Ser Phe Asp
    230                 235                 240 gag atg aat gca gag ctg cag tca aaa ctg aag gat tta ttt aat gtg    884
Glu Met Asn Ala Glu Leu Gln Ser Lys Leu Lys Asp Leu Phe Asn Val
245                 250                 255                 260 gat gct ttt aag ctg gaa tca tta gaa gca aaa aac aga gca ttg aat    932
Asp Ala Phe Lys Leu Glu Ser Leu Glu Ala Lys Asn Arg Ala Leu Asn
```

-continued

| | | | | | | | | | | | | | | |
|---|---|---|---|---|---|---|---|---|---|---|---|---|---|---|
| Asp | Ala | Phe | Lys | Leu | Glu | Ser | Leu | Glu | Ala | Lys | Asn | Arg | Ala | Leu | Asn |
| | | | | 265 | | | | 270 | | | | | 275 | | |

```
gaa cag att gca aga ttg gaa caa gaa aga gaa aaa gaa ccg aat cgt     980
Glu Gln Ile Ala Arg Leu Glu Gln Glu Arg Glu Lys Glu Pro Asn Arg
            280                 285                 290 cta gag tcg ttg aga aaa ctg aag gct tcc tta caa gga gat gtt caa    1028
Leu Glu Ser Leu Arg Lys Leu Lys Ala Ser Leu Gln Gly Asp Val Gln
        295                 300                 305 aag tat cag gca tac atg agc aat ttg gag tct cat tca gcc att ctt    1076
Lys Tyr Gln Ala Tyr Met Ser Asn Leu Glu Ser His Ser Ala Ile Leu
    310                 315                 320 gac cag aaa tta aat ggt ctc aat gag gaa att gct aga gta gaa cta    1124
Asp Gln Lys Leu Asn Gly Leu Asn Glu Glu Ile Ala Arg Val Glu Leu
325                 330                 335                 340 gaa tgt gaa aca ata aaa cag gag aac act cga cta cag aat atc att    1172
Glu Cys Glu Thr Ile Lys Gln Glu Asn Thr Arg Leu Gln Asn Ile Ile
                345                 350                 355 gac aac cag aag tac tca gtt gca gac att gag cga ata aat cat gaa    1220
Asp Asn Gln Lys Tyr Ser Val Ala Asp Ile Glu Arg Ile Asn His Glu
            360                 365                 370 aga aat gaa ttg cag cag act att aat aaa tta acc aag gac ctg gaa    1268
Arg Asn Glu Leu Gln Gln Thr Ile Asn Lys Leu Thr Lys Asp Leu Glu
        375                 380                 385 gct gaa caa cag aag ttg tgg aat gag gag tta aaa tat gcc aga ggc    1316
Ala Glu Gln Gln Lys Leu Trp Asn Glu Glu Leu Lys Tyr Ala Arg Gly
    390                 395                 400 aaa gaa gcg att gaa aca caa tta gca gag tat cac aaa ttg gct aga    1364
Lys Glu Ala Ile Glu Thr Gln Leu Ala Glu Tyr His Lys Leu Ala Arg
405                 410                 415                 420 aaa tta aaa ctt att cct aaa ggt gct gag aat tcc aaa ggt tat gac    1412
Lys Leu Lys Leu Ile Pro Lys Gly Ala Glu Asn Ser Lys Gly Tyr Asp
                425                 430                 435 ttt gaa att aag ttt aat ccc gag gct ggt gcc aac tgc ctt gtc aaa    1460
Phe Glu Ile Lys Phe Asn Pro Glu Ala Gly Ala Asn Cys Leu Val Lys
            440                 445                 450 tac agg gct caa gtt tat gta cct ctt aag gaa ctc ctg aat gaa act    1508
Tyr Arg Ala Gln Val Tyr Val Pro Leu Lys Glu Leu Leu Asn Glu Thr
        455                 460                 465 gaa gaa gaa att aat aaa gcc cta aat aaa aaa atg ggt ttg gag gat    1556
Glu Glu Glu Ile Asn Lys Ala Leu Asn Lys Lys Met Gly Leu Glu Asp
    470                 475                 480 act tta gaa caa ttg aat gca atg ata aca gaa agc aag aga agt gtg    1604
Thr Leu Glu Gln Leu Asn Ala Met Ile Thr Glu Ser Lys Arg Ser Val
485                 490                 495                 500 aga act ctg aaa gaa gaa gtt caa aag ctg gat gat ctt tac caa caa    1652
Arg Thr Leu Lys Glu Glu Val Gln Lys Leu Asp Asp Leu Tyr Gln Gln
                505                 510                 515 aaa att aag gaa gca gag gaa gag gat gaa aaa tgt gcc agt gag ctt    1700
Lys Ile Lys Glu Ala Glu Glu Glu Asp Glu Lys Cys Ala Ser Glu Leu
            520                 525                 530 gag tcc ttg gag aaa cac aag cac ctg cta gaa agt act gtt aac cag    1748
Glu Ser Leu Glu Lys His Lys His Leu Leu Glu Ser Thr Val Asn Gln
        535                 540                 545 ggg ctc agt gaa gct atg aat gaa tta gat gct gtt cag cgg gaa tac    1796
Gly Leu Ser Glu Ala Met Asn Glu Leu Asp Ala Val Gln Arg Glu Tyr
    550                 555                 560 caa cta gtt gtg caa acc acg act gaa gaa aga cga aaa gtg gga aat    1844
Gln Leu Val Val Gln Thr Thr Thr Glu Glu Arg Arg Lys Val Gly Asn
565                 570                 575                 580 aac ttg caa cgt ctg tta gag atg gtt gct aca cat gtt ggg tct gta    1892
```

```
Asn Leu Gln Arg Leu Leu Glu Met Val Ala Thr His Val Gly Ser Val
                585                 590                 595 gag aaa cat ctt gag gag cag att gct aaa gtt gat aga gaa tat gaa    1940
Glu Lys His Leu Glu Glu Gln Ile Ala Lys Val Asp Arg Glu Tyr Glu
            600                 605                 610 gaa tgc atg tca gaa gat ctc tcg gaa aat att aaa gag att aga gat    1988
Glu Cys Met Ser Glu Asp Leu Ser Glu Asn Ile Lys Glu Ile Arg Asp
        615                 620                 625 aag tat gag aag aaa gct act cta att aag tct tct gaa gaa tga        2033
Lys Tyr Glu Lys Lys Ala Thr Leu Ile Lys Ser Ser Glu Glu
    630                 635                 640 agataaaatg ttgatcatgt atatatatcc atagtgaata aaattgtctc agtaaaaaaa  2093
aaaaaaaaaa aaaaaaaaaa aaaaaaaaaa aaaaaaaaaa aaaaaaaaaa aaaaaaa     2150

<210> SEQ ID NO 14
<211> LENGTH: 642
<212> TYPE: PRT
<213> ORGANISM: Homo sapiens

<400> SEQUENCE: 14

Met Lys Arg Ser Ser Val Ser Ser Gly Gly Ala Gly Arg Leu Ser Met
1               5                   10                  15

Gln Glu Leu Arg Ser Gln Asp Val Asn Lys Gln Gly Leu Tyr Thr Pro
            20                  25                  30

Gln Thr Lys Glu Lys Pro Thr Phe Gly Lys Leu Ser Ile Asn Lys Pro
        35                  40                  45

Thr Ser Glu Arg Lys Val Ser Leu Phe Gly Lys Arg Thr Ser Gly His
    50                  55                  60

Gly Ser Arg Asn Ser Gln Leu Gly Ile Phe Ser Ser Glu Lys Ile
65                  70                  75                  80

Lys Asp Pro Arg Pro Leu Asn Asp Lys Ala Phe Ile Gln Gln Cys Ile
                85                  90                  95

Arg Gln Leu Cys Glu Phe Leu Thr Glu Asn Gly Tyr Ala His Asn Val
            100                 105                 110

Ser Met Lys Ser Leu Gln Ala Pro Ser Val Lys Asp Phe Leu Lys Ile
        115                 120                 125

Phe Thr Phe Leu Tyr Gly Phe Leu Cys Pro Ser Tyr Glu Leu Pro Asp
    130                 135                 140

Thr Lys Phe Glu Glu Glu Val Pro Arg Ile Phe Lys Asp Leu Gly Tyr
145                 150                 155                 160

Pro Phe Ala Leu Ser Lys Ser Ser Met Tyr Thr Val Gly Ala Pro His
                165                 170                 175

Thr Trp Pro His Ile Val Ala Ala Leu Val Trp Leu Ile Asp Cys Ile
            180                 185                 190

Lys Ile His Thr Ala Met Lys Glu Ser Ser Pro Leu Phe Asp Asp Gly
        195                 200                 205

Gln Pro Trp Gly Glu Glu Thr Glu Asp Gly Ile Met His Asn Lys Leu
    210                 215                 220

Phe Leu Asp Tyr Thr Ile Lys Cys Tyr Glu Ser Phe Met Ser Gly Ala
225                 230                 235                 240

Asp Ser Phe Asp Glu Met Asn Ala Glu Leu Gln Ser Lys Leu Lys Asp
                245                 250                 255

Leu Phe Asn Val Asp Ala Phe Lys Leu Glu Ser Leu Glu Ala Lys Asn
            260                 265                 270

Arg Ala Leu Asn Glu Gln Ile Ala Arg Leu Glu Gln Glu Arg Glu Lys
        275                 280                 285
```

| | | | | | | | | | | | | |
|---|---|---|---|---|---|---|---|---|---|---|---|---|
|Glu|Pro|Asn|Arg|Leu|Glu|Ser|Leu|Arg|Lys|Leu|Lys|Ala|Ser|Leu|Gln|
| |290| | | |295| | | |300| | | | | | |

Glu Pro Asn Arg Leu Glu Ser Leu Arg Lys Leu Lys Ala Ser Leu Gln
    290                 295                 300

Gly Asp Val Gln Lys Tyr Gln Ala Tyr Met Ser Asn Leu Glu Ser His
305             310                 315                 320

Ser Ala Ile Leu Asp Gln Lys Leu Asn Gly Leu Asn Glu Glu Ile Ala
            325                 330                 335

Arg Val Glu Leu Glu Cys Glu Thr Ile Lys Gln Glu Asn Thr Arg Leu
            340                 345                 350

Gln Asn Ile Ile Asp Asn Gln Lys Tyr Ser Val Ala Asp Ile Glu Arg
            355                 360                 365

Ile Asn His Glu Arg Asn Glu Leu Gln Gln Thr Ile Asn Lys Leu Thr
370                 375                 380

Lys Asp Leu Glu Ala Glu Gln Gln Lys Leu Trp Asn Glu Glu Leu Lys
385                 390                 395                 400

Tyr Ala Arg Gly Lys Glu Ala Ile Glu Thr Gln Leu Ala Glu Tyr His
            405                 410                 415

Lys Leu Ala Arg Lys Leu Lys Leu Ile Pro Lys Gly Ala Glu Asn Ser
            420                 425                 430

Lys Gly Tyr Asp Phe Glu Ile Lys Phe Asn Pro Glu Ala Gly Ala Asn
            435                 440                 445

Cys Leu Val Lys Tyr Arg Ala Gln Val Tyr Val Pro Leu Lys Glu Leu
450                 455                 460

Leu Asn Glu Thr Glu Glu Ile Asn Lys Ala Leu Asn Lys Lys Met
465                 470                 475                 480

Gly Leu Glu Asp Thr Leu Glu Gln Leu Asn Ala Met Ile Thr Glu Ser
            485                 490                 495

Lys Arg Ser Val Arg Thr Leu Lys Glu Val Gln Lys Leu Asp Asp
            500                 505                 510

Leu Tyr Gln Gln Lys Ile Lys Glu Ala Glu Glu Asp Glu Lys Cys
    515                 520                 525

Ala Ser Glu Leu Glu Ser Leu Glu Lys His Lys His Leu Leu Glu Ser
530                 535                 540

Thr Val Asn Gln Gly Leu Ser Glu Ala Met Asn Glu Leu Asp Ala Val
545                 550                 555                 560

Gln Arg Glu Tyr Gln Leu Val Val Gln Thr Thr Thr Glu Glu Arg Arg
            565                 570                 575

Lys Val Gly Asn Asn Leu Gln Arg Leu Leu Glu Met Val Ala Thr His
            580                 585                 590

Val Gly Ser Val Glu Lys His Leu Glu Glu Gln Ile Ala Lys Val Asp
            595                 600                 605

Arg Glu Tyr Glu Glu Cys Met Ser Glu Asp Leu Ser Glu Asn Ile Lys
610                 615                 620

Glu Ile Arg Asp Lys Tyr Glu Lys Lys Ala Thr Leu Ile Lys Ser Ser
625                 630                 635                 640

Glu Glu

<210> SEQ ID NO 15
<211> LENGTH: 2984
<212> TYPE: DNA
<213> ORGANISM: Homo sapiens
<220> FEATURE:
<221> NAME/KEY: CDS
<222> LOCATION: (75)..(2648)

<400> SEQUENCE: 15

```
ggaaattcaa acgtgtttgc ggaaaggagt ttgggttcca tctttcatt tccccagcgc        60
```

| agc ttt ctg t aga | atg | gaa | tcc | gag | gat | tta | agt | ggc | aga | gaa | ttg | aca |     | 110 |
|---|---|---|---|---|---|---|---|---|---|---|---|---|---|---|
|  | Met | Glu | Ser | Glu | Asp | Leu | Ser | Gly | Arg | Glu | Leu | Thr |  |  |
|  | 1 |  |  | 5 |  |  |  |  |  | 10 |  |  |  |  |

| att | gat | tcc | ata | atg | aac | aaa | gtg | aga | gac | att | aaa | aat | aag | ttt | aaa | 158 |
|---|---|---|---|---|---|---|---|---|---|---|---|---|---|---|---|---|
| Ile | Asp | Ser | Ile | Met | Asn | Lys | Val | Arg | Asp | Ile | Lys | Asn | Lys | Phe | Lys |  |
|  |  | 15 |  |  |  |  | 20 |  |  |  |  | 25 |  |  |  |  |

| aat | gaa | gac | ctt | act | gat | gaa | cta | agc | ttg | aat | aaa | att | tct | gct | gat | 206 |
|---|---|---|---|---|---|---|---|---|---|---|---|---|---|---|---|---|
| Asn | Glu | Asp | Leu | Thr | Asp | Glu | Leu | Ser | Leu | Asn | Lys | Ile | Ser | Ala | Asp |  |
|  | 30 |  |  |  |  | 35 |  |  |  |  | 40 |  |  |  |  |  |

| act | aca | gat | aac | tcg | gga | act | gtt | aac | caa | att | atg | atg | atg | gca | aac | 254 |
|---|---|---|---|---|---|---|---|---|---|---|---|---|---|---|---|---|
| Thr | Thr | Asp | Asn | Ser | Gly | Thr | Val | Asn | Gln | Ile | Met | Met | Met | Ala | Asn |  |
| 45 |  |  |  |  | 50 |  |  |  |  | 55 |  |  |  |  | 60 |  |

| aac | cca | gag | gac | tgg | ttg | agt | ttg | ttg | ctc | aaa | cta | gag | aaa | aac | agt | 302 |
|---|---|---|---|---|---|---|---|---|---|---|---|---|---|---|---|---|
| Asn | Pro | Glu | Asp | Trp | Leu | Ser | Leu | Leu | Leu | Lys | Leu | Glu | Lys | Asn | Ser |  |
|  |  |  |  | 65 |  |  |  |  | 70 |  |  |  |  | 75 |  |  |

| gtt | ccg | cta | agt | gat | gct | ctt | tta | aat | aaa | ttg | att | ggt | cgt | tac | agt | 350 |
|---|---|---|---|---|---|---|---|---|---|---|---|---|---|---|---|---|
| Val | Pro | Leu | Ser | Asp | Ala | Leu | Leu | Asn | Lys | Leu | Ile | Gly | Arg | Tyr | Ser |  |
|  |  |  | 80 |  |  |  |  | 85 |  |  |  |  | 90 |  |  |  |

| caa | gca | att | gaa | gcg | ctt | ccc | cca | gat | aaa | tat | ggc | caa | aat | gag | agt | 398 |
|---|---|---|---|---|---|---|---|---|---|---|---|---|---|---|---|---|
| Gln | Ala | Ile | Glu | Ala | Leu | Pro | Pro | Asp | Lys | Tyr | Gly | Gln | Asn | Glu | Ser |  |
|  |  | 95 |  |  |  |  | 100 |  |  |  |  | 105 |  |  |  |  |

| ttt | gct | aga | att | caa | gtg | aga | ttt | gct | gaa | tta | aaa | gct | att | caa | gag | 446 |
|---|---|---|---|---|---|---|---|---|---|---|---|---|---|---|---|---|
| Phe | Ala | Arg | Ile | Gln | Val | Arg | Phe | Ala | Glu | Leu | Lys | Ala | Ile | Gln | Glu |  |
|  | 110 |  |  |  |  | 115 |  |  |  |  | 120 |  |  |  |  |  |

| cca | gat | gat | gca | cgt | gac | tac | ttt | caa | atg | gcc | aga | gca | aac | tgc | aag | 494 |
|---|---|---|---|---|---|---|---|---|---|---|---|---|---|---|---|---|
| Pro | Asp | Asp | Ala | Arg | Asp | Tyr | Phe | Gln | Met | Ala | Arg | Ala | Asn | Cys | Lys |  |
| 125 |  |  |  | 130 |  |  |  |  | 135 |  |  |  |  | 140 |  |  |

| aaa | ttt | gct | ttt | gtt | cat | ata | tct | ttt | gca | caa | ttt | gaa | ctg | tca | caa | 542 |
|---|---|---|---|---|---|---|---|---|---|---|---|---|---|---|---|---|
| Lys | Phe | Ala | Phe | Val | His | Ile | Ser | Phe | Ala | Gln | Phe | Glu | Leu | Ser | Gln |  |
|  |  |  |  | 145 |  |  |  |  | 150 |  |  |  |  | 155 |  |  |

| ggt | aat | gtc | aaa | aaa | agt | aaa | caa | ctt | ctt | caa | aaa | gct | gta | gaa | cgt | 590 |
|---|---|---|---|---|---|---|---|---|---|---|---|---|---|---|---|---|
| Gly | Asn | Val | Lys | Lys | Ser | Lys | Gln | Leu | Leu | Gln | Lys | Ala | Val | Glu | Arg |  |
|  |  |  | 160 |  |  |  |  | 165 |  |  |  |  | 170 |  |  |  |

| gga | gca | gta | cca | cta | gaa | atg | ctg | gaa | att | gcc | ctg | cgg | aat | tta | aac | 638 |
|---|---|---|---|---|---|---|---|---|---|---|---|---|---|---|---|---|
| Gly | Ala | Val | Pro | Leu | Glu | Met | Leu | Glu | Ile | Ala | Leu | Arg | Asn | Leu | Asn |  |
|  |  | 175 |  |  |  |  | 180 |  |  |  |  | 185 |  |  |  |  |

| ctc | caa | aaa | aag | cag | ctg | ctt | tca | gag | gag | gaa | aag | aag | aat | tta | tca | 686 |
|---|---|---|---|---|---|---|---|---|---|---|---|---|---|---|---|---|
| Leu | Gln | Lys | Lys | Gln | Leu | Leu | Ser | Glu | Glu | Glu | Lys | Lys | Asn | Leu | Ser |  |
|  | 190 |  |  |  |  | 195 |  |  |  |  | 200 |  |  |  |  |  |

| gca | tct | acg | gta | tta | act | gcc | caa | gaa | tca | ttt | tcc | ggt | tca | ctt | ggg | 734 |
|---|---|---|---|---|---|---|---|---|---|---|---|---|---|---|---|---|
| Ala | Ser | Thr | Val | Leu | Thr | Ala | Gln | Glu | Ser | Phe | Ser | Gly | Ser | Leu | Gly |  |
| 205 |  |  |  | 210 |  |  |  |  | 215 |  |  |  |  | 220 |  |  |

| cat | tta | cag | aat | agg | aac | aac | agt | tgt | gat | tcc | aga | gga | cag | act | act | 782 |
|---|---|---|---|---|---|---|---|---|---|---|---|---|---|---|---|---|
| His | Leu | Gln | Asn | Arg | Asn | Asn | Ser | Cys | Asp | Ser | Arg | Gly | Gln | Thr | Thr |  |
|  |  |  |  | 225 |  |  |  |  | 230 |  |  |  |  | 235 |  |  |

| aaa | gcc | agg | ttt | tta | tat | gga | gag | aac | atg | cca | cca | caa | gat | gca | gaa | 830 |
|---|---|---|---|---|---|---|---|---|---|---|---|---|---|---|---|---|
| Lys | Ala | Arg | Phe | Leu | Tyr | Gly | Glu | Asn | Met | Pro | Pro | Gln | Asp | Ala | Glu |  |
|  |  |  | 240 |  |  |  |  | 245 |  |  |  |  | 250 |  |  |  |

| ata | ggt | tac | cgg | aat | tca | ttg | aga | caa | act | aac | aaa | act | aaa | cag | tca | 878 |
|---|---|---|---|---|---|---|---|---|---|---|---|---|---|---|---|---|
| Ile | Gly | Tyr | Arg | Asn | Ser | Leu | Arg | Gln | Thr | Asn | Lys | Thr | Lys | Gln | Ser |  |
|  |  | 255 |  |  |  |  | 260 |  |  |  |  | 265 |  |  |  |  |

| tgc | cca | ttt | gga | aga | gtc | cca | gtt | aac | ctt | cta | aat | agc | cca | gat | tgt | 926 |
|---|---|---|---|---|---|---|---|---|---|---|---|---|---|---|---|---|
| Cys | Pro | Phe | Gly | Arg | Val | Pro | Val | Asn | Leu | Leu | Asn | Ser | Pro | Asp | Cys |  |
|  | 270 |  |  |  |  | 275 |  |  |  |  | 280 |  |  |  |  |  |

| gat | gtg | aag | aca | gat | gat | tca | gtt | gta | cct | tgt | ttt | atg | aaa | aga | caa | 974 |
|---|---|---|---|---|---|---|---|---|---|---|---|---|---|---|---|---|
| Asp | Val | Lys | Thr | Asp | Asp | Ser | Val | Val | Pro | Cys | Phe | Met | Lys | Arg | Gln |  |
| 285 |  |  |  | 290 |  |  |  |  | 295 |  |  |  |  | 300 |  |  |

| acc | tct | aga | tca | gaa | tgc | cga | gat | ttg | gtt | gtg | cct | gga | tct | aaa | cca | 1022 |
|---|---|---|---|---|---|---|---|---|---|---|---|---|---|---|---|---|
| Thr | Ser | Arg | Ser | Glu | Cys | Arg | Asp | Leu | Val | Val | Pro | Gly | Ser | Lys | Pro |  |

```
                    305                 310                 315
agt gga aat gat tcc tgt gaa tta aga aat tta aag tct gtt caa aat     1070
Ser Gly Asn Asp Ser Cys Glu Leu Arg Asn Leu Lys Ser Val Gln Asn
            320                 325                 330 agt cat ttc aag gaa cct ctg gtg tca gat gaa aag agt tct gaa ctt     1118
Ser His Phe Lys Glu Pro Leu Val Ser Asp Glu Lys Ser Ser Glu Leu
        335                 340                 345 att att act gat tca ata acc ctg aag aat aaa acg gaa tca agt ctt     1166
Ile Ile Thr Asp Ser Ile Thr Leu Lys Asn Lys Thr Glu Ser Ser Leu
    350                 355                 360 cta gct aaa tta gaa gaa act aaa gag tat caa gaa cca gag gtt cca     1214
Leu Ala Lys Leu Glu Glu Thr Lys Glu Tyr Gln Glu Pro Glu Val Pro
365                 370                 375                 380 gag agt aac cag aaa cag tgg caa tct aag aga aag tca gag tgt att     1262
Glu Ser Asn Gln Lys Gln Trp Gln Ser Lys Arg Lys Ser Glu Cys Ile
                385                 390                 395 aac cag aat cct gct gca tct tca aat cac tgg cag att ccg gag tta     1310
Asn Gln Asn Pro Ala Ala Ser Ser Asn His Trp Gln Ile Pro Glu Leu
            400                 405                 410 gcc cga aaa gtt aat aca gag cag aaa cat acc act ttt gag caa cct     1358
Ala Arg Lys Val Asn Thr Glu Gln Lys His Thr Thr Phe Glu Gln Pro
        415                 420                 425 gtc ttt tca gtt tca aaa cag tca cca cca ata tca aca tct aaa tgg     1406
Val Phe Ser Val Ser Lys Gln Ser Pro Pro Ile Ser Thr Ser Lys Trp
    430                 435                 440 ttt gac cca aaa tct att tgt aag aca cca agc agc aat acc ttg gat     1454
Phe Asp Pro Lys Ser Ile Cys Lys Thr Pro Ser Ser Asn Thr Leu Asp
445                 450                 455                 460 gat tac atg agc tgt ttt aga act cca gtt gta aag aat gac ttt cca     1502
Asp Tyr Met Ser Cys Phe Arg Thr Pro Val Val Lys Asn Asp Phe Pro
                465                 470                 475 cct gct tgt cag ttg tca aca cct tat ggc caa cct gcc tgt ttc cag     1550
Pro Ala Cys Gln Leu Ser Thr Pro Tyr Gly Gln Pro Ala Cys Phe Gln
            480                 485                 490 cag caa cag cat caa ata ctt gcc act cca ctt caa aat tta cag gtt     1598
Gln Gln Gln His Gln Ile Leu Ala Thr Pro Leu Gln Asn Leu Gln Val
        495                 500                 505 tta gca tct tct tca gca aat gaa tgc att tcg gtt aaa gga aga att     1646
Leu Ala Ser Ser Ser Ala Asn Glu Cys Ile Ser Val Lys Gly Arg Ile
    510                 515                 520 tat tcc att tta aag cag ata gga agt gga ggt tca agc aag gta ttt     1694
Tyr Ser Ile Leu Lys Gln Ile Gly Ser Gly Gly Ser Ser Lys Val Phe
525                 530                 535                 540 cag gtg tta aat gaa aag aaa cag ata tat gct ata aaa tat gtg aac     1742
Gln Val Leu Asn Glu Lys Lys Gln Ile Tyr Ala Ile Lys Tyr Val Asn
                545                 550                 555 tta gaa gaa gca gat aac caa act ctt gat agt tac cgg aac gaa ata     1790
Leu Glu Glu Ala Asp Asn Gln Thr Leu Asp Ser Tyr Arg Asn Glu Ile
            560                 565                 570 gct tat ttg aat aaa cta caa caa cac agt gat aag atc atc cga ctt     1838
Ala Tyr Leu Asn Lys Leu Gln Gln His Ser Asp Lys Ile Ile Arg Leu
        575                 580                 585 tat gat tat gaa atc acg gac cag tac atc tac atg gta atg gag tgt     1886
Tyr Asp Tyr Glu Ile Thr Asp Gln Tyr Ile Tyr Met Val Met Glu Cys
    590                 595                 600 gga aat att gat ctt aat agt tgg ctt aaa aag aaa aaa tcc att gat     1934
Gly Asn Ile Asp Leu Asn Ser Trp Leu Lys Lys Lys Lys Ser Ile Asp
605                 610                 615                 620 cca tgg gaa cgc aag agt tac tgg aaa aat atg tta gag gca gtt cac     1982
Pro Trp Glu Arg Lys Ser Tyr Trp Lys Asn Met Leu Glu Ala Val His
```

```
                     625                 630                 635
aca atc cat caa cat ggc att gtt cac agt gat ctt aaa cca gct aac       2030
Thr Ile His Gln His Gly Ile Val His Ser Asp Leu Lys Pro Ala Asn
            640                 645                 650 ttt ctg ata gtt gat gga atg cta aag cta att gat ttt ggg att gca       2078
Phe Leu Ile Val Asp Gly Met Leu Lys Leu Ile Asp Phe Gly Ile Ala
            655                 660                 665 aac caa atg caa cca gat aca aca agt gtt gtt aaa gat tct cag gtt       2126
Asn Gln Met Gln Pro Asp Thr Thr Ser Val Val Lys Asp Ser Gln Val
        670                 675                 680 ggc aca gtt aat tat atg cca cca gaa gca atc aaa gat atg tct tcc       2174
Gly Thr Val Asn Tyr Met Pro Pro Glu Ala Ile Lys Asp Met Ser Ser
685                 690                 695                 700 tcc aga gag aat ggg aaa tct aag tca aag ata agc ccc aaa agt gat       2222
Ser Arg Glu Asn Gly Lys Ser Lys Ser Lys Ile Ser Pro Lys Ser Asp
                705                 710                 715 gtt tgg tcc tta gga tgt att ttg tac tat atg act tac ggg aaa aca       2270
Val Trp Ser Leu Gly Cys Ile Leu Tyr Tyr Met Thr Tyr Gly Lys Thr
            720                 725                 730 cca ttt cag cag ata att aat cag att tct aaa tta cat gcc ata att       2318
Pro Phe Gln Gln Ile Ile Asn Gln Ile Ser Lys Leu His Ala Ile Ile
            735                 740                 745 gat cct aat cat gaa att gaa ttt ccc gat att cca gag aaa gat ctt       2366
Asp Pro Asn His Glu Ile Glu Phe Pro Asp Ile Pro Glu Lys Asp Leu
            750                 755                 760 caa gat gtg tta aag tgt tgt tta aaa agg gac cca aaa cag agg ata       2414
Gln Asp Val Leu Lys Cys Cys Leu Lys Arg Asp Pro Lys Gln Arg Ile
765                 770                 775                 780 tcc att cct gag ctc ctg gct cat ccc tat gtt caa att caa act cat       2462
Ser Ile Pro Glu Leu Leu Ala His Pro Tyr Val Gln Ile Gln Thr His
                785                 790                 795 cca gtt aac caa atg gcc aag gga acc act gaa gaa atg aaa tat gtt       2510
Pro Val Asn Gln Met Ala Lys Gly Thr Thr Glu Glu Met Lys Tyr Val
            800                 805                 810 ctg ggc caa ctt gtt ggt ctg aat tct cct aac tcc att ttg aaa gct       2558
Leu Gly Gln Leu Val Gly Leu Asn Ser Pro Asn Ser Ile Leu Lys Ala
            815                 820                 825 gct aaa act tta tat gaa cac tat agt ggt ggt gaa agt cat aat tct       2606
Ala Lys Thr Leu Tyr Glu His Tyr Ser Gly Gly Glu Ser His Asn Ser
830                 835                 840 tca tcc tcc aag act ttt gaa aaa aag agg gga aaa aaa tga               2648
Ser Ser Ser Lys Thr Phe Glu Lys Lys Arg Gly Lys Lys
845                 850                 855 tttgcagtta ttcgtaatgt caaataccac ctataaaata tattggactg ttatactctt     2708
gaatccctgt ggaaatctac atttgaagac aacatcactc tgaagtgtta tcagcaaaaa     2768
aaattcagta gattatcttt aaaagaaaac tgtaaaaata gcaaccactt atggtactgt     2828
atatattgta gacttgtttt ctctgtttta tgctcttgtg taatctactt gacatcattt     2888
tactcttgga atagtgggtg gatagcaagt atattctaaa aaactttgta aataaagttt     2948
tgtggctaaa atgacactaa aaaaaaaaaa aaaaaa                               2984

<210> SEQ ID NO 16
<211> LENGTH: 857
<212> TYPE: PRT
<213> ORGANISM: Homo sapiens

<400> SEQUENCE: 16

Met Glu Ser Glu Asp Leu Ser Gly Arg Glu Leu Thr Ile Asp Ser Ile
1               5                   10                  15
```

```
Met Asn Lys Val Arg Asp Ile Lys Asn Lys Phe Lys Asn Glu Asp Leu
            20                  25                  30

Thr Asp Glu Leu Ser Leu Asn Lys Ile Ser Ala Asp Thr Thr Asp Asn
            35                  40                  45

Ser Gly Thr Val Asn Gln Ile Met Met Met Ala Asn Asn Pro Glu Asp
50                  55                  60

Trp Leu Ser Leu Leu Lys Leu Glu Lys Asn Ser Val Pro Leu Ser
65                  70                  75                  80

Asp Ala Leu Leu Asn Lys Leu Ile Gly Arg Tyr Ser Gln Ala Ile Glu
                85                  90                  95

Ala Leu Pro Pro Asp Lys Tyr Gly Gln Asn Glu Ser Phe Ala Arg Ile
            100                 105                 110

Gln Val Arg Phe Ala Glu Leu Lys Ala Ile Gln Glu Pro Asp Asp Ala
            115                 120                 125

Arg Asp Tyr Phe Gln Met Ala Arg Ala Asn Cys Lys Lys Phe Ala Phe
130                 135                 140

Val His Ile Ser Phe Ala Gln Phe Glu Leu Ser Gln Gly Asn Val Lys
145                 150                 155                 160

Lys Ser Lys Gln Leu Leu Gln Lys Ala Val Glu Arg Gly Ala Val Pro
                165                 170                 175

Leu Glu Met Leu Glu Ile Ala Leu Arg Asn Leu Asn Leu Gln Lys Lys
            180                 185                 190

Gln Leu Leu Ser Glu Glu Lys Lys Asn Leu Ser Ala Ser Thr Val
            195                 200                 205

Leu Thr Ala Gln Glu Ser Phe Ser Gly Ser Leu Gly His Leu Gln Asn
210                 215                 220

Arg Asn Asn Ser Cys Asp Ser Arg Gly Gln Thr Thr Lys Ala Arg Phe
225                 230                 235                 240

Leu Tyr Gly Glu Asn Met Pro Pro Gln Asp Ala Glu Ile Gly Tyr Arg
                245                 250                 255

Asn Ser Leu Arg Gln Thr Asn Lys Thr Lys Gln Ser Cys Pro Phe Gly
            260                 265                 270

Arg Val Pro Val Asn Leu Leu Asn Ser Pro Asp Cys Asp Val Lys Thr
            275                 280                 285

Asp Asp Ser Val Val Pro Cys Phe Met Lys Arg Gln Thr Ser Arg Ser
290                 295                 300

Glu Cys Arg Asp Leu Val Val Pro Gly Ser Lys Pro Ser Gly Asn Asp
305                 310                 315                 320

Ser Cys Glu Leu Arg Asn Leu Lys Ser Val Gln Asn Ser His Phe Lys
                325                 330                 335

Glu Pro Leu Val Ser Asp Glu Lys Ser Ser Glu Leu Ile Ile Thr Asp
            340                 345                 350

Ser Ile Thr Leu Lys Asn Lys Thr Glu Ser Ser Leu Leu Ala Lys Leu
            355                 360                 365

Glu Glu Thr Lys Glu Tyr Gln Glu Pro Glu Val Pro Glu Ser Asn Gln
370                 375                 380

Lys Gln Trp Gln Ser Lys Arg Lys Ser Glu Cys Ile Asn Gln Asn Pro
385                 390                 395                 400

Ala Ala Ser Ser Asn His Trp Gln Ile Pro Glu Leu Ala Arg Lys Val
                405                 410                 415

Asn Thr Glu Gln Lys His Thr Thr Phe Glu Gln Pro Val Phe Ser Val
            420                 425                 430

Ser Lys Gln Ser Pro Pro Ile Ser Thr Ser Lys Trp Phe Asp Pro Lys
```

```
                435                 440                 445
Ser Ile Cys Lys Thr Pro Ser Ser Asn Thr Leu Asp Asp Tyr Met Ser
450                 455                 460

Cys Phe Arg Thr Pro Val Val Lys Asn Asp Phe Pro Pro Ala Cys Gln
465                 470                 475                 480

Leu Ser Thr Pro Tyr Gly Gln Pro Ala Cys Phe Gln Gln Gln His
                485                 490                 495

Gln Ile Leu Ala Thr Pro Leu Gln Asn Leu Gln Val Leu Ala Ser Ser
                500                 505                 510

Ser Ala Asn Glu Cys Ile Ser Val Lys Gly Arg Ile Tyr Ser Ile Leu
                515                 520                 525

Lys Gln Ile Gly Ser Gly Gly Ser Ser Lys Val Phe Gln Val Leu Asn
530                 535                 540

Glu Lys Lys Gln Ile Tyr Ala Ile Lys Tyr Val Asn Leu Glu Glu Ala
545                 550                 555                 560

Asp Asn Gln Thr Leu Asp Ser Tyr Arg Asn Glu Ile Ala Tyr Leu Asn
                565                 570                 575

Lys Leu Gln Gln His Ser Asp Lys Ile Ile Arg Leu Tyr Asp Tyr Glu
                580                 585                 590

Ile Thr Asp Gln Tyr Ile Tyr Met Val Met Glu Cys Gly Asn Ile Asp
                595                 600                 605

Leu Asn Ser Trp Leu Lys Lys Lys Ser Ile Asp Pro Trp Glu Arg
610                 615                 620

Lys Ser Tyr Trp Lys Asn Met Leu Glu Ala Val His Thr Ile His Gln
625                 630                 635                 640

His Gly Ile Val His Ser Asp Leu Lys Pro Ala Asn Phe Leu Ile Val
                645                 650                 655

Asp Gly Met Leu Lys Leu Ile Asp Phe Gly Ile Ala Asn Gln Met Gln
                660                 665                 670

Pro Asp Thr Thr Ser Val Val Lys Asp Ser Gln Val Gly Thr Val Asn
                675                 680                 685

Tyr Met Pro Pro Glu Ala Ile Lys Asp Met Ser Ser Ser Arg Glu Asn
690                 695                 700

Gly Lys Ser Lys Ser Lys Ile Ser Pro Lys Ser Asp Val Trp Ser Leu
705                 710                 715                 720

Gly Cys Ile Leu Tyr Tyr Met Thr Tyr Gly Lys Thr Pro Phe Gln Gln
                725                 730                 735

Ile Ile Asn Gln Ile Ser Lys Leu His Ala Ile Ile Asp Pro Asn His
                740                 745                 750

Glu Ile Glu Phe Pro Asp Ile Pro Glu Lys Asp Leu Gln Asp Val Leu
                755                 760                 765

Lys Cys Cys Leu Lys Arg Asp Pro Lys Gln Arg Ile Ser Ile Pro Glu
770                 775                 780

Leu Leu Ala His Pro Tyr Val Gln Ile Gln Thr His Pro Val Asn Gln
785                 790                 795                 800

Met Ala Lys Gly Thr Thr Glu Glu Met Lys Tyr Val Leu Gly Gln Leu
                805                 810                 815

Val Gly Leu Asn Ser Pro Asn Ser Ile Leu Lys Ala Ala Lys Thr Leu
                820                 825                 830

Tyr Glu His Tyr Ser Gly Gly Glu Ser His Asn Ser Ser Ser Lys
                835                 840                 845

Thr Phe Glu Lys Lys Arg Gly Lys Lys
850                 855
```

<210> SEQ ID NO 17
<211> LENGTH: 1735
<212> TYPE: DNA
<213> ORGANISM: Homo sapiens
<220> FEATURE:
<221> NAME/KEY: CDS
<222> LOCATION: (242)..(913)

<400> SEQUENCE: 17

```
gttatcagag gtgagcccgt gctcttcagc ggagaagatc ccctacctgg ccgccggcca      60
ctttctgtgg gccgtggggt cctcaaggag acggcccttg ggctcagggg ctgcgtttcc     120
acacgcgcct ttcccagggc tcccgcgccc gttcctgcct ggccgccggc cgctccaaca     180
gcagcacaag gcgggactca gaaccggcgt tcagggccgc cagcggccgc gaggccctga     240
```

| | | |
|---|---|---|
| g atg agg ctc caa aga ccc cga cag gcc ccg gcg ggt ggg agg cgc gcg<br>  Met Arg Leu Gln Arg Pro Arg Gln Ala Pro Ala Gly Gly Arg Arg Ala<br>   1               5                  10                  15 | 289 |
| ccc cgg ggc ggg cgg ggc tcc ccc tac cgg cca gac ccg ggg aga ggc<br>Pro Arg Gly Gly Arg Gly Ser Pro Tyr Arg Pro Asp Pro Gly Arg Gly<br>             20                  25                  30 | 337 |
| gcg cgg agg ctg cga agg ttc cag aag ggc ggg gag ggg gcg ccg cgc<br>Ala Arg Arg Leu Arg Arg Phe Gln Lys Gly Gly Glu Gly Ala Pro Arg<br>         35                  40                  45 | 385 |
| gct gac cct ccc tgg gca ccg ctg ggg acg atg gcg ctg ctc gcc ttg<br>Ala Asp Pro Pro Trp Ala Pro Leu Gly Thr Met Ala Leu Leu Ala Leu<br>     50                  55                  60 | 433 |
| ctg ctg gtc gtg gcc cta ccg cgg gtg tgg aca gac gcc aac ctg act<br>Leu Leu Val Val Ala Leu Pro Arg Val Trp Thr Asp Ala Asn Leu Thr<br> 65                  70                  75                  80 | 481 |
| gcg aga caa cga gat cca gag gac tcc cag cga acg gac gag ggt gac<br>Ala Arg Gln Arg Asp Pro Glu Asp Ser Gln Arg Thr Asp Glu Gly Asp<br>                 85                  90                  95 | 529 |
| aat aga gtg tgg tgt cat gtt tgt gag aga gaa aac act ttc gag tgc<br>Asn Arg Val Trp Cys His Val Cys Glu Arg Glu Asn Thr Phe Glu Cys<br>            100                 105                 110 | 577 |
| cag aac cca agg agg tgc aaa tgg aca gag cca tac tgc gtt ata gcg<br>Gln Asn Pro Arg Arg Cys Lys Trp Thr Glu Pro Tyr Cys Val Ile Ala<br>        115                 120                 125 | 625 |
| gcc gtg aaa ata ttt cca cgt ttt ttc atg gtt gcg aag cag tgc tcc<br>Ala Val Lys Ile Phe Pro Arg Phe Phe Met Val Ala Lys Gln Cys Ser<br>    130                 135                 140 | 673 |
| gct ggt tgt gca gcg atg gag aga ccc aag cca gag gag aag cgg ttt<br>Ala Gly Cys Ala Ala Met Glu Arg Pro Lys Pro Glu Glu Lys Arg Phe<br>145                 150                 155                 160 | 721 |
| ctc ctg gaa gag ccc atg ccc ttc ttt tac ctc aag tgt tgt aaa att<br>Leu Leu Glu Glu Pro Met Pro Phe Phe Tyr Leu Lys Cys Cys Lys Ile<br>                165                 170                 175 | 769 |
| cgc tac tgc aat tta gag ggg cca cct atc aac tca tca gtg ttc aaa<br>Arg Tyr Cys Asn Leu Glu Gly Pro Pro Ile Asn Ser Ser Val Phe Lys<br>            180                 185                 190 | 817 |
| gaa tat gct ggg agc atg ggt gag agc tgt ggt ggg ctg tgg ctg gcc<br>Glu Tyr Ala Gly Ser Met Gly Glu Ser Cys Gly Gly Leu Trp Leu Ala<br>        195                 200                 205 | 865 |
| atc ctc ctg ctg ctg gcc tcc att gca gcc ggc ctc agc ctg tct tga<br>Ile Leu Leu Leu Leu Ala Ser Ile Ala Ala Gly Leu Ser Leu Ser<br>    210                 215                 220 | 913 |

```
gccacgggac tgccacagac tgagccttcc ggagcatgga ctcgctccag accgttgtca     973
cctgttgcat taaacttgtt ttctgttgat tacctcttgg tttgacttcc cagggtcttg    1033
ggatgggaga gtgggggatca ggtgcagttg gctcttaacc ctcaagggtt ctttaactca    1093
```

```
cattcagagg aagtccagat ctcctgagta gtgattttgg tgacaagttt ttctctttga   1153
aatcaaacct tgtaactcat ttattgctga tggccactct tttccttgac tcccctctgc   1213
ctctgagggc ttcagtattg atggggaggg aggcctaagt accactcatg gagagtatgt   1273
gctgagatgc ttccgacctt tcaggtgacg caggaacact gggggagtct gaatgattgg   1333
ggtgaagaca tccctggagt gaaggactcc tcagcatggg gggcagtggg gcacacgtta   1393
gggctgcccc cattccagtg gtggaggcgc tgtggatggc tgcttttcct caacctttcc   1453
taccagattc caggaggcag aagataacta attgtgttga agaaacttag acttcaccca   1513
ccagctggca caggtgcaca gattcataaa ttcccacacg tgtgtgttca acatctgaaa   1573
cttaggccaa gtagagagca tcagggtaaa tggcgttcat ttctctgtta agatgcagcc   1633
atccatgggg agctgagaaa tcagactcaa agttccacca aaaacaaata caagggggact  1693 tcaaaagttc acgaaaaaat tgaattaaaa gataaaaatt aa                      1735
```

<210> SEQ ID NO 18  
<211> LENGTH: 223  
<212> TYPE: PRT  
<213> ORGANISM: Homo sapiens

<400> SEQUENCE: 18

```
Met Arg Leu Gln Arg Pro Arg Gln Ala Pro Ala Gly Gly Arg Arg Ala
1               5                   10                  15

Pro Arg Gly Gly Arg Gly Ser Pro Tyr Arg Pro Asp Pro Gly Arg Gly
            20                  25                  30

Ala Arg Arg Leu Arg Arg Phe Gln Lys Gly Gly Glu Gly Ala Pro Arg
        35                  40                  45

Ala Asp Pro Pro Trp Ala Pro Leu Gly Thr Met Ala Leu Leu Ala Leu
    50                  55                  60

Leu Leu Val Val Ala Leu Pro Arg Val Trp Thr Asp Ala Asn Leu Thr
65                  70                  75                  80

Ala Arg Gln Arg Asp Pro Glu Asp Ser Gln Arg Thr Asp Glu Gly Asp
                85                  90                  95

Asn Arg Val Trp Cys His Val Cys Glu Arg Glu Asn Thr Phe Glu Cys
            100                 105                 110

Gln Asn Pro Arg Arg Cys Lys Trp Thr Glu Pro Tyr Cys Val Ile Ala
        115                 120                 125

Ala Val Lys Ile Phe Pro Arg Phe Phe Met Val Ala Lys Gln Cys Ser
    130                 135                 140

Ala Gly Cys Ala Ala Met Glu Arg Pro Lys Pro Glu Glu Lys Arg Phe
145                 150                 155                 160

Leu Leu Glu Glu Pro Met Pro Phe Phe Tyr Leu Lys Cys Cys Lys Ile
                165                 170                 175

Arg Tyr Cys Asn Leu Glu Gly Pro Pro Ile Asn Ser Ser Val Phe Lys
            180                 185                 190

Glu Tyr Ala Gly Ser Met Gly Glu Ser Cys Gly Gly Leu Trp Leu Ala
        195                 200                 205

Ile Leu Leu Leu Leu Ala Ser Ile Ala Ala Gly Leu Ser Leu Ser
    210                 215                 220
```

<210> SEQ ID NO 19  
<211> LENGTH: 9  
<212> TYPE: PRT  
<213> ORGANISM: artificial  
<220> FEATURE:  
<223> OTHER INFORMATION: An artificially synthesized peptide sequence

```
<400> SEQUENCE: 19

Ile Tyr Glu Val Met Val Leu Ala Met
1               5

<210> SEQ ID NO 20
<211> LENGTH: 9
<212> TYPE: PRT
<213> ORGANISM: artificial
<220> FEATURE:
<223> OTHER INFORMATION: An artificially synthesized peptide sequence

<400> SEQUENCE: 20

Leu Phe Leu Leu Leu Val Leu Leu Leu
1               5

<210> SEQ ID NO 21
<211> LENGTH: 9
<212> TYPE: PRT
<213> ORGANISM: artificial
<220> FEATURE:
<223> OTHER INFORMATION: An artificially synthesized peptide sequence

<400> SEQUENCE: 21

Val Phe Arg Glu Ala Glu Val Thr Leu
1               5

<210> SEQ ID NO 22
<211> LENGTH: 9
<212> TYPE: PRT
<213> ORGANISM: artificial
<220> FEATURE:
<223> OTHER INFORMATION: An artificially synthesized peptide sequence

<400> SEQUENCE: 22

Leu Tyr Val Glu Val Thr Asn Glu Ala
1               5

<210> SEQ ID NO 23
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 23

Lys Tyr Glu Ala His Val Pro Glu Asn
1               5

<210> SEQ ID NO 24
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 24

Lys Tyr Glu Leu Phe Gly His Ala Val
1               5

<210> SEQ ID NO 25
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 25
```

```
Arg Ser Leu Lys Glu Arg Asn Pro Leu
1               5

<210> SEQ ID NO 26
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 26

Arg Gly Pro Leu Ala Ser Leu Leu Leu
1               5

<210> SEQ ID NO 27
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 27

Lys Gly Gly Phe Ile Leu Pro Val Leu
1               5

<210> SEQ ID NO 28
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 28

Thr Tyr Asn Gly Val Val Ala Tyr Ser
1               5

<210> SEQ ID NO 29
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 29

Leu Phe Ser Thr Asp Asn Asp Asp Phe
1               5

<210> SEQ ID NO 30
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 30

Asp Tyr Leu Asn Glu Trp Gly Ser Arg Phe
1               5                   10

<210> SEQ ID NO 31
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 31

Thr Tyr Asn Gly Val Val Ala Tyr Ser Ile
```

<210> SEQ ID NO 32
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 32

Leu Phe Leu Leu Leu Val Leu Leu Leu Leu
1               5                   10

<210> SEQ ID NO 33
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 33

Asp Phe Glu Ala Lys Asn Gln His Thr Leu
1               5                   10

<210> SEQ ID NO 34
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 34

Lys Tyr Glu Ala His Val Pro Glu Asn Ala
1               5                   10

<210> SEQ ID NO 35
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 35

Lys Tyr Glu Leu Phe Gly His Ala Val Ser
1               5                   10

<210> SEQ ID NO 36
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 36

Arg Asn Asn Ile Tyr Glu Val Met Val Leu
1               5                   10

<210> SEQ ID NO 37
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 37

Arg Gly Pro Leu Ala Ser Leu Leu Leu Leu
1               5                   10

```
<210> SEQ ID NO 38
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 38

Arg Ile Leu Arg Asp Pro Ala Gly Trp Leu
1               5                   10

<210> SEQ ID NO 39
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 39

Cys Asn Gln Ser Pro Val Arg Gln Val Leu
1               5                   10

<210> SEQ ID NO 40
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 40

Val Tyr Ile Glu Ile Lys Phe Thr Leu
1               5

<210> SEQ ID NO 41
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 41

Arg Tyr Ser Val Ala Leu Ala Trp Leu
1               5

<210> SEQ ID NO 42
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 42

Val Tyr Pro Ala Asn Glu Val Thr Leu
1               5

<210> SEQ ID NO 43
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 43

His Tyr Thr Pro Gln Gln Asn Gly Leu
1               5

<210> SEQ ID NO 44
```

```
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 44

Phe Tyr Phe Ala Leu Phe Ser Cys Leu
1               5

<210> SEQ ID NO 45
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 45

Gly Tyr Gly Asp Phe Ser Glu Pro Leu
1               5

<210> SEQ ID NO 46
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 46

Lys Phe Gly Gln Ile Val Asn Met Leu
1               5

<210> SEQ ID NO 47
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 47

Ala Tyr Thr Thr Arg Gly Gly Lys Ile
1               5

<210> SEQ ID NO 48
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 48

Lys Tyr Asn Pro Asn Pro Asp Gln Ser
1               5

<210> SEQ ID NO 49
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 49

Arg Asn Ile Leu Val Asn Ser Asn Leu
1               5

<210> SEQ ID NO 50
<211> LENGTH: 9
<212> TYPE: PRT
```

<213> ORGANISM: Artificial
<220> FEATURE:
<223> OTHER INFORMATION: An artificially synthesized peptide sequence

<400> SEQUENCE: 50

Lys Tyr Leu Ser Asp Met Ser Tyr Val
1               5

<210> SEQ ID NO 51
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 51

Lys Leu Ile Arg Asn Pro Asn Ser Leu
1               5

<210> SEQ ID NO 52
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 52

Arg Tyr Lys Asp Asn Phe Thr Ala Ala
1               5

<210> SEQ ID NO 53
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 53

Lys Ala Ile Glu Glu Gly Tyr Arg Leu
1               5

<210> SEQ ID NO 54
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 54

Lys Tyr Ser Lys Ala Lys Gln Glu Ala
1               5

<210> SEQ ID NO 55
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 55

Ala Phe Gln Asp Val Gly Ala Cys Ile
1               5

<210> SEQ ID NO 56
<211> LENGTH: 9
<212> TYPE: PRT
<213> ORGANISM: Artificial
<220> FEATURE:

```
<223> OTHER INFORMATION: An artificially synthesized peptide sequence

<400> SEQUENCE: 56

Trp Leu Val Pro Ile Gly Asn Cys Leu
1               5

<210> SEQ ID NO 57
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 57

Arg Pro Pro Ser Ala Pro Leu Asn Leu
1               5

<210> SEQ ID NO 58
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 58

Lys Cys Pro Leu Thr Val Arg Asn Leu
1               5

<210> SEQ ID NO 59
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 59

Ser Tyr Asn Val Val Cys Lys Lys Cys
1               5

<210> SEQ ID NO 60
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 60

Val Tyr Pro Ala Asn Glu Val Thr Leu Leu
1               5                   10

<210> SEQ ID NO 61
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 61

Met Tyr Cys Gly Ala Asp Gly Glu Trp Leu
1               5                   10

<210> SEQ ID NO 62
<211> LENGTH: 10
<212> TYPE: PRT
<213> ORGANISM: Artificial
<220> FEATURE:
<223> OTHER INFORMATION: An artificially synthesized peptide sequence
```

```
<400> SEQUENCE: 62

Gly Tyr Thr Asp Lys Gln Arg Arg Asp Phe
1               5                   10

<210> SEQ ID NO 63
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 63

Phe Tyr Phe Ala Leu Phe Ser Cys Leu Phe
1               5                   10

<210> SEQ ID NO 64
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 64

Lys Phe Thr Leu Arg Asp Cys Asn Ser Leu
1               5                   10

<210> SEQ ID NO 65
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 65

Ser Tyr Gly Glu Arg Pro Tyr Trp Asp Met
1               5                   10

<210> SEQ ID NO 66
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 66

Ile Phe Tyr Phe Ala Leu Phe Ser Cys Leu
1               5                   10

<210> SEQ ID NO 67
<211> LENGTH: 10
<212> TYPE: PRT
<213> ORGANISM: Artificial
<220> FEATURE:
<223> OTHER INFORMATION: SYGIVMWEVM

<400> SEQUENCE: 67

Ser Tyr Gly Ile Val Met Trp Glu Val Met
1               5                   10

<210> SEQ ID NO 68
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 68
```

```
Glu Phe Gly Glu Val Cys Ser Gly Arg Leu
1               5                   10

<210> SEQ ID NO 69
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 69

Lys Tyr Asn Pro Asn Pro Asp Gln Ser Val
1               5                   10

<210> SEQ ID NO 70
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 70

Asn Phe Thr Ala Ala Gly Tyr Thr Thr Leu
1               5                   10

<210> SEQ ID NO 71
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 71

Gln Phe Asp His Pro Asn Ile Ile His Leu
1               5                   10

<210> SEQ ID NO 72
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 72

Ala Phe Leu Arg Lys Asn Asp Gly Arg Phe
1               5                   10

<210> SEQ ID NO 73
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 73

Lys Gln Glu Ala Asp Glu Glu Lys His Leu
1               5                   10

<210> SEQ ID NO 74
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 74

Arg Gly Ile Gly Ser Gly Met Lys Tyr Leu
1               5                   10
```

```
<210> SEQ ID NO 75
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 75

Arg Val Tyr Ile Glu Ile Lys Phe Thr Leu
1               5                   10

<210> SEQ ID NO 76
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 76

Ser Tyr Val Phe His Val Arg Ala Arg Thr
1               5                   10

<210> SEQ ID NO 77
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 77

Glu Trp Leu Val Pro Ile Gly Asn Cys Leu
1               5                   10

<210> SEQ ID NO 78
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 78

Arg Val Tyr Pro Ala Asn Glu Val Thr Leu
1               5                   10

<210> SEQ ID NO 79
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 79

Glu Tyr Met Glu Asn Gly Ser Leu Asp Ala
1               5                   10

<210> SEQ ID NO 80
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 80

Thr Tyr Pro Pro Phe Val Asn Phe Phe
1               5
```

```
<210> SEQ ID NO 81
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 81

Leu Tyr Cys Thr Ser Met Met Asn Leu
1               5

<210> SEQ ID NO 82
<211> LENGTH: 9
<212> TYPE: PRT
<213> ORGANISM: Artificial
<220> FEATURE:
<223> OTHER INFORMATION: An artificially synthesized peptide seque

<400> SEQUENCE: 82

Leu Tyr Val Val Lys Gln Glu Trp Phe
1               5

<210> SEQ ID NO 83
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 83

Asn Tyr Val Asn Ile Leu Ala Thr Ile
1               5

<210> SEQ ID NO 84
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 84

Ile Tyr Thr Ala Asp Pro Glu Ser Phe
1               5

<210> SEQ ID NO 85
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 85

Leu Tyr Lys Ala Asp Cys Arg Val Ile
1               5

<210> SEQ ID NO 86
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 86

Ser Phe Gln Met Thr Ser Asp Glu Leu
1               5

<210> SEQ ID NO 87
<211> LENGTH: 9
```

```
<212> TYPE: PRT
<213> ORGANISM: Artificial
<220> FEATURE:
<223> OTHER INFORMATION: An artificially synthesized peptide sequence

<400> SEQUENCE: 87

Ile Phe Leu Lys Tyr Ser Lys Asp Leu
1               5

<210> SEQ ID NO 88
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 88

Phe Phe Glu Arg Arg Ser His Thr Leu
1               5

<210> SEQ ID NO 89
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 89

Asp Phe Asn Ser Lys Val Thr His Leu
1               5

<210> SEQ ID NO 90
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 90

Lys Gln Glu Glu Leu Ile Lys Ala Leu
1               5

<210> SEQ ID NO 91
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 91

Arg Gly Glu Gln Val Thr Leu Phe Leu
1               5

<210> SEQ ID NO 92
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 92

Arg Leu Pro Ser Val Ala Leu Leu Leu
1               5

<210> SEQ ID NO 93
<211> LENGTH: 9
<212> TYPE: PRT
<213> ORGANISM: Artificial
```

```
<220> FEATURE:
<223> OTHER INFORMATION: An artificially synthesized peptide sequence

<400> SEQUENCE: 93

Lys Pro Glu Cys Gly Arg Gln Ser Leu
1               5

<210> SEQ ID NO 94
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 94

Ile Phe Gly Ser Ile Pro Asp Ile Phe
1               5

<210> SEQ ID NO 95
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 95

Arg Val Ile Gly Pro Pro Val Val Leu
1               5

<210> SEQ ID NO 96
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 96

Lys Tyr Ser Lys Asp Leu Val Lys Thr
1               5

<210> SEQ ID NO 97
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 97

Asp Phe Tyr Ala Ala Val Asp Asp Phe
1               5

<210> SEQ ID NO 98
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 98

Leu Tyr Glu Lys Ala Asn Thr Pro Glu Leu
1               5                   10

<210> SEQ ID NO 99
<211> LENGTH: 10
<212> TYPE: PRT
<213> ORGANISM: Artificial
<220> FEATURE:
<223> OTHER INFORMATION: An artificially synthesized peptide sequence
```

```
<400> SEQUENCE: 99

Asn Tyr Val Asn Ile Leu Ala Thr Ile Ile
1               5                   10

<210> SEQ ID NO 100
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 100

Ser Tyr Val Glu Glu Glu Met Pro Gln Ile
1               5                   10

<210> SEQ ID NO 101
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 101

Asp Phe Gln Asp Ser Val Phe Asn Asp Leu
1               5                   10

<210> SEQ ID NO 102
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 102

Ser Phe Phe Glu Arg Arg Ser His Thr Leu
1               5                   10

<210> SEQ ID NO 103
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 103

Ser Phe Ser Lys Thr Pro Lys Arg Ala Leu
1               5                   10

<210> SEQ ID NO 104
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 104

Lys Tyr Leu Pro Leu Gly Asp Glu Arg Cys
1               5                   10

<210> SEQ ID NO 105
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 105
```

```
Glu Phe Glu Gly Leu Asp Ser Pro Glu Phe
1               5                   10

<210> SEQ ID NO 106
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 106

Lys Val Pro Pro Phe Gln Asp Cys Ile Leu
1               5                   10

<210> SEQ ID NO 107
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 107

Arg Pro Pro Thr Glu Gln Ala Asn Val Leu
1               5                   10

<210> SEQ ID NO 108
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 108

Lys Tyr Ser Lys Asp Leu Val Lys Thr Tyr
1               5                   10

<210> SEQ ID NO 109
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 109

Val Val Glu Glu Asn Ile Val Lys Asp Leu
1               5                   10

<210> SEQ ID NO 110
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 110

Ile Phe Val Arg Val Met Glu Ser Leu
1               5

<210> SEQ ID NO 111
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 111

Arg Val Met Glu Ser Leu Glu Gly Leu
```

```
<210> SEQ ID NO 112
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 112

Leu Tyr Leu Leu Gly Val Val Leu Thr Leu
1               5                   10

<210> SEQ ID NO 113
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 113

Arg Val Met Glu Ser Leu Glu Gly Leu Leu
1               5                   10

<210> SEQ ID NO 114
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 114

Tyr Leu Leu Gly Val Val Leu Thr Leu
1               5

<210> SEQ ID NO 115
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 115

Val Leu Thr Leu Leu Ser Ile Phe Val
1               5

<210> SEQ ID NO 116
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 116

Thr Leu Leu Ser Ile Phe Val Arg Val
1               5

<210> SEQ ID NO 117
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 117

Val Leu Asn Leu Tyr Leu Leu Gly Val
1               5
```

```
<210> SEQ ID NO 118
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 118

Leu Leu Gly Val Val Leu Thr Leu Leu
1               5

<210> SEQ ID NO 119
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 119

Arg Val Met Glu Ser Leu Glu Gly Leu
1               5

<210> SEQ ID NO 120
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 120

Asn Leu Tyr Leu Leu Gly Val Val Leu
1               5

<210> SEQ ID NO 121
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 121

Tyr Leu Leu Gly Val Val Leu Thr Leu Leu
1               5                   10

<210> SEQ ID NO 122
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 122

Val Val Leu Thr Leu Leu Ser Ile Phe Val
1               5                   10

<210> SEQ ID NO 123
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 123

Gly Leu Leu Glu Ser Pro Ser Pro Gly Thr
1               5                   10

<210> SEQ ID NO 124
```

```
<210> SEQ ID NO 124
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 124

Asn Leu Tyr Leu Leu Gly Val Val Leu Thr
1               5                   10

<210> SEQ ID NO 125
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 125

Val Leu Asn Leu Tyr Leu Leu Gly Val Val
1               5                   10

<210> SEQ ID NO 126
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 126

Thr Leu Leu Ser Ile Phe Val Arg Val Met
1               5                   10

<210> SEQ ID NO 127
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 127

Ser Ile Phe Val Arg Val Met Glu Ser Leu
1               5                   10

<210> SEQ ID NO 128
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 128

Leu Thr Leu Leu Ser Ile Phe Val Arg Val
1               5                   10

<210> SEQ ID NO 129
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 129

Leu Tyr Phe Asp Asp Glu Tyr Asn Ile
1               5

<210> SEQ ID NO 130
<211> LENGTH: 9
<212> TYPE: PRT
```

<213> ORGANISM: Artificial
<220> FEATURE:
<223> OTHER INFORMATION: An artificially synthesized peptide sequence

<400> SEQUENCE: 130

Leu Phe Glu Arg Gly Glu Arg Arg Leu
1               5

<210> SEQ ID NO 131
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 131

Arg Ala Leu Gly Ala Ala Cys Leu Leu
1               5

<210> SEQ ID NO 132
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 132

Glu Tyr Asn Ile Val Lys Arg Asp Val
1               5

<210> SEQ ID NO 133
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 133

Leu Tyr Leu Lys Leu Leu Pro Tyr Val Leu
1               5                   10

<210> SEQ ID NO 134
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 134

Leu Phe Val Val Gln Ala Ser Leu Trp Leu
1               5                   10

<210> SEQ ID NO 135
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 135

Arg Gln Gln Phe Phe Ile Asp Phe Arg Leu
1               5                   10

<210> SEQ ID NO 136
<211> LENGTH: 10
<212> TYPE: PRT
<213> ORGANISM: Artificial
<220> FEATURE:

<223> OTHER INFORMATION: DFLEAVKRHI

<400> SEQUENCE: 136

Asp Phe Leu Glu Ala Val Lys Arg His Ile
1               5                   10

<210> SEQ ID NO 137
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 137

Arg Ala Leu Gly Ala Ala Cys Leu Leu Leu
1               5                   10

<210> SEQ ID NO 138
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 138

Arg Pro Phe Val Val Val Gln Ala Arg Leu
1               5                   10

<210> SEQ ID NO 139
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 139

Ala Tyr Leu Ala Gly Val Pro Gly Ser Ala
1               5                   10

<210> SEQ ID NO 140
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 140

Ser Leu Trp Leu Tyr Leu Lys Leu Leu
1               5

<210> SEQ ID NO 141
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 141

Leu Leu Leu Leu Ala Ala Gly Trp Leu
1               5

<210> SEQ ID NO 142
<211> LENGTH: 9
<212> TYPE: PRT
<213> ORGANISM: Artificial
<220> FEATURE:
<223> OTHER INFORMATION: An artificially synthesized peptide sequence

```
<400> SEQUENCE: 142

Asn Leu Phe Val Val Gln Ala Ser Leu
1               5

<210> SEQ ID NO 143
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 143

Asn Met Val Glu Lys Arg Val Asp Leu
1               5

<210> SEQ ID NO 144
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 144

Phe Val Val Gln Ala Ser Leu Trp Leu
1               5

<210> SEQ ID NO 145
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 145

Gln Gln Phe Phe Ile Asp Phe Arg Leu
1               5

<210> SEQ ID NO 146
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 146

Arg Leu Gly Asp Ser Arg His Arg Ile
1               5

<210> SEQ ID NO 147
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 147

Val Gln Ala Ser Leu Trp Leu Tyr Leu
1               5

<210> SEQ ID NO 148
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 148
```

```
Glu Leu Ala Val Val Pro Val Phe Val
1               5

<210> SEQ ID NO 149
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 149

Arg Leu Ile Gly Trp Asn Asp Trp Ile
1               5

<210> SEQ ID NO 150
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 150

Arg Val Ser Glu Ile Ile Ser Phe Ala
1               5

<210> SEQ ID NO 151
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 151

Gly Leu Ala Ser Ser Arg Val Arg Leu
1               5

<210> SEQ ID NO 152
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 152

Ala Leu Gly Ala Ala Cys Leu Leu Leu
1               5

<210> SEQ ID NO 153
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 153

Val Gln Cys Asp Ser Cys Gln Glu Leu
1               5

<210> SEQ ID NO 154
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 154

Trp Leu Tyr Leu Lys Leu Leu Pro Tyr Val
1               5                   10
```

```
<210> SEQ ID NO 155
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 155

Asn Leu Cys Cys Arg Gln Gln Phe Phe Ile
1               5                   10

<210> SEQ ID NO 156
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 156

Ala Leu Phe Glu Arg Gly Glu Arg Arg Leu
1               5                   10

<210> SEQ ID NO 157
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 157

Met Leu Tyr Phe Asp Asp Glu Tyr Asn Ile
1               5                   10

<210> SEQ ID NO 158
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 158

Cys Leu Leu Leu Leu Ala Ala Gly Trp Leu
1               5                   10

<210> SEQ ID NO 159
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 159

Ala Leu Gly Ala Ala Cys Leu Leu Leu Leu
1               5                   10

<210> SEQ ID NO 160
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 160

Arg Leu Ile Gly Trp Asn Asp Trp Ile Ile
1               5                   10
```

```
<210> SEQ ID NO 161
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 161

Val Val Gln Ala Ser Leu Trp Leu Tyr Leu
1               5                   10

<210> SEQ ID NO 162
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 162

Gln Glu Leu Ala Val Val Pro Val Phe Val
1               5                   10

<210> SEQ ID NO 163
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 163

Phe Ile Ser Asn Glu Gly Asn Gln Asn Leu
1               5                   10

<210> SEQ ID NO 164
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 164

Arg Gln Gln Phe Phe Ile Asp Phe Arg Leu
1               5                   10

<210> SEQ ID NO 165
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 165

Gly Leu Asn Pro Gly Thr Val Asn Ser Cys
1               5                   10

<210> SEQ ID NO 166
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 166

Arg Leu Gln Met Arg Gly Arg Pro Asn Ile
1               5                   10

<210> SEQ ID NO 167
<211> LENGTH: 10
```

```
<212> TYPE: PRT
<213> ORGANISM: Artificial
<220> FEATURE:
<223> OTHER INFORMATION: An artificially synthesized peptide sequence

<400> SEQUENCE: 167

Arg Val Asp Gly Asp Phe Leu Glu Ala Val
1               5                   10

<210> SEQ ID NO 168
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 168

Ile Tyr Asn Glu Leu Leu Tyr Asp Leu
1               5

<210> SEQ ID NO 169
<211> LENGTH: 9
<212> TYPE: PRT
<213> ORGANISM: Artificial
<220> FEATURE:
<223> OTHER INFORMATION: MYEEKLNIL

<400> SEQUENCE: 169

Met Tyr Glu Glu Lys Leu Asn Ile Leu
1               5

<210> SEQ ID NO 170
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 170

Val Tyr Leu Arg Val Arg Pro Leu Leu
1               5

<210> SEQ ID NO 171
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 171

Lys Phe Ser Ala Ile Ala Ser Gln Leu
1               5

<210> SEQ ID NO 172
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 172

Ser Phe Phe Glu Ile Tyr Asn Glu Leu
1               5

<210> SEQ ID NO 173
<211> LENGTH: 9
<212> TYPE: PRT
<213> ORGANISM: Artificial
```

```
<220> FEATURE:
<223> OTHER INFORMATION: An artificially synthesized peptide sequence

<400> SEQUENCE: 173

Ile Phe Asn Ser Leu Gln Gly Gln Leu
1               5

<210> SEQ ID NO 174
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 174

Phe Phe Glu Ile Tyr Asn Glu Leu Leu
1               5

<210> SEQ ID NO 175
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 175

Met Phe Glu Ser Thr Ala Ala Asp Leu
1               5

<210> SEQ ID NO 176
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 176

Ser Phe Asp Ser Gly Ile Ala Gly Leu
1               5

<210> SEQ ID NO 177
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 177

Arg Phe Ser Ile Trp Ile Ser Phe Phe
1               5

<210> SEQ ID NO 178
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 178

Ile Phe Ser Ile Arg Ile Leu His Leu
1               5

<210> SEQ ID NO 179
<211> LENGTH: 9
<212> TYPE: PRT
<213> ORGANISM: Artificial
<220> FEATURE:
<223> OTHER INFORMATION: An artificially synthesized peptide sequence
```

```
<400> SEQUENCE: 179

Lys Ile Glu Glu Leu Glu Ala Leu Leu
1               5

<210> SEQ ID NO 180
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 180

Lys Leu Asn Ile Leu Lys Glu Ser Leu
1               5

<210> SEQ ID NO 181
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 181

Lys Leu Gln Gln Cys Lys Ala Glu Leu
1               5

<210> SEQ ID NO 182
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 182

Phe Thr Ile Asp Val Asp Lys Lys Leu
1               5

<210> SEQ ID NO 183
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 183

Gln Leu Gln Glu Val Lys Ala Lys Leu
1               5

<210> SEQ ID NO 184
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 184

Ile Tyr Asn Glu Leu Leu Tyr Asp Leu Leu
1               5                   10

<210> SEQ ID NO 185
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 185
```

Arg Ser Leu Ala Leu Ile Phe Asn Ser Leu
1               5                   10

<210> SEQ ID NO 186
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 186

Ser Phe Phe Glu Ile Tyr Asn Glu Leu Leu
1               5                   10

<210> SEQ ID NO 187
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 187

Arg Leu Leu Arg Thr Glu Leu Gln Lys Leu
1               5                   10

<210> SEQ ID NO 188
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 188

Lys Asn Ile Arg Leu Leu Arg Thr Glu Leu
1               5                   10

<210> SEQ ID NO 189
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 189

Arg Gln Glu Glu Met Lys Lys Leu Ser Leu
1               5                   10

<210> SEQ ID NO 190
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 190

Arg Val Arg Pro Leu Leu Pro Ser Glu Leu
1               5                   10

<210> SEQ ID NO 191
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 191

Arg Ile Leu Arg Ser Arg Arg Ser Pro Leu

-continued

<210> SEQ ID NO 192
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 192

Arg Ile Glu Asn Val Glu Thr Leu Val Leu
1               5                   10

<210> SEQ ID NO 193
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 193

Lys Asn Gln Ser Phe Ala Ser Thr His Leu
1               5                   10

<210> SEQ ID NO 194
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 194

Lys Val Tyr Leu Arg Val Arg Pro Leu Leu
1               5                   10

<210> SEQ ID NO 195
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 195

Asp Ser Met Glu Lys Val Lys Val Tyr Leu
1               5                   10

<210> SEQ ID NO 196
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 196

Lys Tyr Gln Ala Tyr Met Ser Asn Leu
1               5

<210> SEQ ID NO 197
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 197

Val Tyr Val Pro Leu Lys Glu Leu Leu
1               5

<210> SEQ ID NO 198
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 198

Glu Tyr His Lys Leu Ala Arg Lys Leu
1               5

<210> SEQ ID NO 199
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 199

Ser Tyr Glu Leu Pro Asp Thr Lys Phe
1               5

<210> SEQ ID NO 200
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 200

Lys Tyr Glu Lys Lys Ala Thr Leu Ile
1               5

<210> SEQ ID NO 201
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 201

Lys Tyr Ala Arg Gly Lys Glu Ala Ile
1               5

<210> SEQ ID NO 202
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 202

Asp Phe Leu Lys Ile Phe Thr Phe Leu
1               5

<210> SEQ ID NO 203
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 203

Gly Phe Leu Cys Pro Ser Tyr Glu Leu
1               5

<210> SEQ ID NO 204

```
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 204

Leu Phe Asn Val Asp Ala Phe Lys Leu
1               5

<210> SEQ ID NO 205
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 205

Ser Phe Asp Glu Met Asn Ala Glu Leu
1               5

<210> SEQ ID NO 206
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 206

Ile Phe Thr Phe Leu Tyr Gly Phe Leu
1               5

<210> SEQ ID NO 207
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 207

Lys Phe Glu Glu Glu Val Pro Arg Ile
1               5

<210> SEQ ID NO 208
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 208

Arg Ile Asn His Glu Arg Asn Glu Leu
1               5

<210> SEQ ID NO 209
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 209

Ser Phe Met Ser Gly Ala Asp Ser Phe
1               5

<210> SEQ ID NO 210
<211> LENGTH: 9
<212> TYPE: PRT
```

```
<213> ORGANISM: Artificial
<220> FEATURE:
<223> OTHER INFORMATION: An artificially synthesized peptide sequence

<400> SEQUENCE: 210

Ile Phe Lys Asp Leu Gly Tyr Pro Phe
1               5

<210> SEQ ID NO 211
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 211

Glu Tyr Gln Leu Val Val Gln Thr Thr
1               5

<210> SEQ ID NO 212
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 212

Lys Ala Leu Asn Lys Lys Met Gly Leu
1               5

<210> SEQ ID NO 213
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 213

Glu Val Pro Arg Ile Phe Lys Asp Leu
1               5

<210> SEQ ID NO 214
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 214

Lys Tyr Arg Ala Gln Val Tyr Val Pro Leu
1               5                   10

<210> SEQ ID NO 215
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 215

Glu Tyr Glu Glu Cys Met Ser Glu Asp Leu
1               5                   10

<210> SEQ ID NO 216
<211> LENGTH: 10
<212> TYPE: PRT
<213> ORGANISM: Artificial
<220> FEATURE:
```

<223> OTHER INFORMATION: An artificially synthesized peptide sequence

<400> SEQUENCE: 216

Lys Tyr Ser Val Ala Asp Ile Glu Arg Ile
1               5                   10

<210> SEQ ID NO 217
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 217

Asp Tyr Thr Ile Lys Cys Tyr Glu Ser Phe
1               5                   10

<210> SEQ ID NO 218
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 218

Lys Phe Glu Glu Glu Val Pro Arg Ile Phe
1               5                   10

<210> SEQ ID NO 219
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 219

Ala Phe Ile Gln Gln Cys Ile Arg Gln Leu
1               5                   10

<210> SEQ ID NO 220
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 220

Arg Ser Gln Asp Val Asn Lys Gln Gly Leu
1               5                   10

<210> SEQ ID NO 221
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 221

Arg Thr Leu Lys Glu Glu Val Gln Lys Leu
1               5                   10

<210> SEQ ID NO 222
<211> LENGTH: 10
<212> TYPE: PRT
<213> ORGANISM: Artificial
<220> FEATURE:
<223> OTHER INFORMATION: An artificially synthesized peptide sequence

```
<400> SEQUENCE: 222

Arg Gly Lys Glu Ala Ile Glu Thr Gln Leu
1               5                   10

<210> SEQ ID NO 223
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 223

Arg Ala Leu Asn Glu Gln Ile Ala Arg Leu
1               5                   10

<210> SEQ ID NO 224
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 224

Glu Tyr Gln Leu Val Val Gln Thr Thr Thr
1               5                   10

<210> SEQ ID NO 225
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 225

Glu Thr Glu Glu Glu Ile Asn Lys Ala Leu
1               5                   10

<210> SEQ ID NO 226
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 226

Leu Leu Glu Ser Thr Val Asn Gln Gly Leu
1               5                   10

<210> SEQ ID NO 227
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 227

Tyr Met Ser Cys Phe Arg Thr Pro Val
1               5

<210> SEQ ID NO 228
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 228
```

```
Lys Gln Ile Tyr Ala Ile Lys Tyr Val
1               5

<210> SEQ ID NO 229
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 229

Asn Met Leu Glu Ala Val His Thr Ile
1               5

<210> SEQ ID NO 230
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 230

Leu Leu Asn Ser Pro Asp Cys Asp Val
1               5

<210> SEQ ID NO 231
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 231

Ile Leu Ala Thr Pro Leu Gln Asn Leu
1               5

<210> SEQ ID NO 232
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 232

Tyr Val Leu Gly Gln Leu Val Gly Leu
1               5

<210> SEQ ID NO 233
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 233

Ser Leu Gly Cys Ile Leu Tyr Tyr Met
1               5

<210> SEQ ID NO 234
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 234

Gln Met Gln Pro Asp Thr Thr Ser Val
1               5
```

```
<210> SEQ ID NO 235
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 235

Gly Thr Thr Glu Glu Met Lys Tyr Val
1               5

<210> SEQ ID NO 236
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 236

Leu Ile Val Asp Gly Met Leu Lys Leu
1               5

<210> SEQ ID NO 237
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 237

Ser Leu Leu Ala Lys Leu Glu Glu Thr
1               5

<210> SEQ ID NO 238
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 238

Leu Phe Glu Arg Gly Glu Arg Arg Leu
1               5

<210> SEQ ID NO 239
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 239

Leu Leu Ala His Pro Tyr Val Gln Ile
1               5

<210> SEQ ID NO 240
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 240

Lys Leu Ile Gly Arg Tyr Ser Gln Ala
1               5
```

```
<210> SEQ ID NO 241
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 241

Asn Leu Asn Leu Gln Lys Lys Gln Leu
1               5

<210> SEQ ID NO 242
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 242

Met Gln Pro Asp Thr Thr Ser Val Val
1               5

<210> SEQ ID NO 243
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 243

Lys Leu Gln Gln His Ser Asp Lys Ile
1               5

<210> SEQ ID NO 244
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 244

Phe Ala Phe Val His Ile Ser Phe Ala
1               5

<210> SEQ ID NO 245
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 245

Cys Glu Leu Arg Asn Leu Lys Ser Val
1               5

<210> SEQ ID NO 246
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 246

Ser Ile Leu Lys Ala Ala Lys Thr Leu
1               5

<210> SEQ ID NO 247
<211> LENGTH: 10
```

```
<212> TYPE: PRT
<213> ORGANISM: Artificial
<220> FEATURE:
<223> OTHER INFORMATION: An artificially synthesized peptide sequence

<400> SEQUENCE: 247

Leu Leu Leu Lys Leu Glu Lys Asn Ser Val
1               5                   10

<210> SEQ ID NO 248
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 248

Asn Leu Leu Asn Ser Pro Asp Cys Asp Val
1               5                   10

<210> SEQ ID NO 249
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 249

Phe Leu Ile Val Asp Gly Met Leu Lys Leu
1               5                   10

<210> SEQ ID NO 250
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 250

Thr Thr Phe Glu Gln Pro Val Phe Ser Val
1               5                   10

<210> SEQ ID NO 251
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 251

Val Leu Asn Glu Lys Lys Gln Ile Tyr Ala
1               5                   10

<210> SEQ ID NO 252
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 252

Gly Met Leu Lys Leu Ile Asp Phe Gly Ile
1               5                   10

<210> SEQ ID NO 253
<211> LENGTH: 10
<212> TYPE: PRT
<213> ORGANISM: Artificial
```

```
<220> FEATURE:
<223> OTHER INFORMATION: An artificially synthesized peptide sequence

<400> SEQUENCE: 253

Leu Leu Ser Glu Glu Glu Lys Lys Asn Leu
1               5                   10

<210> SEQ ID NO 254
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 254

Tyr Met Ser Cys Phe Arg Thr Pro Val Val
1               5                   10

<210> SEQ ID NO 255
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 255

Met Met Ala Asn Asn Pro Glu Asp Trp Leu
1               5                   10

<210> SEQ ID NO 256
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 256

Met Val Met Glu Cys Gly Asn Ile Asp Leu
1               5                   10

<210> SEQ ID NO 257
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 257

Tyr Met Pro Pro Glu Ala Ile Lys Asp Met
1               5                   10

<210> SEQ ID NO 258
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 258

Lys Leu Ile Gly Arg Tyr Ser Gln Ala Ile
1               5                   10

<210> SEQ ID NO 259
<211> LENGTH: 10
<212> TYPE: PRT
<213> ORGANISM: Artificial
<220> FEATURE:
<223> OTHER INFORMATION: An artificially synthesized peptide sequence
```

```
<400> SEQUENCE: 259

Asn Gln Met Gln Pro Asp Thr Thr Ser Val
1               5                   10

<210> SEQ ID NO 260
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 260

Gln Ile Leu Ala Thr Pro Leu Gln Asn Leu
1               5                   10

<210> SEQ ID NO 261
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 261

Leu Ile Val Asp Gly Met Leu Lys Leu Ile
1               5                   10

<210> SEQ ID NO 262
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 262

Asn Leu Asn Leu Gln Lys Lys Gln Leu Leu
1               5                   10

<210> SEQ ID NO 263
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 263

Gln Met Gln Pro Asp Thr Thr Ser Val Val
1               5                   10

<210> SEQ ID NO 264
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 264

Lys Gly Thr Thr Glu Glu Met Lys Tyr Val
1               5                   10

<210> SEQ ID NO 265
<211> LENGTH: 10
<212> TYPE: PRT
<213> ORGANISM: Artificial
<220> FEATURE:
<223> OTHER INFORMATION: An artificially synthesized peptide sequenc

<400> SEQUENCE: 265
```

```
Leu Thr Ile Asp Ser Ile Met Asn Lys Val
1               5                   10
```

<210> SEQ ID NO 266
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 266

```
Lys Leu Gln Gln His Ser Asp Lys Ile Ile
1               5                   10
```

<210> SEQ ID NO 267
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 267

```
Lys Ile Phe Pro Arg Phe Phe Met Val
1               5
```

<210> SEQ ID NO 268
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 268

```
Gly Leu Trp Leu Ala Ile Leu Leu Leu
1               5
```

<210> SEQ ID NO 269
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 269

```
Leu Leu Val Val Ala Leu Pro Arg Val
1               5
```

<210> SEQ ID NO 270
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 270

```
Ala Leu Leu Ala Leu Leu Leu Val Val
1               5
```

<210> SEQ ID NO 271
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 271

```
Trp Leu Ala Ile Leu Leu Leu Leu Ala
```

```
<210> SEQ ID NO 272
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 272

Leu Leu Ala Ser Ile Ala Ala Gly Leu
1               5

<210> SEQ ID NO 273
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 273

Leu Leu Leu Leu Ala Ser Ile Ala Ala
1               5

<210> SEQ ID NO 274
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 274

Phe Met Val Ala Lys Gln Cys Ser Ala
1               5

<210> SEQ ID NO 275
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 275

Thr Met Ala Leu Leu Ala Leu Leu Leu
1               5

<210> SEQ ID NO 276
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 276

Met Ala Leu Leu Ala Leu Leu Leu Val
1               5

<210> SEQ ID NO 277
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 277

Ala Ile Leu Leu Leu Leu Ala Ser Ile
1               5
```

<210> SEQ ID NO 278
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 278

Ala Leu Pro Arg Val Trp Thr Asp Ala
1               5

<210> SEQ ID NO 279
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 279

Ser Met Gly Glu Ser Cys Gly Gly Leu
1               5

<210> SEQ ID NO 280
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 280

Leu Leu Ala Leu Leu Leu Val Val Ala
1               5

<210> SEQ ID NO 281
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 281

Val Val Ala Leu Pro Arg Val Trp Thr
1               5

<210> SEQ ID NO 282
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 282

Arg Val Trp Thr Asp Ala Asn Leu Thr
1               5

<210> SEQ ID NO 283
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 283

Phe Leu Leu Glu Glu Pro Met Pro Phe
1               5

<210> SEQ ID NO 284

```
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 284

Leu Ala Leu Leu Leu Val Val Ala Leu
1               5

<210> SEQ ID NO 285
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 285

Gly Thr Met Ala Leu Leu Ala Leu Leu
1               5

<210> SEQ ID NO 286
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 286

Leu Leu Leu Val Val Ala Leu Pro Arg Val
1               5                   10

<210> SEQ ID NO 287
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 287

Gly Leu Trp Leu Ala Ile Leu Leu Leu Leu
1               5                   10

<210> SEQ ID NO 288
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 288

Leu Leu Leu Ala Ser Ile Ala Ala Gly Leu
1               5                   10

<210> SEQ ID NO 289
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 289

Thr Met Ala Leu Leu Ala Leu Leu Leu Val
1               5                   10

<210> SEQ ID NO 290
<211> LENGTH: 10
<212> TYPE: PRT
```

```
<213> ORGANISM: Artificial
<220> FEATURE:
<223> OTHER INFORMATION: An artificially synthesized peptide sequence

<400> SEQUENCE: 290

Leu Leu Ala Leu Leu Val Val Ala Leu
1               5                   10

<210> SEQ ID NO 291
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 291

Phe Leu Leu Glu Glu Pro Met Pro Phe Phe
1               5                   10

<210> SEQ ID NO 292
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 292

Ile Leu Leu Leu Leu Ala Ser Ile Ala Ala
1               5                   10

<210> SEQ ID NO 293
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 293

Lys Ile Phe Pro Arg Phe Phe Met Val Ala
1               5                   10

<210> SEQ ID NO 294
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 294

Ala Leu Leu Ala Leu Leu Leu Val Val Ala
1               5                   10

<210> SEQ ID NO 295
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 295

Leu Val Val Ala Leu Pro Arg Val Trp Thr
1               5                   10

<210> SEQ ID NO 296
<211> LENGTH: 10
<212> TYPE: PRT
<213> ORGANISM: Artificial
<220> FEATURE:
```

```
<223> OTHER INFORMATION: An artificially synthesized peptide sequence

<400> SEQUENCE: 296

Met Ala Leu Leu Ala Leu Leu Val Val
1               5                   10

<210> SEQ ID NO 297
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 297

Arg Leu Gln Arg Pro Arg Gln Ala Pro Ala
1               5                   10

<210> SEQ ID NO 298
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 298

Cys Gln Asn Pro Arg Arg Cys Lys Trp Thr
1               5                   10

<210> SEQ ID NO 299
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 299

Arg Val Trp Thr Asp Ala Asn Leu Thr Ala
1               5                   10

<210> SEQ ID NO 300
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 300

Trp Ala Pro Leu Gly Thr Met Ala Leu Leu
1               5                   10

<210> SEQ ID NO 301
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 301

Thr Glu Pro Tyr Cys Val Ile Ala Ala Val
1               5                   10

<210> SEQ ID NO 302
<211> LENGTH: 10
<212> TYPE: PRT
<213> ORGANISM: Artificial
<220> FEATURE:
<223> OTHER INFORMATION: An artificially synthesized peptide sequence
```

```
<400> SEQUENCE: 302

Leu Glu Glu Pro Met Pro Phe Phe Tyr Leu
1               5                   10

<210> SEQ ID NO 303
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 303

Leu Glu Gly Pro Pro Ile Asn Ser Ser Val
1               5                   10

<210> SEQ ID NO 304
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 304

Tyr Leu Lys Cys Cys Lys Ile Arg Tyr Cys
1               5                   10

<210> SEQ ID NO 305
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 305

Val Lys Ile Phe Pro Arg Phe Phe Met Val
1               5                   10

<210> SEQ ID NO 306
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 306

Lys Ile Phe Pro Ser Lys Arg Ile Leu
1               5

<210> SEQ ID NO 307
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 307

Arg Gly Ser Val Leu Glu Gly Val Leu
1               5

<210> SEQ ID NO 308
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 308
```

```
Phe Leu Leu Leu Val Leu Leu Leu
1               5

<210> SEQ ID NO 309
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 309

Ile Gly Asn Phe Ile Ile Glu Asn Leu
1               5

<210> SEQ ID NO 310
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 310

Thr Ala Val Ala Val Val Glu Ile Leu
1               5

<210> SEQ ID NO 311
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 311

Asn Gln Ser Pro Val Arg Gln Val Leu
1               5

<210> SEQ ID NO 312
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 312

Lys Gln Asp Thr Tyr Asp Val His Leu
1               5

<210> SEQ ID NO 313
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 313

Asp Tyr Glu Gly Ser Gly Ser Asp Ala
1               5

<210> SEQ ID NO 314
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 314

Gly Trp Leu Leu Leu Asn Lys Pro Leu
1               5
```

```
<210> SEQ ID NO 315
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 315

Ile Leu Pro Val Leu Gly Ala Val Leu
1               5

<210> SEQ ID NO 316
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 316

Thr Ala Pro Pro Tyr Asp Thr Leu Leu
1               5

<210> SEQ ID NO 317
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 317

Val Val Leu Ser Leu Lys Lys Phe Leu
1               5

<210> SEQ ID NO 318
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 318

Ala Leu Leu Phe Leu Leu Leu Val Leu
1               5

<210> SEQ ID NO 319
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 319

Val Thr Asn Glu Ala Pro Phe Val Leu
1               5

<210> SEQ ID NO 320
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 320

Ala Val Leu Ala Leu Leu Phe Leu Leu
1               5
```

```
<210> SEQ ID NO 321
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 321

Asp Thr Tyr Asp Val His Leu Ser Leu
1               5

<210> SEQ ID NO 322
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 322

Gly Pro Leu Ala Ser Leu Leu Leu Leu
1               5

<210> SEQ ID NO 323
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 323

Val Leu Asn Ile Thr Asp Lys Asp Leu
1               5

<210> SEQ ID NO 324
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 324

Ala Val Glu Lys Glu Thr Gly Trp Leu
1               5

<210> SEQ ID NO 325
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 325

Asn Asn Ile Tyr Glu Val Met Val Leu
1               5

<210> SEQ ID NO 326
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 326

Leu Leu Leu Leu Gln Val Cys Trp Leu
1               5

<210> SEQ ID NO 327
<211> LENGTH: 9
```

```
<212> TYPE: PRT
<213> ORGANISM: Artificial
<220> FEATURE:
<223> OTHER INFORMATION: An artificially synthesized peptide sequence

<400> SEQUENCE: 327

Gly Cys Pro Gly Gln Glu Pro Ala Leu
1               5

<210> SEQ ID NO 328
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 328

Glu Tyr Thr Leu Thr Ile Gln Ala Thr
1               5

<210> SEQ ID NO 329
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 329

Glu Thr Val Gln Glu Arg Arg Ser Leu
1               5

<210> SEQ ID NO 330
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 330

Ser Tyr Arg Ile Leu Arg Asp Pro Ala
1               5

<210> SEQ ID NO 331
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 331

Gly Gln Val Thr Ala Val Gly Thr Leu
1               5

<210> SEQ ID NO 332
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 332

Gly Ala Val Leu Ala Leu Leu Phe Leu
1               5

<210> SEQ ID NO 333
<211> LENGTH: 9
<212> TYPE: PRT
<213> ORGANISM: Artificial
```

```
<220> FEATURE:
<223> OTHER INFORMATION: An artificially synthesized peptide sequence

<400> SEQUENCE: 333

Gly Ile Leu Thr Thr Arg Lys Gly Leu
1               5

<210> SEQ ID NO 334
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 334

His Pro Glu Ser Asn Gln Gly Ile Leu
1               5

<210> SEQ ID NO 335
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 335

Val Leu Ala Leu Leu Phe Leu Leu Leu
1               5

<210> SEQ ID NO 336
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 336

Glu Gly Asp Thr Val Val Leu Ser Leu
1               5

<210> SEQ ID NO 337
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 337

Thr Ile Ser Val Ile Ser Ser Gly Leu
1               5

<210> SEQ ID NO 338
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 338

Val Leu Gly Ala Val Leu Ala Leu Leu
1               5

<210> SEQ ID NO 339
<211> LENGTH: 9
<212> TYPE: PRT
<213> ORGANISM: Artificial
<220> FEATURE:
<223> OTHER INFORMATION: An artificially synthesized peptide sequence
```

<400> SEQUENCE: 339

Glu Trp Gly Ser Arg Phe Lys Lys Leu
1               5

<210> SEQ ID NO 340
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 340

Lys Val Val Glu Val Gln Glu Gly Ile
1               5

<210> SEQ ID NO 341
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 341

Thr Tyr Asp Val His Leu Ser Leu Ser
1               5

<210> SEQ ID NO 342
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 342

Phe Tyr Ser Ile Thr Gly Pro Gly Ala
1               5

<210> SEQ ID NO 343
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 343

Ile Tyr Thr Tyr Asn Gly Val Val Ala
1               5

<210> SEQ ID NO 344
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 344

Phe Ile Leu Pro Val Leu Gly Ala Val Leu
1               5                   10

<210> SEQ ID NO 345
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 345

Ala Val Leu Ala Leu Leu Phe Leu Leu Leu
1               5                   10

<210> SEQ ID NO 346
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 346

Gly Thr Ile Ser Val Ile Ser Ser Gly Leu
1               5                   10

<210> SEQ ID NO 347
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 347

Asp Tyr Glu Gly Ser Gly Ser Asp Ala Ala
1               5                   10

<210> SEQ ID NO 348
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 348

Thr Val Val Leu Ser Leu Lys Lys Phe Leu
1               5                   10

<210> SEQ ID NO 349
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 349

Phe Ala Val Glu Lys Glu Thr Gly Trp Leu
1               5                   10

<210> SEQ ID NO 350
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 350

Ala Leu Leu Phe Leu Leu Leu Val Leu Leu
1               5                   10

<210> SEQ ID NO 351
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 351

Ser Gln Glu Pro Lys Asp Pro His Asp Leu

```
1               5                   10

<210> SEQ ID NO 352
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 352

Leu Ala Leu Leu Phe Leu Leu Leu Val Leu
1               5                   10

<210> SEQ ID NO 353
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 353

Gly Ala Glu Gln Glu Pro Gly Gln Ala Leu
1               5                   10

<210> SEQ ID NO 354
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 354

Gly Ala Val Leu Ala Leu Leu Phe Leu Leu
1               5                   10

<210> SEQ ID NO 355
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 355

Val Asn Glu Glu Gly Asp Thr Val Val Leu
1               5                   10

<210> SEQ ID NO 356
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 356

Asn Ala Val Gly His Glu Val Gln Arg Leu
1               5                   10

<210> SEQ ID NO 357
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 357

Thr Asn Glu Ala Pro Phe Val Leu Lys Leu
1               5                   10
```

<210> SEQ ID NO 358
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 358

Glu Asn Gln Lys Ile Ser Tyr Arg Ile Leu
1               5                   10

<210> SEQ ID NO 359
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 359

Ser Leu Leu Leu Leu Gln Val Cys Trp Leu
1               5                   10

<210> SEQ ID NO 360
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 360

Gly Leu Glu Ala Arg Pro Glu Val Val Leu
1               5                   10

<210> SEQ ID NO 361
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 361

Glu Val Gln Arg Leu Thr Val Thr Asp Leu
1               5                   10

<210> SEQ ID NO 362
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 362

Gly Leu Pro Arg Gly Pro Leu Ala Ser Leu
1               5                   10

<210> SEQ ID NO 363
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 363

Leu Pro Val Leu Gly Ala Val Leu Ala Leu
1               5                   10

<210> SEQ ID NO 364

```
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 364

Gln Val Leu Asn Ile Thr Asp Lys Asp Leu
1               5                   10

<210> SEQ ID NO 365
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 365

Ala Val Glu Lys Glu Thr Gly Trp Leu Leu
1               5                   10

<210> SEQ ID NO 366
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 366

Ser Gly Gln Val Thr Ala Val Gly Thr Leu
1               5                   10

<210> SEQ ID NO 367
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 367

Gln Gly Ile Leu Thr Thr Arg Lys Gly Leu
1               5                   10

<210> SEQ ID NO 368
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 368

Ser Pro Pro Thr Thr Gly Thr Gly Thr Leu
1               5                   10

<210> SEQ ID NO 369
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 369

Asn Ser Pro Ala Trp Arg Ala Thr Tyr Leu
1               5                   10

<210> SEQ ID NO 370
<211> LENGTH: 10
<212> TYPE: PRT
```

<213> ORGANISM: Artificial
<220> FEATURE:
<223> OTHER INFORMATION: An artificially synthesized peptide sequence

<400> SEQUENCE: 370

Gly Pro Phe Pro Gln Arg Leu Asn Gln Leu
1               5                   10

<210> SEQ ID NO 371
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 371

Glu Ile Gly Asn Phe Ile Ile Glu Asn Leu
1               5                   10

<210> SEQ ID NO 372
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 372

Thr Thr Ala Val Ala Val Val Glu Ile Leu
1               5                   10

<210> SEQ ID NO 373
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 373

Ile Tyr Thr Tyr Asn Gly Val Val Ala Tyr
1               5                   10

<210> SEQ ID NO 374
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 374

Asp Tyr Asp Tyr Leu Asn Glu Trp Gly Ser
1               5                   10

<210> SEQ ID NO 375
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 375

Ala Leu Phe Ser Cys Leu Phe Gly Ile
1               5

<210> SEQ ID NO 376
<211> LENGTH: 9
<212> TYPE: PRT
<213> ORGANISM: Artificial
<220> FEATURE:

```
<223> OTHER INFORMATION: An artificially synthesized peptide sequence

<400> SEQUENCE: 376

Gly Leu Asn Pro Leu Thr Ser Tyr Val
1               5

<210> SEQ ID NO 377
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 377

Cys Leu Phe Gly Ile Cys Asp Ala Val
1               5

<210> SEQ ID NO 378
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 378

Gln Met His Gly Arg Met Val Pro Val
1               5

<210> SEQ ID NO 379
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 379

Lys Leu Asn Thr Glu Ile Arg Asp Val
1               5

<210> SEQ ID NO 380
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 380

Trp Leu Val Pro Ile Gly Asn Cys Leu
1               5

<210> SEQ ID NO 381
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 381

Lys Leu Ile Arg Asn Pro Asn Ser Leu
1               5

<210> SEQ ID NO 382
<211> LENGTH: 9
<212> TYPE: PRT
<213> ORGANISM: Artificial
<220> FEATURE:
<223> OTHER INFORMATION: An artificially synthesized peptide sequence
```

```
<400> SEQUENCE: 382

Val Val Ile Leu Ile Ala Ala Phe Val
1               5

<210> SEQ ID NO 383
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 383

Val Met Trp Glu Val Met Ser Tyr Gly
1               5

<210> SEQ ID NO 384
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 384

Gly Ile Gly Ser Gly Met Lys Tyr Leu
1               5

<210> SEQ ID NO 385
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 385

Asn Ile Leu Val Asn Ser Asn Leu Val
1               5

<210> SEQ ID NO 386
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 386

Thr Thr Leu Glu Ala Val Val His Val
1               5

<210> SEQ ID NO 387
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 387

Tyr Leu Leu Gly Val Val Leu Thr Leu
1               5

<210> SEQ ID NO 388
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 388
```

```
Leu Tyr Leu Leu Gly Val Val Leu Thr
1               5
```

<210> SEQ ID NO 389
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 389

```
Val Met Glu Ser Leu Glu Gly Leu Leu
1               5
```

<210> SEQ ID NO 390
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 390

```
Leu Leu Gly Val Val Leu Thr Leu Leu
1               5
```

<210> SEQ ID NO 391
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 391

```
Tyr Leu Leu Gly Val Val Leu Thr Leu Leu
1               5                   10
```

<210> SEQ ID NO 392
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 392

```
Leu Asn Leu Tyr Leu Leu Gly Val Val Leu
1               5                   10
```

<210> SEQ ID NO 393
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 393

```
Leu Ala Asn Thr Glu Pro Thr Lys Gly Leu
1               5                   10
```

<210> SEQ ID NO 394
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 394

```
Ser Ile Phe Val Arg Val Met Glu Ser Leu
1               5                   10
```

```
<210> SEQ ID NO 395
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 395

Leu Tyr Leu Lys Leu Leu Pro Tyr Val
1               5

<210> SEQ ID NO 396
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 396

Ile Ser Asn Glu Gly Asn Gln Asn Leu
1               5

<210> SEQ ID NO 397
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 397

Arg Ser Gly Trp His Thr Phe Pro Leu
1               5

<210> SEQ ID NO 398
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 398

Ala Ser Leu Trp Leu Tyr Leu Lys Leu
1               5

<210> SEQ ID NO 399
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 399

Ala Tyr Leu Ala Gly Val Pro Gly Ser
1               5

<210> SEQ ID NO 400
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 400

Asn Met Val Glu Lys Arg Val Asp Leu
1               5
```

```
<210> SEQ ID NO 401
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 401

Ala Met Val Thr Ala Leu Arg Lys Leu
1               5

<210> SEQ ID NO 402
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 402

Val Gln Cys Asp Ser Cys Gln Glu Leu
1               5

<210> SEQ ID NO 403
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 403

Asn Ser Cys Cys Ile Pro Thr Lys Leu
1               5

<210> SEQ ID NO 404
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 404

Asn Tyr Cys Glu Gly Ser Cys Pro Ala
1               5

<210> SEQ ID NO 405
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 405

Phe Val Val Gln Ala Ser Leu Trp Leu
1               5

<210> SEQ ID NO 406
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 406

Val Asn Gln Tyr Arg Met Arg Gly Leu
1               5

<210> SEQ ID NO 407
<211> LENGTH: 9
```

```
<212> TYPE: PRT
<213> ORGANISM: Artificial
<220> FEATURE:
<223> OTHER INFORMATION: An artificially synthesized peptide sequence

<400> SEQUENCE: 407

Gln Phe Phe Ile Asp Phe Arg Leu Ile
1               5

<210> SEQ ID NO 408
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 408

Leu Leu Leu Leu Ala Ala Gly Trp Leu
1               5

<210> SEQ ID NO 409
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 409

Gln Gln Phe Phe Ile Asp Phe Arg Leu
1               5

<210> SEQ ID NO 410
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 410

Asn Leu Phe Val Val Gln Ala Ser Leu
1               5

<210> SEQ ID NO 411
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 411

Tyr Tyr Gly Asn Tyr Cys Glu Gly Ser
1               5

<210> SEQ ID NO 412
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 412

Gln Asn Leu Phe Val Val Gln Ala Ser Leu
1               5                   10

<210> SEQ ID NO 413
<211> LENGTH: 10
<212> TYPE: PRT
<213> ORGANISM: Artificial
```

```
<220> FEATURE:
<223> OTHER INFORMATION: An artificially synthesized peptide sequence

<400> SEQUENCE: 413

Asp Val Gln Cys Asp Ser Cys Gln Glu Leu
1               5                   10

<210> SEQ ID NO 414
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 414

Val Val Gln Ala Ser Leu Trp Leu Tyr Leu
1               5                   10

<210> SEQ ID NO 415
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 415

Leu Tyr Phe Asp Asp Glu Tyr Asn Ile Val
1               5                   10

<210> SEQ ID NO 416
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 416

Phe Pro Leu Thr Glu Ala Ile Gln Ala Leu
1               5                   10

<210> SEQ ID NO 417
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 417

Arg Thr Asn Leu Cys Cys Arg Gln Gln Phe
1               5                   10

<210> SEQ ID NO 418
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 418

Ala Ala Met Val Thr Ala Leu Arg Lys Leu
1               5                   10

<210> SEQ ID NO 419
<211> LENGTH: 10
<212> TYPE: PRT
<213> ORGANISM: Artificial
<220> FEATURE:
<223> OTHER INFORMATION: An artificially synthesized peptide sequence
```

<400> SEQUENCE: 419

Val Asn Ser Cys Cys Ile Pro Thr Lys Leu
1               5                   10

<210> SEQ ID NO 420
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 420

Cys Leu Leu Leu Leu Ala Ala Gly Trp Leu
1               5                   10

<210> SEQ ID NO 421
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 421

Val Val Asn Gln Tyr Arg Met Arg Gly Leu
1               5                   10

<210> SEQ ID NO 422
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 422

Asp Gly Leu Ala Ser Ser Arg Val Arg Leu
1               5                   10

<210> SEQ ID NO 423
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 423

Gly Leu Glu Cys Asp Gly Arg Thr Asn Leu
1               5                   10

<210> SEQ ID NO 424
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 424

Asn Tyr Cys Glu Gly Ser Cys Pro Ala Tyr
1               5                   10

<210> SEQ ID NO 425
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 425

Ala Ser Leu Trp Leu Tyr Leu Lys Leu Leu
1               5                   10

<210> SEQ ID NO 426
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 426

Trp Asn Met Val Glu Lys Arg Val Asp Leu
1               5                   10

<210> SEQ ID NO 427
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 427

Phe Leu Glu Ala Val Lys Arg His Ile Leu
1               5                   10

<210> SEQ ID NO 428
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 428

Tyr Cys Glu Gly Ser Cys Pro Ala Tyr Leu
1               5                   10

<210> SEQ ID NO 429
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 429

Ala Val Lys Arg His Ile Leu Ser Arg Leu
1               5                   10

<210> SEQ ID NO 430
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 430

Gln Ala Ser Leu Trp Leu Tyr Leu Lys Leu
1               5                   10

<210> SEQ ID NO 431
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 431

Gly Tyr Tyr Gly Asn Tyr Cys Glu Gly Ser

<210> SEQ ID NO 432
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 432

Leu Tyr Phe Phe Ile Ser Asn Glu Gly Asn
1               5                   10

<210> SEQ ID NO 433
<211> LENGTH: 10
<212> TYPE: PRT
<213> ORGANISM: Artificial
<220> FEATURE:
<223> OTHER INFORMATION: An artificially synthesized peptide sequence

<400> SEQUENCE: 433

Tyr Tyr Gly Asn Tyr Cys Glu Gly Ser Cys
1               5                   10

<210> SEQ ID NO 434
<211> LENGTH: 9
<212> TYPE: PRT
<213> ORGANISM: Artificial
<220> FEATURE:
<223> OTHER INFORMATION: An artificially synthesized peptide sequence

<400> SEQUENCE: 434

Ile Leu Leu Leu Leu Ala Ser Ile Ala
1               5

<210> SEQ ID NO 435
<211> LENGTH: 3218
<212> TYPE: DNA
<213> ORGANISM: Homo sapiens
<220> FEATURE:
<221> NAME/KEY: CDS
<222> LOCATION: (47)..(1270)

<400> SEQUENCE: 435

```
actcggctcg cctcgcggcg ggcgccctcg tcgccagcgg cgcacc atg gac ggg        55
                                                 Met Asp Gly
                                                   1 ctg ccc ggt cgg gcg ctg ggg gcc gcc tgc ctt ctg ctg ctg gcg gcc      103
Leu Pro Gly Arg Ala Leu Gly Ala Ala Cys Leu Leu Leu Leu Ala Ala
      5                  10                  15 ggc tgg ctg ggg cct gag gcc tgg ggc tca ccc acg ccc ccg ccg acg      151
Gly Trp Leu Gly Pro Glu Ala Trp Gly Ser Pro Thr Pro Pro Pro Thr
 20                  25                  30                  35 cct gcc gcg ccg ccg cca ccc ccg cca ccc gga tcc ccg ggt ggc tcg      199
Pro Ala Ala Pro Pro Pro Pro Pro Pro Pro Gly Ser Pro Gly Gly Ser
                 40                  45                  50 cag gac acc tgt acg tcg tgc ggc ggc ttc cgg cgg cca gag gag ctc      247
Gln Asp Thr Cys Thr Ser Cys Gly Gly Phe Arg Arg Pro Glu Glu Leu
             55                  60                  65 ggc cga gtg gac ggc gac ttc ctg gag gcg gtg aag cgg cac atc ttg      295
Gly Arg Val Asp Gly Asp Phe Leu Glu Ala Val Lys Arg His Ile Leu
         70                  75                  80 agc cgc ctg cag atg cgg ggc cgg ccc aac atc acg cac gcc gtg cct      343
Ser Arg Leu Gln Met Arg Gly Arg Pro Asn Ile Thr His Ala Val Pro
     85                  90                  95
```

-continued

| | | |
|---|---|---|
| aag gcc gcc atg gtc acg gcc ctg cgc aag ctg cac gcg ggc aag gtg<br>Lys Ala Ala Met Val Thr Ala Leu Arg Lys Leu His Ala Gly Lys Val<br>100                                 105                              110                           115 | 391 | |
| cgc gag gac ggc cgc gtg gag atc ccg cac ctc gac ggc cac gcc agc<br>Arg Glu Asp Gly Arg Val Glu Ile Pro His Leu Asp Gly His Ala Ser<br>                    120                              125                              130 | 439 | |
| ccg ggc gcc gac ggc cag gag cgc gtt tcc gaa atc atc agc ttc gcc<br>Pro Gly Ala Asp Gly Gln Glu Arg Val Ser Glu Ile Ile Ser Phe Ala<br>                    135                              140                              145 | 487 | |
| gag aca gat ggc ctc gcc tcc tcc cgg gtc cgc cta tac ttc ttc atc<br>Glu Thr Asp Gly Leu Ala Ser Ser Arg Val Arg Leu Tyr Phe Phe Ile<br>             150                              155                              160 | 535 | |
| tcc aac gaa ggc aac cag aac ctg ttt gtg gtc cag gcc agc ctg tgg<br>Ser Asn Glu Gly Asn Gln Asn Leu Phe Val Val Gln Ala Ser Leu Trp<br>        165                            170                              175 | 583 | |
| ctt tac ctg aaa ctc ctg ccc tac gtc ctg gag aag ggc agc cgg cgg<br>Leu Tyr Leu Lys Leu Leu Pro Tyr Val Leu Glu Lys Gly Ser Arg Arg<br>180                                 185                              190                           195 | 631 | |
| aag gtg cgg gtc aaa gtg tac ttc cag gag cag ggc cac ggt gac agg<br>Lys Val Arg Val Lys Val Tyr Phe Gln Glu Gln Gly His Gly Asp Arg<br>                    200                              205                              210 | 679 | |
| tgg aac atg gtg gag aag agg gtg gac ctc aag cgc agc ggc tgg cat<br>Trp Asn Met Val Glu Lys Arg Val Asp Leu Lys Arg Ser Gly Trp His<br>             215                              220                              225 | 727 | |
| acc ttc cca ctc acg gag gcc atc cag gcc ttg ttt gag cgg ggc gag<br>Thr Phe Pro Leu Thr Glu Ala Ile Gln Ala Leu Phe Glu Arg Gly Glu<br>        230                            235                              240 | 775 | |
| cgg cga ctc aac cta gac gtg cag tgt gac agc tgc cag gag ctg gcc<br>Arg Arg Leu Asn Leu Asp Val Gln Cys Asp Ser Cys Gln Glu Leu Ala<br>245                                 250                              255 | 823 | |
| gtg gtg ccg gtg ttc gtg gac cca ggc gaa gag tcg cac cgg ccc ttt<br>Val Val Pro Val Phe Val Asp Pro Gly Glu Glu Ser His Arg Pro Phe<br>260                                 265                              270                           275 | 871 | |
| gtg gtg gtg cag gct cgg ctg ggc gac agc agg cac cgc att cgc aag<br>Val Val Val Gln Ala Arg Leu Gly Asp Ser Arg His Arg Ile Arg Lys<br>                    280                              285                              290 | 919 | |
| cga ggc ctg gag tgc gat ggc cgg acc aac ctc tgt tgc agg caa cag<br>Arg Gly Leu Glu Cys Asp Gly Arg Thr Asn Leu Cys Cys Arg Gln Gln<br>             295                              300                              305 | 967 | |
| ttc ttc att gac ttc cgc ctc atc ggc tgg aac gac tgg atc ata gca<br>Phe Phe Ile Asp Phe Arg Leu Ile Gly Trp Asn Asp Trp Ile Ile Ala<br>        310                            315                              320 | 1015 | |
| ccc acc ggc tac tac ggg aac tac tgt gag ggc agc tgc cca gcc tac<br>Pro Thr Gly Tyr Tyr Gly Asn Tyr Cys Glu Gly Ser Cys Pro Ala Tyr<br>325                               330                              335 | 1063 | |
| ctg gca ggg gtc ccc ggc tct gcc tcc tcc ttc cac acg gct gtg gtg<br>Leu Ala Gly Val Pro Gly Ser Ala Ser Ser Phe His Thr Ala Val Val<br>340                                 345                              350                           355 | 1111 | |
| aac cag tac cgc atg cgg ggt ctg aac ccc ggc acg gtg aac tcc tgc<br>Asn Gln Tyr Arg Met Arg Gly Leu Asn Pro Gly Thr Val Asn Ser Cys<br>                    360                              365                              370 | 1159 | |
| tgc att ccc acc aag ctg agc acc atg tcc atg ctg tac ttc gat gat<br>Cys Ile Pro Thr Lys Leu Ser Thr Met Ser Met Leu Tyr Phe Asp Asp<br>             375                              380                              385 | 1207 | |
| gag tac aac atc gtc aag cgg gac gtg ccc aac atg att gtg gag gag<br>Glu Tyr Asn Ile Val Lys Arg Asp Val Pro Asn Met Ile Val Glu Glu<br>        390                            395                              400 | 1255 | |
| tgc ggc tgc gcc tga cagtgcaagg caggggcacg gtggtggggc acggagggca<br>Cys Gly Cys Ala<br>        405 | 1310 | |

```
gtcccgggtg ggcttcttcc agcccccgcg ggaacggggg tacacggtgg gctgagtaca   1370
gtcattctgt tgggctgtgg agatagtgcc agggtgcggc ctgagatatt tttctacagc   1430
ttcatagagc aaccagtcaa aaccagagcg agaaccctca actgacatga aatactttaa   1490
aatgcacacg tagccacgca cagccagacg catcctgcca cccacacagc agcctccagg   1550
ataccagcaa atggatgcgg tgacaaatgg cagcttagct acaaatgcct gtcagtcgga   1610
gagaatgggg tgagcagcca ccattcccac cagctggccc ggccactctg aattgcgcct   1670
tccgagcaca cataaaagca caaagacaga gacgcagaga gagagagaga gccacggaga   1730
ggaaaagcag atgcagggt ggggagcgca gctcggcgga ggctgcgtgt gccccgtggc   1790
ttttaccagg cctgctctgc ctggctcgat gtctgcttct tccccagcct gggatccttc   1850
gtgcttcaag gctggggag cctgtccttc catgcccttg tcgagggaaa gagacccaga   1910
aaggacacaa cccgtcagag acctgggagc aggggcaatg accgtttgac tgtttgtggc   1970
ttgggcctct gacatgactt atgtgtgtgt gtgttttgg ggtggggagg gagggagaga   2030
agagggggct aaatttgatg ctttaactga tctccaacag ttgacaggtc atccttgcca   2090
gttgtataac tgaaaaagga cttttctacc aggtatgacc ttttaagtga aaatctgaat   2150
tgttctaaat ggaaagaaaa aaagttgcaa tctgtgccct tcattgggga cattcctcta   2210
ggactggttt ggggacgggt gggaatgacc cctaggcaag gggatgagac cgcaggagga   2270
aatggcgggg aggaggcatt cttgaactgc tgaggatggg gggtgtcccc tcagcggagg   2330 ccaaggggagg ggagcagcct agttggtctt ggagagatgg ggaaggcttt cagctgattt   2390
gcagaagttg cccatgtggg ccccagccat cagggctggc cgtggacgtg gcccctgccc   2450
actcacctgc ccgcctgccc gcccgcccgc atagcacttg cagacctgcc tgaacgcaca   2510
tgacatagca cttgccgatc tgcgtgtgtc cagaagtggc ccttggccga gcgccgaact   2570
cgctcgccct ctagatgtcc aagtgccacg tgaactatgc aatttaaagg gttgacccac   2630
actagacgaa actggactcg tacgactctt tttatatttt ttatacttga aatgaaatcc   2690
tttgcttctt ttttaagcga atgattgctt ttaatgtttg cactgattta gttgcatgat   2750
tagtcagaaa ctgccatttg aaaaaaagtt atttttatag cagcaaaaaa aaaaaaaaa   2810 gaatacagtt aaatgtatta tacataattt tggaaccaaa gaggccaaca gatcagtttt   2870 aatttatta gacggtgagg ccatctgaga tgaggtggac gttctgagca gtcccttgag   2930
tggcctgcca acgtttcagg gtatgaatgg attttgttta ttcggtttga tgtgtctttt   2990
ccatccttac acaccagaa ggtagagtaa aaatgactat gatagaatgc aggtgtgtat   3050
ccttaaatcc tcatctttat gtttatttaa taaagctccc cttagattct gtttcataat   3110
aatttaaaac caaacaattt tcccatagac ttgctgttaa agtattgtac gtttgtgtac   3170
agtttaagaa aataaaagat tgagtgccac gggaaaaaaa aaaaaaaa   3218
```

<210> SEQ ID NO 436
<211> LENGTH: 407
<212> TYPE: PRT
<213> ORGANISM: Homo sapiens

<400> SEQUENCE: 436

Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Ser Pro Thr Pro
                20                  25                  30

Pro Pro Thr Pro Ala Ala Pro Pro Pro Pro Pro Gly Ser Pro
        35                  40                  45

```
Gly Gly Ser Gln Asp Thr Cys Thr Ser Cys Gly Gly Phe Arg Arg Pro
    50              55                  60
Glu Glu Leu Gly Arg Val Asp Gly Asp Phe Leu Glu Ala Val Lys Arg
65                  70                  75                  80
His Ile Leu Ser Arg Leu Gln Met Arg Gly Arg Pro Asn Ile Thr His
                85                  90                  95
Ala Val Pro Lys Ala Ala Met Val Thr Ala Leu Arg Lys Leu His Ala
            100                 105                 110
Gly Lys Val Arg Glu Asp Gly Arg Val Glu Ile Pro His Leu Asp Gly
            115                 120                 125
His Ala Ser Pro Gly Ala Asp Gly Gln Glu Arg Val Ser Glu Ile Ile
130                 135                 140
Ser Phe Ala Glu Thr Asp Gly Leu Ala Ser Ser Arg Val Arg Leu Tyr
145                 150                 155                 160
Phe Phe Ile Ser Asn Glu Gly Asn Gln Asn Leu Phe Val Val Gln Ala
                165                 170                 175
Ser Leu Trp Leu Tyr Leu Lys Leu Leu Pro Tyr Val Leu Glu Lys Gly
            180                 185                 190
Ser Arg Arg Lys Val Arg Val Lys Val Tyr Phe Gln Glu Gln Gly His
            195                 200                 205
Gly Asp Arg Trp Asn Met Val Glu Lys Arg Val Asp Leu Lys Arg Ser
210                 215                 220
Gly Trp His Thr Phe Pro Leu Thr Glu Ala Ile Gln Ala Leu Phe Glu
225                 230                 235                 240
Arg Gly Glu Arg Arg Leu Asn Leu Asp Val Gln Cys Asp Ser Cys Gln
                245                 250                 255
Glu Leu Ala Val Val Pro Val Phe Val Asp Pro Gly Glu Glu Ser His
            260                 265                 270
Arg Pro Phe Val Val Val Gln Ala Arg Leu Gly Asp Ser Arg His Arg
            275                 280                 285
Ile Arg Lys Arg Gly Leu Glu Cys Asp Gly Arg Thr Asn Leu Cys Cys
290                 295                 300
Arg Gln Gln Phe Phe Ile Asp Phe Arg Leu Ile Gly Trp Asn Asp Trp
305                 310                 315                 320
Ile Ile Ala Pro Thr Gly Tyr Tyr Gly Asn Tyr Cys Glu Gly Ser Cys
                325                 330                 335
Pro Ala Tyr Leu Ala Gly Val Pro Gly Ser Ala Ser Ser Phe His Thr
            340                 345                 350
Ala Val Val Asn Gln Tyr Arg Met Arg Gly Leu Asn Pro Gly Thr Val
            355                 360                 365
Asn Ser Cys Cys Ile Pro Thr Lys Leu Ser Thr Met Ser Met Leu Tyr
            370                 375                 380
Phe Asp Asp Glu Tyr Asn Ile Val Lys Arg Asp Val Pro Asn Met Ile
385                 390                 395                 400
Val Glu Glu Cys Gly Cys Ala
                405
```